(12) United States Patent
Loessner et al.

(10) Patent No.: US 9,382,298 B2
(45) Date of Patent: Jul. 5, 2016

(54) POLYPEPTIDE

(75) Inventors: Martin Johannes Loessner, Ebmatingen (CH); Fritz Eichenseher, Zürich (CH)

(73) Assignee: Micreos Human Health B.V., Wageningen (NL)

( * ) Notice: Subject to any disclaimer, the term of this patent is extended or adjusted under 35 U.S.C. 154(b) by 0 days.

(21) Appl. No.: 14/115,609

(22) PCT Filed: May 4, 2011

(86) PCT No.: PCT/NL2011/050307
§ 371 (c)(1),
(2), (4) Date: Jan. 6, 2014

(87) PCT Pub. No.: WO2012/150858
PCT Pub. Date: Nov. 8, 2012

(65) Prior Publication Data
US 2014/0127168 A1      May 8, 2014

(51) Int. Cl.
*C07K 14/31* (2006.01)
*C12N 9/36* (2006.01)
*G01N 33/569* (2006.01)

(52) U.S. Cl.
CPC .............. *C07K 14/31* (2013.01); *C12N 9/2462* (2013.01); *G01N 33/56938* (2013.01)

(58) Field of Classification Search
USPC .................. 424/93.6, 94.63, 447, 94.61, 430, 424/164.1, 78.07, 94.6, 9.1; 435/195, 69.1, 435/253.4, 69.7; 514/2.6, 2.4, 2.7; 536/23.2
See application file for complete search history.

(56) References Cited

FOREIGN PATENT DOCUMENTS

| WO | 2009024327 A2 | 2/2009 |
|---|---|---|
| WO | 2010002959 A2 | 1/2010 |
| WO | 2010020657 A1 | 2/2010 |

OTHER PUBLICATIONS

Kwan et al (The complete genomes and proteomes of 27 *Staphylococcus aureus* bacteriophages Journal Proc. Natl. Acad. Sci. U.S.A. 102 (14), 5174-5179 (2005).*
Donovan (Peptidoglycan Hydrolase Fusions Maintain Their Parental Specificities Applied and Environmental Microbiology, vol. 72, No. 4, p. 2988-2996, Apr. 2006).*
Becker, Stephen C. et al., Differentially conserved staphylococcal SH3b_5 cell wall binding domains confer increased staphylolytic and streptolytic activity to a streptococcal prophage endolysin domain, Gene, Aug. 15, 2009; 443 (1-2):32-41.*
Loessner, Martin J. et al., C-terminal domains of Listeria monocytogenes bacteriophage murein hydrolases determine specific recognition and high-affinity binding to bacterial cell wall carbohydrates, Molecular Microbiology, Wiley-Blackwell Publishing Ltd., GB, vol. 44, No. 2, Apr. 1, 2002, pp. 335-349.
Sass Peter and Bierbaum, Gabriele, Lytic Activity of Recombinant Bacteriophage ϕ11 and ϕ12 Endolysins on Whole Cells and Biofilms of *Staphylococcus aureus*, Applied and Environmental Microbiology, American Society for Microbiology, US, vol. 73, No. 1, Jan. 2007, pp. 347-352.
International Search Report for Int. App. No. PCT/NL2011/050307, mailed Jan. 16, 2012.

* cited by examiner

*Primary Examiner* — Kagnew H Gebreyesus
(74) *Attorney, Agent, or Firm* — McDonnell Boehnen Hulbert & Berghoff LLP

(57) ABSTRACT

The invention relates to a polypeptide, a corresponding nucleic acid molecule, a construct and/or vector and/or cell comprising such nucleic acid molecule and/or a composition comprising said polypeptide, nucleic acid molecule, construct, vector and/or cell. The invention further relates to such composition for medical use, preferably for use in treating an infectious disease. Furthermore, the invention relates to the use of said polypeptide, nucleic acid molecule, construct, vector, cell and/or composition as an antimicrobial, preferably as a food additive or disinfectant, or for detecting bacteria, preferably in a diagnostic application.

21 Claims, 5 Drawing Sheets

SEQUENCE LISTING

<160> NUMBER OF SEQ ID NOS: 67

<210> SEQ ID NO 1
<211> LENGTH: 1461
<212> TYPE: DNA
<213> ORGANISM: Staphylococcus aureus bacteriophage 2638a

<400> SEQUENCE: 1

```
atgctaactg ctattgacta tcttacgaaa aaaggttgga aaatatcatc tgaccctcgc    60
acttacgatg gttaccctaa aaactacggc tacagaaatt accatgaaaa cggcattaat   120
tatgatgagt tttgtggtgg ttatcataga gcttttgatg tttacagtaa cgaaactaac   180
gacgtgcctg ctgttactag cggaacagtt attgaagcaa acgattacgg taattttggt   240
ggtacattcg ttattagaga cgctaacgat aacgattgga tatatgggca tctacaacgt   300
ggctcaatgc gatttgttgt aggcgacaaa gtcaatcaag tgacattat ggtttacaa     360 ggtaatagca actattacga caatcctatg agtgtacatt tacatttaca attacgccct   420
aaagacgcaa agaaagatga aaaatcacaa gtatgtagtg gtttggctat ggaaaaatat   480
```

```
gacattacaa atttaaatgc taaacaagat aaatcaaaga atgggagcgt gaaagagttg      540
aaacatatct attcaaacca tattaaaggt aacaagatta cagcaccaaa acctagtatt      600
caaggtgtgg tcatccacaa tgattatggt agtatgacac ctagtcaata cttaccatgg      660
ttatatgcac gtgagaataa cggtacacac gttaacggtt gggctagtgt ttatgcaaat      720
agaaacgaag tgctttggta tcatccgaca gactacgtag agtggcattg tggtaatcaa      780
tgggcaaatg ctaacttaat cggatttgaa gtgtgtgagt cgtatcctgg tagaatctcg      840
gacaaattat tcttagaaaa tgaagaagcg acattgaaag tagctgcgga tgtgatgaag      900
tcgtacggat taccagttaa tcgcaacact gtacgtctgc ataacgaatt cttcggaact      960
tcttgtccac atcgttcgtg ggacttgcat gttggcaaag gtgagcctta cacaactact     1020
aatattaata aaatgaaaga ctacttcatc aaacgcatca acattatta tgacggtgga     1080 aagctagaag taagcaaagc agcaactatc aaacaatctg acgttaagca agaagttaaa     1140
aagcaagaag caaaacaaat tgtgaaagca acagattgga aacagaataa agatggcatt     1200
tggtataaag ctgaacatgc ttcgttcaca gtgacagcac cagagggaat tatcacaaga     1260
tacaaaggtc cttggactgg tcacccacaa gctggtgtat acaaaaagg tcaaacgatt     1320 aaatatgatg aggttcaaaa atttgacggt catgtttggg tatcgtggga aacgtttgag     1380
ggcgaaactg tatacatgcc ggtacgcaca tgggacgcta aaactggtaa agttggtaag     1440
ttgtggggcg aaattaaata a                                              1461
```

<210> SEQ ID NO 2
<211> LENGTH: 1086
<212> TYPE: DNA
<213> ORGANISM: artificial
<220> FEATURE:
<223> OTHER INFORMATION: His-tagged Ami2638_CBD2368

<400> SEQUENCE: 2

```
atgagaggat cgcatcacca tcaccatcac ggatccttac gccctaaaga cgcaaagaaa       60
gatgaaaaat cacaagtatg tagtggtttg gctatggaaa aatatgacat tacaaattta      120
aatgctaaac aagataaatc aaagaatggg agcgtgaaag agttgaaaca tatctattca      180
aaccatatta aggtaacaa gattacagca ccaaaaccta gtattcaagg tgtggtcatc      240
cacaatgatt atggtagtat gacacctagt caatacttac catggttata tgcacgtgag      300
aataacggta cacacgttaa cggttgggct agtgtttatg caaatagaaa cgaagtgctt      360
tggtatcatc cgacagacta cgtagagtgg cattgtggta atcaatgggc aaatgctaac      420
ttaatcggat ttgaagtgtg tgagtcgtat cctggtagaa tctcggacaa attattctta      480
gaaaatgaag aagcgacatt gaaagtagct gcggatgtga tgaagtcgta cggattacca      540
gttaatcgca acactgtacg tctgcataac gaattcttcg gaacttcttg tccacatcgt      600
tcgtgggact tgcatgttgg caaaggtgag ccttacacaa ctactaatat taataaaatg      660
aaagactact tcatcaaacg catcaaacat tattatgacg gtggaaagct agaagtaagc      720
aaagcagcaa ctatcaaaca atctgacgtt aagcaagaag ttaaaaagca agaagcaaaa      780
caaattgtga agcaacaga ttggaaacag aataaagatg gcatttggta taagctgaa      840 catgcttcgt tcacagtgac agcaccagag ggaattatca agatacaa aggtccttgg      900 actggtcacc cacaagctgg tgtattacaa aaaggtcaaa cgattaaata tgatgaggtt      960
caaaaatttg acggtcatgt ttgggtatcg tgggaaacgt ttgagggcga aactgtatac     1020
atgccggtac gcacatggga cgctaaaact ggtaaagttg gtaagttgtg gggcgaaatt     1080
``` aaataa                                                              1086

<210> SEQ ID NO 3
<211> LENGTH: 1035
<212> TYPE: DNA
<213> ORGANISM: artificial
<220> FEATURE:
<223> OTHER INFORMATION: His-tagged M23-2638_CBD2638

<400> SEQUENCE: 3
atgagaggat cgcatcacca tcaccatcac ggatccatgc taactgctat tgactatctt      60
acgaaaaaag gttggaaaat atcatctgac cctcgcactt acgatggtta ccctaaaaac     120
tacggctaca gaaattacca tgaaaacggc attaattatg atgagttttg tggtggttat     180
catagagctt ttgatgttta cagtaacgaa actaacgacg tgcctgctgt tactagcgga     240
acagttattg aagcaaacga ttacggtaat tttggtggta cattcgttat tagagacgct     300
aacgataacg attggatata tgggcatcta caacgtggct caatgcgatt tgttgtaggc     360
gacaaagtca atcaaggtga cattattggt ttacaaggta atagcaacta ttacgacaat     420
cctatgagtg tacatttaca tttacaatta cgccctaaag acgcaaagaa agatgaaaaa     480
tcacaagtat gtagtggttt ggctatggaa aaatatgaca ttacaaattt aaatgctaaa     540
caagataaat caagaatgg gagcgtgaaa gagttgaaac atatctattc aaaccatatt     600
aaaggtaaca agattacagc accaaaacct agtattcaag gtgagctcgg tggaaagcta     660
gaagtaagca aagcagcaac tatcaaacaa tctgacgtta agcaagaagt taaaaagcaa     720
gaagcaaaac aaattgtgaa agcaacagat tggaaacaga ataaagatgg catttggtat     780
aaagctgaac atgcttcgtt cacagtgaca gcaccagagg gaattatcac aagatacaaa     840
ggtccttgga ctggtcaccc acaagctggt gtattacaaa aaggtcaaac gattaaatat     900
gatgaggttc aaaaatttga cggtcatgtt tgggtatcgt gggaaacgtt tgagggcgaa     960
actgtataca tgccggtacg cacatgggac gctaaaactg gtaaagttgg taagttgtgg    1020
ggcgaaatta aataa                                                    1035

<210> SEQ ID NO 4
<211> LENGTH: 2961
<212> TYPE: DNA
<213> ORGANISM: artificial
<220> FEATURE:
<223> OTHER INFORMATION: His-tagged Ply2638_Ply2638

<400> SEQUENCE: 4
atgagaggat cgcatcacca tcaccatcac ggatccatgc taactgctat tgactatctt      60
acgaaaaaag gttggaaaat atcatctgac cctcgcactt acgatggtta ccctaaaaac     120
tacggctaca gaaattacca tgaaaacggc attaattatg atgagttttg tggtggttat     180
catagagctt ttgatgttta cagtaacgaa actaacgacg tgcctgctgt tactagcgga     240
acagttattg aagcaaacga ttacggtaat tttggtggta cattcgttat tagagacgct     300
aacgataacg attggatata tgggcatcta caacgtggct caatgcgatt tgttgtaggc     360
gacaaagtca atcaaggtga cattattggt ttacaaggta atagcaacta ttacgacaat     420
cctatgagtg tacatttaca tttacaatta cgccctaaag acgcaaagaa agatgaaaaa     480
tcacaagtat gtagtggttt ggctatggaa aaatatgaca ttacaaattt aaatgctaaa     540
caagataaat caagaatgg gagcgtgaaa gagttgaaac atatctattc aaaccatatt     600

```
aaaggtaaca agattacagc accaaaacct agtattcaag gtgtggtcat ccacaatgat    660
tatggtagta tgacacctag tcaatactta ccatggttat atgcacgtga gaataacggt    720
acacacgtta acggttgggc tagtgtttat gcaaatagaa acgaagtgct ttggtatcat    780
ccgacagact acgtagagtg gcattgtggt aatcaatggg caaatgctaa cttaatcgga    840
tttgaagtgt gtgagtcgta tcctggtaga atctcggaca aattattctt agaaaatgaa    900
gaagcgacat tgaaagtagc tgcggatgtg atgaagtcgt acggattacc agttaatcgc    960
aacactgtac gtctgcataa cgaattcttc ggaacttctt gtccacatcg ttcgtgggac   1020
ttgcatgttg gcaaaggtga gccttacaca actactaata ttaataaaat gaaagactac   1080
ttcatcaaac gcatcaaaca ttattatgac ggtggaaagc tagaagtaag caaagcagca   1140
actatcaaac aatctgacgt taagcaagaa gttaaaaagc aagaagcaaa acaaattgtg   1200
aaagcaacag attggaaaca gaataaagat ggcatttggt ataaagctga acatgcttcg   1260
ttcacagtga cagcaccaga gggaattatc acaagataca aaggtccttg gactggtcac   1320
ccacaagctg gtgtattaca aaaaggtcaa acgattaaat atgatgaggt tcaaaaattt   1380
gacggtcatg tttgggtatc gtgggaaacg tttgagggcg aaactgtata catgccggta   1440
cgcacatggg acgctaaaac tggtaaagtt ggtaagttgt ggggcgaaat taagagctc    1500
atgctaactg ctattgacta tcttacgaaa aaaggttgga aatatcatc tgaccctcgc    1560
acttacgatg gttaccctaa aaactacggc tacagaaatt accatgaaaa cggcattaat   1620
tatgatgagt tttgtggtgg ttatcataga gcttttgatg tttacagtaa cgaaactaac   1680
gacgtgcctg ctgttactag cggaacagtt attgaagcaa acgattacgg taattttggt   1740
ggtacattcg ttattagaga cgctaacgat aacgattgga tatatgggca tctacaacgt   1800
ggctcaatgc gatttgttgt aggcgacaaa gtcaatcaag gtgacattat tggtttacaa   1860
ggtaatagca actattacga caatcctatg agtgtacatt tacatttaca attacgccct   1920
aaagacgcaa agaaagatga aaaatcacaa gtatgtagtg gtttggctat ggaaaaatat   1980
gacattacaa atttaaatgc taaacaagat aaatcaaaga atgggagcgt gaaagagttg   2040
aaacatatct attcaaacca tattaaaggt aacaagatta cagcaccaaa acctagtatt   2100
caaggtgtgg tcatccacaa tgattatggt agtatgacac ctagtcaata cttaccatgg   2160
ttatatgcac gtgagaataa cggtacacac gttaacggtt gggctagtgt ttatgcaaat   2220
agaaacgaag tgctttggta tcatccgaca gactacgtag agtggcattg tggtaatcaa   2280
tgggcaaatg ctaacttaat cggatttgaa gtgtgtgagt cgtatcctgg tagaatctcg   2340
gacaaattat tcttagaaaa tgaagaagcg acattgaaag tagctgcgga tgtgatgaag   2400
tcgtacggat taccagttaa tcgcaacact gtacgtctgc ataacgaatt cttcggaact   2460
tcttgtccac atcgttcgtg ggacttgcat gttggcaaag gtgagcctta cacaactact   2520
aatattaata aaatgaaaga ctacttcatc aaacgcatca aacattatta tgacggtgga   2580
aagctagaag taagcaaagc agcaactatc aaacaatctg acgttaagca agaagttaaa   2640
aagcaagaag caaaacaaat tgtgaaagca acagattgga aacagaataa agatggcatt   2700
tggtataaag ctgaacatgc ttcgttcaca gtgacagcac cagagggaat tatcacaaga   2760
tacaaaggtc cttggactgg tcacccacaa gctggtgtat acaaaaagg tcaaacgatt   2820
aaatatgatg aggttcaaaa atttgacggt catgtttggg tatcgtggga aacgtttgag   2880
ggcgaaactg tatacatgcc ggtacgcaca tgggacgcta aaactggtaa agttggtaag   2940
ttgtggggcg aaattaaata a                                              2961
```

<210> SEQ ID NO 5
<211> LENGTH: 1983
<212> TYPE: DNA
<213> ORGANISM: artificial
<220> FEATURE:
<223> OTHER INFORMATION: CHAP11_M23-2638_Ami2638_CBD2638

<400> SEQUENCE: 5

```
atgcaagcaa aattaactaa aaatgagttt atagagtggt tgaaaacttc tgagggaaaa      60
caattcaatg tggacttatg gtatggattt caatgctttg attatgccaa tgctggttgg     120
aaagttttgt ttggattact tctaaaaggt ttaggtgcaa aagatattcc gttcgctaac     180
aacttcgacg gattagctac tgtataccaa aatacaccgg acttcttagc acaacctggc     240
gacatggtgg tattcggtag caactacggt gctggatatg gtcacgttgc atgggtaatt     300
gaagcaactt tagattacat cattgtatat gagcagaatt ggctaggcgg tggctggact     360
gacgaatcg aacaacccgg ctggggttgg gaaaaagtta caagacgaca acatgcttat     420
gatttcccta tgtggtttat ccgtccgaat tttaaaagtg agacagcgcc acgatcagtt     480
caatctccta cacaagcacc taaaaaagaa acagctggat ccatgctaac tgctattgac     540
tatcttacga aaaaggttg gaaaatatca tctgaccctc gcacttacga tggttaccct     600
aaaaactacg gctacagaaa ttaccatgaa acggcatta attatgatga gttttgtggt     660
ggttatcata gagcttttga tgtttacagt aacgaaacta acgacgtgcc tgctgttact     720
agcggaacag ttattgaagc aaacgattac ggtaattttg gtggtacatt cgttattaga     780
gacgctaacg ataacgattg gatatatggg catctacaac gtggctcaat gcgatttgtt     840
gtaggcgaca aagtcaatca aggtgacatt attggtttac aaggtaatag caactattac     900
gacaatccta tgagtgtaca tttacattta caattacgcc ctaaagacgc aaagaaagat     960
gaaaaatcac aagtatgtag tggtttggct atggaaaaat atgacattac aaatttaaat    1020
gctaaacaag ataaatcaaa gaatgggagc gtgaaagagt tgaaacatat ctattcaaac    1080
catattaaag gtaacaagat tacagcacca aaacctagta ttcaaggtgt ggtcatccac    1140
aatgattatg gtagtatgac acctagtcaa tacttaccat ggttatatgc acgtgagaat    1200
aacggtacac acgttaacgg ttgggctagt gtttatgcaa atagaaacga agtgctttgg    1260
tatcatccga cagactacgt agagtggcat tgtggtaatc aatgggcaaa tgctaactta    1320
atcggatttg aagtgtgtga gtcgtatcct ggtagaatct cggacaaatt attcttagaa    1380
aatgaagaag cgacattgaa agtagctgcg gatgtgatga gtcgtacgg attaccagtt    1440
aatcgcaaca ctgtacgtct gcataacgaa ttcttcggaa cttcttgtcc acatcgttcg    1500
tgggacttgc atgttggcaa aggtgagcct tacacaacta ctaatattaa taaaatgaaa    1560
gactacttca tcaaacgcat caaacattat tatgacggtg aaagctaga agtaagcaaa    1620
gcagcaacta tcaaacaatc tgacgttaag caagaagtta aaaagcaaga agcaaaacaa    1680
attgtgaaag caacagattg gaaacagaat aaagatggca tttggtataa agctgaacat    1740
gcttcgttca cagtgacagc accagaggga attatcacaa gatacaaagg tccttggact    1800
ggtcacccac aagctggtgt attacaaaaa ggtcaaacga ttaaatatga tgaggttcaa    1860
aaatttgacg gtcatgtttg ggtatcgtgg gaaacgtttg agggcgaaac tgtatacatg    1920
ccggtacgca catgggacgc taaaactggt aaagttggta agttgtgggg cgaaattaaa    1980
taa                                                                  1983
```

<210> SEQ ID NO 6
<211> LENGTH: 2109
<212> TYPE: DNA
<213> ORGANISM: artificial
<220> FEATURE:
<223> OTHER INFORMATION: Ami11_M23-2638_Ami2638_CBD2638

<400> SEQUENCE: 6

| | | | | | |
|---|---|---|---|---|---|
| aagccacaac | ctaaagcagt | agaacttaaa | atcatcaaag | atgtggttaa | aggttatgac | 60 |
| ctacctaagc | gtggtagtaa | ccctaaaggt | atagttatac | acaacgacgc | agggagcaaa | 120 |
| ggggcgactg | ctgaagcata | tcgtaacgga | ttagtaaatg | cacctttatc | aagattagaa | 180 |
| gcgggcattg | cgcatagtta | cgtatcaggc | aacacagttt | ggcaagcctt | agatgaatca | 240 |
| caagtaggtt | ggcataccgc | taatcaaata | ggtaataaat | attattacgg | tattgaagta | 300 |
| tgtcaatcaa | tgggcgcaga | taacgcgaca | ttcttaaaaa | atgaacaggc | aactttccaa | 360 |
| gaatgcgcta | gattgttgaa | aaaatgggga | ttaccagcaa | acagaaatac | aatcagattg | 420 |
| cacaatgaat | ttacttcaac | atcatgccct | catagaagtt | cggttttaca | cactggtttt | 480 |
| gacccagtaa | ctcgcggtct | attgccagaa | gacaagcggt | tgcaacttaa | agactacttt | 540 |
| atcaagcaga | ttagggcgta | catggatggt | aaaataccgg | ttgccactgt | ctctaatgag | 600 |
| tcaagcgctt | caagtaatac | agttaaacca | gttgcaagtg | caggatccat | gctaactgct | 660 |
| attgactatc | ttacgaaaaa | aggttggaaa | atatcatctg | accctcgcac | ttacgatggt | 720 |
| taccctaaaa | actacggcta | cagaaattac | catgaaaacg | gcattaatta | tgatgagttt | 780 |
| tgtggtggtt | atcatagagc | ttttgatgtt | tacagtaacg | aaactaacga | cgtgcctgct | 840 |
| gttactagcg | gaacagttat | tgaagcaaac | gattacggta | attttggtgg | tacattcgtt | 900 |
| attagagacg | ctaacgataa | cgattggata | tatgggcatc | tacaacgtgg | ctcaatgcga | 960 |
| tttgttgtag | gcgacaaagt | caatcaaggt | gacattattg | gtttacaagg | taatagcaac | 1020 |
| tattacgaca | tcctatgag | tgtacattta | catttacaat | tacgccctaa | agacgcaaag | 1080 |
| aaagatgaaa | aatcacaagt | atgtagtggt | ttggctatgg | aaaaatatga | cattacaaat | 1140 |
| ttaaatgcta | acaagataa | atcaaagaat | gggagcgtga | aagagttgaa | acatatctat | 1200 |
| tcaaaccata | ttaaaggtaa | caagattaca | gcaccaaaac | ctagtattca | aggtgtggtc | 1260 |
| atccacaatg | attatggtag | tatgacaccct | agtcaatact | taccatggtt | atatgcacgt | 1320 |
| gagaataacg | gtacacacgt | taacggttgg | gctagtgttt | atgcaaatag | aaacgaagtg | 1380 |
| ctttggtatc | atccgacaga | ctacgtagag | tggcattgtg | gtaatcaatg | ggcaaatgct | 1440 |
| aacttaatcg | gatttgaagt | gtgtgagtcg | tatcctggta | gaatctcgga | caaattattc | 1500 |
| ttagaaaatg | aagaagcgac | attgaaagta | gctgcggatg | tgatgaagtc | gtacggatta | 1560 |
| ccagttaatc | gcaacactgt | acgtctgcat | aacgaattct | tcggaacttc | ttgtccacat | 1620 |
| cgttcgtggg | acttgcatgt | tggcaaaggt | gagccttaca | caactactaa | tattaataaa | 1680 |
| atgaaagact | acttcatcaa | acgcatcaaa | cattattatg | acggtggaaa | gctagaagta | 1740 |
| agcaaagcag | caactatcaa | acaatctgac | gttaagcaag | aagttaaaaa | gcaagaagca | 1800 |
| aaacaaattg | tgaaagcaac | agattggaaa | cagaataaag | atggcatttg | gtataaagct | 1860 |
| gaacatgctt | cgttcacagt | gacagcacca | gagggaatta | tcacaagata | caaaggtcct | 1920 |
| tggactggtc | acccacaagc | tggtgtatta | caaaaaggtc | aaacgattaa | atatgatgag | 1980 |
| gttcaaaaat | ttgacggtca | tgtttgggta | tcgtgggaaa | cgtttgaggg | cgaaactgta | 2040 |
| tacatgccgg | tacgcacatg | ggacgctaaa | actggtaaag | ttggtaagtt | gtggggcgaa | 2100 | attaaataa 2109

<210> SEQ ID NO 7
<211> LENGTH: 1923
<212> TYPE: DNA
<213> ORGANISM: artificial
<220> FEATURE:
<223> OTHER INFORMATION: CHAPTw_Ami2638_M23-LST_CBD2638

<400> SEQUENCE: 7

| | |
|---|---:|
| atgaaaaccc tgaaacaagc agagtcctac attaagagta aagtaaatac aggaactgat | 60 |
| tttgatggtt tatatgggta tcagtgtatg gacttagcag tagattatat ttaccatgta | 120 |
| acagatggta aaataagaat gtggggtaat gctaaggatg cgataaataa ctcttttggt | 180 |
| ggtactgcta cggtatataa aaactaccct gcttttagac ctaagtacgg tgatgtagtc | 240 |
| gtatggacta ctggtaattt tgcaacttat ggtcatatcg caatagttac taaccctgac | 300 |
| ccttatggag accttcaata tgttacagtt cttgaacaaa actggaacgg taacgggatt | 360 |
| tataaaaccg agttagctac aatcagaaca cacgattaca caggaattac acattttatt | 420 |
| aaagacgcaa agaagatga aaaatcacaa gtatgtagtg gtttggctat ggaaaaatat | 480 |
| gacattacaa atttaaatgc taaacaagat aaatcaaaga atgggagcgt gaaagagttg | 540 |
| aaacatatct attcaaacca tattaaaggt aacaagatta cagcaccaaa acctagtatt | 600 |
| caaggtgtgg tcatccacaa tgattatggt agtatgacac tagtcaata cttaccatgg | 660 |
| ttatatgcac gtgagaataa cggtacacac gttaacggtt gggctagtgt ttatgcaaat | 720 |
| agaaacgaag tgctttggta tcatccgaca gactacgtag agtggcattg tggtaatcaa | 780 |
| tgggcaaatg ctaacttaat cggatttgaa gtgtgtgagt cgtatcctgg tagaatctcg | 840 |
| gacaaattat tcttagaaaa tgaagaagcg acattgaaag tagctgcgga tgtgatgaag | 900 |
| tcgtacggat taccagttaa tcgcaacact gtacgtctgc ataacgaatt cttcggaact | 960 |
| tcttgtccac atcgttcgtg ggacttgcat gttggcaaag gtgagcctta cacaactact | 1020 |
| aatattaata aaatgaaaga ctacttcatc aaacgcatca acattatta tgacggtgga | 1080 |
| aagctagaag taagcaaagc agcaactatc aaacaatctg acgttaagca agaagttaaa | 1140 |
| aagcaagaag caaacaaat tgtgaaagca acagatgctg caacacatga acattcagca | 1200 |
| caatggttga ataattacaa aaaggatat ggttacggtc cttatccatt aggtataaat | 1260 |
| ggcggtatgc actacggagt tgattttttt atgaatattg aacaccagt aaaagctatt | 1320 |
| tcaagcggaa aaatagttga agctggttgg agtaattacg gaggaggtaa tcaaataggt | 1380 |
| cttattgaaa atgatggagt gcatagacaa tggtatatgc atctaagtaa atataatgtt | 1440 |
| aaagtaggag attatgtcaa agctggtcaa ataatcggtt ggtctggaag cactggttat | 1500 |
| tctacagcac acatttaca cttccaaaga atggttaatt catttcaaa ttcaactgcc | 1560 |
| caagatccaa tgccttctt aaagagcgca ggatatggaa aagcaggtgg tacagtaact | 1620 |
| ccaacgccga atacaggttg gaaacagaat aaagatggca tttggtataa agctgaacat | 1680 |
| gcttcgttca cagtgacagc accagaggga attatcacaa gatacaaagg tccttggact | 1740 |
| ggtcacccac aagctggtgt attacaaaaa ggtcaaacga ttaaatatga tgaggttcaa | 1800 |
| aaatttgacg gtcatgtttg gtatcgtgg gaaacgtttg agggcgaaac tgtatacatg | 1860 |
| ccggtacgca catgggacgc taaaactggt aaagttggta agttgtgggg cgaaattaaa | 1920 |
| taa | 1923 |

<210> SEQ ID NO 8
<211> LENGTH: 1953
<212> TYPE: DNA
<213> ORGANISM: artificial
<220> FEATURE:
<223> OTHER INFORMATION: His-tagged CHAPTw_Ami2638_M23-LST_CWT-LST

<400> SEQUENCE: 8

| | | | | | |
|---|---|---|---|---|---|
| atgagaggat | cgcatcacca | tcaccatcac | ggatccatga | aaaccctgaa | acaagcagag | 60 |
| tcctacatta | agagtaaagt | aaatacagga | actgattttg | atggtttata | tgggtatcag | 120 |
| tgtatggact | tagcagtaga | ttatatttac | catgtaacag | atggtaaaat | aagaatgtgg | 180 |
| ggtaatgcta | aggatgcgat | aaataactct | tttggtggta | ctgctacggt | atataaaaac | 240 |
| taccctgctt | ttagacctaa | gtacggtgat | gtagtcgtat | ggactactgg | taattttgca | 300 |
| acttatggtc | atatcgcaat | agttactaac | cctgacccct | tatggagacct | tcaatatgtt | 360 |
| acagttcttg | aacaaaactg | gaacggtaac | gggatttata | aaccgagtt | agctacaatc | 420 |
| agaacacacg | attacacagg | aattacacat | tttattaaag | acgcaaagaa | agatgaaaaa | 480 |
| tcacaagtat | gtagtggttt | ggctatggaa | aaatatgaca | ttacaaattt | aaatgctaaa | 540 |
| caagataaat | caaagaatgg | gagcgtgaaa | gagttgaaac | atatctattc | aaaccatatt | 600 |
| aaaggtaaca | agattacagc | accaaaacct | agtattcaag | gtgtggtcat | ccacaatgat | 660 |
| tatggtagta | tgacacctag | tcaatactta | ccatggttat | atgcacgtga | ataacggt | 720 |
| acacacgtta | acggtgggc | tagtgtttat | gcaaatagaa | acgaagtgct | ttggtatcat | 780 |
| ccgacagact | acgtagagtg | gcattgtggt | aatcaatggg | caaatgctaa | cttaatcgga | 840 |
| tttgaagtgt | gtgagtcgta | tcctggtaga | atctcggaca | aattattctt | agaaaatgaa | 900 |
| gaagcgacat | tgaaagtagc | tgcggatgtg | atgaagtcgt | acggattacc | agttaatcgc | 960 |
| aacactgtac | gtctgcataa | cgaattcttc | ggaacttctt | gtccacatcg | ttcgtgggac | 1020 |
| ttgcatgttg | gcaaaggtga | gccttacaca | actactaata | ttaataaaat | gaaagactac | 1080 |
| ttcatcaaac | gcatcaaaca | ttattatgac | ggtggaaagc | tagaagtaag | caaagcagca | 1140 |
| actatcaaac | aatctgacgt | taagcaagaa | gttaaaaagc | aagaagcaaa | acaaattgtg | 1200 |
| aaagcaacag | atgctgcaac | acatgaacat | tcagcacaat | ggttgaataa | ttacaaaaaa | 1260 |
| ggatatggtt | acggtccta | tccattaggt | ataaatggcg | gtatgcacta | cggagttgat | 1320 |
| ttttttatga | atattggaac | accagtaaaa | gctatttcaa | gcggaaaaat | agttgaagct | 1380 |
| ggttggagta | attacggagg | aggtaatcaa | ataggtctta | ttgaaaatga | tggagtgcat | 1440 |
| agacaatggt | atatgcatct | aagtaaatat | aatgttaaag | taggagatta | tgtcaaagct | 1500 |
| ggtcaaataa | tcggttggtc | tggaagcact | ggttattcta | cagcaccaca | tttacacttc | 1560 |
| caaagaatgg | ttaattcatt | tcaaattca | actgcccaag | atccaatgcc | tttcttaaag | 1620 |
| agcgcaggat | atgaaaagc | aggtggtaca | gtaactccaa | cgccgaatac | aggttggaaa | 1680 |
| acaaacaaat | atggcacact | atataaatca | gagtcagcta | gcttcacacc | taatacagat | 1740 |
| ataataacaa | gaacgactgg | tccatttaga | agcatgccgc | agtcaggagt | cttaaaagca | 1800 |
| ggtcaaacaa | ttcattatga | tgaagtgatg | aaacaagacg | tcatgtttg | ggtaggttat | 1860 |
| acaggtaaca | gtggccaacg | tatttacttg | cctgtaagaa | catggaataa | atctactaat | 1920 |
| actttaggtg | ttctttgggg | aactataaag | taa | | | 1953 |

<210> SEQ ID NO 9
<211> LENGTH: 1518

```
<212> TYPE: DNA
<213> ORGANISM: artificial
<220> FEATURE:
<223> OTHER INFORMATION: M23-LST_Ami2638_CBD2638

<400> SEQUENCE: 9
gctgcaacac atgaacattc agcacaatgg ttgaataatt acaaaaaagg atatggttac      60
ggtccttatc cattaggtat aaatggcggt atgcactacg gagttgattt ttttatgaat     120
attggaacac cagtaaaagc tatttcaagc ggaaaaatag ttgaagctgg ttggagtaat     180
tacggaggag gtaatcaaat aggtcttatt gaaaatgatg gagtgcatag acaatggtat     240
atgcatctaa gtaaatataa tgttaaagta ggagattatg tcaaagctgg tcaaataatc     300
ggttggtctg gaagcactgg ttattctaca gcaccacatt tacacttcca agaatggtt     360
aattcatttt caaattcaac tgcccaagat ccaatgcctt tcttaaagag cgcaggatat     420
ggaaaagcag gtggtacagt aactccaacg ccgaatacag gtgagctctt acgccctaaa     480
gacgcaaaga aagatgaaaa atcacaagta tgtagtggtt tggctatgga aaaatatgac     540
attacaaatt taaatgctaa acaagataaa tcaaagaatg ggagcgtgaa agagttgaaa     600
catatctatt caaaccatat taaggtaac aagattacag caccaaaacc tagtattcaa     660
ggtgtggtca tccacaatga ttatggtagt atgacaccta gtcaatactt accatggtta     720
tatgcacgtg agaataacgg tacacacgtt aacggttggg ctagtgtttta tgcaaataga     780
aacgaagtgc tttggtatca tccgacagac tacgtagagt ggcattgtgg taatcaatgg     840
gcaaatgcta acttaatcgg atttgaagtg tgtgagtcgt atcctggtag aatctcggac     900
aaattattct tagaaaatga agaagcgaca ttgaaagtag ctgcggatgt gatgaagtcg     960
tacggattac cagttaatcg caacactgta cgtctgcata cgaattctt cggaacttct    1020
tgtccacatc gttcgtggga cttgcatgtt ggcaaaggtg agccttacac aactactaat    1080
attaataaaa tgaaagacta cttcatcaaa cgcatcaaac attattatga cggtggaaag    1140
ctagaagtaa gcaaagcagc aactatcaaa caatctgacg ttaagcaaga agttaaaaag    1200
caagaagcaa aacaaattgt gaaagcaaca gattggaaac agaataaaga tggcatttgg    1260
tataaagctg aacatgcttc gttcacagtg acagcaccag agggaattat cacaagatac    1320
aaaggtccctt ggactggtca cccacaagct ggtgtattac aaaaaggtca acgattaaa    1380
tatgatgagg ttcaaaaatt tgacggtcat gtttgggtat cgtgggaaac gtttgagggc    1440
gaaactgtat acatgccggt acgcacatgg gacgctaaaa ctggtaaagt tggtaagttg    1500
tggggcgaaa ttaaataa                                                 1518

<210> SEQ ID NO 10
<211> LENGTH: 1521
<212> TYPE: DNA
<213> ORGANISM: artificial
<220> FEATURE:
<223> OTHER INFORMATION: His-tagged LST_LST

<400> SEQUENCE: 10
atgagaggat cgcatcacca tcaccatcac ggatccgctg caacacatga acattcagca      60
caatggttga ataattacaa aaaggatat ggttacggtc cttatccatt aggtataaat     120
ggcggtatgc actacggagt tgatttttt atgaatattg aacaccagt aaaagctatt     180
tcaagcggaa aaatagttga agctggttgg agtaattacg gaggaggtaa tcaaataggt     240
cttattgaaa atgatggagt gcatagacaa tggtatatgc atctaagtaa atataatgtt     300
```

| | |
|---|---|
| aaagtaggag attatgtcaa agctggtcaa ataatcggtt ggtctggaag cactggttat | 360 |
| tctacagcac cacatttaca cttccaaaga atggttaatt cattttcaaa ttcaactgcc | 420 |
| caagatccaa tgcctttctt aaagagcgca ggatatggaa aagcaggtgg tacagtaact | 480 |
| ccaacgccga atacaggttg gaaaacaaac aaatatggca cactatataa atcagagtca | 540 |
| gctagcttca cacctaatac agatataata acaagaacga ctggtccatt tagaagcatg | 600 |
| ccgcagtcag gagtcttaaa agcaggtcaa acaattcatt atgatgaagt gatgaaacaa | 660 |
| gacggtcatg tttgggtagg ttatacaggt aacagtggcc aacgtattta cttgcctgta | 720 |
| agaacatgga ataaatctac taatacttta ggtgttcttt ggggaactat aaaggagctc | 780 |
| gctgcaacac atgaacattc agcacaatgg ttgaataatt acaaaaaagg atatggttac | 840 |
| ggtccttatc cattaggtat aaatggcggt atgcactacg gagttgattt ttttatgaat | 900 |
| attggaacac cagtaaaagc tatttcaagc ggaaaaatag ttgaagctgg ttggagtaat | 960 |
| tacggaggag gtaatcaaat aggtcttatt gaaaatgatg gagtgcatag acaatggtat | 1020 |
| atgcatctaa gtaaatataa tgttaaagta ggagattatg tcaaagctgg tcaaataatc | 1080 |
| ggttggtctg gaagcactgg ttattctaca gcaccacatt tacacttcca agaatggtt | 1140 |
| aattcatttt caaattcaac tgcccaagat ccaatgcctt tcttaaagag cgcaggatat | 1200 |
| ggaaaagcag gtggtacagt aactccaacg ccgaatacag gttggaaaac aaacaaatat | 1260 |
| ggcacactat ataatcaga gtcagctagc ttcacaccta atacagatat aataacaaga | 1320 |
| acgactggtc catttagaag catgccgcag tcaggagtct taaaagcagg tcaaacaatt | 1380 |
| cattatgatg aagtgatgaa acaagacggt catgtttggg taggttatac aggtaacagt | 1440 |
| ggccaacgta tttacttgcc tgtaagaaca tggaataaat ctactaatac tttaggtgtt | 1500 |
| ctttggggaa ctataaagtg a | 1521 |

<210> SEQ ID NO 11
<211> LENGTH: 1245
<212> TYPE: DNA
<213> ORGANISM: artificial
<220> FEATURE:
<223> OTHER INFORMATION: His-tagged M23-LST_M23_LST-CWT-LST

<400> SEQUENCE: 11

| | |
|---|---|
| atgagaggat cgcatcacca tcaccatcac ggatccgctg caacacatga acattcagca | 60 |
| caatggttga ataattacaa aaaggatat ggttacggtc cttatccatt aggtataaat | 120 |
| ggcggtatgc actacggagt tgattttttt atgaatattg aacaccagt aaaagctatt | 180 |
| tcaagcggaa aaatagttga agctggttgg agtaattacg gaggaggtaa tcaaataggt | 240 |
| cttattgaaa atgatggagt gcatagacaa tggtatatgc atctaagtaa atataatgtt | 300 |
| aaagtaggag attatgtcaa agctggtcaa ataatcggtt ggtctggaag cactggttat | 360 |
| tctacagcac cacatttaca cttccaaaga atggttaatt cattttcaaa ttcaactgcc | 420 |
| caagatccaa tgcctttctt aaagagcgca ggatatggaa aagcaggtgg tacagtaact | 480 |
| ccaacgccga atacaggtga gctcgctgca acacatgaac attcagcaca atggttgaat | 540 |
| aattacaaaa aaggatatgg ttacggtcct tatccattag gtataaatgg cggtatgcac | 600 |
| tacggagttg atttttttat gaatattgga acaccagtaa aagctatttc aagcggaaaa | 660 |
| atagttgaag ctggttggag taattacgga ggaggtaatc aaataggtct tattgaaaat | 720 |
| gatggagtgc atagacaatg gtatatgcat ctaagtaaat ataatgttaa agtaggagat | 780 |
| tatgtcaaag ctggtcaaat aatcggttgg tctggaagca ctggttattc tacagcacca | 840 |

```
catttacact tccaaagaat ggttaattca ttttcaaatt caactgccca agatccaatg      900
cctttcttaa agagcgcagg atatggaaaa gcaggtggta cagtaactcc aacgccgaat      960
acaggttgga aaacaaacaa atatggcaca ctatataaat cagagtcagc tagcttcaca     1020
cctaatacag atataataac aagaacgact ggtccattta gaagcatgcc gcagtcagga     1080
gtcttaaaag caggtcaaac aattcattat gatgaagtga tgaaacaaga cggtcatgtt     1140
tgggtaggtt atacaggtaa cagtggccaa cgtatttact tgcctgtaag aacatggaat     1200
aaatctacta atactttagg tgttcttttgg ggaactataa agtga                    1245
```

<210> SEQ ID NO 12
<211> LENGTH: 285
<212> TYPE: DNA
<213> ORGANISM: Staphylococcus aureus bacteriophage 2638a

<400> SEQUENCE: 12

```
tggaaacaga ataaagatgg catttggtat aaagctgaac atgcttcgtt cacagtgaca       60
gcaccagagg gaattatcac aagatacaaa ggtccttgga ctggtcaccc acaagctggt      120
gtattacaaa aaggtcaaac gattaaatat gatgaggttc aaaaatttga cggtcatgtt      180
tgggtatcgt gggaaacgtt tgagggcgaa actgtataca tgccggtacg cacatgggac      240
gctaaaactg gtaaagttgg taagttgtgg ggcgaaatta ataa                       285
```

<210> SEQ ID NO 13
<211> LENGTH: 279
<212> TYPE: DNA
<213> ORGANISM: Staphylococcus simulans

<400> SEQUENCE: 13

```
tggaaaacaa acaaatatgg cacactatat aaatcagagt cagctagctt cacacctaat       60
acagatataa taacaagaac gactggtcca tttagaagca tgccgcagtc aggagtctta      120
aaagcaggtc aaacaattca ttatgatgaa gtgatgaaac aagacggtca tgtttgggta      180
ggttatacag gtaacagtgg ccaacgtatt tacttgcctg taagaacatg gaataaatct      240
actaatactt taggtgttct ttggggaact ataaagtga                            279
```

<210> SEQ ID NO 14
<211> LENGTH: 438
<212> TYPE: DNA
<213> ORGANISM: Staphylococcus aureus bacteriophage 2638a

<400> SEQUENCE: 14

```
atgctaactg ctattgacta tcttacgaaa aaaggttgga aaatatcatc tgaccctcgc       60
acttacgatg gttaccctaa aaactacggc tacagaaatt accatgaaaa cggcattaat      120
tatgatgagt tttgtggtgg ttatcataga gcttttgatg tttacagtaa cgaaactaac      180
gacgtgcctg ctgttactag cggaacagtt attgaagcaa acgattacgg taattttggt      240
ggtacattcg ttattagaga cgctaacgat aacgattgga tatatgggca tctacaacgt      300
ggctcaatgc gatttgttgt aggcgacaaa gtcaatcaag gtgacattat tggtttacaa      360
ggtaatagca actattacga caatcctatg agtgtacatt tacatttaca attacgccct      420
aaagacgcaa agaaagat                                                    438
```

<210> SEQ ID NO 15
<211> LENGTH: 420
<212> TYPE: DNA

<213> ORGANISM: Staphylococcus simulans

<400> SEQUENCE: 15

```
gctgcaacac atgaacattc agcacaatgg ttgaataatt acaaaaaagg atatggttac    60
ggtccttatc cattaggtat aaatggcggt atgcactacg gagttgattt ttttatgaat   120
attggaacac cagtaaaagc tatttcaagc ggaaaaatag ttgaagctgg ttggagtaat   180
tacggaggag gtaatcaaat aggtcttatt gaaaatgatg gagtgcatag acaatggtat   240
atgcatctaa gtaaatataa tgttaaagta ggagattatg tcaaagctgg tcaaataatc   300
ggttggtctg gaagcactgg ttattctaca gcaccacatt tacacttcca agaatggtt    360
aattcatttt caaattcaac tgcccaagat ccaatgcctt tcttaaagag cgcaggatat   420
```

<210> SEQ ID NO 16
<211> LENGTH: 510
<212> TYPE: DNA
<213> ORGANISM: Staphylococcus aureus bacteriophage 2638a

<400> SEQUENCE: 16

```
ggtaacaaga ttacagcacc aaaacctagt attcaaggtg tggtcatcca caatgattat    60
ggtagtatga caccctagtca atacttacca tggttatatg cacgtgagaa taacggtaca   120
cacgttaacg gttgggctag tgtttatgca aatagaaacg aagtgctttg gtatcatccg   180
acagactacg tagagtggca ttgtggtaat caatgggcaa atgctaactt aatcggattt   240
gaagtgtgtg agtcgtatcc tggtagaatc tcggacaaat tattcttaga aaatgaagaa   300
gcgacattga agtagctgc ggatgtgatg aagtcgtacg gattaccagt taatcgcaac   360
actgtacgtc tgcataacga attcttcgga acttcttgtc cacatcgttc gtgggacttg   420
catgttggca aaggtgagcc ttacacaact actaatatta ataaaatgaa agactacttc   480
atcaaacgca tcaaacatta ttatgacggt                                    510
```

<210> SEQ ID NO 17
<211> LENGTH: 642
<212> TYPE: DNA
<213> ORGANISM: Staphylococcus aureus phage phi 11

<400> SEQUENCE: 17

```
aagccacaac ctaaagcagt agaacttaaa atcatcaaag atgtggttaa aggttatgac    60
ctacctaagc gtggtagtaa ccctaaaggt atagttatac acaacgacgc agggagcaaa   120
ggggcgactg ctgaagcata tcgtaacgga ttagtaaatg caccttttatc aagattagaa   180
gcgggcattg cgcatagtta cgtatcaggc aacacagttt ggcaagcctt agatgaatca   240
caagtaggtt ggcataccgc taatcaaata ggtaataaat attattacgg tattgaagta   300
tgtcaatcaa tgggcgcaga taacgcgaca ttcttaaaaa atgaacaggc aactttccaa   360
gaatgcgcta gattgttgaa aaaatgggga ttaccagcaa acagaaatac aatcagattg   420
cacaatgaat ttacttcaac atcatgccct catagaagtt cggttttaca cactggtttt   480
gacccagtaa ctcgcggtct attgccagaa gacaagcggt tgcaacttaa agactacttt   540
atcaagcaga ttagggcgta catggatggt aaaataccgg ttgccactgt ctctaatgag   600
tcaagcgctt caagtaatac agttaaacca gttgcaagtg ca                      642
```

<210> SEQ ID NO 18
<211> LENGTH: 516
<212> TYPE: DNA
<213> ORGANISM: Staphylococcus aureus phage phi 11

<400> SEQUENCE: 18

```
atgcaagcaa aattaactaa aaatgagttt atagagtggt tgaaaacttc tgagggaaaa        60
caattcaatg tggacttatg gtatggattt caatgctttg attatgccaa tgctggttgg       120
aaagttttgt ttggattact tctaaaaggt ttaggtgcaa aagatattcc gttcgctaac       180
aacttcgacg gattagctac tgtataccaa aatacaccgg acttcttagc acaacctggc       240
gacatggtgg tattcggtag caactacggt gctggatatg gtcacgttgc atgggtaatt       300
gaagcaactt tagattacat cattgtatat gagcagaatt ggctaggcgg tggctggact       360 gacgaatcg aacaacccgg ctggggttgg gaaaaagtta caagacgaca acatgcttat       420
gatttcccta tgtggtttat ccgtccgaat tttaaaagtg agacagcgcc acgatcagtt       480
caatctccta cacaagcacc taaaaaagaa acagct                                 516
```

<210> SEQ ID NO 19
<211> LENGTH: 420
<212> TYPE: DNA
<213> ORGANISM: Staphylococcus phage Twort

<400> SEQUENCE: 19

```
atgaaaaccc tgaaacaagc agagtcctac attaagagta aagtaaatac aggaactgat        60
tttgatggtt atatgggta tcagtgtatg gacttagcag tagattatat ttaccatgta       120
acagatggta aaataagaat gtggggtaat gctaaggatg cgataaataa ctcttttggt       180
ggtactgcta cggtatataa aaactaccct gcttttagac ctaagtacgg tgatgtagtc       240
gtatggacta ctggtaattt tgcaacttat ggtcatatcg caatagttac taaccctgac       300
ccttatggag accttcaata tgttacagtt cttgaacaaa actggaacgg taacgggatt       360
tataaaaccg agttagctac aatcagaaca cacgattaca caggaattac acattttatt       420
```

<210> SEQ ID NO 20
<211> LENGTH: 1851
<212> TYPE: DNA
<213> ORGANISM: artificial
<220> FEATURE:
<223> OTHER INFORMATION: M23-2638_Ami2638_CBD2638_CBD2638

<400> SEQUENCE: 20

```
atgctaactg ctattgacta tcttacgaaa aaaggttgga aatatcatc tgaccctcgc        60 acttacgatg ttaccctaa aaactacggc tacagaaatt accatgaaaa cggcattaat       120
tatgatgagt tttgtggtgg ttatcataga gcttttgatg tttacagtaa cgaaactaac       180
gacgtgcctg ctgttactag cggaacagtt attgaagcaa acgattacgg taattttggt       240
ggtacattcg ttattagaga cgctaacgat aacgattgga tatatgggca tctacaacgt       300
ggctcaatgc gatttgttgt aggcgacaaa gtcaatcaag gtgacattat tggtttacaa       360
ggtaatagca actattacga caatcctatg agtgtacatt acatttaca attacgccct       420 aaagacgcaa agaaagatga aaaatcacaa gtatgtagtg gtttggctat ggaaaaatat       480
gacattacaa atttaaatgc taaacaagat aaatcaaaga atgggagcgt gaaagagttg       540
aaacatatct attcaaacca tattaaaggt aacaagatta cagcaccaaa acctagtatt       600
caaggtgtgg tcatccacaa tgattatggt agtatgacac tagtcaata cttaccatgg       660 ttatatgcac gtgagaataa cggtacacac gttaacggtt gggctagtgt ttatgcaaat       720
agaaacgaag tgctttggta tcatccgaca gactacgtag agtggcattg tggtaatcaa       780
```

-continued

```
tgggcaaatg ctaacttaat cggatttgaa gtgtgtgagt cgtatcctgg tagaatctcg    840
gacaaattat tcttagaaaa tgaagaagcg acattgaaag tagctgcgga tgtgatgaag    900
tcgtacggat taccagttaa tcgcaacact gtacgtctgc ataacgaatt cttcggaact    960
tcttgtccac atcgttcgtg ggacttgcat gttggcaaag gtgagcctta cacaactact   1020
aatattaata aaatgaaaga ctacttcatc aaacgcatca acattatta tgacggtgga    1080
aagctagaag taagcaaagc agcaactatc aaacaatctg acgttaagca agaagttaaa   1140
aagcaagaag caaaacaaat tgtgaaagca acagattgga aacagaataa agatggcatt   1200
tggtataaag ctgaacatgc ttcgttcaca gtgacagcac cagagggaat tatcacaaga   1260
tacaaaggtc cttggactgg tcacccacaa gctggtgtat tacaaaaagg tcaaacgatt   1320
aaatatgatg aggttcaaaa atttgacggt catgtttggg tatcgtggga aacgtttgag   1380
ggcgaaactg tatacatgcc ggtacgcaca tgggacgcta aaactggtaa agttggtaag   1440
ttgtggggcg aaattaaaga gctcggtgga aagctagaag taagcaaagc agcaactatc   1500
aaacaatctg acgttaagca agaagttaaa aagcaagaag caaaacaaat tgtgaaagca   1560
acagattgga aacagaataa agatggcatt tggtataaag ctgaacatgc ttcgttcaca   1620
gtgacagcac cagagggaat tatcacaaga tacaaaggtc cttggactgg tcacccacaa   1680
gctggtgtat tacaaaaagg tcaaacgatt aaatatgatg aggttcaaaa atttgacggt   1740
catgtttggg tatcgtggga aacgtttgag ggcgaaactg tatacatgcc ggtacgcaca   1800
tgggacgcta aaactggtaa agttggtaag ttgtggggcg aaattaaata a             1851
```

<210> SEQ ID NO 21
<211> LENGTH: 498
<212> TYPE: PRT
<213> ORGANISM: artificial
<220> FEATURE:
<223> OTHER INFORMATION: His-tagged Ply2638

<400> SEQUENCE: 21

```
Met Arg Gly Ser His His His His His His Gly Ser Met Leu Thr Ala
1               5                   10                  15

Ile Asp Tyr Leu Thr Lys Lys Gly Trp Lys Ile Ser Ser Asp Pro Arg
            20                  25                  30

Thr Tyr Asp Gly Tyr Pro Lys Asn Tyr Gly Tyr Arg Asn Tyr His Glu
        35                  40                  45

Asn Gly Ile Asn Tyr Asp Glu Phe Cys Gly Gly Tyr His Arg Ala Phe
    50                  55                  60

Asp Val Tyr Ser Asn Glu Thr Asn Asp Val Pro Ala Val Thr Ser Gly
65                  70                  75                  80

Thr Val Ile Glu Ala Asn Asp Tyr Gly Asn Phe Gly Gly Thr Phe Val
                85                  90                  95

Ile Arg Asp Ala Asn Asp Asn Trp Ile Tyr Gly His Leu Gln Arg
            100                 105                 110

Gly Ser Met Arg Phe Val Val Gly Asp Lys Val Asn Gln Gly Asp Ile
        115                 120                 125

Ile Gly Leu Gln Gly Asn Ser Asn Tyr Tyr Asp Asn Pro Met Ser Val
    130                 135                 140

His Leu His Leu Gln Leu Arg Pro Lys Asp Ala Lys Lys Asp Glu Lys
145                 150                 155                 160

Ser Gln Val Cys Ser Gly Leu Ala Met Glu Lys Tyr Asp Ile Thr Asn
                165                 170                 175
```

```
Leu Asn Ala Lys Gln Asp Lys Ser Lys Asn Gly Ser Val Lys Glu Leu
            180                 185                 190

Lys His Ile Tyr Ser Asn His Ile Lys Gly Asn Lys Ile Thr Ala Pro
        195                 200                 205

Lys Pro Ser Ile Gln Gly Val Val Ile His Asn Asp Tyr Gly Ser Met
    210                 215                 220

Thr Pro Ser Gln Tyr Leu Pro Trp Leu Tyr Ala Arg Glu Asn Asn Gly
225                 230                 235                 240

Thr His Val Asn Gly Trp Ala Ser Val Tyr Ala Asn Arg Asn Glu Val
                245                 250                 255

Leu Trp Tyr His Pro Thr Asp Tyr Val Glu Trp His Cys Gly Asn Gln
            260                 265                 270

Trp Ala Asn Ala Asn Leu Ile Gly Phe Glu Val Cys Glu Ser Tyr Pro
        275                 280                 285

Gly Arg Ile Ser Asp Lys Leu Phe Leu Glu Asn Glu Glu Ala Thr Leu
    290                 295                 300

Lys Val Ala Ala Asp Val Met Lys Ser Tyr Gly Leu Pro Val Asn Arg
305                 310                 315                 320

Asn Thr Val Arg Leu His Asn Glu Phe Phe Gly Thr Ser Cys Pro His
                325                 330                 335

Arg Ser Trp Asp Leu His Val Gly Lys Gly Glu Pro Tyr Thr Thr Thr
            340                 345                 350

Asn Ile Asn Lys Met Lys Asp Tyr Phe Ile Lys Arg Ile Lys His Tyr
        355                 360                 365

Tyr Asp Gly Gly Lys Leu Glu Val Ser Lys Ala Thr Ile Lys Gln
    370                 375                 380

Ser Asp Val Lys Gln Glu Val Lys Lys Gln Glu Ala Lys Gln Ile Val
385                 390                 395                 400

Lys Ala Thr Asp Trp Lys Gln Asn Lys Asp Gly Ile Trp Tyr Lys Ala
                405                 410                 415

Glu His Ala Ser Phe Thr Val Thr Ala Pro Gly Ile Ile Thr Arg
            420                 425                 430

Tyr Lys Gly Pro Trp Thr Gly His Pro Gln Ala Gly Val Leu Gln Lys
        435                 440                 445

Gly Gln Thr Ile Lys Tyr Asp Glu Val Gln Lys Phe Asp Gly His Val
    450                 455                 460

Trp Val Ser Trp Glu Thr Phe Glu Gly Glu Thr Val Tyr Met Pro Val
465                 470                 475                 480

Arg Thr Trp Asp Ala Lys Thr Gly Lys Val Gly Lys Leu Trp Gly Glu
                485                 490                 495

Ile Lys

<210> SEQ ID NO 22
<211> LENGTH: 361
<212> TYPE: PRT
<213> ORGANISM: artificial
<220> FEATURE:
<223> OTHER INFORMATION: His-tagged Ami2638_CBD2638

<400> SEQUENCE: 22

Met Arg Gly Ser His His His His His His Gly Ser Leu Arg Pro Lys
1               5                   10                  15

Asp Ala Lys Lys Asp Glu Lys Ser Gln Val Cys Ser Gly Leu Ala Met
            20                  25                  30

Glu Lys Tyr Asp Ile Thr Asn Leu Asn Ala Lys Gln Asp Lys Ser Lys
```

```
                35                  40                  45
Asn Gly Ser Val Lys Glu Leu Lys His Ile Tyr Ser Asn His Ile Lys
 50                  55                  60
Gly Asn Lys Ile Thr Ala Pro Lys Pro Ser Ile Gln Gly Val Val Ile
 65                  70                  75                  80
His Asn Asp Tyr Gly Ser Met Thr Pro Ser Gln Tyr Leu Pro Trp Leu
                     85                  90                  95
Tyr Ala Arg Glu Asn Asn Gly Thr His Val Asn Gly Trp Ala Ser Val
            100                 105                 110
Tyr Ala Asn Arg Asn Glu Val Leu Trp Tyr His Pro Thr Asp Tyr Val
            115                 120                 125
Glu Trp His Cys Gly Asn Gln Trp Ala Asn Ala Asn Leu Ile Gly Phe
            130                 135                 140
Glu Val Cys Glu Ser Tyr Pro Gly Arg Ile Ser Asp Lys Leu Phe Leu
145                 150                 155                 160
Glu Asn Glu Glu Ala Thr Leu Lys Val Ala Ala Asp Val Met Lys Ser
                    165                 170                 175
Tyr Gly Leu Pro Val Asn Arg Asn Thr Val Arg Leu His Asn Glu Phe
                180                 185                 190
Phe Gly Thr Ser Cys Pro His Arg Ser Trp Asp Leu His Val Gly Lys
            195                 200                 205
Gly Glu Pro Tyr Thr Thr Thr Asn Ile Asn Lys Met Lys Asp Tyr Phe
            210                 215                 220
Ile Lys Arg Ile Lys His Tyr Tyr Asp Gly Gly Lys Leu Glu Val Ser
225                 230                 235                 240
Lys Ala Ala Thr Ile Lys Gln Ser Asp Val Lys Gln Glu Val Lys Lys
                    245                 250                 255
Gln Glu Ala Lys Gln Ile Val Lys Ala Thr Asp Trp Lys Gln Asn Lys
                260                 265                 270
Asp Gly Ile Trp Tyr Lys Ala Glu His Ala Ser Phe Thr Val Thr Ala
            275                 280                 285
Pro Glu Gly Ile Ile Thr Arg Tyr Lys Gly Pro Trp Thr Gly His Pro
290                 295                 300
Gln Ala Gly Val Leu Gln Lys Gly Gln Thr Ile Lys Tyr Asp Glu Val
305                 310                 315                 320
Gln Lys Phe Asp Gly His Val Trp Val Ser Trp Glu Thr Phe Glu Gly
                325                 330                 335
Glu Thr Val Tyr Met Pro Val Arg Thr Trp Asp Ala Lys Thr Gly Lys
                340                 345                 350
Val Gly Lys Leu Trp Gly Glu Ile Lys
                355                 360

<210> SEQ ID NO 23
<211> LENGTH: 344
<212> TYPE: PRT
<213> ORGANISM: artificial
<220> FEATURE:
<223> OTHER INFORMATION: His-tagged M23-2638_CBD2638

<400> SEQUENCE: 23

Met Arg Gly Ser His His His His His His Gly Ser Met Leu Thr Ala
 1               5                  10                  15
Ile Asp Tyr Leu Thr Lys Lys Gly Trp Lys Ile Ser Ser Asp Pro Arg
                20                  25                  30
Thr Tyr Asp Gly Tyr Pro Lys Asn Tyr Gly Tyr Arg Asn Tyr His Glu
```

```
                    35                  40                  45

Asn Gly Ile Asn Tyr Asp Glu Phe Cys Gly Gly Tyr His Arg Ala Phe
 50                  55                  60

Asp Val Tyr Ser Asn Glu Thr Asn Asp Val Pro Ala Val Thr Ser Gly
 65                  70                  75                  80

Thr Val Ile Glu Ala Asn Asp Tyr Gly Asn Phe Gly Thr Phe Val
                 85                  90                  95

Ile Arg Asp Ala Asn Asp Asn Trp Ile Tyr Gly His Leu Gln Arg
                100                 105                 110

Gly Ser Met Arg Phe Val Val Gly Asp Lys Val Asn Gln Gly Asp Ile
                115                 120                 125

Ile Gly Leu Gln Gly Asn Ser Asn Tyr Tyr Asp Asn Pro Met Ser Val
130                 135                 140

His Leu His Leu Gln Leu Arg Pro Lys Asp Ala Lys Lys Asp Glu Lys
145                 150                 155                 160

Ser Gln Val Cys Ser Gly Leu Ala Met Glu Lys Tyr Asp Ile Thr Asn
                165                 170                 175

Leu Asn Ala Lys Gln Asp Lys Ser Lys Asn Gly Ser Val Lys Glu Leu
                180                 185                 190

Lys His Ile Tyr Ser Asn His Ile Lys Gly Asn Lys Ile Thr Ala Pro
                195                 200                 205

Lys Pro Ser Ile Gln Gly Glu Leu Gly Gly Lys Leu Glu Val Ser Lys
210                 215                 220

Ala Ala Thr Ile Lys Gln Ser Asp Val Lys Gln Glu Val Lys Lys Gln
225                 230                 235                 240

Glu Ala Lys Gln Ile Val Lys Ala Thr Asp Trp Lys Gln Asn Lys Asp
                245                 250                 255

Gly Ile Trp Tyr Lys Ala Glu His Ala Ser Phe Thr Val Thr Ala Pro
                260                 265                 270

Glu Gly Ile Ile Thr Arg Tyr Lys Gly Pro Trp Thr Gly His Pro Gln
                275                 280                 285

Ala Gly Val Leu Gln Lys Gly Gln Thr Ile Lys Tyr Asp Glu Val Gln
290                 295                 300

Lys Phe Asp Gly His Val Trp Val Ser Trp Glu Thr Phe Glu Gly Glu
305                 310                 315                 320

Thr Val Tyr Met Pro Val Arg Thr Trp Asp Ala Lys Thr Gly Lys Val
                325                 330                 335

Gly Lys Leu Trp Gly Glu Ile Lys
                340

<210> SEQ ID NO 24
<211> LENGTH: 986
<212> TYPE: PRT
<213> ORGANISM: artificial
<220> FEATURE:
<223> OTHER INFORMATION: His-tagged Ply2638_Ply2638

<400> SEQUENCE: 24

Met Arg Gly Ser His His His His His His Gly Ser Met Leu Thr Ala
  1               5                  10                  15

Ile Asp Tyr Leu Thr Lys Lys Gly Trp Lys Ile Ser Ser Asp Pro Arg
                 20                  25                  30

Thr Tyr Asp Gly Tyr Pro Lys Asn Tyr Gly Tyr Arg Asn Tyr His Glu
                 35                  40                  45

Asn Gly Ile Asn Tyr Asp Glu Phe Cys Gly Gly Tyr His Arg Ala Phe
```

```
              50                  55                  60
Asp Val Tyr Ser Asn Glu Thr Asn Asp Val Pro Ala Val Thr Ser Gly
 65                  70                  75                  80

Thr Val Ile Glu Ala Asn Asp Tyr Gly Asn Phe Gly Gly Thr Phe Val
                     85                  90                  95

Ile Arg Asp Ala Asn Asp Asn Asp Trp Ile Tyr Gly His Leu Gln Arg
                    100                 105                 110

Gly Ser Met Arg Phe Val Val Gly Asp Lys Val Asn Gln Gly Asp Ile
                    115                 120                 125

Ile Gly Leu Gln Gly Asn Ser Asn Tyr Tyr Asp Asn Pro Met Ser Val
                    130                 135                 140

His Leu His Leu Gln Leu Arg Pro Lys Asp Ala Lys Lys Asp Glu Lys
145                 150                 155                 160

Ser Gln Val Cys Ser Gly Leu Ala Met Glu Lys Tyr Asp Ile Thr Asn
                    165                 170                 175

Leu Asn Ala Lys Gln Asp Lys Ser Lys Asn Gly Ser Val Lys Glu Leu
                    180                 185                 190

Lys His Ile Tyr Ser Asn His Ile Lys Gly Asn Lys Ile Thr Ala Pro
                    195                 200                 205

Lys Pro Ser Ile Gln Gly Val Val Ile His Asn Asp Tyr Gly Ser Met
210                 215                 220

Thr Pro Ser Gln Tyr Leu Pro Trp Leu Tyr Ala Arg Glu Asn Asn Gly
225                 230                 235                 240

Thr His Val Asn Gly Trp Ala Ser Val Tyr Ala Asn Arg Asn Glu Val
                    245                 250                 255

Leu Trp Tyr His Pro Thr Asp Tyr Val Glu Trp His Cys Gly Asn Gln
                    260                 265                 270

Trp Ala Asn Ala Asn Leu Ile Gly Phe Glu Val Cys Glu Ser Tyr Pro
                    275                 280                 285

Gly Arg Ile Ser Asp Lys Leu Phe Leu Glu Asn Glu Glu Ala Thr Leu
                    290                 295                 300

Lys Val Ala Ala Asp Val Met Lys Ser Tyr Gly Leu Pro Val Asn Arg
305                 310                 315                 320

Asn Thr Val Arg Leu His Asn Glu Phe Phe Gly Thr Ser Cys Pro His
                    325                 330                 335

Arg Ser Trp Asp Leu His Val Gly Lys Gly Glu Pro Tyr Thr Thr Thr
                    340                 345                 350

Asn Ile Asn Lys Met Lys Asp Tyr Phe Ile Lys Arg Ile Lys His Tyr
                    355                 360                 365

Tyr Asp Gly Gly Lys Leu Glu Val Ser Lys Ala Ala Thr Ile Lys Gln
                    370                 375                 380

Ser Asp Val Lys Gln Glu Val Lys Lys Gln Ala Lys Gln Ile Val
385                 390                 395                 400

Lys Ala Thr Asp Trp Lys Gln Asn Lys Asp Gly Ile Trp Tyr Lys Ala
                    405                 410                 415

Glu His Ala Ser Phe Thr Val Thr Ala Pro Glu Gly Ile Ile Thr Arg
                    420                 425                 430

Tyr Lys Gly Pro Trp Thr Gly His Pro Gln Ala Gly Val Leu Gln Lys
                    435                 440                 445

Gly Gln Thr Ile Lys Tyr Asp Glu Val Gln Lys Phe Asp Gly His Val
                    450                 455                 460

Trp Val Ser Trp Glu Thr Phe Glu Gly Glu Thr Val Tyr Met Pro Val
465                 470                 475                 480
```

-continued

```
Arg Thr Trp Asp Ala Lys Thr Gly Lys Val Gly Lys Leu Trp Gly Glu
                485                 490                 495
Ile Lys Glu Leu Met Leu Thr Ala Ile Asp Tyr Leu Thr Lys Lys Gly
            500                 505                 510
Trp Lys Ile Ser Ser Asp Pro Arg Thr Tyr Asp Gly Tyr Pro Lys Asn
        515                 520                 525
Tyr Gly Tyr Arg Asn Tyr His Glu Asn Gly Ile Asn Tyr Asp Glu Phe
    530                 535                 540
Cys Gly Gly Tyr His Arg Ala Phe Asp Val Tyr Ser Asn Glu Thr Asn
545                 550                 555                 560
Asp Val Pro Ala Val Thr Ser Gly Thr Val Ile Glu Ala Asn Asp Tyr
                565                 570                 575
Gly Asn Phe Gly Gly Thr Phe Val Ile Arg Asp Ala Asn Asp Asn Asp
            580                 585                 590
Trp Ile Tyr Gly His Leu Gln Arg Gly Ser Met Arg Phe Val Val Gly
        595                 600                 605
Asp Lys Val Asn Gln Gly Asp Ile Ile Gly Leu Gln Gly Asn Ser Asn
    610                 615                 620
Tyr Tyr Asp Asn Pro Met Ser Val His Leu His Leu Gln Leu Arg Pro
625                 630                 635                 640
Lys Asp Ala Lys Lys Asp Glu Lys Ser Gln Val Cys Ser Gly Leu Ala
                645                 650                 655
Met Glu Lys Tyr Asp Ile Thr Asn Leu Asn Ala Lys Gln Asp Lys Ser
            660                 665                 670
Lys Asn Gly Ser Val Lys Glu Leu Lys His Ile Tyr Ser Asn His Ile
        675                 680                 685
Lys Gly Asn Lys Ile Thr Ala Pro Lys Pro Ser Ile Gln Gly Val Val
    690                 695                 700
Ile His Asn Asp Tyr Gly Ser Met Thr Pro Ser Gln Tyr Leu Pro Trp
705                 710                 715                 720
Leu Tyr Ala Arg Glu Asn Asn Gly Thr His Val Asn Gly Trp Ala Ser
                725                 730                 735
Val Tyr Ala Asn Arg Asn Glu Val Leu Trp Tyr His Pro Thr Asp Tyr
            740                 745                 750
Val Glu Trp His Cys Gly Asn Gln Trp Ala Asn Ala Asn Leu Ile Gly
        755                 760                 765
Phe Glu Val Cys Glu Ser Tyr Pro Gly Arg Ile Ser Asp Lys Leu Phe
    770                 775                 780
Leu Glu Asn Glu Glu Ala Thr Leu Lys Val Ala Ala Asp Val Met Lys
785                 790                 795                 800
Ser Tyr Gly Leu Pro Val Asn Arg Asn Thr Val Arg Leu His Asn Glu
                805                 810                 815
Phe Phe Gly Thr Ser Cys Pro His Arg Ser Trp Asp Leu His Val Gly
            820                 825                 830
Lys Gly Glu Pro Tyr Thr Thr Asn Ile Asn Lys Met Lys Asp Tyr
        835                 840                 845
Phe Ile Lys Arg Ile Lys His Tyr Tyr Asp Gly Gly Lys Leu Glu Val
    850                 855                 860
Ser Lys Ala Ala Thr Ile Lys Gln Ser Asp Val Lys Gln Glu Val Lys
865                 870                 875                 880
Lys Gln Glu Ala Lys Gln Ile Val Lys Ala Thr Asp Trp Lys Gln Asn
                885                 890                 895
```

```
Lys Asp Gly Ile Trp Tyr Lys Ala Glu His Ala Ser Phe Thr Val Thr
                900                 905                 910
Ala Pro Glu Gly Ile Ile Thr Arg Tyr Lys Gly Pro Trp Thr Gly His
            915                 920                 925
Pro Gln Ala Gly Val Leu Gln Lys Gly Gln Thr Ile Lys Tyr Asp Glu
        930                 935                 940
Val Gln Lys Phe Asp Gly His Val Trp Val Ser Trp Glu Thr Phe Glu
945                 950                 955                 960
Gly Glu Thr Val Tyr Met Pro Val Arg Thr Trp Asp Ala Lys Thr Gly
                965                 970                 975
Lys Val Gly Lys Leu Trp Gly Glu Ile Lys
            980                 985
```

<210> SEQ ID NO 25
<211> LENGTH: 672
<212> TYPE: PRT
<213> ORGANISM: artificial
<220> FEATURE:
<223> OTHER INFORMATION: His-tagged CHAP11_M23-2638_Ami2638_CBD2638

<400> SEQUENCE: 25

```
Met Arg Gly Ser His His His His His Gly Ser Met Gln Ala Lys
1               5                   10                  15
Leu Thr Lys Asn Glu Phe Ile Glu Trp Leu Lys Thr Ser Glu Gly Lys
            20                  25                  30
Gln Phe Asn Val Asp Leu Trp Tyr Gly Phe Gln Cys Phe Asp Tyr Ala
        35                  40                  45
Asn Ala Gly Trp Lys Val Leu Phe Gly Leu Leu Leu Lys Gly Leu Gly
    50                  55                  60
Ala Lys Asp Ile Pro Phe Ala Asn Asn Phe Asp Gly Leu Ala Thr Val
65                  70                  75                  80
Tyr Gln Asn Thr Pro Asp Phe Leu Ala Gln Pro Gly Asp Met Val Val
                85                  90                  95
Phe Gly Ser Asn Tyr Gly Ala Gly Tyr Gly His Val Ala Trp Val Ile
            100                 105                 110
Glu Ala Thr Leu Asp Tyr Ile Ile Val Tyr Gln Asn Trp Leu Gly
        115                 120                 125
Gly Gly Trp Thr Asp Gly Ile Glu Gln Pro Gly Trp Gly Trp Glu Lys
    130                 135                 140
Val Thr Arg Arg Gln His Ala Tyr Asp Phe Pro Met Trp Phe Ile Arg
145                 150                 155                 160
Pro Asn Phe Lys Ser Glu Thr Ala Pro Arg Ser Val Gln Ser Pro Thr
                165                 170                 175
Gln Ala Pro Lys Lys Glu Thr Ala Gly Ser Met Leu Thr Ala Ile Asp
            180                 185                 190
Tyr Leu Thr Lys Lys Gly Trp Lys Ile Ser Ser Asp Pro Arg Thr Tyr
        195                 200                 205
Asp Gly Tyr Pro Lys Asn Tyr Gly Tyr Arg Asn Tyr His Glu Asn Gly
    210                 215                 220
Ile Asn Tyr Asp Glu Phe Cys Gly Gly Tyr His Arg Ala Phe Asp Val
225                 230                 235                 240
Tyr Ser Asn Glu Thr Asn Asp Val Pro Ala Val Thr Ser Gly Thr Val
                245                 250                 255
Ile Glu Ala Asn Asp Tyr Gly Asn Phe Gly Gly Thr Phe Val Ile Arg
            260                 265                 270
```

```
Asp Ala Asn Asp Asn Asp Trp Ile Tyr Gly His Leu Gln Arg Gly Ser
            275                 280                 285

Met Arg Phe Val Val Gly Asp Lys Val Asn Gln Gly Asp Ile Ile Gly
290                 295                 300

Leu Gln Gly Asn Ser Asn Tyr Tyr Asp Asn Pro Met Ser Val His Leu
305                 310                 315                 320

His Leu Gln Leu Arg Pro Lys Asp Ala Lys Lys Asp Glu Lys Ser Gln
                325                 330                 335

Val Cys Ser Gly Leu Ala Met Glu Lys Tyr Asp Ile Thr Asn Leu Asn
            340                 345                 350

Ala Lys Gln Asp Lys Ser Lys Asn Gly Ser Val Lys Glu Leu Lys His
        355                 360                 365

Ile Tyr Ser Asn His Ile Lys Gly Asn Lys Ile Thr Ala Pro Lys Pro
    370                 375                 380

Ser Ile Gln Gly Val Val Ile His Asn Asp Tyr Gly Ser Met Thr Pro
385                 390                 395                 400

Ser Gln Tyr Leu Pro Trp Leu Tyr Ala Arg Glu Asn Asn Gly Thr His
                405                 410                 415

Val Asn Gly Trp Ala Ser Val Tyr Ala Asn Arg Asn Glu Val Leu Trp
            420                 425                 430

Tyr His Pro Thr Asp Tyr Val Glu Trp His Cys Gly Asn Gln Trp Ala
        435                 440                 445

Asn Ala Asn Leu Ile Gly Phe Glu Val Cys Glu Ser Tyr Pro Gly Arg
    450                 455                 460

Ile Ser Asp Lys Leu Phe Leu Glu Asn Glu Ala Thr Leu Lys Val
465                 470                 475                 480

Ala Ala Asp Val Met Lys Ser Tyr Gly Leu Pro Val Asn Arg Asn Thr
                485                 490                 495

Val Arg Leu His Asn Glu Phe Phe Gly Thr Ser Cys Pro His Arg Ser
            500                 505                 510

Trp Asp Leu His Val Gly Lys Gly Glu Pro Tyr Thr Thr Thr Asn Ile
        515                 520                 525

Asn Lys Met Lys Asp Tyr Phe Ile Lys Arg Ile Lys His Tyr Tyr Asp
    530                 535                 540

Gly Gly Lys Leu Glu Val Ser Lys Ala Ala Thr Ile Lys Gln Ser Asp
545                 550                 555                 560

Val Lys Gln Glu Val Lys Gln Glu Ala Lys Gln Ile Val Lys Ala
                565                 570                 575

Thr Asp Trp Lys Gln Asn Lys Asp Gly Ile Trp Tyr Lys Ala Glu His
            580                 585                 590

Ala Ser Phe Thr Val Thr Ala Pro Glu Gly Ile Ile Thr Arg Tyr Lys
        595                 600                 605

Gly Pro Trp Thr Gly His Pro Gln Ala Gly Val Leu Gln Lys Gly Gln
    610                 615                 620

Thr Ile Lys Tyr Asp Glu Val Gln Lys Phe Asp Gly His Val Trp Val
625                 630                 635                 640

Ser Trp Glu Thr Phe Glu Gly Glu Thr Val Tyr Met Pro Val Arg Thr
                645                 650                 655

Trp Asp Ala Lys Thr Gly Lys Val Gly Lys Leu Trp Gly Glu Ile Lys
            660                 665                 670

<210> SEQ ID NO 26
<211> LENGTH: 714
<212> TYPE: PRT
```

<213> ORGANISM: artificial
<220> FEATURE:
<223> OTHER INFORMATION: His-tagged Ami11_M23-2638_Ami2638_CBD2638

<400> SEQUENCE: 26

Met Arg Gly Ser His His His His His His Gly Ser Lys Pro Gln Pro
1               5                   10                  15

Lys Ala Val Glu Leu Lys Ile Ile Lys Asp Val Val Lys Gly Tyr Asp
                20                  25                  30

Leu Pro Lys Arg Gly Ser Asn Pro Lys Gly Ile Val Ile His Asn Asp
            35                  40                  45

Ala Gly Ser Lys Gly Ala Thr Ala Glu Ala Tyr Arg Asn Gly Leu Val
        50                  55                  60

Asn Ala Pro Leu Ser Arg Leu Glu Ala Gly Ile Ala His Ser Tyr Val
65                  70                  75                  80

Ser Gly Asn Thr Val Trp Gln Ala Leu Asp Glu Ser Gln Val Gly Trp
                85                  90                  95

His Thr Ala Asn Gln Ile Gly Asn Lys Tyr Tyr Tyr Gly Ile Glu Val
            100                 105                 110

Cys Gln Ser Met Gly Ala Asp Asn Ala Thr Phe Leu Lys Asn Glu Gln
        115                 120                 125

Ala Thr Phe Gln Glu Cys Ala Arg Leu Leu Lys Lys Trp Gly Leu Pro
    130                 135                 140

Ala Asn Arg Asn Thr Ile Arg Leu His Asn Glu Phe Thr Ser Thr Ser
145                 150                 155                 160

Cys Pro His Arg Ser Ser Val Leu His Thr Gly Phe Asp Pro Val Thr
                165                 170                 175

Arg Gly Leu Leu Pro Glu Asp Lys Arg Leu Gln Leu Lys Asp Tyr Phe
            180                 185                 190

Ile Lys Gln Ile Arg Ala Tyr Met Asp Gly Lys Ile Pro Val Ala Thr
        195                 200                 205

Val Ser Asn Glu Ser Ser Ala Ser Ser Asn Thr Val Lys Pro Val Ala
    210                 215                 220

Ser Ala Gly Ser Met Leu Thr Ala Ile Asp Tyr Leu Thr Lys Lys Gly
225                 230                 235                 240

Trp Lys Ile Ser Ser Asp Pro Arg Thr Tyr Asp Gly Tyr Pro Lys Asn
                245                 250                 255

Tyr Gly Tyr Arg Asn Tyr His Glu Asn Gly Ile Asn Tyr Asp Glu Phe
            260                 265                 270

Cys Gly Gly Tyr His Arg Ala Phe Asp Val Tyr Ser Asn Glu Thr Asn
        275                 280                 285

Asp Val Pro Ala Val Thr Ser Gly Thr Val Ile Glu Ala Asn Asp Tyr
    290                 295                 300

Gly Asn Phe Gly Gly Thr Phe Val Ile Arg Asp Ala Asn Asp Asn Asp
305                 310                 315                 320

Trp Ile Tyr Gly His Leu Gln Arg Gly Ser Met Arg Phe Val Val Gly
                325                 330                 335

Asp Lys Val Asn Gln Gly Asp Ile Ile Gly Leu Gln Gly Asn Ser Asn
            340                 345                 350

Tyr Tyr Asp Asn Pro Met Ser Val His Leu His Leu Gln Leu Arg Pro
        355                 360                 365

Lys Asp Ala Lys Lys Asp Glu Lys Ser Gln Val Cys Ser Gly Leu Ala
    370                 375                 380

Met Glu Lys Tyr Asp Ile Thr Asn Leu Asn Ala Lys Gln Asp Lys Ser

```
                385                 390                 395                 400
Lys Asn Gly Ser Val Lys Glu Leu Lys His Ile Tyr Ser Asn His Ile
                    405                 410                 415

Lys Gly Asn Lys Ile Thr Ala Pro Lys Pro Ser Ile Gln Gly Val Val
                420                 425                 430

Ile His Asn Asp Tyr Gly Ser Met Thr Pro Ser Gln Tyr Leu Pro Trp
            435                 440                 445

Leu Tyr Ala Arg Glu Asn Asn Gly Thr His Val Asn Gly Trp Ala Ser
        450                 455                 460

Val Tyr Ala Asn Arg Asn Glu Val Leu Trp Tyr His Pro Thr Asp Tyr
465                 470                 475                 480

Val Glu Trp His Cys Gly Asn Gln Trp Ala Asn Ala Asn Leu Ile Gly
                485                 490                 495

Phe Glu Val Cys Glu Ser Tyr Pro Gly Arg Ile Ser Asp Lys Leu Phe
                500                 505                 510

Leu Glu Asn Glu Glu Ala Thr Leu Lys Val Ala Ala Asp Val Met Lys
            515                 520                 525

Ser Tyr Gly Leu Pro Val Asn Arg Asn Thr Val Arg Leu His Asn Glu
        530                 535                 540

Phe Phe Gly Thr Ser Cys Pro His Arg Ser Trp Asp Leu His Val Gly
545                 550                 555                 560

Lys Gly Glu Pro Tyr Thr Thr Thr Asn Ile Asn Lys Met Lys Asp Tyr
                565                 570                 575

Phe Ile Lys Arg Ile Lys His Tyr Tyr Asp Gly Gly Lys Leu Glu Val
            580                 585                 590

Ser Lys Ala Ala Thr Ile Lys Gln Ser Asp Val Lys Gln Glu Val Lys
        595                 600                 605

Lys Gln Glu Ala Lys Gln Ile Val Lys Ala Thr Asp Trp Lys Gln Asn
610                 615                 620

Lys Asp Gly Ile Trp Tyr Lys Ala Glu His Ala Ser Phe Thr Val Thr
625                 630                 635                 640

Ala Pro Glu Gly Ile Ile Thr Arg Tyr Lys Gly Pro Trp Thr Gly His
                645                 650                 655

Pro Gln Ala Gly Val Leu Gln Lys Gly Gln Thr Ile Lys Tyr Asp Glu
            660                 665                 670

Val Gln Lys Phe Asp Gly His Val Trp Val Ser Trp Glu Thr Phe Glu
        675                 680                 685

Gly Glu Thr Val Tyr Met Pro Val Arg Thr Trp Asp Ala Lys Thr Gly
690                 695                 700

Lys Val Gly Lys Leu Trp Gly Glu Ile Lys
705                 710

<210> SEQ ID NO 27
<211> LENGTH: 652
<212> TYPE: PRT
<213> ORGANISM: artificial
<220> FEATURE:
<223> OTHER INFORMATION: His-tagged CHAPTw_Ami2638_M23-LST_CBD2638

<400> SEQUENCE: 27

Met Arg Gly Ser His His His His His His Gly Ser Met Lys Thr Leu
1               5                   10                  15

Lys Gln Ala Glu Ser Tyr Ile Lys Ser Lys Val Asn Thr Gly Thr Asp
            20                  25                  30

Phe Asp Gly Leu Tyr Gly Tyr Gln Cys Met Asp Leu Ala Val Asp Tyr
```

```
            35                  40                  45
Ile Tyr His Val Thr Asp Gly Lys Ile Arg Met Trp Gly Asn Ala Lys
 50                  55                  60

Asp Ala Ile Asn Asn Ser Phe Gly Gly Thr Ala Thr Val Tyr Lys Asn
 65                  70                  75                  80

Tyr Pro Ala Phe Arg Pro Lys Tyr Gly Asp Val Val Trp Thr Thr
                 85                  90                  95

Gly Asn Phe Ala Thr Tyr Gly His Ile Ala Ile Val Thr Asn Pro Asp
                100                 105                 110

Pro Tyr Gly Asp Leu Gln Tyr Val Thr Val Leu Glu Gln Asn Trp Asn
                115                 120                 125

Gly Asn Gly Ile Tyr Lys Thr Glu Leu Ala Thr Ile Arg Thr His Asp
                130                 135                 140

Tyr Thr Gly Ile Thr His Phe Ile Lys Asp Ala Lys Lys Asp Glu Lys
145                 150                 155                 160

Ser Gln Val Cys Ser Gly Leu Ala Met Glu Lys Tyr Asp Ile Thr Asn
                165                 170                 175

Leu Asn Ala Lys Gln Asp Lys Ser Lys Asn Gly Ser Val Lys Glu Leu
                180                 185                 190

Lys His Ile Tyr Ser Asn His Ile Lys Gly Asn Lys Ile Thr Ala Pro
                195                 200                 205

Lys Pro Ser Ile Gln Gly Val Val Ile His Asn Asp Tyr Gly Ser Met
210                 215                 220

Thr Pro Ser Gln Tyr Leu Pro Trp Leu Tyr Ala Arg Glu Asn Asn Gly
225                 230                 235                 240

Thr His Val Asn Gly Trp Ala Ser Val Tyr Ala Asn Arg Asn Glu Val
                245                 250                 255

Leu Trp Tyr His Pro Thr Asp Tyr Val Glu Trp His Cys Gly Asn Gln
                260                 265                 270

Trp Ala Asn Ala Asn Leu Ile Gly Phe Glu Val Cys Glu Ser Tyr Pro
                275                 280                 285

Gly Arg Ile Ser Asp Lys Leu Phe Leu Glu Asn Glu Glu Ala Thr Leu
                290                 295                 300

Lys Val Ala Ala Asp Val Met Lys Ser Tyr Gly Leu Pro Val Asn Arg
305                 310                 315                 320

Asn Thr Val Arg Leu His Asn Glu Phe Phe Gly Thr Ser Cys Pro His
                325                 330                 335

Arg Ser Trp Asp Leu His Val Gly Lys Gly Glu Pro Tyr Thr Thr Thr
                340                 345                 350

Asn Ile Asn Lys Met Lys Asp Tyr Phe Ile Lys Arg Ile Lys His Tyr
                355                 360                 365

Tyr Asp Gly Gly Lys Leu Glu Val Ser Lys Ala Ala Thr Ile Lys Gln
                370                 375                 380

Ser Asp Val Lys Gln Glu Val Lys Gln Glu Ala Lys Gln Ile Val
385                 390                 395                 400

Lys Ala Thr Asp Ala Ala Thr His Glu His Ser Ala Gln Trp Leu Asn
                405                 410                 415

Asn Tyr Lys Gly Tyr Gly Tyr Gly Pro Tyr Pro Leu Gly Ile Asn
                420                 425                 430

Gly Gly Met His Tyr Gly Val Asp Phe Phe Met Asn Ile Gly Thr Pro
                435                 440                 445

Val Lys Ala Ile Ser Ser Gly Lys Ile Val Glu Ala Gly Trp Ser Asn
450                 455                 460
```

```
Tyr Gly Gly Gly Asn Gln Ile Gly Leu Ile Glu Asn Asp Gly Val His
465                 470                 475                 480

Arg Gln Trp Tyr Met His Leu Ser Lys Tyr Asn Val Lys Val Gly Asp
            485                 490                 495

Tyr Val Lys Ala Gly Gln Ile Ile Gly Trp Ser Gly Ser Thr Gly Tyr
        500                 505                 510

Ser Thr Ala Pro His Leu His Phe Gln Arg Met Val Asn Ser Phe Ser
    515                 520                 525

Asn Ser Thr Ala Gln Asp Pro Met Pro Phe Leu Lys Ser Ala Gly Tyr
530                 535                 540

Gly Lys Ala Gly Gly Thr Val Thr Pro Thr Pro Asn Thr Gly Trp Lys
545                 550                 555                 560

Gln Asn Lys Asp Gly Ile Trp Tyr Lys Ala Glu His Ala Ser Phe Thr
                565                 570                 575

Val Thr Ala Pro Glu Gly Ile Ile Thr Arg Tyr Lys Gly Pro Trp Thr
            580                 585                 590

Gly His Pro Gln Ala Gly Val Leu Gln Lys Gly Gln Thr Ile Lys Tyr
        595                 600                 605

Asp Glu Val Gln Lys Phe Asp Gly His Val Trp Val Ser Trp Glu Thr
610                 615                 620

Phe Glu Gly Glu Thr Val Tyr Met Pro Val Arg Thr Trp Asp Ala Lys
625                 630                 635                 640

Thr Gly Lys Val Gly Lys Leu Trp Gly Glu Ile Lys
                645                 650

<210> SEQ ID NO 28
<211> LENGTH: 650
<212> TYPE: PRT
<213> ORGANISM: artificial
<220> FEATURE:
<223> OTHER INFORMATION: His-tagged CHAPTw_Ami2638_M23-LST_CWT-LST

<400> SEQUENCE: 28

Met Arg Gly Ser His His His His His His Gly Ser Met Lys Thr Leu
1               5                   10                  15

Lys Gln Ala Glu Ser Tyr Ile Lys Ser Lys Val Asn Thr Gly Thr Asp
            20                  25                  30

Phe Asp Gly Leu Tyr Gly Tyr Gln Cys Met Asp Leu Ala Val Asp Tyr
        35                  40                  45

Ile Tyr His Val Thr Asp Gly Lys Ile Arg Met Trp Gly Asn Ala Lys
    50                  55                  60

Asp Ala Ile Asn Asn Ser Phe Gly Gly Thr Ala Thr Val Tyr Lys Asn
65                  70                  75                  80

Tyr Pro Ala Phe Arg Pro Lys Tyr Gly Asp Val Val Val Trp Thr Thr
                85                  90                  95

Gly Asn Phe Ala Thr Tyr Gly His Ile Ala Ile Val Thr Asn Pro Asp
            100                 105                 110

Pro Tyr Gly Asp Leu Gln Tyr Val Thr Val Leu Glu Gln Asn Trp Asn
        115                 120                 125

Gly Asn Gly Ile Tyr Lys Thr Glu Leu Ala Thr Ile Arg Thr His Asp
    130                 135                 140

Tyr Thr Gly Ile Thr His Phe Ile Lys Asp Ala Lys Lys Asp Glu Lys
145                 150                 155                 160

Ser Gln Val Cys Ser Gly Leu Ala Met Glu Lys Tyr Asp Ile Thr Asn
                165                 170                 175
```

```
Leu Asn Ala Lys Gln Asp Lys Ser Lys Asn Gly Ser Val Lys Glu Leu
            180                 185                 190

Lys His Ile Tyr Ser Asn His Ile Lys Gly Asn Lys Ile Thr Ala Pro
            195                 200                 205

Lys Pro Ser Ile Gln Gly Val Val Ile His Asn Asp Tyr Gly Ser Met
210                 215                 220

Thr Pro Ser Gln Tyr Leu Pro Trp Leu Tyr Ala Arg Glu Asn Asn Gly
225                 230                 235                 240

Thr His Val Asn Gly Trp Ala Ser Val Tyr Ala Asn Arg Asn Glu Val
            245                 250                 255

Leu Trp Tyr His Pro Thr Asp Tyr Val Glu Trp His Cys Gly Asn Gln
            260                 265                 270

Trp Ala Asn Ala Asn Leu Ile Gly Phe Glu Val Cys Glu Ser Tyr Pro
            275                 280                 285

Gly Arg Ile Ser Asp Lys Leu Phe Leu Glu Asn Glu Glu Ala Thr Leu
            290                 295                 300

Lys Val Ala Ala Asp Val Met Lys Ser Tyr Gly Leu Pro Val Asn Arg
305                 310                 315                 320

Asn Thr Val Arg Leu His Asn Glu Phe Phe Gly Thr Ser Cys Pro His
            325                 330                 335

Arg Ser Trp Asp Leu His Val Gly Lys Gly Glu Pro Tyr Thr Thr Thr
            340                 345                 350

Asn Ile Asn Lys Met Lys Asp Tyr Phe Ile Lys Arg Ile Lys His Tyr
            355                 360                 365

Tyr Asp Gly Gly Lys Leu Glu Val Ser Lys Ala Ala Thr Ile Lys Gln
            370                 375                 380

Ser Asp Val Lys Gln Glu Val Lys Lys Gln Glu Ala Lys Gln Ile Val
385                 390                 395                 400

Lys Ala Thr Asp Ala Ala Thr His Glu His Ser Ala Gln Trp Leu Asn
            405                 410                 415

Asn Tyr Lys Lys Gly Tyr Gly Tyr Gly Pro Tyr Pro Leu Gly Ile Asn
            420                 425                 430

Gly Gly Met His Tyr Gly Val Asp Phe Phe Met Asn Ile Gly Thr Pro
            435                 440                 445

Val Lys Ala Ile Ser Ser Gly Lys Ile Val Glu Ala Gly Trp Ser Asn
            450                 455                 460

Tyr Gly Gly Gly Asn Gln Ile Gly Leu Ile Glu Asn Asp Gly Val His
465                 470                 475                 480

Arg Gln Trp Tyr Met His Leu Ser Lys Tyr Asn Val Lys Val Gly Asp
            485                 490                 495

Tyr Val Lys Ala Gly Gln Ile Ile Gly Trp Ser Gly Ser Thr Gly Tyr
            500                 505                 510

Ser Thr Ala Pro His Leu His Phe Gln Arg Met Val Asn Ser Phe Ser
            515                 520                 525

Asn Ser Thr Ala Gln Asp Pro Met Pro Phe Leu Lys Ser Ala Gly Tyr
            530                 535                 540

Gly Lys Ala Gly Gly Thr Val Thr Pro Thr Asn Thr Gly Trp Lys
545                 550                 555                 560

Thr Asn Lys Tyr Gly Thr Leu Tyr Lys Ser Glu Ser Ala Ser Phe Thr
            565                 570                 575

Pro Asn Thr Asp Ile Ile Thr Arg Thr Thr Gly Pro Phe Arg Ser Met
            580                 585                 590
```

```
Pro Gln Ser Gly Val Leu Lys Ala Gly Gln Thr Ile His Tyr Asp Glu
            595                 600                 605

Val Met Lys Gln Asp Gly His Val Trp Val Gly Tyr Thr Gly Asn Ser
    610                 615                 620

Gly Gln Arg Ile Tyr Leu Pro Val Arg Thr Trp Asn Lys Ser Thr Asn
625                 630                 635                 640

Thr Leu Gly Val Leu Trp Gly Thr Ile Lys
                645                 650

<210> SEQ ID NO 29
<211> LENGTH: 517
<212> TYPE: PRT
<213> ORGANISM: artificial
<220> FEATURE:
<223> OTHER INFORMATION: His-tagged M23-LST_Ami2638_CBD2638

<400> SEQUENCE: 29

Met Arg Gly Ser His His His His His His Gly Ser Ala Ala Thr His
1               5                   10                  15

Glu His Ser Ala Gln Trp Leu Asn Asn Tyr Lys Lys Gly Tyr Gly Tyr
            20                  25                  30

Gly Pro Tyr Pro Leu Gly Ile Asn Gly Gly Met His Tyr Gly Val Asp
        35                  40                  45

Phe Phe Met Asn Ile Gly Thr Pro Val Lys Ala Ile Ser Ser Gly Lys
50                  55                  60

Ile Val Glu Ala Gly Trp Ser Asn Tyr Gly Gly Gly Asn Gln Ile Gly
65                  70                  75                  80

Leu Ile Glu Asn Asp Gly Val His Arg Gln Trp Tyr Met His Leu Ser
                85                  90                  95

Lys Tyr Asn Val Lys Val Gly Asp Tyr Val Lys Ala Gly Gln Ile Ile
            100                 105                 110

Gly Trp Ser Gly Ser Thr Gly Tyr Ser Thr Ala Pro His Leu His Phe
        115                 120                 125

Gln Arg Met Val Asn Ser Phe Ser Asn Ser Thr Ala Gln Asp Pro Met
130                 135                 140

Pro Phe Leu Lys Ser Ala Gly Tyr Gly Lys Ala Gly Gly Thr Val Thr
145                 150                 155                 160

Pro Thr Pro Asn Thr Gly Glu Leu Leu Arg Pro Lys Asp Ala Lys Lys
                165                 170                 175

Asp Glu Lys Ser Gln Val Cys Ser Gly Leu Ala Met Glu Lys Tyr Asp
            180                 185                 190

Ile Thr Asn Leu Asn Ala Lys Gln Asp Lys Ser Lys Asn Gly Ser Val
        195                 200                 205

Lys Glu Leu Lys His Ile Tyr Ser Asn His Ile Lys Gly Asn Lys Ile
210                 215                 220

Thr Ala Pro Lys Pro Ser Ile Gln Gly Val Val Ile His Asn Asp Tyr
225                 230                 235                 240

Gly Ser Met Thr Pro Ser Gln Tyr Leu Pro Trp Leu Tyr Ala Arg Glu
                245                 250                 255

Asn Asn Gly Thr His Val Asn Gly Trp Ala Ser Val Tyr Ala Asn Arg
            260                 265                 270

Asn Glu Val Leu Trp Tyr His Pro Thr Asp Tyr Val Glu Trp His Cys
        275                 280                 285

Gly Asn Gln Trp Ala Asn Ala Asn Leu Ile Gly Phe Glu Val Cys Glu
        290                 295                 300
```

Ser Tyr Pro Gly Arg Ile Ser Asp Lys Leu Phe Leu Glu Asn Glu Glu
305                 310                 315                 320

Ala Thr Leu Lys Val Ala Ala Asp Val Met Lys Ser Tyr Gly Leu Pro
            325                 330                 335

Val Asn Arg Asn Thr Val Arg Leu His Asn Glu Phe Phe Gly Thr Ser
        340                 345                 350

Cys Pro His Arg Ser Trp Asp Leu His Val Gly Lys Gly Glu Pro Tyr
    355                 360                 365

Thr Thr Thr Asn Ile Asn Lys Met Lys Asp Tyr Phe Ile Lys Arg Ile
370                 375                 380

Lys His Tyr Tyr Asp Gly Gly Lys Leu Glu Val Ser Lys Ala Ala Thr
385                 390                 395                 400

Ile Lys Gln Ser Asp Val Lys Gln Glu Val Lys Lys Gln Glu Ala Lys
            405                 410                 415

Gln Ile Val Lys Ala Thr Asp Trp Lys Gln Asn Lys Asp Gly Ile Trp
        420                 425                 430

Tyr Lys Ala Glu His Ala Ser Phe Thr Val Thr Ala Pro Glu Gly Ile
    435                 440                 445

Ile Thr Arg Tyr Lys Gly Pro Trp Thr Gly His Pro Gln Ala Gly Val
450                 455                 460

Leu Gln Lys Gly Gln Thr Ile Lys Tyr Asp Glu Val Gln Lys Phe Asp
465                 470                 475                 480

Gly His Val Trp Val Ser Trp Glu Thr Phe Glu Gly Thr Val Tyr
            485                 490                 495

Met Pro Val Arg Thr Trp Asp Ala Lys Thr Lys Val Gly Lys Leu
        500                 505                 510

Trp Gly Glu Ile Lys
        515

<210> SEQ ID NO 30
<211> LENGTH: 506
<212> TYPE: PRT
<213> ORGANISM: artificial
<220> FEATURE:
<223> OTHER INFORMATION: His-tagged LST_LST

<400> SEQUENCE: 30

Met Arg Gly Ser His His His His His His Gly Ser Ala Ala Thr His
1               5                   10                  15

Glu His Ser Ala Gln Trp Leu Asn Asn Tyr Lys Lys Gly Tyr Gly Tyr
            20                  25                  30

Gly Pro Tyr Pro Leu Gly Ile Asn Gly Gly Met His Tyr Gly Val Asp
        35                  40                  45

Phe Phe Met Asn Ile Gly Thr Pro Val Lys Ala Ile Ser Ser Gly Lys
    50                  55                  60

Ile Val Glu Ala Gly Trp Ser Asn Tyr Gly Gly Asn Gln Ile Gly
65                  70                  75                  80

Leu Ile Glu Asn Asp Gly Val His Arg Gln Trp Tyr Met His Leu Ser
                85                  90                  95

Lys Tyr Asn Val Lys Val Gly Asp Tyr Val Lys Ala Gly Gln Ile Ile
            100                 105                 110

Gly Trp Ser Gly Ser Thr Gly Tyr Ser Thr Ala Pro His Leu His Phe
        115                 120                 125

Gln Arg Met Val Asn Ser Phe Ser Asn Ser Thr Ala Gln Asp Pro Met
    130                 135                 140

```
Pro Phe Leu Lys Ser Ala Gly Tyr Gly Lys Ala Gly Gly Thr Val Thr
145                 150                 155                 160

Pro Thr Pro Asn Thr Gly Trp Lys Thr Asn Lys Tyr Gly Thr Leu Tyr
            165                 170                 175

Lys Ser Glu Ser Ala Ser Phe Thr Pro Asn Thr Asp Ile Ile Thr Arg
        180                 185                 190

Thr Thr Gly Pro Phe Arg Ser Met Pro Gln Ser Gly Val Leu Lys Ala
            195                 200                 205

Gly Gln Thr Ile His Tyr Asp Glu Val Met Lys Gln Asp Gly His Val
        210                 215                 220

Trp Val Gly Tyr Thr Gly Asn Ser Gly Gln Arg Ile Tyr Leu Pro Val
225                 230                 235                 240

Arg Thr Trp Asn Lys Ser Thr Asn Thr Leu Gly Val Leu Trp Gly Thr
            245                 250                 255

Ile Lys Glu Leu Ala Ala Thr His Glu His Ser Ala Gln Trp Leu Asn
        260                 265                 270

Asn Tyr Lys Lys Gly Tyr Gly Tyr Gly Pro Tyr Pro Leu Gly Ile Asn
            275                 280                 285

Gly Gly Met His Tyr Gly Val Asp Phe Phe Met Asn Ile Gly Thr Pro
290                 295                 300

Val Lys Ala Ile Ser Ser Gly Lys Ile Val Glu Ala Gly Trp Ser Asn
305                 310                 315                 320

Tyr Gly Gly Gly Asn Gln Ile Gly Leu Ile Glu Asn Asp Gly Val His
            325                 330                 335

Arg Gln Trp Tyr Met His Leu Ser Lys Tyr Asn Val Lys Val Gly Asp
        340                 345                 350

Tyr Val Lys Ala Gly Gln Ile Ile Gly Trp Ser Gly Ser Thr Gly Tyr
        355                 360                 365

Ser Thr Ala Pro His Leu His Phe Gln Arg Met Val Asn Ser Phe Ser
        370                 375                 380

Asn Ser Thr Ala Gln Asp Pro Met Pro Phe Leu Lys Ser Ala Gly Tyr
385                 390                 395                 400

Gly Lys Ala Gly Gly Thr Val Thr Pro Thr Pro Asn Thr Gly Trp Lys
            405                 410                 415

Thr Asn Lys Tyr Gly Thr Leu Tyr Lys Ser Glu Ser Ala Ser Phe Thr
        420                 425                 430

Pro Asn Thr Asp Ile Ile Thr Arg Thr Thr Gly Pro Phe Arg Ser Met
            435                 440                 445

Pro Gln Ser Gly Val Leu Lys Ala Gly Gln Thr Ile His Tyr Asp Glu
        450                 455                 460

Val Met Lys Gln Asp Gly His Val Trp Val Gly Tyr Thr Gly Asn Ser
465                 470                 475                 480

Gly Gln Arg Ile Tyr Leu Pro Val Arg Thr Trp Asn Lys Ser Thr Asn
            485                 490                 495

Thr Leu Gly Val Leu Trp Gly Thr Ile Lys
            500                 505

<210> SEQ ID NO 31
<211> LENGTH: 414
<212> TYPE: PRT
<213> ORGANISM: artificial
<220> FEATURE:
<223> OTHER INFORMATION: His-tagged M23-LST_M23-LST_CWT-LST

<400> SEQUENCE: 31
```

```
Met Arg Gly Ser His His His His His Gly Ser Ala Ala Thr His
1               5                   10                  15

Glu His Ser Ala Gln Trp Leu Asn Asn Tyr Lys Lys Gly Tyr Gly Tyr
            20                  25                  30

Gly Pro Tyr Pro Leu Gly Ile Asn Gly Gly Met His Tyr Gly Val Asp
        35                  40                  45

Phe Phe Met Asn Ile Gly Thr Pro Val Lys Ala Ile Ser Ser Gly Lys
50                  55                  60

Ile Val Glu Ala Gly Trp Ser Asn Tyr Gly Gly Asn Gln Ile Gly
65              70                  75                  80

Leu Ile Glu Asn Asp Gly Val His Arg Gln Trp Tyr Met His Leu Ser
                85                  90                  95

Lys Tyr Asn Val Lys Val Gly Asp Tyr Val Lys Ala Gly Gln Ile Ile
            100                 105                 110

Gly Trp Ser Gly Ser Thr Gly Tyr Ser Thr Ala Pro His Leu His Phe
            115                 120                 125

Gln Arg Met Val Asn Ser Phe Ser Asn Ser Thr Ala Gln Asp Pro Met
        130                 135                 140

Pro Phe Leu Lys Ser Ala Gly Tyr Gly Lys Ala Gly Gly Thr Val Thr
145                 150                 155                 160

Pro Thr Pro Asn Thr Gly Glu Leu Ala Ala Thr His Glu His Ser Ala
                165                 170                 175

Gln Trp Leu Asn Asn Tyr Lys Lys Gly Tyr Gly Tyr Gly Pro Tyr Pro
            180                 185                 190

Leu Gly Ile Asn Gly Gly Met His Tyr Gly Val Asp Phe Phe Met Asn
        195                 200                 205

Ile Gly Thr Pro Val Lys Ala Ile Ser Ser Gly Lys Ile Val Glu Ala
        210                 215                 220

Gly Trp Ser Asn Tyr Gly Gly Asn Gln Ile Gly Leu Ile Glu Asn
225                 230                 235                 240

Asp Gly Val His Arg Gln Trp Tyr Met His Leu Ser Lys Tyr Asn Val
                245                 250                 255

Lys Val Gly Asp Tyr Val Lys Ala Gly Gln Ile Ile Gly Trp Ser Gly
            260                 265                 270

Ser Thr Gly Tyr Ser Thr Ala Pro His Leu His Phe Gln Arg Met Val
        275                 280                 285

Asn Ser Phe Ser Asn Ser Thr Ala Gln Asp Pro Met Pro Phe Leu Lys
        290                 295                 300

Ser Ala Gly Tyr Gly Lys Ala Gly Gly Thr Val Thr Pro Thr Pro Asn
305                 310                 315                 320

Thr Gly Trp Lys Thr Asn Lys Tyr Gly Thr Leu Tyr Lys Ser Glu Ser
                325                 330                 335

Ala Ser Phe Thr Pro Asn Thr Asp Ile Ile Thr Arg Thr Thr Gly Pro
            340                 345                 350

Phe Arg Ser Met Pro Gln Ser Gly Val Leu Lys Ala Gly Gln Thr Ile
            355                 360                 365

His Tyr Asp Glu Val Met Lys Gln Asp Gly His Val Trp Val Gly Tyr
        370                 375                 380

Thr Gly Asn Ser Gly Gln Arg Ile Tyr Leu Pro Val Arg Thr Trp Asn
385                 390                 395                 400

Lys Ser Thr Asn Thr Leu Gly Val Leu Trp Gly Thr Ile Lys
            405                 410
```

<210> SEQ ID NO 32
<211> LENGTH: 628
<212> TYPE: PRT
<213> ORGANISM: artificial
<220> FEATURE:
<223> OTHER INFORMATION: His-tagged M23-2638_Ami2638_CBD2638_CBD2638

<400> SEQUENCE: 32

Met Arg Gly Ser His His His His His His Gly Ser Met Leu Thr Ala
1               5                   10                  15

Ile Asp Tyr Leu Thr Lys Lys Gly Trp Lys Ile Ser Ser Asp Pro Arg
            20                  25                  30

Thr Tyr Asp Gly Tyr Pro Lys Asn Tyr Gly Tyr Arg Asn Tyr His Glu
        35                  40                  45

Asn Gly Ile Asn Tyr Asp Glu Phe Cys Gly Gly Tyr His Arg Ala Phe
    50                  55                  60

Asp Val Tyr Ser Asn Glu Thr Asn Asp Val Pro Ala Val Thr Ser Gly
65                  70                  75                  80

Thr Val Ile Glu Ala Asn Asp Tyr Gly Asn Phe Gly Gly Thr Phe Val
                85                  90                  95

Ile Arg Asp Ala Asn Asp Asn Asp Trp Ile Tyr Gly His Leu Gln Arg
            100                 105                 110

Gly Ser Met Arg Phe Val Val Gly Asp Lys Val Asn Gln Gly Asp Ile
        115                 120                 125

Ile Gly Leu Gln Gly Asn Ser Asn Tyr Tyr Asp Asn Pro Met Ser Val
    130                 135                 140

His Leu His Leu Gln Leu Arg Pro Lys Asp Ala Lys Lys Asp Glu Lys
145                 150                 155                 160

Ser Gln Val Cys Ser Gly Leu Ala Met Glu Lys Tyr Asp Ile Thr Asn
                165                 170                 175

Leu Asn Ala Lys Gln Asp Lys Ser Lys Asn Gly Ser Val Lys Glu Leu
            180                 185                 190

Lys His Ile Tyr Ser Asn His Ile Lys Gly Asn Lys Ile Thr Ala Pro
        195                 200                 205

Lys Pro Ser Ile Gln Gly Val Val Ile His Asn Asp Tyr Gly Ser Met
    210                 215                 220

Thr Pro Ser Gln Tyr Leu Pro Trp Leu Tyr Ala Arg Glu Asn Asn Gly
225                 230                 235                 240

Thr His Val Asn Gly Trp Ala Ser Val Tyr Ala Asn Arg Asn Glu Val
                245                 250                 255

Leu Trp Tyr His Pro Thr Asp Tyr Val Glu Trp His Cys Gly Asn Gln
            260                 265                 270

Trp Ala Asn Ala Asn Leu Ile Gly Phe Glu Val Cys Glu Ser Tyr Pro
        275                 280                 285

Gly Arg Ile Ser Asp Lys Leu Phe Leu Glu Asn Glu Ala Thr Leu
    290                 295                 300

Lys Val Ala Ala Asp Val Met Lys Ser Tyr Gly Leu Pro Val Asn Arg
305                 310                 315                 320

Asn Thr Val Arg Leu His Asn Glu Phe Phe Gly Thr Ser Cys Pro His
                325                 330                 335

Arg Ser Trp Asp Leu His Val Gly Lys Gly Glu Pro Tyr Thr Thr Thr
            340                 345                 350

Asn Ile Asn Lys Met Lys Asp Tyr Phe Ile Lys Arg Ile Lys His Tyr
        355                 360                 365

Tyr Asp Gly Gly Lys Leu Glu Val Ser Lys Ala Ala Thr Ile Lys Gln

```
                370             375             380
Ser Asp Val Lys Gln Glu Val Lys Lys Gln Glu Ala Lys Gln Ile Val
385                 390                 395                 400

Lys Ala Thr Asp Trp Lys Gln Asn Lys Asp Gly Ile Trp Tyr Lys Ala
                405                 410                 415

Glu His Ala Ser Phe Thr Val Thr Ala Pro Glu Gly Ile Ile Thr Arg
                420                 425                 430

Tyr Lys Gly Pro Trp Thr Gly His Pro Gln Ala Gly Val Leu Gln Lys
                435                 440                 445

Gly Gln Thr Ile Lys Tyr Asp Glu Val Gln Lys Phe Asp Gly His Val
        450                 455                 460

Trp Val Ser Trp Glu Thr Phe Glu Gly Glu Thr Val Tyr Met Pro Val
465                 470                 475                 480

Arg Thr Trp Asp Ala Lys Thr Gly Lys Val Gly Lys Leu Trp Gly Glu
                485                 490                 495

Ile Lys Glu Leu Gly Gly Lys Leu Glu Val Ser Lys Ala Ala Thr Ile
                500                 505                 510

Lys Gln Ser Asp Val Lys Gln Glu Val Lys Lys Gln Glu Ala Lys Gln
        515                 520                 525

Ile Val Lys Ala Thr Asp Trp Lys Gln Asn Lys Asp Gly Ile Trp Tyr
        530                 535                 540

Lys Ala Glu His Ala Ser Phe Thr Val Thr Ala Pro Glu Gly Ile Ile
545                 550                 555                 560

Thr Arg Tyr Lys Gly Pro Trp Thr Gly His Pro Gln Ala Gly Val Leu
                565                 570                 575

Gln Lys Gly Gln Thr Ile Lys Tyr Asp Glu Val Gln Lys Phe Asp Gly
                580                 585                 590

His Val Trp Val Ser Trp Glu Thr Phe Glu Gly Glu Thr Val Tyr Met
                595                 600                 605

Pro Val Arg Thr Trp Asp Ala Lys Thr Gly Lys Val Gly Lys Leu Trp
610                 615                 620

Gly Glu Ile Lys
625

<210> SEQ ID NO 33
<211> LENGTH: 741
<212> TYPE: DNA
<213> ORGANISM: Staphylococcus simulans

<400> SEQUENCE: 33
gctgcaacac atgaacattc agcacaatgg ttgaataatt acaaaaaagg atatggttac      60
ggtccttatc cattaggtat aaatggcggt atgcactacg agttgatttt ttttatgaat     120
attggaacac cagtaaaagc tatttcaagc ggaaaaatag ttgaagctgg ttggagtaat     180
tacggaggag gtaatcaaat aggtcttatt gaaaatgatg gagtgcatag acaatggtat     240
atgcatctaa gtaaatataa tgttaaagta ggagattatg tcaaagctgg tcaaataatc     300
ggttggtctg gaagcactgg ttattctaca gcaccacatt tacacttcca agaatggtt      360 aattcatttt caaattcaac tgcccaagat ccaatgcctt tcttaaagag cgcaggatat     420
ggaaaagcag gtggtacagt aactccaacg ccgaatacag gttggaaaac aaacaaatat     480
ggcacactat ataatcaga gtcagctagc ttcacaccta atacagatat aataacaaga     540
acgactggtc catttagaag catgccgcag tcaggagtct aaaagcagg tcaaacaatt     600 cattatgatg aagtgatgaa acaagacggt catgtttggg taggttatac aggtaacagt     660
```

-continued

```
ggccaacgta tttacttgcc tgtaagaaca tggaataaat ctactaatac tttaggtgtt    720
ctttggggaa ctataaagtg a                                              741
```

<210> SEQ ID NO 34
<211> LENGTH: 246
<212> TYPE: PRT
<213> ORGANISM: Staphylococcus simulans

<400> SEQUENCE: 34

```
Ala Ala Thr His Glu His Ser Ala Gln Trp Leu Asn Asn Tyr Lys Lys
1               5                   10                  15

Gly Tyr Gly Tyr Gly Pro Tyr Pro Leu Gly Ile Asn Gly Gly Met His
            20                  25                  30

Tyr Gly Val Asp Phe Phe Met Asn Ile Gly Thr Pro Val Lys Ala Ile
        35                  40                  45

Ser Ser Gly Lys Ile Val Glu Ala Gly Trp Ser Asn Tyr Gly Gly Gly
    50                  55                  60

Asn Gln Ile Gly Leu Ile Glu Asn Asp Gly Val His Arg Gln Trp Tyr
65                  70                  75                  80

Met His Leu Ser Lys Tyr Asn Val Lys Val Gly Asp Tyr Val Lys Ala
                85                  90                  95

Gly Gln Ile Ile Gly Trp Ser Gly Ser Thr Gly Tyr Ser Thr Ala Pro
            100                 105                 110

His Leu His Phe Gln Arg Met Val Asn Ser Phe Ser Asn Ser Thr Ala
        115                 120                 125

Gln Asp Pro Met Pro Phe Leu Lys Ser Ala Gly Tyr Gly Lys Ala Gly
    130                 135                 140

Gly Thr Val Thr Pro Thr Pro Asn Thr Gly Trp Lys Thr Asn Lys Tyr
145                 150                 155                 160

Gly Thr Leu Tyr Lys Ser Glu Ser Ala Ser Phe Thr Pro Asn Thr Asp
                165                 170                 175

Ile Ile Thr Arg Thr Thr Gly Pro Phe Arg Ser Met Pro Gln Ser Gly
            180                 185                 190

Val Leu Lys Ala Gly Gln Thr Ile His Tyr Asp Glu Val Met Lys Gln
        195                 200                 205

Asp Gly His Val Trp Val Gly Tyr Thr Gly Asn Ser Gly Gln Arg Ile
    210                 215                 220

Tyr Leu Pro Val Arg Thr Trp Asn Lys Ser Thr Asn Thr Leu Gly Val
225                 230                 235                 240

Leu Trp Gly Thr Ile Lys
                245
```

<210> SEQ ID NO 35
<211> LENGTH: 94
<212> TYPE: PRT
<213> ORGANISM: Staphylococcus aureus bacteriophage 2638a

<400> SEQUENCE: 35

```
Trp Lys Gln Asn Lys Asp Gly Ile Trp Tyr Lys Ala Glu His Ala Ser
1               5                   10                  15

Phe Thr Val Thr Ala Pro Glu Gly Ile Ile Thr Arg Tyr Lys Gly Pro
            20                  25                  30

Trp Thr Gly His Pro Gln Ala Gly Val Leu Gln Lys Gly Gln Thr Ile
        35                  40                  45

Lys Tyr Asp Glu Val Gln Lys Phe Asp Gly His Val Trp Val Ser Trp
```

```
                    50                  55                  60

Glu Thr Phe Glu Gly Glu Thr Val Tyr Met Pro Val Arg Thr Trp Asp
 65                  70                  75                  80

Ala Lys Thr Gly Lys Val Gly Lys Leu Trp Gly Glu Ile Lys
                     85                  90

<210> SEQ ID NO 36
<211> LENGTH: 92
<212> TYPE: PRT
<213> ORGANISM: Staphylococcus simulans

<400> SEQUENCE: 36

Trp Lys Thr Asn Lys Tyr Gly Thr Leu Tyr Lys Ser Glu Ser Ala Ser
  1               5                  10                  15

Phe Thr Pro Asn Thr Asp Ile Ile Thr Arg Thr Thr Gly Pro Phe Arg
                 20                  25                  30

Ser Met Pro Gln Ser Gly Val Leu Lys Ala Gly Gln Thr Ile His Tyr
             35                  40                  45

Asp Glu Val Met Lys Gln Asp Gly His Val Trp Val Gly Tyr Thr Gly
 50                  55                  60

Asn Ser Gly Gln Arg Ile Tyr Leu Pro Val Arg Thr Trp Asn Lys Ser
 65                  70                  75                  80

Thr Asn Thr Leu Gly Val Leu Trp Gly Thr Ile Lys
                 85                  90

<210> SEQ ID NO 37
<211> LENGTH: 146
<212> TYPE: PRT
<213> ORGANISM: Staphylococcus aureus bacteriophage 2638a

<400> SEQUENCE: 37

Met Leu Thr Ala Ile Asp Tyr Leu Thr Lys Lys Gly Trp Lys Ile Ser
  1               5                  10                  15

Ser Asp Pro Arg Thr Tyr Asp Gly Tyr Pro Lys Asn Tyr Gly Tyr Arg
                 20                  25                  30

Asn Tyr His Glu Asn Gly Ile Asn Tyr Asp Glu Phe Cys Gly Gly Tyr
             35                  40                  45

His Arg Ala Phe Asp Val Tyr Ser Asn Glu Thr Asn Asp Val Pro Ala
 50                  55                  60

Val Thr Ser Gly Thr Val Ile Glu Ala Asn Asp Tyr Gly Asn Phe Gly
 65                  70                  75                  80

Gly Thr Phe Val Ile Arg Asp Ala Asn Asp Asn Asp Trp Ile Tyr Gly
                 85                  90                  95

His Leu Gln Arg Gly Ser Met Arg Phe Val Val Gly Asp Lys Val Asn
            100                 105                 110

Gln Gly Asp Ile Ile Gly Leu Gln Gly Asn Ser Asn Tyr Tyr Asp Asn
            115                 120                 125

Pro Met Ser Val His Leu His Leu Gln Leu Arg Pro Lys Asp Ala Lys
        130                 135                 140

Lys Asp
145

<210> SEQ ID NO 38
<211> LENGTH: 140
<212> TYPE: PRT
<213> ORGANISM: Staphylococcus simulans

<400> SEQUENCE: 38
```

```
Ala Ala Thr His Glu His Ser Ala Gln Trp Leu Asn Asn Tyr Lys Lys
1               5                   10                  15

Gly Tyr Gly Tyr Gly Pro Tyr Pro Leu Gly Ile Asn Gly Met His
            20                  25                  30

Tyr Gly Val Asp Phe Phe Met Asn Ile Gly Thr Pro Val Lys Ala Ile
            35                  40                  45

Ser Ser Gly Lys Ile Val Glu Ala Gly Trp Ser Asn Tyr Gly Gly
    50                  55                  60

Asn Gln Ile Gly Leu Ile Glu Asn Asp Gly Val His Arg Gln Trp Tyr
65                  70                  75                  80

Met His Leu Ser Lys Tyr Asn Val Lys Val Gly Asp Tyr Val Lys Ala
                85                  90                  95

Gly Gln Ile Ile Gly Trp Ser Gly Ser Thr Gly Tyr Ser Thr Ala Pro
            100                 105                 110

His Leu His Phe Gln Arg Met Val Asn Ser Phe Ser Asn Ser Thr Ala
            115                 120                 125

Gln Asp Pro Met Pro Phe Leu Lys Ser Ala Gly Tyr
    130                 135                 140

<210> SEQ ID NO 39
<211> LENGTH: 169
<212> TYPE: PRT
<213> ORGANISM: Staphylococcus aureus bacteriophage 2638a

<400> SEQUENCE: 39

Asn Lys Ile Thr Ala Pro Lys Pro Ser Ile Gln Gly Val Val Ile His
1               5                   10                  15

Asn Asp Tyr Gly Ser Met Thr Pro Ser Gln Tyr Leu Pro Trp Leu Tyr
            20                  25                  30

Ala Arg Glu Asn Asn Gly Thr His Val Asn Gly Trp Ala Ser Val Tyr
        35                  40                  45

Ala Asn Arg Asn Glu Val Leu Trp Tyr His Pro Thr Asp Tyr Val Glu
    50                  55                  60

Trp His Cys Gly Asn Gln Trp Ala Asn Ala Asn Leu Ile Gly Phe Glu
65                  70                  75                  80

Val Cys Glu Ser Tyr Pro Gly Arg Ile Ser Asp Lys Leu Phe Leu Glu
                85                  90                  95

Asn Glu Glu Ala Thr Leu Lys Val Ala Ala Asp Val Met Lys Ser Tyr
            100                 105                 110

Gly Leu Pro Val Asn Arg Asn Thr Val Arg Leu His Asn Glu Phe Phe
            115                 120                 125

Gly Thr Ser Cys Pro His Arg Ser Trp Asp Leu His Val Gly Lys Gly
            130                 135                 140

Glu Pro Tyr Thr Thr Thr Asn Ile Asn Lys Met Lys Asp Tyr Phe Ile
145                 150                 155                 160

Lys Arg Ile Lys His Tyr Tyr Asp Gly
                165

<210> SEQ ID NO 40
<211> LENGTH: 163
<212> TYPE: PRT
<213> ORGANISM: Staphylococcus aureus phage phi 11

<400> SEQUENCE: 40

Asn Pro Lys Gly Ile Val Ile His Asn Asp Ala Gly Ser Lys Gly Ala
1               5                   10                  15
```

```
Thr Ala Glu Ala Tyr Arg Asn Gly Leu Val Asn Ala Pro Leu Ser Arg
            20                  25                  30

Leu Glu Ala Gly Ile Ala His Ser Tyr Val Ser Gly Asn Thr Val Trp
        35                  40                  45

Gln Ala Leu Asp Glu Ser Gln Val Gly Trp His Thr Ala Asn Gln Ile
50                  55                  60

Gly Asn Lys Tyr Tyr Gly Ile Glu Val Cys Gln Ser Met Gly Ala
65                  70                  75                  80

Asp Asn Ala Thr Phe Leu Lys Asn Glu Gln Ala Thr Phe Gln Glu Cys
                85                  90                  95

Ala Arg Leu Leu Lys Lys Trp Gly Leu Pro Ala Asn Arg Asn Thr Ile
            100                 105                 110

Arg Leu His Asn Glu Phe Thr Ser Thr Ser Cys Pro His Arg Ser Ser
        115                 120                 125

Val Leu His Thr Gly Phe Asp Pro Val Thr Arg Gly Leu Leu Pro Glu
    130                 135                 140

Asp Lys Arg Leu Gln Leu Lys Asp Tyr Phe Ile Lys Gln Ile Arg Ala
145                 150                 155                 160

Tyr Met Asp

<210> SEQ ID NO 41
<211> LENGTH: 158
<212> TYPE: PRT
<213> ORGANISM: Staphylococcus aureus phage phi 11

<400> SEQUENCE: 41

Met Ser Ile Ile Met Glu Val Ala Thr Met Gln Ala Lys Leu Thr Lys
1               5                   10                  15

Asn Glu Phe Ile Glu Trp Leu Lys Thr Ser Glu Gly Lys Gln Phe Asn
            20                  25                  30

Val Asp Leu Trp Tyr Gly Phe Gln Cys Phe Asp Tyr Ala Asn Ala Gly
        35                  40                  45

Trp Lys Val Leu Phe Gly Leu Leu Lys Gly Leu Gly Ala Lys Asp
    50                  55                  60

Ile Pro Phe Ala Asn Asn Phe Asp Gly Leu Ala Thr Val Tyr Gln Asn
65                  70                  75                  80

Thr Pro Asp Phe Leu Ala Gln Pro Gly Asp Met Val Val Phe Gly Ser
                85                  90                  95

Asn Tyr Gly Ala Gly Tyr Gly His Val Ala Trp Val Ile Glu Ala Thr
            100                 105                 110

Leu Asp Tyr Ile Ile Val Tyr Glu Gln Asn Trp Leu Gly Gly Gly Trp
        115                 120                 125

Thr Asp Gly Ile Glu Gln Pro Gly Trp Gly Trp Glu Lys Val Thr Arg
    130                 135                 140

Arg Gln His Ala Tyr Asp Phe Pro Met Trp Phe Ile Arg Pro
145                 150                 155

<210> SEQ ID NO 42
<211> LENGTH: 140
<212> TYPE: PRT
<213> ORGANISM: Staphylococcus phage Twort

<400> SEQUENCE: 42

Met Lys Thr Leu Lys Gln Ala Glu Ser Tyr Ile Lys Ser Lys Val Asn
1               5                   10                  15
```

```
Thr Gly Thr Asp Phe Asp Gly Leu Tyr Gly Tyr Gln Cys Met Asp Leu
            20                  25                  30

Ala Val Asp Tyr Ile Tyr His Val Thr Asp Gly Lys Ile Arg Met Trp
        35                  40                  45

Gly Asn Ala Lys Asp Ala Ile Asn Asn Ser Phe Gly Gly Thr Ala Thr
    50                  55                  60

Val Tyr Lys Asn Tyr Pro Ala Phe Arg Pro Lys Tyr Gly Asp Val Val
65                  70                  75                  80

Val Trp Thr Thr Gly Asn Phe Ala Thr Tyr Gly His Ile Ala Ile Val
                85                  90                  95

Thr Asn Pro Asp Pro Tyr Gly Asp Leu Gln Tyr Val Thr Val Leu Glu
            100                 105                 110

Gln Asn Trp Asn Gly Asn Gly Ile Tyr Lys Thr Glu Leu Ala Thr Ile
        115                 120                 125

Arg Thr His Asp Tyr Thr Gly Ile Thr His Phe Ile
    130                 135                 140
```

<210> SEQ ID NO 43
<211> LENGTH: 12
<212> TYPE: PRT
<213> ORGANISM: artificial
<220> FEATURE:
<223> OTHER INFORMATION: His-tag

<400> SEQUENCE: 43

```
Met Arg Gly Ser His His His His His His Gly Ser
1               5                   10
```

<210> SEQ ID NO 44
<211> LENGTH: 1497
<212> TYPE: DNA
<213> ORGANISM: artificial
<220> FEATURE:
<223> OTHER INFORMATION: His-tagged Ply2638

<400> SEQUENCE: 44

```
atgagaggat cgcatcacca tcaccatcac ggatccatgc taactgctat tgactatctt      60
acgaaaaaag gttggaaaat atcatctgac cctcgcactt acgatggtta ccctaaaaac     120
tacggctaca gaaattacca tgaaaacggc attaattatg atgagttttg tggtggttat     180
catagagctt ttgatgttta cagtaacgaa actaacgacg tgcctgctgt tactagcgga     240
acagttattg aagcaaacga ttacggtaat tttggtggta cattcgttat tagagacgct     300
aacgataacg attggatata tgggcatcta caacgtggct caatgcgatt tgttgtaggc     360
gacaaagtca atcaaggtga cattattggt ttacaaggta atagcaacta ttacgacaat     420
cctatgagtg tacatttaca tttacaatta cgccctaaag acgcaaagaa agatgaaaaa     480
tcacaagtat gtagtggttt ggctatggaa aaatatgaca ttacaaattt aaatgctaaa     540
caagataaat caaagaatgg gagcgtgaaa gagttgaaac atatctattc aaaccatatt     600
aaaggtaaca agattacagc accaaaacct agtattcaag gtgtggtcat ccacaatgat     660
tatggtagta tgcacctag tcaatactta ccatggttat atgcacgtga gaataacggt     720
acacacgtta acgttgggc tagtgtttat gcaaatagaa acgaagtgct ttggtatcat     780
ccgacagact acgtagagtg gcattgtggt aatcaatggg caaatgctaa cttaatcgga     840
tttgaagtgt gtgagtcgta tcctggtaga atctcggaca attattcttt agaaaatgaa     900
gaagcgacat tgaaagtagc tgcggatgtg atgaagtcgt acggattacc agttaatcgc     960
```

```
aacactgtac gtctgcataa cgaattcttc ggaacttctt gtccacatcg ttcgtgggac    1020
ttgcatgttg gcaaaggtga gccttacaca actactaata ttaataaaat gaaagactac    1080
ttcatcaaac gcatcaaaca ttattatgac ggtggaaagc tagaagtaag caaagcagca    1140
actatcaaac aatctgacgt taagcaagaa gttaaaaagc aagaagcaaa acaaattgtg    1200
aaagcaacag attggaaaca gaataaagat ggcatttggt ataaagctga acatgcttcg    1260
ttcacagtga cagcaccaga gggaattatc acaagataca aaggtccttg gactggtcac    1320
ccacaagctg gtgtattaca aaaaggtcaa acgattaaat atgatgaggt tcaaaaattt    1380
gacggtcatg tttgggtatc gtgggaaacg tttgagggcg aaactgtata catgccggta    1440
cgcacatggg acgctaaaac tggtaaagtt ggtaagttgt ggggcgaaat taaataa      1497
```

<210> SEQ ID NO 45
<211> LENGTH: 2019
<212> TYPE: DNA
<213> ORGANISM: artificial
<220> FEATURE:
<223> OTHER INFORMATION: His-tagged CHAP11-M23-2638_Ami2638_CBD2638

<400> SEQUENCE: 45

```
atgagaggat cgcatcacca tcaccatcac ggatccatgc aagcaaaatt aactaaaaat      60
gagtttatag agtggttgaa aacttctgag ggaaaacaat tcaatgtgga cttatggtat    120
ggatttcaat gctttgatta tgccaatgct ggttggaaag ttttgtttgg attacttcta    180
aaaggtttag gtgcaaaaga tattccgttc gctaacaact tcgacggatt agctactgta    240
taccaaaata caccggactt cttagcacaa cctggcgaca tggtggtatt cggtagcaac    300
tacggtgctg gatatggtca cgttgcatgg gtaattgaag caactttaga ttacatcatt    360
gtatatgagc agaattggct aggcggtggc tggactgacg gaatcgaaca acccggctgg    420
ggttgggaaa aagttacaag acgacaacat gcttatgatt tccctatgtg gtttatccgt    480
ccgaatttta aaagtgagac agcgccacga tcagttcaat ctcctacaca agcacctaaa    540
aaagaaacag ctggatccat gctaactgct attgactatc ttacgaaaaa aggttggaaa    600
atatcatctg accctcgcac ttacgatggt taccctaaaa actacggcta cagaaattac    660
catgaaaacg gcattaatta tgatgagttt gtggtggtt atcatagagc ttttgatgtt    720
tacagtaacg aaactaacga cgtgcctgct gttactagcg aacagttat tgaagcaaac    780 gattacggta attttggtgg tacattcgtt attagagacg ctaacgataa cgattggata    840
tatgggcatc tacaacgtgg ctcaatgcga tttgttgtag cgacaaagt caatcaaggt    900 gacattattg gtttacaagg taatagcaac tattacgaca atcctatgag tgtacattta    960
catttacaat tacgccctaa agacgcaaag aaagatgaaa atcacaagt atgtagtggt   1020 ttggctatgg aaaaatatga cattacaaat ttaaatgcta acaagataa atcaaagaat   1080 gggagcgtga agagttgaa acatatctat tcaaaccata ttaaaggtaa caagattaca   1140
gcaccaaaac ctagtattca aggtgtggtc atccacaatg attatggtag tatgacacct   1200
agtcaatact taccatggtt atatgcacgt gagaataacg gtacacacgt taacggttgg   1260
gctagtgttt atgcaaatag aaacgaagtg ctttggtatc atccgacaga ctacgtagag   1320
tggcattgtg gtaatcaatg ggcaaatgct aacttaatcg gatttgaagt gtgtgagtcg   1380
tatcctggta gaatctcgga caaattattc ttagaaaatg aagaagcgac attgaaagta   1440 gctgcgatg tgatgaagtc gtacggatta ccagttaatc gcaacactgt acgtctgcat   1500
aacgaattct tcggaacttc ttgtccacat cgttcgtggg acttgcatgt tggcaaaggt   1560
```

```
gagccttaca caactactaa tattaataaa atgaaagact acttcatcaa acgcatcaaa    1620
cattattatg acggtggaaa gctagaagta agcaaagcag caactatcaa acaatctgac    1680
gttaagcaag aagttaaaaa gcaagaagca aaacaaattg tgaaagcaac agattggaaa    1740
cagaataaag atggcatttg gtataaagct gaacatgctt cgttcacagt gacagcacca    1800
gagggaatta tcacaagata caaaggtcct tggactggtc acccacaagc tggtgtatta    1860
caaaaaggtc aaacgattaa atatgatgag gttcaaaaat ttgacggtca tgtttgggta    1920
tcgtgggaaa cgtttgaggg cgaaactgta tacatgccgg tacgcacatg gacgctaaa     1980 actggtaaag ttggtaagtt gtggggcgaa attaaataa                           2019
```

<210> SEQ ID NO 46
<211> LENGTH: 2145
<212> TYPE: DNA
<213> ORGANISM: artificial
<220> FEATURE:
<223> OTHER INFORMATION: His-tagged Ami11_M23-2638_Ami2638_CBD2638

<400> SEQUENCE: 46

```
atgagaggat cgcatcacca tcaccatcac ggatccaagc cacaacctaa agcagtagaa      60
cttaaaatca tcaaagatgt ggttaaaggt tatgacctac ctaagcgtgg tagtaaccct     120
aaaggtatag ttatacacaa cgacgcaggg agcaaagggg cgactgctga agcatatcgt     180
aacggattag taaatgcacc tttatcaaga ttagaagcgg gcattgcgca tagttacgta     240
tcaggcaaca cagtttggca agccttagat gaatcacaag taggttggca taccgctaat     300
caaataggta ataaatatta ttacggtatt gaagtatgtc aatcaatggg cgcagataac     360
gcgacattct taaaaaatga acaggcaact ttccaagaat cgctagatt gttgaaaaaa      420 tggggattac cagcaaacag aaatacaatc agattgcaca atgaatttac ttcaacatca     480
tgccctcata gaagttcggt tttacacact ggttttgacc cagtaactcg cggtctattg     540
ccagaagaca agcggttgca acttaaagac tactttatca agcagattag gcgtacatg     600 gatggtaaaa taccggttgc cactgtctct aatgagtcaa gcgcttcaag taatacagtt     660
aaaccagttg caagtgcagg atccatgcta actgctattg actatcttac gaaaaaaggt     720
tggaaaatat catctgaccc tcgcacttac gatggttacc ctaaaaacta cggctacaga     780
aattaccatg aaaacggcat taattatgat gagttttgtg gtggttatca tagagctttt     840
gatgtttaca gtaacgaaac taacgacgtg cctgctgtta ctagcggaac agttattgaa     900
gcaaacgatt acggtaattt tggtggtaca ttcgttatta gagacgctaa cgataacgat     960
tggatatatg ggcatctaca acgtggctca atgcgatttg ttgtaggcga caaagtcaat    1020
caaggtgaca ttattggttt acaaggtaat agcaactatt acgacaatcc tatgagtgta    1080
catttacatt tacaattacg ccctaaagac gcaagaaag atgaaaaatc acaagtatgt    1140
agtggtttgg ctatggaaaa atatgacatt acaaatttaa atgctaaaca agataaatca    1200
aagaatggga gcgtgaaaga gttgaaacat atctattcaa accatattaa aggtaacaag    1260
attacagcac caaacctag tattcaaggt gtggtcatcc acaatgatta tggtagtatg    1320
acacctagtc aatacttacc atggttatat gcacgtgaga ataacggtac acacgttaac    1380
ggttgggcta gtgtttatgc aaatagaaac gaagtgcttt ggtatcatcc gacagactac    1440
gtagagtggc attgtggtaa tcaatgggca aatgctaact taatcggatt tgaagtgtgt    1500
gagtcgtatc ctggtagaat ctcggacaaa ttattcttag aaaatgaaga agcgacattg    1560
```

| | |
|---|---|
| aaagtagctg cggatgtgat gaagtcgtac ggattaccag ttaatcgcaa cactgtacgt | 1620 |
| ctgcataacg aattcttcgg aacttcttgt ccacatcgtt cgtgggactt gcatgttggc | 1680 |
| aaaggtgagc cttacacaac tactaatatt aataaaatga aagactactt catcaaacgc | 1740 |
| atcaaacatt attatgacgg tggaaagcta gaagtaagca aagcagcaac tatcaaacaa | 1800 |
| tctgacgtta agcaagaagt taaaaagcaa gaagcaaaac aaattgtgaa agcaacagat | 1860 |
| tggaaacaga ataagatgg catttggtat aaagctgaac atgcttcgtt cacagtgaca | 1920 |
| gcaccagagg gaattatcac aagatacaaa ggtccttgga ctggtcaccc acaagctggt | 1980 |
| gtattacaaa aaggtcaaac gattaaatat gatgaggttc aaaaatttga cggtcatgtt | 2040 |
| tgggtatcgt gggaaacgtt tgagggcgaa actgtataca tgccggtacg cacatgggac | 2100 |
| gctaaaactg gtaaagttgg taagttgtgg ggcgaaatta aataa | 2145 |

<210> SEQ ID NO 47
<211> LENGTH: 1959
<212> TYPE: DNA
<213> ORGANISM: artificial
<220> FEATURE:
<223> OTHER INFORMATION: His-tagged CHAPTw_Ami2638_M23-LST_CBD2638

<400> SEQUENCE: 47

| | |
|---|---|
| atgagaggat cgcatcacca tcaccatcac ggatccatga aaccctgaa caagcagag | 60 |
| tcctacatta agagtaaagt aaatacagga actgattttg atggtttata tgggtatcag | 120 |
| tgtatggact tagcagtaga ttatatttac catgtaacag atggtaaaat aagaatgtgg | 180 |
| ggtaatgcta aggatgcgat aaataactct tttggtggta ctgctacggt atataaaaac | 240 |
| taccctgctt ttagacctaa gtacggtgat gtagtcgtat ggactactgg taattttgca | 300 |
| acttatggtc atatcgcaat agttactaac cctgacccctt atggagacct tcaatatgtt | 360 |
| acagttcttg aacaaaactg gaacggtaac gggatttata aaccgagtt agctacaatc | 420 |
| agaacacacg attacacagg aattacacat tttattaaag acgcaaagaa agatgaaaaa | 480 |
| tcacaagtat gtagtggttt ggctatggaa aaatatgaca ttacaaattt aaatgctaaa | 540 |
| caagataaat caagaatgg gagcgtgaaa gagttgaaac atatctattc aaaccatatt | 600 |
| aaaggtaaca agattacagc accaaaacct agtattcaag gtgtggtcat ccacaatgat | 660 |
| tatggtagta tgacacctag tcaatactta ccatggttat atgcacgtga gaataacggt | 720 |
| acacacgtta acggttgggc tagtgtttat gcaaatagaa acgaagtgct ttggtatcat | 780 |
| ccgacagact acgtagagtg gcattgtggt aatcaatggg caaatgctaa cttaatcgga | 840 |
| tttgaagtgt gtgagtcgta tcctggtaga atctcggaca aattattctt agaaaatgaa | 900 |
| gaagcgacat tgaaagtagc tgcggatgtg atgaagtcgt acggattacc agttaatcgc | 960 |
| aacactgtac gtctgcataa cgaattcttc ggaacttctt gtccacatcg ttcgtgggac | 1020 |
| ttgcatgttg gcaaaggtga gccttacaca actactaata ttaataaaat gaaagactac | 1080 |
| ttcatcaaac gcatcaaaca ttattatgac ggtggaaagc tagaagtaag caaagcagca | 1140 |
| actatcaaac aatctgacgt taagcaagaa gttaaaaagc aagaagcaaa acaaattgtg | 1200 |
| aaagcaacag atgctgcaac acatgaacat tcagcacaat ggttgaataa ttacaaaaaa | 1260 |
| ggatatggtt acggtcctta tccattaggt ataaatggcg gtatgcacta cggagttgat | 1320 |
| ttttttatga atattggaac accagtaaaa gctatttcaa gcggaaaaat agttgaagct | 1380 |
| ggttggagta attacggagg aggtaatcaa ataggtctta ttgaaaatga tggagtgcat | 1440 |
| agacaatggt atatgcatct aagtaaatat aatgttaaag taggagatta tgtcaaagct | 1500 |

```
ggtcaaataa tcggttggtc tggaagcact ggttattcta cagcaccaca tttacacttc    1560
caaagaatgg ttaattcatt ttcaaattca actgcccaag atccaatgcc tttcttaaag    1620
agcgcaggat atggaaaagc aggtggtaca gtaactccaa cgccgaatac aggttggaaa    1680
cagaataaag atggcatttg gtataaagct gaacatgctt cgttcacagt gacagcacca    1740
gagggaatta tcacaagata caaaggtcct tggactggtc acccacaagc tggtgtatta    1800
caaaaaggtc aaacgattaa atatgatgag gttcaaaaat ttgacggtca tgtttgggta    1860
tcgtgggaaa cgtttgaggg cgaaactgta tacatgccgg tacgcacatg ggacgctaaa    1920
actggtaaag ttggtaagtt gtggggcgaa attaaataa                           1959
```

<210> SEQ ID NO 48
<211> LENGTH: 1554
<212> TYPE: DNA
<213> ORGANISM: artificial
<220> FEATURE:
<223> OTHER INFORMATION: His-tagged M23-LST_Ami2638_CBD2638

<400> SEQUENCE: 48

```
atgagaggat cgcatcacca tcaccatcac ggatccgctg caacacatga acattcagca      60
caatggttga ataattacaa aaaggatat ggttacggtc cttatccatt aggtataaat     120
ggcggtatgc actacggagt tgattttttt atgaatattg aacaccagt aaaagctatt     180 tcaagcggaa aaatagttga agctggttgg agtaattacg gaggaggtaa tcaaataggt     240
cttattgaaa atgatggagt gcatagacaa tggtatatgc atctaagtaa atataatgtt     300
aaagtaggag attatgtcaa agctggtcaa ataatcggtt ggtctggaag cactggttat     360
tctacagcac cacatttaca cttccaaaga atggttaatt cattttcaaa ttcaactgcc     420
caagatccaa tgccttttctt aaagagcgca ggatatggaa aagcaggtgg tacagtaact     480
ccaacgccga atacaggtga gctcttacgc cctaaagacg caaagaaaga tgaaaaatca     540
caagtatgta gtggtttggc tatggaaaaa tatgacatta caaatttaaa tgctaaacaa     600
gataaatcaa agaatgggag cgtgaaagag ttgaaacata tctattcaaa ccatattaaa     660
ggtaacaaga ttacagcacc aaaacctagt attcaaggtg tggtcatcca caatgattat     720
ggtagtatga cacctagtca atacttacca tggttatatg cacgtgagaa taacggtaca     780
cacgttaacg gttgggctag tgtttatgca aatagaaacg aagtgctttg gtatcatccg     840
acagactacg tagagtggca ttgtggtaat caatgggcaa atgctaactt aatcggattt     900
gaagtgtgtg agtcgtatcc tggtagaatc tcggacaaat tattcttaga aaatgaagaa     960
gcgacattga agtagctgc ggatgtgatg aagtcgtacg gattaccagt taatcgcaac    1020
actgtacgtc tgcataacga attcttcgga acttcttgtc cacatcgttc gtgggacttg    1080
catgttggca aggtgagcc ttacacaact actaatatta taaaatgaa agactacttc    1140 atcaaacgca tcaaacatta ttatgacggt ggaaagctag aagtaagcaa agcagcaact    1200
atcaaacaat ctgacgttaa gcaagaagtt aaaaagcaag aagcaaaaca aattgtgaaa    1260
gcaacagatt ggaaacagaa taagatggc atttggtata aagctgaaca tgcttcgttc    1320
acagtgacag caccagaggg aattatcaca agatacaaag gtccttggac tggtcaccca    1380
caagctggtg tattacaaaa aggtcaaacg attaaatatg atgaggttca aaaatttgac    1440
ggtcatgttt gggtatcgtg ggaaacgttt gagggcgaaa ctgtatacat gccggtacgc    1500
acatgggacg ctaaaactgg taagttggt aagttgtggg gcgaaattaa ataa           1554
```

<210> SEQ ID NO 49
<211> LENGTH: 1887
<212> TYPE: DNA
<213> ORGANISM: artificial
<220> FEATURE:
<223> OTHER INFORMATION: His-tagged M23-2638_Ami2638_CBD2638_CBD2638

<400> SEQUENCE: 49

| | | | | | | |
|---|---|---|---|---|---|---|
| atgagaggat | cgcatcacca | tcaccatcac | ggatccatgc | taactgctat | tgactatctt | 60 |
| acgaaaaaag | gttggaaaat | atcatctgac | cctcgcactt | acgatggtta | ccctaaaaac | 120 |
| tacggctaca | gaaattacca | tgaaaacggc | attaattatg | atgagttttg | tggtggttat | 180 |
| catagagctt | ttgatgttta | cagtaacgaa | actaacgacg | tgcctgctgt | tactagcgga | 240 |
| acagttattg | aagcaaacga | ttacggtaat | tttggtggta | cattcgttat | tagagacgct | 300 |
| aacgataacg | attggatata | tgggcatcta | caacgtggct | caatgcgatt | tgttgtaggc | 360 |
| gacaaagtca | tcaaggtga | cattattggt | ttacaaggta | atagcaacta | ttacgacaat | 420 |
| cctatgagtg | tacatttaca | tttacaatta | cgccctaaag | acgcaaagaa | agatgaaaaa | 480 |
| tcacaagtat | gtagtggttt | ggctatggaa | aaatatgaca | ttacaaattt | aaatgctaaa | 540 |
| caagataaat | caaagaatgg | gagcgtgaaa | gagttgaaac | atatctattc | aaaccatatt | 600 |
| aaaggtaaca | agattacagc | accaaaacct | agtattcaag | gtgtggtcat | ccacaatgat | 660 |
| tatggtagta | tgacacctag | tcaatactta | ccatggttat | atgcacgtga | gaataacggt | 720 |
| acacacgtta | acggttgggc | tagtgtttat | gcaaatagaa | acgaagtgct | ttggtatcat | 780 |
| ccgacagact | acgtagagtg | gcattgtggt | aatcaatggg | caaatgctaa | cttaatcgga | 840 |
| tttgaagtgt | gtgagtcgta | tcctggtaga | atctcggaca | aattattctt | agaaaatgaa | 900 |
| gaagcgacat | tgaaagtagc | tgcggatgtg | atgaagtcgt | acggattacc | agttaatcgc | 960 |
| aacactgtac | gtctgcataa | cgaattcttc | ggaacttctt | gtccacatcg | ttcgtgggac | 1020 |
| ttgcatgttg | gcaaaggtga | gccttacaca | actactaata | ttaataaaat | gaaagactac | 1080 |
| ttcatcaaac | gcatcaaaca | ttattatgac | ggtggaaagc | tagaagtaag | caaagcagca | 1140 |
| actatcaaac | aatctgacgt | taagcaagaa | gttaaaaagc | aagaagcaaa | acaaattgtg | 1200 |
| aaagcaacag | attggaaaca | gaataaagat | ggcatttggt | ataaagctga | acatgcttcg | 1260 |
| ttcacagtga | cagcaccaga | gggaattatc | acaagataca | aggtccttg | gactggtcac | 1320 |
| ccacaagctg | gtgtattaca | aaaaggtcaa | acgattaaat | atgatgaggt | tcaaaaattt | 1380 |
| gacggtcatg | tttgggtatc | gtgggaaacg | tttgagggcg | aaactgtata | catgccggta | 1440 |
| cgcacatggg | acgctaaaac | tggtaaagtt | ggtaagttgt | ggggcgaaat | taagagctc | 1500 |
| ggtggaaagc | tagaagtaag | caaagcagca | actatcaaac | aatctgacgt | taagcaagaa | 1560 |
| gttaaaaagc | aagaagcaaa | acaaattgtg | aaagcaacag | attggaaaca | gaataaagat | 1620 |
| ggcatttggt | ataaagctga | acatgcttcg | ttcacagtga | cagcaccaga | gggaattatc | 1680 |
| acaagataca | aggtccttg | gactggtcac | ccacaagctg | gtgtattaca | aaaaggtcaa | 1740 |
| acgattaaat | atgatgaggt | tcaaaaattt | gacggtcatg | tttgggtatc | gtgggaaacg | 1800 |
| tttgagggcg | aaactgtata | catgccggta | cgcacatggg | acgctaaaac | tggtaaagtt | 1860 |
| ggtaagttgt | ggggcgaaat | taaataa | | | | 1887 |

<210> SEQ ID NO 50
<211> LENGTH: 3461
<212> TYPE: DNA
<213> ORGANISM: artificial
<220> FEATURE:
<223> OTHER INFORMATION: pQE-30 vector

<400> SEQUENCE: 50

```
ctcgagaaat cataaaaaat ttatttgctt tgtgagcgga taacaattat aatagattca      60
attgtgagcg ataacaatt tcacacagaa ttcattaaag aggagaaatt aactatgaga     120
ggatcgcatc accatcacca tcacggatcc gcatgcgagc tcggtacccc gggtcgacct     180
gcagccaagc ttaattagct gagcttggac tcctgttgat agatccagta atgacctcag     240
aactccatct ggatttgttc agaacgctcg gttgccgccg ggcgtttttt attggtgaga     300
atccaagcta gcttggcgag attttcagga gctaaggaag ctaaaatgga gaaaaaaatc     360
actggatata ccaccgttga tatatcccaa tggcatcgta agaacatttt gaggcatttt    420
cagtcagttg ctcaatgtac ctataaccag accgttcagc tggatattac ggcctttta     480
aagaccgtaa agaaaaataa gcacaagttt tatccggcct ttattcacat tcttgcccgc     540
ctgatgaatg ctcatccgga atttcgtatg gcaatgaaag acggtgagct ggtgatatgg     600
gatagtgttc acccttgtta caccgttttc catgagcaaa ctgaaacgtt ttcatcgctc     660
tggagtgaat accacgacga tttccggcag tttctacaca tatattcgca agatgtggcg     720
tgttacggtg aaaacctggc ctatttccct aaagggttta ttgagaatat gttttttcgtc    780
tcagccaatc cctgggtgag tttcaccagt tttgatttaa acgtggccaa tatggacaac     840
ttcttcgccc ccgttttcac catgggcaaa tattatacgc aaggcgacaa ggtgctgatg     900
ccgctggcga ttcaggttca tcatgccgtt tgtgatggct tccatgtcgg cagaatgctt     960
aatgaattac aacagtactg cgatgagtgg cagggcgggg cgtaattttt ttaaggcagt    1020
tattggtgcc cttaaacgcc tggggtaatg actctctagc ttgaggcatc aaataaaacg    1080
aaaggctcag tcgaaagact gggcctttcg ttttatctgt tgtttgtcgg tgaacgctct    1140
cctgagtagg acaaatccgc cctctagagc tgcctcgcgc gtttcggtga tgacggtgaa    1200
aacctctgac acatgcagct cccggagacg gtcacagctt gtctgtaagc ggatgccggg    1260
agcagacaag cccgtcaggg cgcgtcagcg ggtgttggcg ggtgtcgggg cgcagccatg    1320
acccagtcac gtagcgatag cggagtgtat actggcttaa ctatgcggca tcagagcaga    1380
ttgtactgag agtgcaccat atgcggtgtg aaataccgca cagatgcgta aggagaaaat    1440
accgcatcag gcgctcttcc gcttcctcgc tcactgactc gctgcgctcg tcgttcggc     1500
tgcggcgagc ggtatcagct cactcaaagg cggtaatacg ttatccaca gaatcagggg    1560
ataacgcagg aaagaacatg tgagcaaaag gccagcaaaa ggccaggaac cgtaaaaagg    1620
ccgcgttgct ggcgtttttc cataggctcc gcccccctga cgagcatcac aaaaatcgac    1680
gctcaagtca gaggtggcga aacccgacag gactataaag ataccaggcg tttccccctg    1740
gaagctccct cgtgcgctct cctgttccga cctgccgct taccggatac ctgtccgcct    1800
ttctccccttc gggaagcgtg gcgctttctc atagctcacg ctgtaggtat ctcagttcgg    1860
tgtaggtcgt tcgctccaag ctgggctgtg tgcacgaacc ccccgttcag cccgaccgct    1920
gcgccttatc cggtaactat cgtcttgagt ccaacccggt aagacacgac ttatcgccac    1980
tggcagcagc cactggtaac aggattagca gagcgaggta tgtaggcggt gctacagagt    2040
tcttgaagtg gtggcctaac tacggctaca ctagaaggac agtatttggt atctgcgctc    2100
tgctgaagcc agttaccttc ggaaaaagag ttggtagctc ttgatccggc aaacaaacca    2160
ccgctggtag cggtggtttt tttgtttgca agcagcagat tacgcgcaga aaaaaaggat    2220
```

-continued

| | |
|---|---|
| ctcaagaaga tcctttgatc ttttctacgg ggtctgacgc tcagtggaac gaaaactcac | 2280 |
| gttaagggat tttggtcatg agattatcaa aaaggatctt cacctagatc cttttaaatt | 2340 |
| aaaaatgaag ttttaaatca atctaaagta tatatgagta aacttggtct gacagttacc | 2400 |
| aatgcttaat cagtgaggca cctatctcag cgatctgtct atttcgttca tccatagttg | 2460 |
| cctgactccc cgtcgtgtag ataactacga tacgggaggg cttaccatct ggccccagtg | 2520 |
| ctgcaatgat accgcgagac ccacgctcac cggctccaga tttatcagca ataaaccagc | 2580 |
| cagccggaag ggccgagcgc agaagtggtc ctgcaacttt atccgcctcc atccagtcta | 2640 |
| ttaattgttg ccgggaagct agagtaagta gttcgccagt taatagtttg cgcaacgttg | 2700 |
| ttgccattgc tacaggcatc gtggtgtcac gctcgtcgtt tggtatggct tcattcagct | 2760 |
| ccggttccca acgatcaagg cgagttacat gatcccccat gttgtgcaaa aaagcggtta | 2820 |
| gctccttcgg tcctccgatc gttgtcagaa gtaagttggc cgcagtgtta tcactcatgg | 2880 |
| ttatggcagc actgcataat tctcttactg tcatgccatc cgtaagatgc ttttctgtga | 2940 |
| ctggtgagta ctcaaccaag tcattctgag aatagtgtat gcggcgaccg agttgctctt | 3000 |
| gcccggcgtc aatacgggat aataccgcgc cacatagcag aactttaaaa gtgctcatca | 3060 |
| ttggaaaacg ttcttcgggg cgaaaactct caaggatctt accgctgttg agatccagtt | 3120 |
| cgatgtaacc cactcgtgca cccaactgat cttcagcatc ttttactttc accagcgttt | 3180 |
| ctgggtgagc aaaaacagga aggcaaaatg ccgcaaaaaa gggaataagg gcgacacgga | 3240 |
| aatgttgaat actcatactc ttcctttttc aatattattg aagcatttat cagggttatt | 3300 |
| gtctcatgag cggatacata tttgaatgta tttagaaaaa taaacaaata ggggttccgc | 3360 |
| gcacatttcc ccgaaaagtg ccacctgacg tctaagaaac cattattatc atgacattaa | 3420 |
| cctataaaaa taggcgtatc acgaggccct ttcgtcttca c | 3461 |

<210> SEQ ID NO 51
<211> LENGTH: 127
<212> TYPE: PRT
<213> ORGANISM: Staphylococcus aureus bacteriophage 2638a

<400> SEQUENCE: 51

Gly Lys Leu Glu Val Ser Lys Ala Ala Thr Ile Lys Gln Ser Asp Val
1               5                   10                  15

Lys Gln Glu Val Lys Lys Gln Glu Ala Lys Gln Ile Val Lys Ala Thr
            20                  25                  30

Asp Trp Lys Gln Asn Lys Asp Gly Ile Trp Tyr Lys Ala Glu His Ala
        35                  40                  45

Ser Phe Thr Val Thr Ala Pro Glu Gly Ile Ile Thr Arg Tyr Lys Gly
    50                  55                  60

Pro Trp Thr Gly His Pro Gln Ala Gly Val Leu Gln Lys Gly Gln Thr
65                  70                  75                  80

Ile Lys Tyr Asp Glu Val Gln Lys Phe Asp Gly His Val Trp Val Ser
                85                  90                  95

Trp Glu Thr Phe Glu Gly Glu Thr Val Tyr Met Pro Val Arg Thr Trp
            100                 105                 110

Asp Ala Lys Thr Gly Lys Val Gly Lys Leu Trp Gly Glu Ile Lys
        115                 120                 125

<210> SEQ ID NO 52
<211> LENGTH: 106
<212> TYPE: PRT
<213> ORGANISM: Staphylococcus simulans

<400> SEQUENCE: 52

```
Gly Lys Ala Gly Gly Thr Val Thr Pro Thr Pro Asn Thr Gly Trp Lys
1               5                   10                  15

Thr Asn Lys Tyr Gly Thr Leu Tyr Lys Ser Glu Ser Ala Ser Phe Thr
            20                  25                  30

Pro Asn Thr Asp Ile Ile Thr Arg Thr Thr Gly Pro Phe Arg Ser Met
        35                  40                  45

Pro Gln Ser Gly Val Leu Lys Ala Gly Gln Thr Ile His Tyr Asp Glu
    50                  55                  60

Val Met Lys Gln Asp Gly His Val Trp Val Gly Tyr Thr Gly Asn Ser
65                  70                  75                  80

Gly Gln Arg Ile Tyr Leu Pro Val Arg Thr Trp Asn Lys Ser Thr Asn
                85                  90                  95

Thr Leu Gly Val Leu Trp Gly Thr Ile Lys
            100                 105
```

<210> SEQ ID NO 53
<211> LENGTH: 190
<212> TYPE: PRT
<213> ORGANISM: Staphylococcus aureus bacteriophage 2638a

<400> SEQUENCE: 53

```
Met Leu Thr Ala Ile Asp Tyr Leu Thr Lys Lys Gly Trp Lys Ile Ser
1               5                   10                  15

Ser Asp Pro Arg Thr Tyr Asp Gly Tyr Pro Lys Asn Tyr Gly Tyr Arg
            20                  25                  30

Asn Tyr His Glu Asn Gly Ile Asn Tyr Asp Glu Phe Cys Gly Gly Tyr
        35                  40                  45

His Arg Ala Phe Asp Val Tyr Ser Asn Glu Thr Asn Asp Val Pro Ala
    50                  55                  60

Val Thr Ser Gly Thr Val Ile Glu Ala Asn Asp Tyr Gly Asn Phe Gly
65                  70                  75                  80

Gly Thr Phe Val Ile Arg Asp Ala Asn Asp Asn Asp Trp Ile Tyr Gly
                85                  90                  95

His Leu Gln Arg Gly Ser Met Arg Phe Val Val Gly Asp Lys Val Asn
            100                 105                 110

Gln Gly Asp Ile Ile Gly Leu Gln Gly Asn Ser Asn Tyr Tyr Asp Asn
        115                 120                 125

Pro Met Ser Val His Leu His Leu Gln Leu Arg Pro Lys Asp Ala Lys
    130                 135                 140

Lys Asp Glu Lys Ser Gln Val Cys Ser Gly Leu Ala Met Glu Lys Tyr
145                 150                 155                 160

Asp Ile Thr Asn Leu Asn Ala Lys Gln Asp Lys Ser Lys Asn Gly Ser
                165                 170                 175

Val Lys Glu Leu Lys His Ile Tyr Ser Asn His Ile Lys Gly
            180                 185                 190
```

<210> SEQ ID NO 54
<211> LENGTH: 154
<212> TYPE: PRT
<213> ORGANISM: Staphylococcus simulans

<400> SEQUENCE: 54

```
Ala Ala Thr His Glu His Ser Ala Gln Trp Leu Asn Asn Tyr Lys Lys
1               5                   10                  15
```

```
Gly Tyr Gly Tyr Gly Pro Tyr Pro Leu Gly Ile Asn Gly Met His
            20                  25                  30

Tyr Gly Val Asp Phe Phe Met Asn Ile Gly Thr Pro Val Lys Ala Ile
        35                  40                  45

Ser Ser Gly Lys Ile Val Glu Ala Gly Trp Ser Asn Tyr Gly Gly
50                  55                  60

Asn Gln Ile Gly Leu Ile Glu Asn Asp Gly Val His Arg Gln Trp Tyr
65                  70                  75                  80

Met His Leu Ser Lys Tyr Asn Val Lys Val Gly Asp Tyr Val Lys Ala
                85                  90                  95

Gly Gln Ile Ile Gly Trp Ser Gly Ser Thr Gly Tyr Ser Thr Ala Pro
            100                 105                 110

His Leu His Phe Gln Arg Met Val Asn Ser Phe Ser Asn Ser Thr Ala
        115                 120                 125

Gln Asp Pro Met Pro Phe Leu Lys Ser Ala Gly Tyr Gly Lys Ala Gly
130                 135                 140

Gly Thr Val Thr Pro Thr Pro Asn Thr Gly
145                 150
```

<210> SEQ ID NO 55
<211> LENGTH: 246
<212> TYPE: PRT
<213> ORGANISM: Staphylococcus aureus bacteriophage 2638a

<400> SEQUENCE: 55

```
Glu Lys Ser Gln Val Cys Ser Gly Leu Ala Met Glu Lys Tyr Asp Ile
1               5                   10                  15

Thr Asn Leu Asn Ala Lys Gln Asp Lys Ser Lys Asn Gly Ser Val Lys
            20                  25                  30

Glu Leu Lys His Ile Tyr Ser Asn His Ile Lys Gly Asn Lys Ile Thr
        35                  40                  45

Ala Pro Lys Pro Ser Ile Gln Gly Val Val Ile His Asn Asp Tyr Gly
    50                  55                  60

Ser Met Thr Pro Ser Gln Tyr Leu Pro Trp Leu Tyr Ala Arg Glu Asn
65                  70                  75                  80

Asn Gly Thr His Val Asn Gly Trp Ala Ser Val Tyr Ala Asn Arg Asn
                85                  90                  95

Glu Val Leu Trp Tyr His Pro Thr Asp Tyr Val Glu Trp His Cys Gly
            100                 105                 110

Asn Gln Trp Ala Asn Ala Asn Leu Ile Gly Phe Glu Val Cys Glu Ser
        115                 120                 125

Tyr Pro Gly Arg Ile Ser Asp Lys Leu Phe Leu Glu Asn Glu Glu Ala
    130                 135                 140

Thr Leu Lys Val Ala Ala Asp Val Met Lys Ser Tyr Gly Leu Pro Val
145                 150                 155                 160

Asn Arg Asn Thr Val Arg Leu His Asn Glu Phe Phe Gly Thr Ser Cys
                165                 170                 175

Pro His Arg Ser Trp Asp Leu His Val Gly Lys Gly Glu Pro Tyr Thr
            180                 185                 190

Thr Thr Asn Ile Asn Lys Met Lys Asp Tyr Phe Ile Lys Arg Ile Lys
        195                 200                 205

His Tyr Tyr Asp Gly Gly Lys Leu Glu Val Ser Lys Ala Ala Thr Ile
    210                 215                 220

Lys Gln Ser Asp Val Lys Gln Glu Val Lys Gln Glu Ala Lys Gln
225                 230                 235                 240
```

```
Ile Val Lys Ala Thr Asp
                245

<210> SEQ ID NO 56
<211> LENGTH: 220
<212> TYPE: PRT
<213> ORGANISM: Staphylococcus aureus phage phi 11

<400> SEQUENCE: 56

Pro Lys Lys Glu Thr Ala Lys Pro Gln Pro Lys Ala Val Glu Leu Lys
1               5                   10                  15

Ile Ile Lys Asp Val Val Lys Gly Tyr Asp Leu Pro Lys Arg Gly Ser
            20                  25                  30

Asn Pro Lys Gly Ile Val Ile His Asn Asp Ala Gly Ser Lys Gly Ala
        35                  40                  45

Thr Ala Glu Ala Tyr Arg Asn Gly Leu Val Asn Ala Pro Leu Ser Arg
    50                  55                  60

Leu Glu Ala Gly Ile Ala His Ser Tyr Val Ser Gly Asn Thr Val Trp
65                  70                  75                  80

Gln Ala Leu Asp Glu Ser Gln Val Gly Trp His Thr Ala Asn Gln Ile
                85                  90                  95

Gly Asn Lys Tyr Tyr Tyr Gly Ile Glu Val Cys Gln Ser Met Gly Ala
            100                 105                 110

Asp Asn Ala Thr Phe Leu Lys Asn Glu Gln Ala Thr Phe Gln Glu Cys
        115                 120                 125

Ala Arg Leu Leu Lys Lys Trp Gly Leu Pro Ala Asn Arg Asn Thr Ile
    130                 135                 140

Arg Leu His Asn Glu Phe Thr Ser Thr Ser Cys Pro His Arg Ser Ser
145                 150                 155                 160

Val Leu His Thr Gly Phe Asp Pro Val Thr Arg Gly Leu Leu Pro Glu
                165                 170                 175

Asp Lys Arg Leu Gln Leu Lys Asp Tyr Phe Ile Lys Gln Ile Arg Ala
            180                 185                 190

Tyr Met Asp Gly Lys Ile Pro Val Ala Thr Val Ser Asn Glu Ser Ser
        195                 200                 205

Ala Ser Ser Asn Thr Val Lys Pro Val Ala Ser Ala
    210                 215                 220

<210> SEQ ID NO 57
<211> LENGTH: 206
<212> TYPE: PRT
<213> ORGANISM: Staphylococcus aureus phage phi 11

<400> SEQUENCE: 57

Met Ser Ile Ile Met Glu Val Ala Thr Met Gln Ala Lys Leu Thr Lys
1               5                   10                  15

Asn Glu Phe Ile Glu Trp Leu Lys Thr Ser Glu Gly Lys Gln Phe Asn
            20                  25                  30

Val Asp Leu Trp Tyr Gly Phe Gln Cys Phe Asp Tyr Ala Asn Ala Gly
        35                  40                  45

Trp Lys Val Leu Phe Gly Leu Leu Leu Lys Gly Leu Gly Ala Lys Asp
    50                  55                  60

Ile Pro Phe Ala Asn Asn Phe Asp Gly Leu Ala Thr Val Tyr Gln Asn
65                  70                  75                  80

Thr Pro Asp Phe Leu Ala Gln Pro Gly Asp Met Val Val Phe Gly Ser
                85                  90                  95
```

Asn Tyr Gly Ala Gly Tyr Gly His Val Ala Trp Val Ile Glu Ala Thr
                100                 105                 110

Leu Asp Tyr Ile Ile Val Tyr Glu Gln Asn Trp Leu Gly Gly Gly Trp
            115                 120                 125

Thr Asp Gly Ile Glu Gln Pro Gly Trp Gly Trp Glu Lys Val Thr Arg
        130                 135                 140

Arg Gln His Ala Tyr Asp Phe Pro Met Trp Phe Ile Arg Pro Asn Phe
145                 150                 155                 160

Lys Ser Glu Thr Ala Pro Arg Ser Val Gln Ser Pro Thr Gln Ala Pro
                165                 170                 175

Lys Lys Glu Thr Ala Lys Pro Gln Pro Lys Ala Val Glu Leu Lys Ile
            180                 185                 190

Ile Lys Asp Val Val Lys Gly Tyr Asp Leu Pro Lys Arg Gly
        195                 200                 205

<210> SEQ ID NO 58
<211> LENGTH: 187
<212> TYPE: PRT
<213> ORGANISM: Staphylococcus phage Twort

<400> SEQUENCE: 58

Met Lys Thr Leu Lys Gln Ala Glu Ser Tyr Ile Lys Ser Lys Val Asn
1               5                   10                  15

Thr Gly Thr Asp Phe Asp Gly Leu Tyr Gly Tyr Gln Cys Met Asp Leu
            20                  25                  30

Ala Val Asp Tyr Ile Tyr His Val Thr Asp Gly Lys Ile Arg Met Trp
        35                  40                  45

Gly Asn Ala Lys Asp Ala Ile Asn Asn Ser Phe Gly Gly Thr Ala Thr
    50                  55                  60

Val Tyr Lys Asn Tyr Pro Ala Phe Arg Pro Lys Tyr Gly Asp Val Val
65                  70                  75                  80

Val Trp Thr Thr Gly Asn Phe Ala Thr Tyr Gly His Ile Ala Ile Val
                85                  90                  95

Thr Asn Pro Asp Pro Tyr Gly Asp Leu Gln Tyr Val Thr Val Leu Glu
            100                 105                 110

Gln Asn Trp Asn Gly Asn Gly Ile Tyr Lys Thr Glu Leu Ala Thr Ile
        115                 120                 125

Arg Thr His Asp Tyr Thr Gly Ile Thr His Phe Ile Arg Pro Asn Phe
    130                 135                 140

Ala Thr Glu Ser Ser Val Lys Lys Lys Asp Thr Lys Lys Lys Pro Lys
145                 150                 155                 160

Pro Ser Asn Arg Asp Gly Ile Asn Lys Asp Lys Ile Val Tyr Asp Arg
                165                 170                 175

Thr Asn Ile Asn Tyr Asn Met Val Lys Arg Gly
            180                 185

<210> SEQ ID NO 59
<211> LENGTH: 4546
<212> TYPE: DNA
<213> ORGANISM: artificial
<220> FEATURE:
<223> OTHER INFORMATION: pHGFP_CBD2638_c vector

<400> SEQUENCE: 59
ctcgagaaat cataaaaaat ttatttgctt tgtgagcgga taacaattat aatagattca      60
attgtgagcg gataacaatt tcacacagaa ttcattaaag aggagaaatt aactatgaga     120

```
ggatcgcatc accatcacca tcacggatcc atgagtaaag gagaagaact tttcactgga    180
gttgtcccaa ttcttgttga attagatggt gatgttaatg ggcacaaatt ttctgtcagt    240
ggagagggtg aaggtgatgc aacatacgga aaacttaccc ttaaatttat ttgcactact    300
ggaaaactac ctgttccatg gccaacactt gtcactactt tcgcgtatgg tcttcaatgc    360
tttgcgagat acccagatca tatgaaacgg catgactttt tcaagagtgc catgcccgaa    420
ggttatgtac aggaaagaac tatatttttc aaagatgacg ggaactacaa gacacgtgct    480
gaagtcaagt ttgaaggtga tacccttgtt aatagaatcg agttaaaagg tattgatttt    540
aaagaagatg aaacattct tggacacaaa ttggaataca actataactc acacaatgta    600
tacatcatgg cagacaaaca aaagaatgga atcaaagtta acttcaaaat tagacacaac    660
attgaagatg gaagcgttca actagcagac cattatcaac aaaatactcc aattggcgat    720
ggccctgtcc ttttaccaga caaccattac ctgtccacac aatctgccct tcgaaagat     780
cccaacgaaa agagagacca catggtcctt cttgagtttg taacagctgc tgggattaca    840
catggcatgg atgaactata caaagagctc ggtggaaagc tagaagtaag caaagcagca    900
actatcaaac aatctgacgt taagcaagaa gttaaaaagc aagaagcaaa acaaattgtg    960
aaagcaacag attggaaaca gaataaagat ggcatttggt ataaagctga acatgcttcg   1020
ttcacagtga cagcaccaga gggaattatc acaagataca aagtccttg gactggtcac    1080
ccacaagctg gtgtattaca aaaggtcaa acgattaaat atgatgaggt tcaaaaattt     1140
gacggtcatg tttgggtatc gtgggaaacg tttgagggcg aaactgtata catgccggta   1200
cgcacatggg acgctaaaac tggtaaagtt ggtaagttgt ggggcgaaat taaataagtc   1260
gacctgcagc caagcttaat tagctgagct tggactcctg ttgatagatc cagtaatgac   1320
ctcagaactc catctggatt tgttcagaac gctcggttgc cgccgggcgt tttttattgg   1380
tgagaatcca agctagcttg gcgagatttt caggagctaa ggaagctaaa atggagaaaa   1440
aaatcactgg atataccacc gttgatatat cccaatggca tcgtaaagaa catttttgagg   1500
catttcagtc agttgctcaa tgtacctata accagaccgt tcagctggat attacggcct   1560
ttttaaagac cgtaaagaaa aataagcaca gttttatcc ggcctttatt cacattcttg     1620
cccgcctgat gaatgctcat ccggaatttc gtatggcaat gaaagacggt gagctggtga   1680
tatgggatag tgttcaccct tgttacaccg ttttccatga gcaaactgaa acgttttcat   1740
cgctctggag tgaataccac gacgatttcc ggcagtttct acacatatat tcgcaagatg   1800
tggcgtgtta cggtgaaaac ctggcctatt tccctaaagg gtttattgag aatatgttt     1860
tcgtctcagc caatccctgg gtgagtttca ccagttttga tttaaacgtg gccaatatgg   1920
acaacttctt cgcccccgtt ttcaccatgg gcaaatatta tacgcaaggc gacaaggtgc   1980
tgatgccgct ggcgattcag gttcatcatg ccgtttgtga tggcttccat gtcggcagaa   2040
tgcttaatga attacaacag tactgcgatg agtggcaggg cggggcgtaa tttttttaag   2100
gcagttattg gtgcccttaa acgcctgggg taatgactct ctagcttgag gcatcaaata   2160
aaacgaaagg ctcagtcgaa agactgggcc tttcgtttta tctgttgttt gtcggtgaac   2220
gctctcctga gtaggacaaa tccgccctct agagctgcct cgcgcgtttc ggtgatgacg   2280
gtgaaaacct ctgacacatg cagctcccgg agacggtcac agcttgtctg taagcggatg   2340
ccgggagcag acaagcccgt cagggcgcgt cagcgggtgt tggcgggtgt cggggcgcag   2400
ccatgaccca gtcacgtagc gatagcggag tgtatactgg cttaactatg cggcatcaga   2460
```

|  |  |  |  |  |  |
|---|---|---|---|---|---|
| gcagattgta | ctgagagtgc | accatatgcg | gtgtgaaata | ccgcacagat | gcgtaaggag | 2520 |
| aaaataccgc | atcaggcgct | cttccgcttc | ctcgctcact | gactcgctgc | gctcggtcgt | 2580 |
| tcggctgcgg | cgagcggtat | cagctcactc | aaaggcggta | atacggttat | ccacagaatc | 2640 |
| aggggataac | gcaggaaaga | acatgtgagc | aaaaggccag | caaaaggcca | ggaaccgtaa | 2700 |
| aaaggccgcg | ttgctggcgt | ttttccatag | gctccgcccc | cctgacgagc | atcacaaaaa | 2760 |
| tcgacgctca | agtcagaggt | ggcgaaaccc | gacaggacta | taaagatacc | aggcgtttcc | 2820 |
| ccctggaagc | tccctcgtgc | gctctcctgt | tccgaccctg | ccgcttaccg | gatacctgtc | 2880 |
| cgcctttctc | ccttcgggaa | gcgtggcgct | ttctcatagc | tcacgctgta | ggtatctcag | 2940 |
| ttcggtgtag | gtcgttcgct | ccaagctggg | ctgtgtgcac | gaaccccccg | ttcagcccga | 3000 |
| ccgctgcgcc | ttatccggta | actatcgtct | tgagtccaac | ccggtaagac | acgacttatc | 3060 |
| gccactggca | gcagccactg | gtaacaggat | tagcagagcg | aggtatgtag | gcggtgctac | 3120 |
| agagttcttg | aagtggtggc | ctaactacgg | ctacactaga | aggacagtat | ttggtatctg | 3180 |
| cgctctgctg | aagccagtta | ccttcggaaa | aagagttggt | agctcttgat | ccggcaaaca | 3240 |
| aaccaccgct | ggtagcggtg | gtttttttgt | ttgcaagcag | cagattacgc | gcagaaaaaa | 3300 |
| aggatctcaa | gaagatcctt | tgatcttttc | tacggggtct | gacgctcagt | ggaacgaaaa | 3360 |
| ctcacgttaa | gggattttgg | tcatgagatt | atcaaaaagg | atcttcacct | agatcctttt | 3420 |
| aaattaaaaa | tgaagtttta | aatcaatcta | agtatatat | gagtaaactt | ggtctgacag | 3480 |
| ttaccaatgc | ttaatcagtg | aggcacctat | ctcagcgatc | tgtctatttc | gttcatccat | 3540 |
| agttgcctga | ctccccgtcg | tgtagataac | tacgatacgg | gagggcttac | catctggccc | 3600 |
| cagtgctgca | atgataccgc | gagacccacg | ctcaccggct | ccagatttat | cagcaataaa | 3660 |
| ccagccagcc | ggaagggccg | agcgcagaag | tggtcctgca | actttatccg | cctccatcca | 3720 |
| gtctattaat | tgttgccggg | aagctagagt | aagtagttcg | ccagttaata | gtttgcgcaa | 3780 |
| cgttgttgcc | attgctacag | gcatcgtggt | gtcacgctcg | tcgtttggta | tggcttcatt | 3840 |
| cagctccggt | tcccaacgat | caaggcgagt | tacatgatcc | cccatgttgt | gcaaaaaagc | 3900 |
| ggttagctcc | ttcggtcctc | cgatcgttgt | cagaagtaag | ttggccgcag | tgttatcact | 3960 |
| catggttatg | gcagcactgc | ataattctct | tactgtcatg | ccatccgtaa | gatgcttttc | 4020 |
| tgtgactggt | gagtactcaa | ccaagtcatt | ctgagaatag | tgtatgcggc | gaccgagttg | 4080 |
| ctcttgcccg | gcgtcaatac | gggataatac | cgcgccacat | agcagaactt | taaaagtgct | 4140 |
| catcattgga | aaacgttctt | cggggcgaaa | actctcaagg | atcttaccgc | tgttgagatc | 4200 |
| cagttcgatg | taacccactc | gtgcacccaa | ctgatcttca | gcatctttta | ctttcaccag | 4260 |
| cgtttctggg | tgagcaaaaa | caggaaggca | aaatgccgca | aaaaagggaa | taagggcgac | 4320 |
| acggaaatgt | tgaatactca | tactcttcct | ttttcaatat | tattgaagca | tttatcaggg | 4380 |
| ttattgtctc | atgagcggat | acatatttga | atgtatttag | aaaaataaac | aaataggggt | 4440 |
| tccgcgcaca | tttccccgaa | aagtgccacc | tgacgtctaa | gaaaccatta | ttatcatgac | 4500 |
| attaacctat | aaaaataggc | gtatcacgag | gcccttcgt | cttcac |  | 4546 |

<210> SEQ ID NO 60
<211> LENGTH: 1143
<212> TYPE: DNA
<213> ORGANISM: artificial
<220> FEATURE:
<223> OTHER INFORMATION: His-tagged GFP_CBD2638

<400> SEQUENCE: 60

| | |
|---|---|
| atgagaggat cgcatcacca tcaccatcac ggatccatga gtaaaggaga agaactttc | 60 |
| actggagttg tcccaattct tgttgaatta gatggtgatg ttaatgggca caaattttct | 120 |
| gtcagtggag agggtgaagg tgatgcaaca tacggaaaac ttacccttaa atttatttgc | 180 |
| actactggaa aactacctgt tccatggcca acacttgtca ctactttcgc gtatggtctt | 240 |
| caatgctttg cgagataccc agatcatatg aaacggcatg acttttcaa gagtgccatg | 300 |
| cccgaaggtt atgtacagga agaactata tttttcaaag atgacgggaa ctacaagaca | 360 |
| cgtgctgaag tcaagtttga aggtgatacc cttgttaata aatcgagtt aaaaggtatt | 420 |
| gattttaaag aagatggaaa cattcttgga cacaaattgg aatacaacta taactcacac | 480 |
| aatgtataca tcatggcaga caaacaaaag aatggaatca agttaactt caaaattaga | 540 |
| cacaacattg aagatggaag cgttcaacta gcagaccatt atcaacaaaa tactccaatt | 600 |
| ggcgatggcc ctgtcctttt accagacaac cattacctgt ccacacaatc tgcccttcg | 660 |
| aaagatccca acgaaaagag agaccacatg gtccttcttg agtttgtaac agctgctggg | 720 |
| attacacatg gcatggatga actatacaaa gagctcggtg aaagctaga agtaagcaaa | 780 |
| gcagcaacta tcaaacaatc tgacgttaag caagaagtta aaagcaaga agcaaaacaa | 840 |
| attgtgaaag caacagattg gaaacagaat aaagatggca tttggtataa agctgaacat | 900 |
| gcttcgttca cagtgacagc accagaggga attatcacaa gatacaaagg tccttggact | 960 |
| ggtcacccac aagctggtgt attacaaaaa ggtcaaacga ttaaatatga tgaggttcaa | 1020 |
| aaatttgacg gtcatgtttg ggtatcgtgg gaaacgtttg agggcgaaac tgtatacatg | 1080 |
| ccggtacgca catgggacgc taaaactggt aaagttggta agttgtgggg cgaaattaaa | 1140 |
| taa | 1143 |

<210> SEQ ID NO 61
<211> LENGTH: 1539
<212> TYPE: DNA
<213> ORGANISM: artificial
<220> FEATURE:
<223> OTHER INFORMATION: His-tagged GFP_CBD2638_CBD2638 var.1

<400> SEQUENCE: 61

| | |
|---|---|
| atgagaggat cgcatcacca tcaccatcac ggatccatga gtaaaggaga agaactttc | 60 |
| actggagttg tcccaattct tgttgaatta gatggtgatg ttaatgggca caaattttct | 120 |
| gtcagtggag agggtgaagg tgatgcaaca tacggaaaac ttacccttaa atttatttgc | 180 |
| actactggaa aactacctgt tccatggcca acacttgtca ctactttcgc gtatggtctt | 240 |
| caatgctttg cgagataccc agatcatatg aaacggcatg acttttcaa gagtgccatg | 300 |
| cccgaaggtt atgtacagga agaactata tttttcaaag atgacgggaa ctacaagaca | 360 |
| cgtgctgaag tcaagtttga aggtgatacc cttgttaata aatcgagtt aaaaggtatt | 420 |
| gattttaaag aagatggaaa cattcttgga cacaaattgg aatacaacta taactcacac | 480 |
| aatgtataca tcatggcaga caaacaaaag aatggaatca agttaactt caaaattaga | 540 |
| cacaacattg aagatggaag cgttcaacta gcagaccatt atcaacaaaa tactccaatt | 600 |
| ggcgatggcc ctgtcctttt accagacaac cattacctgt ccacacaatc tgcccttcg | 660 |
| aaagatccca acgaaaagag agaccacatg gtccttcttg agtttgtaac agctgctggg | 720 |
| attacacatg gcatggatga actatacaaa gagctcggtg aaagctaga agtaagcaaa | 780 |
| gcagcaacta tcaaacaatc tgacgttaag caagaagtta aaagcaaga agcaaaacaa | 840 |

```
attgtgaaag caacagattg aaacagaat aaagatggca tttggtataa agctgaacat      900
gcttcgttca cagtgacagc accagaggga attatcacaa gatacaaagg tccttggact     960
ggtcacccac aagctggtgt attacaaaaa ggtcaaacga ttaaatatga tgaggttcaa    1020
aaatttgacg gtcatgtttg ggtatcgtgg gaaacgtttg agggcgaaac tgtatacatg    1080
ccggtacgca catgggacgc taaaactggt aaagttggta agttgtgggg cgaaattaaa    1140
gagctcggtg aaagctaga agtaagcaaa gcagcaacta tcaaacaatc tgacgttaag    1200
caagaagtta aaaagcaaga agcaaaacaa attgtgaaag caacagattg aaacagaat    1260
aaagatggca tttggtataa agctgaacat gcttcgttca cagtgacagc accagaggga    1320
attatcacaa gatacaaagg tccttggact ggtcacccac aagctggtgt attacaaaaa    1380
ggtcaaacga ttaaatatga tgaggttcaa aaatttgacg gtcatgtttg ggtatcgtgg    1440
gaaacgtttg agggcgaaac tgtatacatg ccggtacgca catgggacgc taaaactggt    1500
aaagttggta agttgtgggg cgaaattaaa taagtcgac                            1539

<210> SEQ ID NO 62
<211> LENGTH: 1560
<212> TYPE: DNA
<213> ORGANISM: artificial
<220> FEATURE:
<223> OTHER INFORMATION: Hist-tagged GFP_CBD2638_CBD2638 var. 2

<400> SEQUENCE: 62
atgagaggat cgcatcacca tcaccatcac ggatccatga gtaaaggaga agaacttttc      60
actggagttg tcccaattct tgttgaatta gatggtgatg ttaatgggca caaattttct    120
gtcagtggag agggtgaagg tgatgcaaca tacggaaaac ttacccttaa atttatttgc    180
actactggaa aactacctgt tccatggcca acacttgtca ctactttcgc gtatggtctt    240
caatgctttg cgagataccc agatcatatg aaacagcatg acttttccaa gagtgccatg    300
cccgaaggtt atgtacagga agaactata ttttttcaaag atgacgggaa ctacaagaca    360
cgtgctgaag tcaagtttga aggtgatacc cttgttaata gaatcgagtt aaaaggtatt    420
gattttaaag aagatggaaa cattcttgga cacaaattgg aatacaacta taactcacac    480
aatgtataca tcatggcaga caaacaaaag aatggaatca aagttaactt caaaattaga    540
cacaacattg aagatggaag cgttcaacta gcagaccatt atcaacaaaa tactccaatt    600
ggcgatggcc ctgtcctttt accagacaac cattacctgt ccacacaatc tgccctttcg    660
aaagatccca acgaaaagag agaccacatg gtccttcttg agtttgtaac agctgctggg    720
attacacatg gcatggatga actatacaaa gagctcggtg aaagctaga agtaagcaaa    780
gcagcaacta tcaaacaatc tgacgttaag caagaagtta aaaagcaaga agcaaaacaa    840
attgtgaaag caacagattg aaacagaat aaagatggca tttggtataa agctgaacat    900
gcttcgttca cagtgacagc accagaggga attatcacaa gatacaaagg tccttggact    960
ggtcacccac aagctggtgt attacaaaaa ggtcaaacga ttaaatatga tgaggttcaa   1020
aaatttgacg gtcatgtttg ggtatcgtgg gaaacgtttg agggcgaaac tgtatacatg   1080
ccggtacgca catgggacgc taaaactggt aaagttggta agttgtgggg cgaaattaaa   1140
ggtaccggtg aaagctaga agtaagcaaa gcagcaacta tcaaacaatc tgacgttaag   1200
caagaagtta aaaagcaaga agcaaaacaa attgtgaaag caacagattg aaacagaat   1260
aaagatggca tttggtataa agctgaacat gcttcgttca cagtgacagc accagaggga   1320
attatcacaa gatacaaagg tccttggact ggtcacccac aagctggtgt attacaaaaa   1380
```

```
ggtcaaacga ttaaatatga tgaggttcaa aaatttgacg gtcatgtttg ggtatcgtgg      1440
gaaacgtttg agggcgaaac tgtatacatg ccggtacgca catgggacgc taaaactggt      1500
aaagttggta agttgtgggg cgaaattaaa gtcgacctgc agccaagctt aattagctga      1560
```

<210> SEQ ID NO 63
<211> LENGTH: 1944
<212> TYPE: DNA
<213> ORGANISM: artificial
<220> FEATURE:
<223> OTHER INFORMATION: His-tagged GFP_CBD2638_CBD2638_CBD2638

<400> SEQUENCE: 63

```
atgagaggat cgcatcacca tcaccatcac ggatccatga gtaaaggaga agaacttttc       60
actggagttg tcccaattct tgttgaatta gatggtgatg ttaatgggca caaattttct      120
gtcagtggag agggtgaagg tgatgcaaca tacggaaaac ttacccttaa atttatttgc      180
actactggaa aactacctgt tccatggcca acacttgtca ctactttcgc gtatggtctt      240
caatgctttg cgagataccc agatcatatg aaacagcatg acttttcaa gagtgccatg       300 cccgaaggtt atgtacagga agaactatat tttcaaag atgacgggaa ctacaagaca        360
cgtgctgaag tcaagtttga aggtgatacc cttgttaata aatcgagtt aaaaggtatt      420 gattttaaag aagatggaaa cattcttgga cacaaattgg aatacaacta taactcacac      480
aatgtataca tcatggcaga caaacaaaag aatggaatca aagttaactt caaaattaga      540
cacaacattg aagatggaag cgttcaacta gcagaccatt atcaacaaaa tactccaatt      600
ggcgatggcc ctgtcctttt accagacaac cattacctgt ccacacaatc tgccctttcg      660
aaagatccca acgaaaagag agaccacatg gtccttcttg agtttgtaac agctgctggg      720
attacacatg gcatggatga actatacaaa gagctcggtg aaagctagag agtaagcaaa      780
gcagcaacta tcaaacaatc tgacgttaag caagaagtta aaaagcaaga agcaaaacaa      840
attgtgaaag caacagattg gaaacagaat aaagatggca tttggtataa agctgaacat      900
gcttcgttca cagtgacagc accagaggga attatcacaa gatacaaagg tccttggact      960
ggtcacccac aagctggtgt attacaaaaa ggtcaaacga ttaaatatga tgaggttcaa     1020
aaatttgacg gtcatgtttg ggtatcgtgg gaaacgtttg agggcgaaac tgtatacatg     1080
ccggtacgca catgggacgc taaaactggt aaagttggta agttgtgggg cgaaattaaa     1140
ggtaccggtg aaagctagag agtaagcaaa gcagcaacta tcaaacaatc tgacgttaag     1200
caagaagtta aaaagcaaga agcaaaacaa attgtgaaag caacagattg gaaacagaat     1260
aaagatggca tttggtataa agctgaacat gcttcgttca cagtgacagc accagaggga     1320
attatcacaa gatacaaagg tccttggact ggtcacccac aagctggtgt attacaaaaa     1380
ggtcaaacga ttaaatatga tgaggttcaa aaatttgacg gtcatgtttg ggtatcgtgg     1440
gaaacgtttg agggcgaaac tgtatacatg ccggtacgca catgggacgc taaaactggt     1500
aaagttggta agttgtgggg cgaaattaaa gtcgacggtg aaagctagag agtaagcaaa     1560
gcagcaacta tcaaacaatc tgacgttaag caagaagtta aaaagcaaga agcaaaacaa     1620
attgtgaaag caacagattg gaaacagaat aaagatggca tttggtataa agctgaacat     1680
gcttcgttca cagtgacagc accagaggga attatcacaa gatacaaagg tccttggact     1740
ggtcacccac aagctggtgt attacaaaaa ggtcaaacga ttaaatatga tgaggttcaa     1800
aaatttgacg gtcatgtttg ggtatcgtgg gaaacgtttg agggcgaaac tgtatacatg     1860
```

```
ccggtacgca catgggacgc taaaactggt aaagttggta agttgtgggg cgaaattaaa    1920
ctgcagccaa gcttaattag ctga                                          1944
```

<210> SEQ ID NO 64
<211> LENGTH: 380
<212> TYPE: PRT
<213> ORGANISM: artificial
<220> FEATURE:
<223> OTHER INFORMATION: His-tagged GFP_CBD2638

<400> SEQUENCE: 64

```
Met Arg Gly Ser His His His His His Gly Ser Met Ser Lys Gly
1               5                   10                  15

Glu Glu Leu Phe Thr Gly Val Val Pro Ile Leu Val Glu Leu Asp Gly
            20                  25                  30

Asp Val Asn Gly His Lys Phe Ser Val Ser Gly Glu Gly Glu Gly Asp
        35                  40                  45

Ala Thr Tyr Gly Lys Leu Thr Leu Lys Phe Ile Cys Thr Thr Gly Lys
    50                  55                  60

Leu Pro Val Pro Trp Pro Thr Leu Val Thr Thr Phe Ala Tyr Gly Leu
65                  70                  75                  80

Gln Cys Phe Ala Arg Tyr Pro Asp His Met Lys Arg His Asp Phe Phe
                85                  90                  95

Lys Ser Ala Met Pro Glu Gly Tyr Val Gln Glu Arg Thr Ile Phe Phe
            100                 105                 110

Lys Asp Asp Gly Asn Tyr Lys Thr Arg Ala Glu Val Lys Phe Glu Gly
        115                 120                 125

Asp Thr Leu Val Asn Arg Ile Glu Leu Lys Gly Ile Asp Phe Lys Glu
    130                 135                 140

Asp Gly Asn Ile Leu Gly His Lys Leu Glu Tyr Asn Tyr Asn Ser His
145                 150                 155                 160

Asn Val Tyr Ile Met Ala Asp Lys Gln Lys Asn Gly Ile Lys Val Asn
                165                 170                 175

Phe Lys Ile Arg His Asn Ile Glu Asp Gly Ser Val Gln Leu Ala Asp
            180                 185                 190

His Tyr Gln Gln Asn Thr Pro Ile Gly Asp Gly Pro Val Leu Leu Pro
        195                 200                 205

Asp Asn His Tyr Leu Ser Thr Gln Ser Ala Leu Ser Lys Asp Pro Asn
    210                 215                 220

Glu Lys Arg Asp His Met Val Leu Leu Glu Phe Val Thr Ala Ala Gly
225                 230                 235                 240

Ile Thr His Gly Met Asp Glu Leu Tyr Lys Glu Leu Gly Gly Lys Leu
                245                 250                 255

Glu Val Ser Lys Ala Ala Thr Ile Lys Gln Ser Asp Val Lys Gln Glu
            260                 265                 270

Val Lys Lys Gln Glu Ala Lys Gln Ile Val Lys Ala Thr Asp Trp Lys
        275                 280                 285

Gln Asn Lys Asp Gly Ile Trp Tyr Lys Ala Glu His Ala Ser Phe Thr
    290                 295                 300

Val Thr Ala Pro Glu Gly Ile Ile Thr Arg Tyr Lys Gly Pro Trp Thr
305                 310                 315                 320

Gly His Pro Gln Ala Gly Val Leu Gln Lys Gly Gln Thr Ile Lys Tyr
                325                 330                 335

Asp Glu Val Gln Lys Phe Asp Gly His Val Trp Val Ser Trp Glu Thr
            340                 345                 350
```

Phe Glu Gly Glu Thr Val Tyr Met Pro Val Arg Thr Trp Asp Ala Lys
            355                 360                 365

Thr Gly Lys Val Gly Lys Leu Trp Gly Glu Ile Lys
    370                 375                 380

<210> SEQ ID NO 65
<211> LENGTH: 510
<212> TYPE: PRT
<213> ORGANISM: artificial
<220> FEATURE:
<223> OTHER INFORMATION: His-tagged GFP_CBD2638_CBD2638 var.1

<400> SEQUENCE: 65

Met Arg Gly Ser His His His His His Gly Ser Met Ser Lys Gly
1               5                   10                  15

Glu Glu Leu Phe Thr Gly Val Val Pro Ile Leu Val Glu Leu Asp Gly
            20                  25                  30

Asp Val Asn Gly His Lys Phe Ser Val Ser Gly Glu Gly Glu Gly Asp
            35                  40                  45

Ala Thr Tyr Gly Lys Leu Thr Leu Lys Phe Ile Cys Thr Thr Gly Lys
    50                  55                  60

Leu Pro Val Pro Trp Pro Thr Leu Val Thr Thr Phe Ala Tyr Gly Leu
65              70                  75                  80

Gln Cys Phe Ala Arg Tyr Pro Asp His Met Lys Arg His Asp Phe Phe
                85                  90                  95

Lys Ser Ala Met Pro Glu Gly Tyr Val Gln Glu Arg Thr Ile Phe Phe
            100                 105                 110

Lys Asp Asp Gly Asn Tyr Lys Thr Arg Ala Glu Val Lys Phe Glu Gly
        115                 120                 125

Asp Thr Leu Val Asn Arg Ile Glu Leu Lys Gly Ile Asp Phe Lys Glu
    130                 135                 140

Asp Gly Asn Ile Leu Gly His Lys Leu Glu Tyr Asn Tyr Asn Ser His
145                 150                 155                 160

Asn Val Tyr Ile Met Ala Asp Lys Gln Lys Asn Gly Ile Lys Val Asn
                165                 170                 175

Phe Lys Ile Arg His Asn Ile Glu Asp Gly Ser Val Gln Leu Ala Asp
            180                 185                 190

His Tyr Gln Gln Asn Thr Pro Ile Gly Asp Gly Pro Val Leu Leu Pro
        195                 200                 205

Asp Asn His Tyr Leu Ser Thr Gln Ser Ala Leu Ser Lys Asp Pro Asn
    210                 215                 220

Glu Lys Arg Asp His Met Val Leu Leu Glu Phe Val Thr Ala Ala Gly
225                 230                 235                 240

Ile Thr His Gly Met Asp Glu Leu Tyr Lys Glu Leu Gly Gly Lys Leu
                245                 250                 255

Glu Val Ser Lys Ala Ala Thr Ile Lys Gln Ser Asp Val Lys Gln Glu
            260                 265                 270

Val Lys Lys Gln Glu Ala Lys Gln Ile Val Lys Ala Thr Asp Trp Lys
        275                 280                 285

Gln Asn Lys Asp Gly Ile Trp Tyr Lys Ala Glu His Ala Ser Phe Thr
    290                 295                 300

Val Thr Ala Pro Glu Gly Ile Ile Thr Arg Tyr Lys Gly Pro Trp Thr
305                 310                 315                 320

Gly His Pro Gln Ala Gly Val Leu Gln Lys Gly Gln Thr Ile Lys Tyr
                325                 330                 335

```
Asp Glu Val Gln Lys Phe Asp Gly His Val Trp Val Ser Trp Glu Thr
            340                 345                 350

Phe Glu Gly Glu Thr Val Tyr Met Pro Val Arg Thr Trp Asp Ala Lys
            355                 360                 365

Thr Gly Lys Val Gly Lys Leu Trp Gly Glu Ile Lys Glu Leu Gly Gly
        370                 375                 380

Lys Leu Glu Val Ser Lys Ala Ala Thr Ile Lys Gln Ser Asp Val Lys
385                 390                 395                 400

Gln Glu Val Lys Lys Gln Glu Ala Lys Gln Ile Val Lys Ala Thr Asp
                405                 410                 415

Trp Lys Gln Asn Lys Asp Gly Ile Trp Tyr Lys Ala Glu His Ala Ser
                420                 425                 430

Phe Thr Val Thr Ala Pro Glu Gly Ile Ile Thr Arg Tyr Lys Gly Pro
            435                 440                 445

Trp Thr Gly His Pro Gln Ala Gly Val Leu Gln Lys Gly Gln Thr Ile
        450                 455                 460

Lys Tyr Asp Glu Val Gln Lys Phe Asp Gly His Val Trp Val Ser Trp
465                 470                 475                 480

Glu Thr Phe Glu Gly Glu Thr Val Tyr Met Pro Val Arg Thr Trp Asp
                485                 490                 495

Ala Lys Thr Gly Lys Val Gly Lys Leu Trp Gly Glu Ile Lys
            500                 505                 510
```

<210> SEQ ID NO 66
<211> LENGTH: 519
<212> TYPE: PRT
<213> ORGANISM: artificial
<220> FEATURE:
<223> OTHER INFORMATION: His-tagged GFP_CBD2638_CBD2638 var. 2

<400> SEQUENCE: 66

```
Met Arg Gly Ser His His His His His Gly Ser Met Ser Lys Gly
1               5                   10                  15

Glu Glu Leu Phe Thr Gly Val Val Pro Ile Leu Val Glu Leu Asp Gly
            20                  25                  30

Asp Val Asn Gly His Lys Phe Ser Val Ser Gly Glu Gly Glu Gly Asp
        35                  40                  45

Ala Thr Tyr Gly Lys Leu Thr Leu Lys Phe Ile Cys Thr Thr Gly Lys
    50                  55                  60

Leu Pro Val Pro Trp Pro Thr Leu Val Thr Thr Phe Ala Tyr Gly Leu
65                  70                  75                  80

Gln Cys Phe Ala Arg Tyr Pro Asp His Met Lys Gln His Asp Phe Phe
                85                  90                  95

Lys Ser Ala Met Pro Glu Gly Tyr Val Gln Glu Arg Thr Ile Phe Phe
            100                 105                 110

Lys Asp Asp Gly Asn Tyr Lys Thr Arg Ala Glu Val Lys Phe Glu Gly
        115                 120                 125

Asp Thr Leu Val Asn Arg Ile Glu Leu Lys Gly Ile Asp Phe Lys Glu
    130                 135                 140

Asp Gly Asn Ile Leu Gly His Lys Leu Glu Tyr Asn Tyr Asn Ser His
145                 150                 155                 160

Asn Val Tyr Ile Met Ala Asp Lys Gln Lys Asn Gly Ile Lys Val Asn
                165                 170                 175

Phe Lys Ile Arg His Asn Ile Glu Asp Gly Ser Val Gln Leu Ala Asp
            180                 185                 190
```

His Tyr Gln Gln Asn Thr Pro Ile Gly Asp Gly Pro Val Leu Leu Pro
            195                 200                 205

Asp Asn His Tyr Leu Ser Thr Gln Ser Ala Leu Ser Lys Asp Pro Asn
210                 215                 220

Glu Lys Arg Asp His Met Val Leu Leu Glu Phe Val Thr Ala Ala Gly
225                 230                 235                 240

Ile Thr His Gly Met Asp Glu Leu Tyr Lys Glu Leu Gly Gly Lys Leu
            245                 250                 255

Glu Val Ser Lys Ala Ala Thr Ile Lys Gln Ser Asp Val Lys Gln Glu
            260                 265                 270

Val Lys Lys Gln Glu Ala Lys Gln Ile Val Lys Ala Thr Asp Trp Lys
275                 280                 285

Gln Asn Lys Asp Gly Ile Trp Tyr Lys Ala Glu His Ala Ser Phe Thr
            290                 295                 300

Val Thr Ala Pro Glu Gly Ile Ile Thr Arg Tyr Lys Gly Pro Trp Thr
305                 310                 315                 320

Gly His Pro Gln Ala Gly Val Leu Gln Lys Gly Gln Thr Ile Lys Tyr
            325                 330                 335

Asp Glu Val Gln Lys Phe Asp Gly His Val Trp Val Ser Trp Glu Thr
            340                 345                 350

Phe Glu Gly Glu Thr Val Tyr Met Pro Val Arg Thr Trp Asp Ala Lys
            355                 360                 365

Thr Gly Lys Val Gly Lys Leu Trp Gly Glu Ile Lys Gly Thr Gly Gly
            370                 375                 380

Lys Leu Glu Val Ser Lys Ala Ala Thr Ile Lys Gln Ser Asp Val Lys
385                 390                 395                 400

Gln Glu Val Lys Lys Gln Glu Ala Lys Gln Ile Val Lys Ala Thr Asp
            405                 410                 415

Trp Lys Gln Asn Lys Asp Gly Ile Trp Tyr Lys Ala Glu His Ala Ser
            420                 425                 430

Phe Thr Val Thr Ala Pro Glu Gly Ile Ile Thr Arg Tyr Lys Gly Pro
            435                 440                 445

Trp Thr Gly His Pro Gln Ala Gly Val Leu Gln Lys Gly Gln Thr Ile
            450                 455                 460

Lys Tyr Asp Glu Val Gln Lys Phe Asp Gly His Val Trp Val Ser Trp
465                 470                 475                 480

Glu Thr Phe Glu Gly Glu Thr Val Tyr Met Pro Val Arg Thr Trp Asp
            485                 490                 495

Ala Lys Thr Gly Lys Val Gly Lys Leu Trp Gly Glu Ile Lys Val Asp
            500                 505                 510

Leu Gln Pro Ser Leu Ile Ser
            515

<210> SEQ ID NO 67
<211> LENGTH: 647
<212> TYPE: PRT
<213> ORGANISM: artificial
<220> FEATURE:
<223> OTHER INFORMATION: His-tagged GFP_CBD2638_CBD2638_CBD2638

<400> SEQUENCE: 67

Met Arg Gly Ser His His His His His His Gly Ser Met Ser Lys Gly
1               5                   10                  15

Glu Glu Leu Phe Thr Gly Val Val Pro Ile Leu Val Glu Leu Asp Gly
            20                  25                  30

```
Asp Val Asn Gly His Lys Phe Ser Val Ser Gly Glu Gly Glu Gly Asp
            35                  40                  45

Ala Thr Tyr Gly Lys Leu Thr Leu Lys Phe Ile Cys Thr Thr Gly Lys
50                  55                  60

Leu Pro Val Pro Trp Pro Thr Leu Val Thr Thr Phe Ala Tyr Gly Leu
65                  70                  75                  80

Gln Cys Phe Ala Arg Tyr Pro Asp His Met Lys Gln His Asp Phe Phe
                85                  90                  95

Lys Ser Ala Met Pro Glu Gly Tyr Val Gln Glu Arg Thr Ile Phe Phe
                100                 105                 110

Lys Asp Asp Gly Asn Tyr Lys Thr Arg Ala Glu Val Lys Phe Glu Gly
                115                 120                 125

Asp Thr Leu Val Asn Arg Ile Glu Leu Lys Gly Ile Asp Phe Lys Glu
            130                 135                 140

Asp Gly Asn Ile Leu Gly His Lys Leu Glu Tyr Asn Tyr Asn Ser His
145                 150                 155                 160

Asn Val Tyr Ile Met Ala Asp Lys Gln Lys Asn Gly Ile Lys Val Asn
                165                 170                 175

Phe Lys Ile Arg His Asn Ile Glu Asp Gly Ser Val Gln Leu Ala Asp
                180                 185                 190

His Tyr Gln Gln Asn Thr Pro Ile Gly Asp Gly Pro Val Leu Leu Pro
            195                 200                 205

Asp Asn His Tyr Leu Ser Thr Gln Ser Ala Leu Ser Lys Asp Pro Asn
210                 215                 220

Glu Lys Arg Asp His Met Val Leu Leu Glu Phe Val Thr Ala Ala Gly
225                 230                 235                 240

Ile Thr His Gly Met Asp Glu Leu Tyr Lys Glu Leu Gly Gly Lys Leu
                245                 250                 255

Glu Val Ser Lys Ala Ala Thr Ile Lys Gln Ser Asp Val Lys Gln Glu
                260                 265                 270

Val Lys Lys Gln Glu Ala Lys Gln Ile Val Lys Ala Thr Asp Trp Lys
            275                 280                 285

Gln Asn Lys Asp Gly Ile Trp Tyr Lys Ala Glu His Ala Ser Phe Thr
290                 295                 300

Val Thr Ala Pro Glu Gly Ile Ile Thr Arg Tyr Lys Gly Pro Trp Thr
305                 310                 315                 320

Gly His Pro Gln Ala Gly Val Leu Gln Lys Gly Gln Thr Ile Lys Tyr
                325                 330                 335

Asp Glu Val Gln Lys Phe Asp Gly His Val Trp Val Ser Trp Glu Thr
                340                 345                 350

Phe Glu Gly Glu Thr Val Tyr Met Pro Val Arg Thr Trp Asp Ala Lys
            355                 360                 365

Thr Gly Lys Val Gly Lys Leu Trp Gly Glu Ile Lys Gly Thr Gly Gly
370                 375                 380

Lys Leu Glu Val Ser Lys Ala Ala Thr Ile Lys Gln Ser Asp Val Lys
385                 390                 395                 400

Gln Glu Val Lys Lys Gln Glu Ala Lys Gln Ile Val Lys Ala Thr Asp
                405                 410                 415

Trp Lys Gln Asn Lys Asp Gly Ile Trp Tyr Lys Ala Glu His Ala Ser
                420                 425                 430

Phe Thr Val Thr Ala Pro Glu Gly Ile Ile Thr Arg Tyr Lys Gly Pro
            435                 440                 445
```

-continued

```
Trp Thr Gly His Pro Gln Ala Gly Val Leu Gln Lys Gly Gln Thr Ile
    450                 455                 460

Lys Tyr Asp Glu Val Gln Lys Phe Asp Gly His Val Trp Val Ser Trp
465                 470                 475                 480

Glu Thr Phe Glu Gly Glu Thr Val Tyr Met Pro Val Arg Thr Trp Asp
                485                 490                 495

Ala Lys Thr Gly Lys Val Gly Lys Leu Trp Gly Glu Ile Lys Val Asp
                500                 505                 510

Gly Gly Lys Leu Glu Val Ser Lys Ala Ala Thr Ile Lys Gln Ser Asp
        515                 520                 525

Val Lys Gln Glu Val Lys Lys Gln Glu Ala Lys Gln Ile Val Lys Ala
530                 535                 540

Thr Asp Trp Lys Gln Asn Lys Asp Gly Ile Trp Tyr Lys Ala Glu His
545                 550                 555                 560

Ala Ser Phe Thr Val Thr Ala Pro Glu Gly Ile Ile Thr Arg Tyr Lys
                565                 570                 575

Gly Pro Trp Thr Gly His Pro Gln Ala Gly Val Leu Gln Lys Gly Gln
                580                 585                 590

Thr Ile Lys Tyr Asp Glu Val Gln Lys Phe Asp Gly His Val Trp Val
        595                 600                 605

Ser Trp Glu Thr Phe Glu Gly Glu Thr Val Tyr Met Pro Val Arg Thr
    610                 615                 620

Trp Asp Ala Lys Thr Gly Lys Val Gly Lys Leu Trp Gly Glu Ile Lys
625                 630                 635                 640

Leu Gln Pro Ser Leu Ile Ser
                645
```

POLYPEPTIDE

This application is a U.S. National Phase Application under 35 U.S.C. §371 of International Application No. PCT/NL2011/050307, filed on May 4, 2011.

FIELD OF THE INVENTION

The invention relates to a polypeptide, a corresponding nucleic acid molecule, a construct and/or a vector and/or a cell comprising such nucleic acid molecule and/or a composition comprising said polypeptide, nucleic acid molecule, construct, vector and/or cell. The invention further relates to such polypeptide, corresponding nucleic acid molecule, construct and/or vector and/or cell comprising such nucleic acid molecule and/or composition for medical use, preferably for use in treating an infectious disease. Furthermore, the invention relates to the use of said polypeptide, nucleic acid molecule, construct, vector, cell and/or composition as an antimicrobial, preferably as a food additive or disinfectant, or for detecting bacteria, preferably in a diagnostic application.

BACKGROUND OF THE INVENTION

*Staphylococcus aureus* is a major human pathogen frequently implicated in several serious infectious diseases and food poisoning. Its treatment becomes more and more difficult because of emerging antibiotic resistant strains. Endolysins from phages infecting *Staphylococcus aureus* have been shown to potentially control these pathogens and can be used for their specific detection. In most cases, major obstacles in the application of endolysins targeting *Staphylococcus* species are low enzyme activity, difficult production in large quantities and/or protein stability.

There is always a need for new antimicrobials with improved characteristics on for example antimicrobial activity and/or stability.

DESCRIPTION OF THE INVENTION

Reported here is the newly characterised Ply2638, the endolysin of *S. aureus* bacteriophage Φ2638a. The enzyme and several engineered derivatives were expressed in a soluble way in *E. Coli* and showed surprising stability after lyophilisation as proven by their lytic activity after reconstitution. In addition to a cell wall-binding domain which binds the cell wall of *Staphylococcus* genera, we showed that two functional domains, i.e. an M23 endopeptidase domain and an amidase domain, are crucial for optimal lytic activity.

We showed that retrofitting of the enzyme with catalytic domains and/or duplication of the cell wall-binding domain originating from *S. aureus* Φ11 endolysin, Φ Twort endolysin, and Lysostaphin resulted in a heterologous polypeptide fusion product with an enhanced lytic activity and/or a shifted pH optimum and/or an increased stability after lyophilisation and reconstitution.

Nucleic Acid Molecule

In a first aspect, there is provided a nucleic acid molecule comprising or consisting of a first nucleotide sequence, said nucleotide sequence having 80, 81, 82, 83, 84, 85, 86, 87, 88, 89, 90, 91, 92, 93, 94, 95, 96, 97, 98, 99 or 100% sequence identity with SEQ ID NO: 12 (referred is to Table 1 for an overview of all SEQ ID NOs used herein). Preferably, said first nucleotide sequence has a length of at least 282, 285, 290, 300, 310, 320, 330, 340, 350, 360 or 370 nucleotides, more preferably, at least 381 nucleotides and/or a length of at most 510, 480, 450, 420 or 390 nucleotides. Preferably, said nucleic acid molecule has a length of at least 282, 285, 290, 300, 310, 320, 330, 340, 350, 360, 370 nucleotides, more preferably at least 381 nucleotides and/or a length of at most 4500, 4200, 3900 and/or 3600 nucleotides. Preferably, said nucleic acid molecule has a length of at least 1200, 1230, 1260, 1290, 1320, 1350, 1380, 1410, 1440, 1470, 1500, 1530 or 1560 nucleotides and/or a length of at most 4500, 4200, 3900 and/or 3600 nucleotides. Also preferred is a nucleic acid molecule according to the invention with a length of at least 1890, 1920, 1950, 1980, 2010, 2040, 2070, 2100, 2130 or 2160 nucleotides and/or a length of at most 4500, 4200, 3900 and/or 3600 nucleotides. Preferably, said first nucleotide sequence encodes a cell wall-binding domain which binds the peptidoglycan cell wall of *Staphylococcus* genera. Preferably, said first nucleotide sequence originates from *S. aureus* bacteriophage Φ2638a endolysin.

As estimated from alignments with the crystal structure of the C-terminal 92 residues of ALE-1 (Lu et al., J. Biol. Chem., 2006, 281(1):549-58), it was estimated that a minimum of 94 amino acids from the cell wall-binding domain originating from *S. aureus* bacteriophage Φ2638a endolysin may be sufficient to direct the enzyme to the cell wall of *Staphylococcus* genera.

Binding of a domain to the peptidoglycan cell wall of *Staphylococcus* genera may be assessed using assays well known to the artisan. In a preferred embodiment, an immunohistochemical technique and/or a gene fusion technique resulting in labelled constructs are used for assessing specific binding of peptides, polypeptides or proteins to the peptidoglycan cell wall of *Staphylococcus* genera. Quantification methods of signals used in the above mentioned immunohistochemical or fusion techniques are well known in the art.

In one embodiment, *Staphylococcus* peptidoglycan cell wall-binding can be quantified using a fluorescent fusion construct comprising a polypeptide comprising a domain encoded by a first nucleotide sequence. Such a cell wall-binding assay is described in detail by Loessner et al (Molecular Microbiology 2002, 44(2): 335-349) and in Example 1. In this assay a solution comprising said fluorescent fusion construct or a negative control, preferably Green Fluorescent Protein (GFP), is subjected to *Staphylococcus* cells, preferably *S. aureus* cells, more preferably *S. aureus* BB255 for an indicated time period where after the cells are sedimented by centrifugation together with the bound fluorescent fusion constructs. The fluorescent signal of the *Staphylococcus* cells exposed to a fluorescent fusion construct subtracted by the fluorescence signal of the *Staphylococcus* cells exposed to a negative control, preferably GPF, is a measure for cell binding as meant in this disclosure.

Preferably, within the context of the invention a nucleic acid molecule will be said to encode a polypeptide domain that binds the peptidoglycan cell wall of *Staphylococcus* genera when using this assay an increase in fluorescent signal of the sedimented cells above the negative control as defined herein is detected. The binding is preferably said to be specific. Preferably, the invention relates to a nucleic acid molecule encoding a polypeptide or a domain which exhibits binding as defined herein of at least 50, 60, 70, 80, 90 or 100, 150 or 200% of peptidoglycan cell wall binding of *S. aureus* bacteriophage Φ2638a endolysin (Ply2638) encoded by SEQ ID NO: 1.

In an embodiment, the invention relates to a nucleic acid molecule that has 80, 81, 82, 83, 84, 85, 86, 87, 88, 89, 90, 91, 92, 93, 94, 95, 96, 97, 98, 99 or 100% sequence identity with SEQ ID NO: 1 encoding for *S. aureus* bacteriophage Φ2638 endolysin.

The present invention further relates to a nucleic acid molecule comprising in addition to said first nucleotide sequence, a heterologous nucleotide sequence encoding a lytic domain. Preferably, said lytic domain exhibits peptidoglycan hydrolase activity as defined later herein. Said nucleic acid molecule comprising heterologous nucleotide sequences being defined herein as a "retrofitted construct".

As used herein the term "heterologous sequence" or "heterologous nucleic acid" is one that is not naturally found operably linked as neighbouring sequence of said first nucleotide sequence. As used herein, the term "heterologous" may mean "recombinant". "Recombinant" refers to a genetic entity distinct from that generally found in nature. As applied to a nucleotide sequence or nucleic acid molecule, this means that said nucleotide sequence or nucleic acid molecule is the product of various combinations of cloning, restriction and/or ligation steps, and other procedures that result in the production of a construct that is distinct from a sequence or molecule found in nature.

A "peptidoglycan hydrolase activity" herein also defined as a "lytic activity" can be assessed by methods well known to the artisan. In an embodiment, lytic activity can be assessed spectrophotometrically by measuring the drop in turbidity of substrate cell suspensions. Preferably, lytic activity can be assessed spectrophotometrically measuring the drop in turbidity of a *S. aureus* suspension, wherein turbidity is quantified by measuring $OD_{595}$ spectrophotometrically (Libra S22, Biochrom). More preferably, 200 nM of a polypeptide encoded by a nucleic acid molecule as identified herein is incubated together with an *S. aureus* suspension having an initial $OD_{600}$ of 1±0.05, as assessed spectrophotometrically (Libra S22, Biochrom), in PBS buffer pH 7.4, 120 mM sodium chloride for 30 min at 37° C. The drop in turbidity is calculated by subtracting the $OD_{595}$ after 30 min of incubation from the $OD_{595}$ before 30 min of incubation. Within the context of the invention a nucleic acid molecule will be said to comprise a nucleic acid sequence encoding a lytic domain when using this assay a drop in turbidity of at least 10, 20, 30, 40, 50 or 60% is detected. Preferably, a drop of at least 70% is detected. Preferably, the invention relates to a nucleic acid molecule encoding a polypeptide which exhibits a lytic activity of at least 50, 60, 70, 80, 90, 100, 150 or 200% or more of a lytic activity of *S. aureus* bacteriophage Φ2638a endolysin (Ply2638) encoded by SEQ ID NO: 1.

In an embodiment a nucleic acid molecule of the invention may not comprise or consist of SEQ ID NO:1. SEQ ID NO: 1 encodes for *S. aureus* bacteriophage Φ2638 endolysin.

A preferred embodiment encompasses a nucleic acid molecule comprising said first nucleotide sequence as identified herein and further comprising as a lytic domain a second and third nucleotide sequences, wherein said second sequence encodes an endopeptidase domain and third nucleotide sequence encodes an amidase domain. Accordingly, the invention relates to a nucleic acid molecule comprising said first nucleotide sequence, wherein said nucleic acid molecule has 80, 81, 82, 83, 84, 85, 86, 87, 88, 89, 90, 91, 92, 93, 94, 95, 96, 97, 98, 99 or 100% sequence identity with SEQ ID NO: 1, or wherein said nucleic acid molecule further comprises a heterologous nucleotide sequence encoding a lytic domain.

An endopeptidase domain as used herein preferably cleaves the pentaglycine cross-bridges (Trayer, H. R. and Buckley, C. E. (1970) *Molecular properties of lysostaphin, a bacteriolytic agent specific for Staphylococcus aureus. J. Biol. Chem.* 245, 4842-4846) that are found in the cell wall of *Staphylococcus* genera, preferably in the cell wall of *S. aureus, S. simulans* and *S. carnosus*. An amidase domain as used herein preferably hydrolyzes gamma-glutamyl-containing substrates. The functionality and activity of these domains in a polypeptide can be confirmed by characterizing the cleavage products upon incubation of said polypeptides containing any of these domains with purified peptidoglycan. Preferably, each of the nucleotide sequences encoding the second or third domain is of bacterial or bacteriophage origin. In a preferred embodiment, said second and third nucleotide sequences originate from a gene encoding for an enzyme selected from the group consisting of *S. aureus* bacteriophage Φ2638a endolysin, *S. aureus* bacteriophage Φ11 endolysin, *S. aureus* bacteriophage ΦTwort endolysin and *S. Simulans* lysostaphin. Preferably, said second nucleotide sequence has 80, 81, 82, 83, 84, 85, 86, 87, 88, 89, 90, 91, 92, 93, 94, 95, 96, 97, 98, 99 or 100% sequence identity with SEQ ID NO: 14 or 15 and said third nucleotide sequence has 80, 81, 82, 83, 84, 85, 86, 87, 88, 89, 90, 91, 92, 93, 94, 95, 96, 97, 98, 99 or 100% sequence identity with SEQ ID NO: 17 or 18.

The invention encompasses all constructs as defined herein containing the functional domains as meant in the invention at any possible location within the construct. In a preferred embodiment, a nucleic acid molecule as defined herein encodes for a polypeptide with a C-terminal domain encoded by a first nucleic acid sequence as identified herein, which is shown herein to encode for functional polypeptides able to target for *Staphylococcus* genera. Even more preferred is a nucleic acid molecule as defined herein comprising a nucleic acid molecule that has 80, 81, 82, 83, 84, 85, 86, 87, 88, 89, 90, 91, 92, 93, 94, 95, 96, 97, 98, 99 or 100% sequence identity with SEQ ID NO: 9. SEQ ID NO: 9 comprises a first nucleotide sequence encoding a C-terminal SH3b homologue cell wall-binding domain (both domains from Ply2638 encoded by SEQ ID NO: 1: Leu138-Lys486), a second nucleotide sequence encoding a polypeptide comprising an N-terminal M23 glycyl-glycine endopeptidase homologue domain (mature Lysostaphin encoded by SEQ ID NO: 33: Ala1-Gly154) and a third nucleotide sequence encoding a central amidase-2 homologue domain. It has a theoretical size of 58.266 kDa. A polypeptide encoded by SEQ ID NO: 9 differs from *S. aureus* bacteriophage Φ2638a endolysin in that the N-terminal M23 endopeptidase domain is substituted by an M23 endopeptidase domain from *S. Simulans* lysostaphin. We showed here that a polypeptide encoded by SEQ ID NO: 9 demonstrated at least 20% increased lytic activity as compared to *S. aureus* bacteriophage Φ2638a endolysin while the lytic activity is maintained after lyophilisation and reconstitution. In a preferred embodiment, a nucleic acid molecule comprising said first, second and third nucleotide sequences encodes for a polypeptide exhibiting a lytic activity of at least 0.7, 0.8, 0.9, 1.0, 1.1, 1.2, 1.3, 1.4, 1.5, 1.6, 1.7, 1.8, 1.9 or 2 fold as compared to a lytic activity of *S. aureus* bacteriophage Φ2638a endolysin encoded by SEQ ID NO:1. In a preferred embodiment, a nucleic acid molecule comprising said first, second and third nucleotide sequences encodes for a polypeptide exhibiting a decrease in lytic activity of at most 1, 2, 3, 4, 5, 6, 7, 8, 9 or 10% after lyophilisation and reconstitution as defined herein as compared to freshly prepared polypeptide, wherein "freshly prepared" is preferably defined herein as at most 2 days storage at 1.63 mg/mL in lyophilisation buffer (50 mM Tris, 500 mM sucrose, 200 mM mannitol, 0.05% polysorbate 20+50% glycerol) at −20° C. and thawed immediately before assessing lytic activity in an assay as identified herein.

Lyophilisation and reconstitution is defined herein as dehydration by freeze-drying and subsequent reconstitution of the sample by adding water. In an embodiment, lyophilisation and reconstitution may be done by dialyzing against 3 changes of 300 ml lyophilization buffer (50 mM phosphate or Tris, 500 mM sucrose, 200 mM mannitol, pH 7.4) aliquot and freezing in the gaseous phase of liquid nitrogen. The freeze-drying can be done under standard conditions, preferably at −40° C. and vacuum at 75 mTorr for 60 minutes, followed by increasing temperature during 5 hours to −10° C. and another 60 minutes at −10° C. at the same vacuum levels. As final step, temperature is preferably increased to 25° C. during 10 hours. Samples are reconstituted by the addition of water.

In another preferred embodiment, a nucleic acid molecule as defined herein comprises in addition to the above identified first, second and third nucleotide sequences at least one duplicate identical or heterologous first, second and/or third nucleotide sequence. Preferably, a nucleic acid molecule as defined herein comprises in addition to said first, second and third nucleotide sequences, a duplicate identical first nucleotide sequence. We showed here that duplication of the first nucleotide sequence as defined herein encoding a cell wall-binding domain results in a polypeptide preferably as encoded by SEQ ID NO: 20 which exposes at least 5, 10, 20, 30, 20 or 40% increased lytic activity as compared to a lytic activity of a reference polypeptide encoded by a nucleic acid molecule lacking such duplicate first domain or as compared to a lytic activity of *S. aureus* bacteriophage Φ2638a endolysin encoded by SEQ ID NO:1 as assessed in an assay as identified herein, more specifically using equimolar amount of a polypeptide and a modified PBS buffer containing 200, 300, 400, or 1000 nM NaCl. This embodiment also encompasses a heterologous nucleic acid molecule in which said first, second and third nucleotide sequences originate form the same source being *S. aureus* bacteriophage Φ2638a, said nucleic acid molecule comprising a sequence that has 80, 81, 82, 83, 84, 85, 86, 87, 88, 89, 90, 91, 92, 93, 94, 95, 96, 97, 98, 99 or 100% sequence identity with SEQ ID NO:1 and an additional duplicate identical or heterologous first, second and/or third nucleotide sequence. Also preferred is a nucleic acid molecule as defined herein comprising a nucleotide sequence that has 80, 81, 82, 83, 84, 85, 86, 87, 88, 89, 90, 91, 92, 93, 94, 95, 96, 97, 98, 99 or 100% sequence identity with SEQ ID NO: 6 and 20.

In another preferred embodiment, a nucleic acid molecule as defined herein comprises a fourth nucleotide sequence encoding a CHAP (cysteine, histidine-dependent amidohydrolases/peptidases) domain. More preferably, said fourth nucleotide sequences originates from *S. aureus* bacteriophage ΦΦ11 or *S. aureus* bacteriophage ΦTwort endolysin. Even more preferably, said fourth nucleotide sequence has 80, 81, 82, 83, 84, 85, 86, 87, 88, 89, 90, 91, 92, 93, 94, 95, 96, 97, 98, 99 or 100% sequence identity with SEQ ID NO: 18 or SEQ ID NO: 19. Preferably, a nucleic acid molecule as defined herein comprises a nucleotide sequence that has 80, 81, 82, 83, 84, 85, 86, 87, 88, 89, 90, 91, 92, 93, 94, 95, 96, 97, 98, 99 or 100% sequence identity with SEQ ID NO: 5 or 7. We showed here that a molecule comprising said first, second, third and fourth nucleotide sequences as defined by SEQ ID NO: 5 encodes for a polypeptide exhibiting an increased lytic activity and/or a shifted, preferably decreased pH optimum as compared to a polypeptide encoded by a construct lacking said fourth domain and/or compared to *S. aureus* bacteriophage Φ2638a endolysin encoded by SEQ ID NO:1. Lytic activity was assessed spectrophotometrically and under the conditions as earlier defined herein. Preferably, said polypeptide exhibits an increase in a lytic activity of at least 0.7, 0.8, 0.9, 1.0, 1.1, 1.2, 1.3, 1.4, 1.5, 1.6, 1.7, 1.8, 1.9, or 2 fold as compared to a lytic activity of a polypeptide encoded by a reference polypeptide differing from said polypeptide only in lacking said fourth domain or as compared to a lytic activity of *S. aureus* bacteriophage Φ2638a endolysin encoded by SEQ ID NO:1. Even more preferably, said polypeptide exhibits an increase in a lytic activity of at least 2.5 fold as compared to the defined reference polypeptide or a polypeptide encoded by SEQ ID NO:1.

A shifted or decreased pH optimum is defined herein as a shift or decrease in optimal lytic activity to a lower pH value, where ionic strength is kept constant. Lytic activity is preferably assessed spectrophotometrically as defined herein. Preferably, the pH optimum of a lytic activity is decreased 0.5-1 pH unit as compared to a lytic activity of a polypeptide encoded by a reference polypeptide differing from said polypeptide only in lacking said fourth domain or as compared to a lytic activity of *S. aureus* bacteriophage Φ2638a endolysin encoded by SEQ ID NO:1.

The invention preferably relates to a nucleic acid molecule comprising a first, second, third and optionally fourth nucleotide sequences as identified herein encoding a polypeptide which has the same lytic activity and/or the same pH optimum or which has an increased lytic activity and/or a decreased pH optimum as compared to a lytic activity of *S. aureus* bacteriophage Φ2638a endolysin encoded by SEQ ID NO:1. The same being identified herein as no detectable difference when using the assay as identified herein or a method well known by the artisan. The current invention also relates to a nucleic acid molecule comprising a first, second, and fourth nucleotide sequence as identified herein encoding a polypeptide which has the same lytic activity and/or the same pH optimum or which has an increased lytic activity and/or a decreased pH optimum as compared to a lytic activity of *S. aureus* bacteriophage Φ2638a endolysin encoded by SEQ ID NO:1. The current invention also relates to a nucleic acid molecule comprising a first, third, and fourth nucleotide sequence as identified herein encoding a polypeptide which has the same lytic activity and/or the same pH optimum or which has an increased lytic activity and/or a decreased pH optimum as compared to a lytic activity of *S. aureus* bacteriophage Φ2638a endolysin encoded by SEQ ID NO:1. Each of the nucleotide sequences identified herein, i.e. first, second, third, fourth nucleotide sequences, encoding the individual domain of a polypeptide defined herein can be assembled by any usual method known for constructing and assembling nucleic acid fragments which are well known to those skilled in the art and widely described in the literature (Sambrook, Maniatis et al. (1989) and illustrated experimental part of the disclosure. In a preferred embodiment, a first, second, third and/or fourth nucleotide sequences are operably linked together.

Accordingly, a nucleic acid molecule of the invention encodes a polypeptide, preferably a polypeptide as identified herein which is able to bind *Staphylococcus* genera via the cell wall-binding domain encoded by a first nucleotide sequence as defined herein and/or lyse said bacteria via an endopeptidase and/or amidase domain and optionally a CHAP domain encoded by a second, third and fourth nucleotide sequence, respectively, as defined herein.

In a preferred embodiment, a nucleic acid molecule of the invention as defined herein optionally comprises a sequence encoding a tag for ease of purification. Preferably, said tag is selected from, but is not limited to, the group consisting of a FLAG-tag, poly(His)-tag, HA-tag and Myc-tag. More preferably said tag is a 6×His-tag. Even more preferably said tag is an N-terminal 6×His-tag identical to SEQ ID NO: 43.

Polypeptide

In a further aspect, there is provided a polypeptide encoded by a nucleic acid molecule as earlier identified herein. This polypeptide comprises a cell wall-binding domain and preferably an endopeptidase domain and/or an amidase domain as defined in the previous section.

A polypeptide domain encompassed by the current invention preferably has 80, 81, 82, 83, 84, 85, 86, 87, 88, 89, 90, 91, 92, 93, 94, 95, 96, 97, 98, 99 or 100% sequence identity with SEQ ID NO: 35, 36, 37, 38, 39, 40, 41 and/or 42. Preferably, a polypeptide domain encompassed by the current invention preferably comprises one ore more putative linkers and has 80, 81, 82, 83, 84, 85, 86, 87, 88, 89, 90, 91, 92, 93, 94, 95, 96, 97, 98, 99 or 100% sequence identity with SEQ ID NO: 51, 52, 53, 54, 55, 56, 57 and/or 58.

A polypeptide encompassed by the current invention preferably has 80, 81, 82, 83, 84, 85, 86, 87, 88, 89, 90, 91, 92, 93, 94, 95, 96, 97, 98, 99 or 100% sequence identity with SEQ ID NO: 21, 25, 26, 27, 29 and/or 32. More preferably, a polypeptide encompassed by the current invention preferably has 80, 81, 82, 83, 84, 85, 86, 87, 88, 89, 90, 91, 92, 93, 94, 95, 96, 97, 98, 99 or 100% sequence identity with SEQ ID NO: 25, 26, 27, 29 and/or 32 with SEQ ID NO: 25, 26, 27, 29 and/or 32.

In an embodiment of the current invention, a polypeptide preferably has at least 80% sequence identity with SEQ ID NO: 21, 25, 26, 27, 29, 32, 35, 36, 37, 38, 39, 40, 41, and/or 42 encoded by a nucleic acid construct with at least 80% identity with SEQ ID NO: 1, 5, 6, 7, 9, 20, 12, 13, 14, 15, 16, 17, 18 and/or 19, respectively. More preferably, a polypeptide of the current invention has at least 80% sequence identity with SEQ ID NO: 25, 26, 27, 29, 32, 35, 36, 37, 38, 39, 40, 41, and/or 42 encoded by a nucleic acid construct with at least 80% identity with SEQ ID NO: 5, 6, 7, 9, 20, 12, 13, 14, 15, 16, 17, 18 and/or 19, respectively.

A polypeptide according to the invention may have a length of at least 94, 95, 96, 100, 110 or 120 amino acids, preferably 127 amino acids and/or at most 1500, 1400, 1300 or 1200 amino acids. Preferably, said polypeptide has a length of at least 400, 410, 420, 430, 440, 450, 460, 470, 480, 490, 500, 510 or 520 amino acids and/or at most 1500, 1400, 1300 or 1200 amino acids. Also preferred is a polypeptide according to the invention with a length of at least 630, 640, 650, 660, 670, 680, 690, 700, 710 or 720 amino acids and/or at most 1500, 1400, 1300 or 1200 amino acids.

An amino acid or nucleotide sequence, encompassed by the present invention, may be derived from one of the sequences as identified herein by substituting, inserting, deleting, or adding one, 2, 3, 4, 5, 6, 7, 8, 9, 10, 12, 14, 16, 18, 20 or more nucleotides or amino acids, respectively. An amino acid sequence, encompassed by the present invention, may be derived from one of the sequences as identified herein by adding an additional N- or C-terminal amino acids or chemical moieties to increase stability, solubility and activity.

An embodiment of the invention encompasses a variant polypeptide. A variant polypeptide may be a non-naturally occurring form of the polypeptide. A polypeptide variant may differ in some engineered way from the polypeptide isolated from its native source. A variant may be made by site-directed mutagenesis starting from the nucleotide sequence of SEQ ID NO: 1, 5, 6, 7, 9, 12, 13, 14, 15, 16, 17, 18, 19 and/or 20. Preferably, a polypeptide variant contains mutations that do not alter the biological function of the encoded polypeptide. According to a preferred embodiment, a polypeptide variant exhibits *Staphylococcus* peptidoglycan cell wall-binding and/or a lytic activity which is the same or enhanced as compared to the *Staphylococcus* peptidoglycan cell-wall binding and/or lytic activity of *S. aureus* bacteriophage Φ2638a endolysin encoded by SEQ ID NO:1. A polypeptide variant of the invention preferably is a variant of SEQ ID NO: 21, 25, 26, 27, 29, 32, 35, 36, 37, 38, 39, 40, 41 and/or 42. A polypeptide variant with the same or an enhanced *Staphylococcus* peptidoglycan cell-wall binding and/or lytic activity is a polypeptide exhibiting a *Staphylococcus aureus* peptidoglycan cell-wall binding and/or lytic activity, which is the same or increased compared to the *Staphylococcus* peptidoglycan cell-wall binding and/or lytic activity of *S. aureus* bacteriophage Φ2638a endolysin encoded by SEQ ID NO:1 measured in an assay as earlier identified herein.

According to another preferred embodiment, a nucleotide sequence of the invention is a variant of the nucleotide sequences of SEQ ID NO: 1, 5, 6, 7, 9, 12, 13, 14, 15, 16, 17, 18, 19 and/or 20. Nucleotide sequence variants may be used for preparing a polypeptide variant as defined earlier. A nucleic acid variant may be a fragment of any of the nucleotide sequences as defined above. A nucleic acid variant may also be a nucleotide sequence that differs from SEQ ID NO: 1, 5, 6, 7, 9, 12, 13, 14, 15, 16, 17, 18, 19 and/or 20 by virtue of the degeneracy of the genetic code. A nucleic acid variant may also be an allelic variant of SEQ ID NO: 1, 5, 6, 7, 9, 12, 13, 14, 15, 16, 17, 18, 19 and/or 20. An allelic variant denotes any of two or more alternative forms of a gene occupying the same chromosome locus. A preferred nucleic acid variant is a nucleotide sequence, which contains silent mutation(s). Alternatively or in combination, a nucleic acid variant may also be obtained by introduction of nucleotide substitutions, which do not give rise to another amino acid sequence of the polypeptide encoded by the nucleotide sequence, but which corresponds to the codon usage of the host organism intended for production of the polypeptide of the invention. According to a preferred embodiment, a nucleic acid variant encodes a polypeptide still exhibiting its biological function. More preferably, a nucleotide sequence variant encodes a polypeptide exhibiting *Staphylococcus* peptidoglycan cell wall-binding and/or a lytic activity. Even more preferably, a nucleic acid variant encodes a polypeptide with enhanced *Staphylococcus* peptidoglycan cell wall-binding and/or lytic activity as defined earlier. Nucleic acids encoding a polypeptide exhibiting S *Staphylococcus* peptidoglycan cell wall-binding and/or lytic activity may be isolated from any microorganism.

All these variants can be obtained using techniques known to the skilled person, such as screening of library by hybridisation (southern blotting procedures) under low to medium to high hybridisation conditions with for the nucleotide sequence SEQ ID NO: 1, 5, 6, 7, 9, 12, 13, 14, 15, 16, 17, 18, 19 and/or 20 or a variant thereof which can be used to design a probe. Low to medium to high stringency conditions means prehybridization and hybridization at 42° C. in 5×SSPE, 0.3% SDS, 200 pg/ml sheared and denatured salmon sperm DNA, and either 25% 35% or 50% formamide for low to medium to high stringencies respectively. Subsequently, the hybridization reaction is washed three times for 30 minutes each using 2×SSC, 0.2% SDS and either 55° C., 65° C., or 75° C. for low to medium to high stringencies.

The sequence information as provided herein should not be so narrowly construed as to require inclusion of erroneously identified bases. The skilled person is capable of identifying such erroneously identified bases and knows how to correct for such errors.

Nucleic Acid Construct

In a further aspect, there is provided a nucleic acid construct comprising a nucleic acid molecule as identified in the previous section. This nucleic acid construct may comprise a first nucleic acid sequence encoding a polypeptide comprising a cell wall-binding domain, possibly further comprising a second and third and optionally fourth nucleic acid sequence as defined in the previous section.

The invention also relates to an expression vector comprising a nucleic acid construct of the invention. Preferably, an expression vector comprises a nucleotide sequence of the invention, which is operably linked to one or more control sequences, which direct the production or expression of the encoded polypeptide in a cell, a subject, or a cell-free expression system.

An expression vector may be seen as a recombinant expression vector. This vector can be constituted by a plasmid, a cosmid, a bacteriophage or a virus which is transformed by introducing a nucleic acid molecule according to the invention. Such transformation vectors according to the host organism to be transformed are well known to those skilled in the art and widely described in the literature.

A further subject of the invention is a process for the transformation of host organisms, by integrating a least one nucleic acid molecule of the invention, which transformation may be carried out by any suitable known means which have been widely described in the specialist literature and in particular in the references cited in the present application, more particularly by the vector according to the invention.

Cell

In a further aspect, the present invention relates to a cell, which comprises a nucleic acid construct or an expression vector of the invention as defined herein. A cell may be any microbial, prokaryotic or eukaryotic cell, which is suitable for expression of the polypeptide of the invention. In a preferred embodiment, said cell is an *E. Coli*. In an even more preferred embodiment, said cell is *E. coli* CL1blue MRF.

Method

In a further aspect, there is provided a method for producing, optionally purifying and optionally freeze-drying a polypeptide as defined in the previous section. Said method comprising the steps of:
  i) producing said polypeptide in a cell comprising a nucleic acid construct as defined in the previous section, optionally
  ii) purifying said polypeptide, and optionally
  iii) freeze-drying said purified polypeptide.

In a preferred embodiment, an *E. Coli* is used in step i) for producing a polypeptide using recombinant technologies. More preferably an *E. coli* XL1blueMRF is used in step i) for producing a polypeptide using recombinant technologies Preferably, in step ii), IMAC and Econo-Pac Chromatography columns (Biorad) packed with 5 mL low density Nickel chelating agarose beads (ABT beads) in combination with gravity flow is used to purify said (6xHis-tagged recombinant) polypeptides. The eluted polypeptide can be dialyzed for 2, 4, and 12 hours against 3×1 l lyophilization buffer, said buffer preferably comprising 50 mM phosphate, 500 mM sucrose, 200 mM mannitol, 0.005% polysorbate 20, pH 7.4.

Method

In a further aspect, the invention also relates to a method for producing a polypeptide with an enhanced lytic activity by treating a polypeptide as defined in the previous section or as obtainable by the method described above. Said treatment comprises substituting a divalent metal ion for increasing a lytic activity as compared to an untreated polypeptide, preferably said method comprising the steps of:
  i) dialyzing said polypeptide against a buffer comprising a chelating compound;
  ii) dialyzing said polypeptide against a divalent metal ion-containing buffer, preferably said divalent metal ion being selected from the group consisting of $Mn^{2+}$, $Co^{2+}$, $Cu^{2+}$, and $Zn^{2+}$.

A "chelating compound" being defined herein as a compound that binds a metal ion. Well known chelating compounds are ethylene diammine tetraacetic acid (EDTA) and ethylene glycol tetraacetic acid (EGTA). Preferably EDTA is used in step i) of the method of the invention.

Preferably, the divalent metal ion of step ii) is selected from the group consisting $Mn^{2+}$, $Co^{2+}$, $Cu^{2+}$, more preferably, said divalent metal ion is selected from the group consisting of $Mn^{2+}$ and $Co^{2+}$, even more preferably said divalent metal ion is $Mn^{2+}$.

We showed that substituting a divalent metal ion by any of the above defined resulted in an increase of a lytic activity of Ply2638 of 2-2.5 fold. Lytic activity was assessed spectrophotometrically as defined herein. Preferably, said method leads to an increase in a lytic activity of at least 1.1, 1.2, 1.3, 1.4, 1.5, 1.6, 1.7, 1.8, 1.9 or 2 fold as compared to an untreated polypeptide. Even more preferably, the method leads to an increase in a lytic activity of at least 2.5 fold. Preferably, the treated polypeptide exhibits a 0.7, 0.8, 0.9, 1.0, 1.1, 1.2, 1.3, 1.4, 1.5, 1.6, 1.7, 1.8, 1.9 to 2 fold increase in lytic activity as compared to the untreated polypeptide encoded by SEQ ID NO: 1.

Composition

In a further aspect, there is provided a composition comprising a nucleic acid molecule or a nucleic acid construct or a polypeptide or a vector or a cell as identified herein or obtainable by a method described herein. Preferably, the invention relates to a composition exhibiting a lytic activity as defined herein. More preferably, said composition is for use as a medicament. This medicament is preferably for treating, preventing and/or delaying an infectious disease. The invention also relates to a pharmaceutical or medical composition. Even more preferably, the invention relates to a pharmaceutical or medical composition for the treatment of an infectious disease. Preferably, the invention relates to a pharmaceutical or medical composition for the treatment of an infectious disease caused by a bacterium, preferably a bacterium of the genus *Staphylococcus*, more preferably a bacterium of the species *S. aureus*. Preferably, said infectious disease is a skin infection, mastitis, pneumonia, meningitis, endocarditis, Toxic Shock Syndrome (TSS), sepsis, septicemia, bacteremia, or osteomyelitis. Preferably, said skin infection is selected from the group of pimples, impetigo, boils, furuncles, cellulitis folliculitis, carbuncles, scaled skin syndrome and abscesses.

A composition as defined herein may comprise a mixture of different nucleic acid molecules, and/or nucleic acid constructs and/or polypeptides an/or vectors and/or cells as identified herein or obtainable by a method described herein.

A composition as defined herein may comprise one or more additional active ingredients. Active preferably being defined herein as showing a lytic activity as defined herein. Preferably, said one or more additional active ingredients are selected from the group consisting of a bacteriophage or phage and antibiotic. A phage encompassed herein can be any phage known in literature. Preferably, a phage encompassed by the present invention belongs, but is not limited, to a family of the list consisting of Myoviridae, Siphoviridae and Podoviridae. A phage encompassed by the present invention may also belong to a family of the list consisting of Tectiviridae, Corticoviridae, Lipothrixviridae, Plasmaviridae, Rudiviridae, Fuselloviridae, Inoviridae, Microviridae, Leviviridae and Cystoviridae. More preferably, said one or more active ingredients comprise and/or consist of lysostaphin, preferably *S. Simulans* lysostaphin having 80, 81, 82, 83, 84, 85, 86, 87, 88, 89, 90, 91, 92, 93, 94, 95, 96, 97, 98, 99 or 100% sequence identity with SEQ ID NO: 34, more preferably *S. Simulans* lysostaphin of SEQ ID NO: 34.). Even more preferably, said one or more active ingredients comprise and/or consist of both one or more different bacteriophages and lysostaphin, preferably, one or more different phages and *S. Simulans* lysostaphin (SEQ ID NO: 34). Within the context of this invention, a combination of active ingredients as defined herein can be administered sequentially and/or simultaneously.

A composition as defined herein may further comprise a pharmaceutically acceptable carrier. Such composition is preferably for use as a medicine or as a medicament. Preferably the medicament is used in the treatment of infectious diseases. A composition may be in the liquid, solid or semi-liquid or semi-solid form.

A composition of the invention can be used to treat animals, including humans, infected with *S. aureus*. Any suitable route of administration can be used to administer said composition including but not limited to: oral, aerosol or other device for delivery to the lungs, nasal spray, intravenous, intramuscular, intraperitoneal, intrathecal, vaginal, rectal, topical, lumbar puncture, intrathecal, and direct application to the brain and/or meninges.

A composition comprising a nucleic acid molecule or a nucleic acid construct or a polypeptide or a vector or a cell as identified herein or obtainable by a method described herein is preferably said to be active, functional or therapeutically active or able to treat, prevent and/or delay an infectious disease when it decreases the amount of a *Staphylococcus* genera present in a patient or in a cell of said patient or in a cell line or in a cell free in vitro system and preferably means that 99%, 90%, 80%, 70%, 60%, 50%, 40%, 30%, 20%, 10%, 5% or less of the initial amount of a *Staphylococcus* genera, is still detectable. Preferably no *Staphylococcus* genera is detectable. In this paragraph, the expression "amount of *Staphylococcus* genera" preferably means alive *Staphylococcus* genera. *Staphylococcus* genera may be detected using standard techniques known by the artisan such as immunohistochemical techniques using *Staphylococcus* specific antibodies, tube coagulase tests that detect staphylocoagulase or "free coagulase", detection of surface proteins such as clumping factor (slide coagulase test) and/or protein A (commercial latex tests). Alive *Staphylococcus* genera may be detected using standard techniques known by the artisan such as microbiological bacterial culture techniques and/or real-time quantitative reverse transcription polymerase chain reaction to assay for bacterial mRNA.

Said decrease is preferably assessed in a tissue or in a cell of an individual or a patient by comparison to the amount present in said individual or patient before treatment with said composition or polypeptide of the invention. Alternatively, the comparison can be made with a tissue or cell of said individual or patient which has not yet been treated with said composition or polypeptide in case the treatment is local.

A composition comprising a nucleic acid molecule or a nucleic acid construct or a polypeptide or a vector or a cell as identified herein or obtainable by a method described herein may be administered to a patient or of a cell, tissue or organ or said patient at least one week, one month, six month, one year or more.

In another embodiment, the invention relates to a non-medical composition exhibiting a binding and/or lytic activity as defined herein. Preferably the invention relates to an antimicrobial. Preferably, the invention relates to an antimicrobial for lysing a bacterium, preferably a bacterium of the genus *Staphylococcus*, more preferably a bacterium of the species *S. aureus*. Preferably the invention relates to an antimicrobial as food preservative or disinfectant.

Use

In a further aspect, the invention relates to the use of a polypeptide comprising domains encoded by a first, second, third and optionally fourth nucleic acid sequence as defined herein, a nucleic acid molecule encoding such polypeptide, a construct comprising such nucleic acid molecule, a vector comprising such construct, a cell comprising such vector and/or a composition comprising any of the above, preferably as antimicrobial. Preferably, the invention relates the use as an antimicrobial for lysing a bacterium, preferably a bacterium of the genus *Staphylococcus*, more preferably a bacterium of the species *S. aureus*. Preferably the invention relates to an antimicrobial as food preservative or disinfectant. Possibly, such food preservatives or disinfectants are used together with other antimicrobial agents. Preferably, such food preservatives or disinfectants are used in combination with one or more additional active ingredients as defined herein. Preferably, said one or more additional active ingredients are selected from the group consisting of a bacteriophage or phage and antibiotic as defined herein.

The above-referenced polypeptide, nucleic acid molecule, construct, vector, cell and/or composition can be applied on or into food products, and/or into various physical sites to be disinfected, by a number of means including, but not limited to, admixing said polypeptide and/or cell containing polypeptide of the invention into the food products, spraying said polypeptide and/or cell containing the polypeptide of the invention onto the foodstuffs or physical sites to be disinfected.

A polypeptide of the invention can be isolated from a cell or a cell containing said polypeptide of the invention can be directly applied or administered without isolation of said polypeptide. For example, a cell which produces a polypeptide of the invention could be administered to a subject (human or animal) or applied to a surface where the polypeptide of the invention would be secreted into food, onto a surface or into the subject's gut. The polypeptide of the invention can then bind and optionally lyse bacterial cells, preferably a bacterium of the genus *Staphylococcus*, more preferably a bacterium of the species *S. aureus*, present in this environment.

Further encompassed is the use of a polypeptide comprising a domain encoded by a first nucleic acid sequence as defined herein, a nucleic acid molecule encoding such polypeptide, a construct comprising such nucleic acid molecule, a vector comprising such construct, a cell comprising such vector and/or a composition comprising any of the above, preferably for detecting bacteria, more preferably for detecting bacteria of the genus *Staphylococcus*, more preferably a bacterium of the species *S. aureus*. Preferably, said polypeptide, nucleic acid molecule, construct, vector, cell and/or composition is used in a diagnostic application. Possibly said polypeptide, nucleic acid molecule, a construct, a vector, cell and/or a composition is used together with other detection agents.

Method

The invention further relates in a further aspect to a method for treating, delaying and/or preventing an infectious disease by administering a composition as earlier defined herein. All features of this method have already been defined herein.

DEFINITIONS

Sequence Identity

"Sequence identity" is herein defined as a relationship between two or more amino acid (peptide, polypeptide, or protein) sequences or two or more nucleic acid (nucleotide, polynucleotide) sequences, as determined by comparing the sequences. In the art, "identity" also means the degree of sequence relatedness between amino acid or nucleotide sequences, as the case may be, as determined by the match between strings of such sequences. "Similarity" between two amino acid sequences is determined by comparing the amino acid sequence and its conserved amino acid substitutes of one peptide or polypeptide to the sequence of a second peptide or polypeptide. In a preferred embodiment, identity or similarity is calculated over the whole SEQ ID NO as identified herein. "Identity" and "similarity" can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988).

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215:403-410 (1990). The well-known Smith Waterman algorithm may also be used to determine identity.

Preferred parameters for polypeptide sequence comparison include the following: Algorithm: Needleman and Wunsch, J. Mol. Biol. 48:443-453 (1970); Comparison matrix: BLOSSUM62 from Hentikoff and Hentikoff, Proc. Natl. Acad. Sci. USA. 89:10915-10919 (1992); Gap Penalty: 12; and Gap Length Penalty: 4. A program useful with these parameters is publicly available as the "Ogap" program from Genetics Computer Group, located in Madison, Wis. The aforementioned parameters are the default parameters for amino acid comparisons (along with no penalty for end gaps).

Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to ser; Arg to lys; Asn to gln or his; Asp to glu; Cys to ser or ala; Gln to asn; Glu to asp; Gly to pro; His to asn or gln; Ile to leu or val; Leu to ile or val; Lys to arg; gln or glu; Met to leu or ile; Phe to met, leu or tyr; Ser to thr; Thr to ser; Trp to tyr; Tyr to trp or phe; and, Val to ile or leu.

Nucleic Acid Construct, Transformation, Expression Vector, Operably Linked, Expression, Control Sequences, Polypeptide Construct A nucleic acid molecule is represented by a nucleotide sequence. A polypeptide is represented by an amino acid sequence. A nucleic acid construct is defined as a nucleic acid molecule which is isolated from a naturally occurring gene or which has been modified to contain segments of nucleic acids which are combined or juxtaposed in a manner which would not otherwise exist in nature. A nucleic acid molecule is represented by a nucleotide sequence. Optionally, a nucleotide sequence present in a nucleic acid construct is operably linked to one or more control sequences, which direct the production or expression of said peptide or polypeptide in a cell or in a subject.

"Operably linked" is defined herein as a configuration in which a control sequence is appropriately placed at a position relative to the nucleotide sequence coding for the polypeptide of the invention such that the control sequence directs the production/expression of the peptide or polypeptide of the invention in a cell and/or in a subject.

"Operably linked" may also be used for defining a configuration in which a sequence is appropriately placed at a position relative to another sequence coding for a functional domain such that a chimeric polypeptide is encoded in a cell and/or in a subject.

Expression will be understood to include any step involved in the production of the peptide or polypeptide including, but not limited to, transcription, post-transcriptional modification, translation, post-translational modification and secretion.

Control sequence is defined herein to include all components which are necessary or advantageous for the expression of a polypeptide. At a minimum, the control sequences include a promoter and transcriptional and translational stop signals. Optionally, a promoter represented by a nucleotide sequence present in a nucleic acid construct is operably linked to another nucleotide sequence encoding a peptide or polypeptide as identified herein.

The term "transformation" refers to a permanent or transient genetic change induced in a cell following the incorporation of new DNA (i.e. DNA exogenous to the cell). When the cell is a bacterial cell, as is intended in the current invention, the term usually refers to an extrachromosomal, self-replicating vector which harbors a selectable antibiotic resistance.

An expression vector may be any vector which can be conveniently subjected to recombinant DNA procedures and can bring about the expression of a nucleotide sequence encoding a polypeptide of the invention in a cell and/or in a subject. As used herein, the term "promoter" refers to a nucleic acid fragment that functions to control the transcription of one or more genes or nucleic acids, located upstream with respect to the direction of transcription of the transcription initiation site of the gene. It is related to the binding site identified by the presence of a binding site for DNA-dependent RNA polymerase, transcription initiation sites, and any other DNA sequences, including, but not limited to, transcription factor binding sites, repressor and activator protein binding sites, and any other sequences of nucleotides known to one skilled in the art to act directly or indirectly to regulate the amount of transcription from the promoter. Within the context of the invention, a promoter preferably ends at nucleotide −1 of the transcription start site (TSS).

"Polypeptide" as used herein refers to any peptide, oligopeptide, polypeptide, gene product, expression product, or protein. A polypeptide is comprised of consecutive amino acids. The term "polypeptide" encompasses naturally occurring or synthetic molecules.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a product or a composition or a nucleic acid molecule or a peptide or polypeptide of a nucleic acid construct or vector or cell as defined herein may comprise additional component(s) than the ones specifically identified; said additional component(s) not altering the unique characteristic of the invention. In addition, reference to an element by the indefinite article "a" or "an" does not exclude the possibility that more than one of the elements is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

EXAMPLES

Materials and Methods

Figure 1:
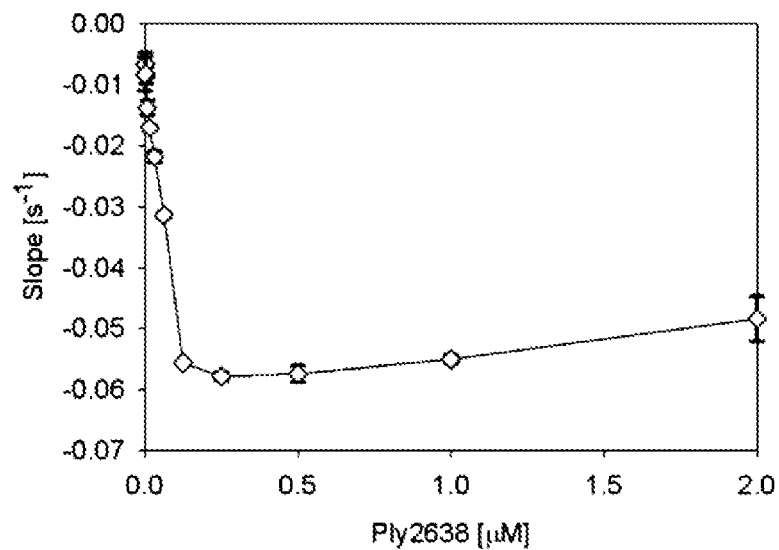
FIG. 1. Linear relationship of Ply2638 (SEQ ID NO: 21 encoded by SEQ ID NO: 44) activity against *S. aureus* SA2638/2854 cells in dependency of endolysin concentration. Assays were performed under standard conditions (PBS buffer pH 7.4, 120 mM sodium chloride) in photometric lysis assays. Maximum activity was determined from the first derivative of regression fits from sigmoidal lysis curves, calculated with SigmaPlot software. Error bars represent standard deviation calculated from technical triplicate experiments.
Figure 2:
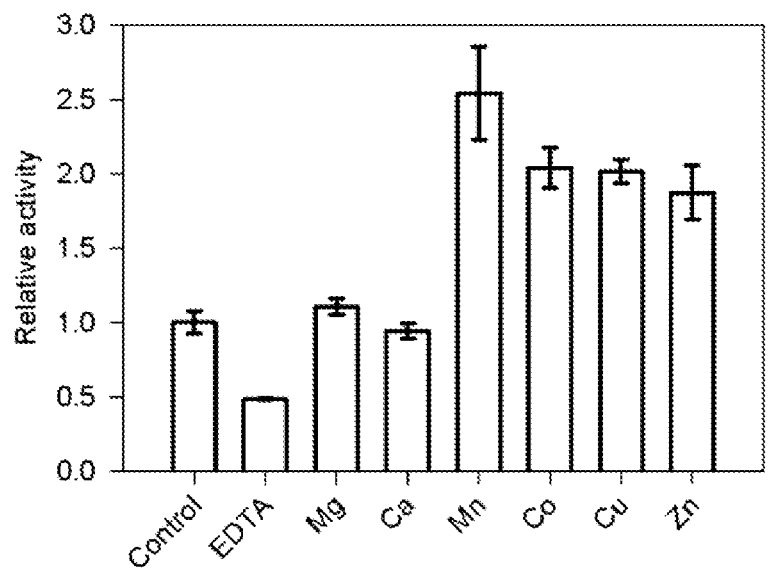
FIG. 2. Influence of divalent cations on lytic activity of Ply2638 (SEQ ID NO: 21, encoded by SEQ ID NO: 44). The enzyme was EDTA treated with subsequent substitution of metal ions by dialysis against MOPS buffer containing $MgCl_2$, $CaCl_2$, $ZnCl_2$, $CuCl_2$, $CoCl_2$, or $MnSO_4$. Ply2638 dialyzed against MOPS buffer omitting EDTA treatment served as reference. Error bars represent standard deviation, calculated from technical triplicate experiments.
Figure 3:
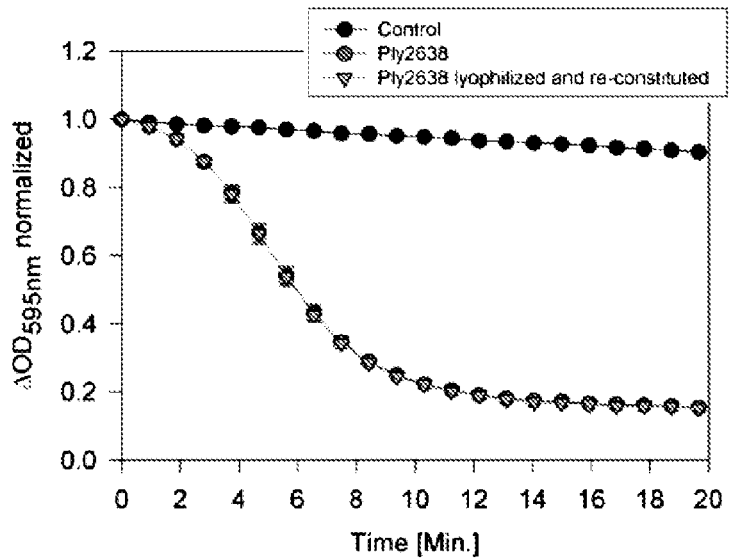
FIG. 3. Lytic activity of 50 nM Ply2638 (SEQ ID NO: 21, encoded by SEQ ID NO: 44) on *S. aureus* SA2638/2854 cells after lyophilization and reconstitution. Activity was measured in a turbidity reduction assay under standard conditions. Lyophilization buffer was taken as a control. The triple domain enzyme recovers full lytic activity after freeze-drying.
Figure 4:
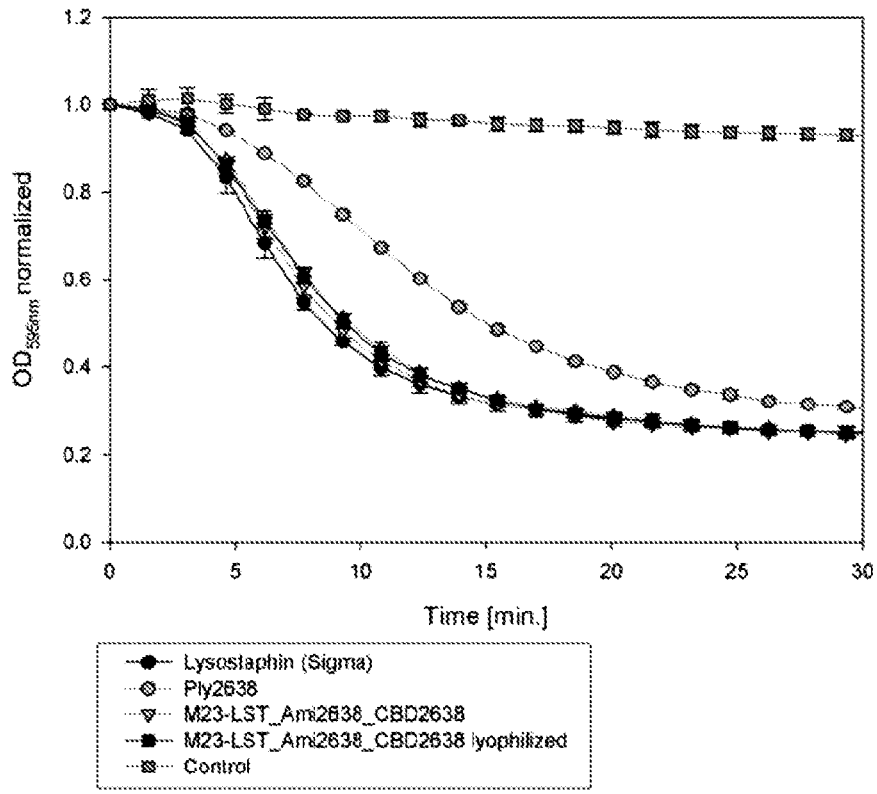
FIG. 4. Lytic activity of 50 nM M23-LST_Ami2638_CBD2638 (SEQ ID NO: 29, encoded by SEQ ID NO: 48) on *S. aureus* SA2638/2854 cells after lyophilization and reconstitution (indicated as lyophilized) as compared to freshly prepared M23-LST_Ami2638_CBD2638 (SEQ ID NO: 29, encoded by SEQ ID NO: 48) and Ply2638 (SEQ ID NO: 21, encoded by SEQ ID NO: 44). Lyophilization buffer was taken as a control. Activity was measured in a turbidity reduction assay under standard conditions. The triple domain enzyme recovers full lytic activity after freeze-drying.
Figure 5:
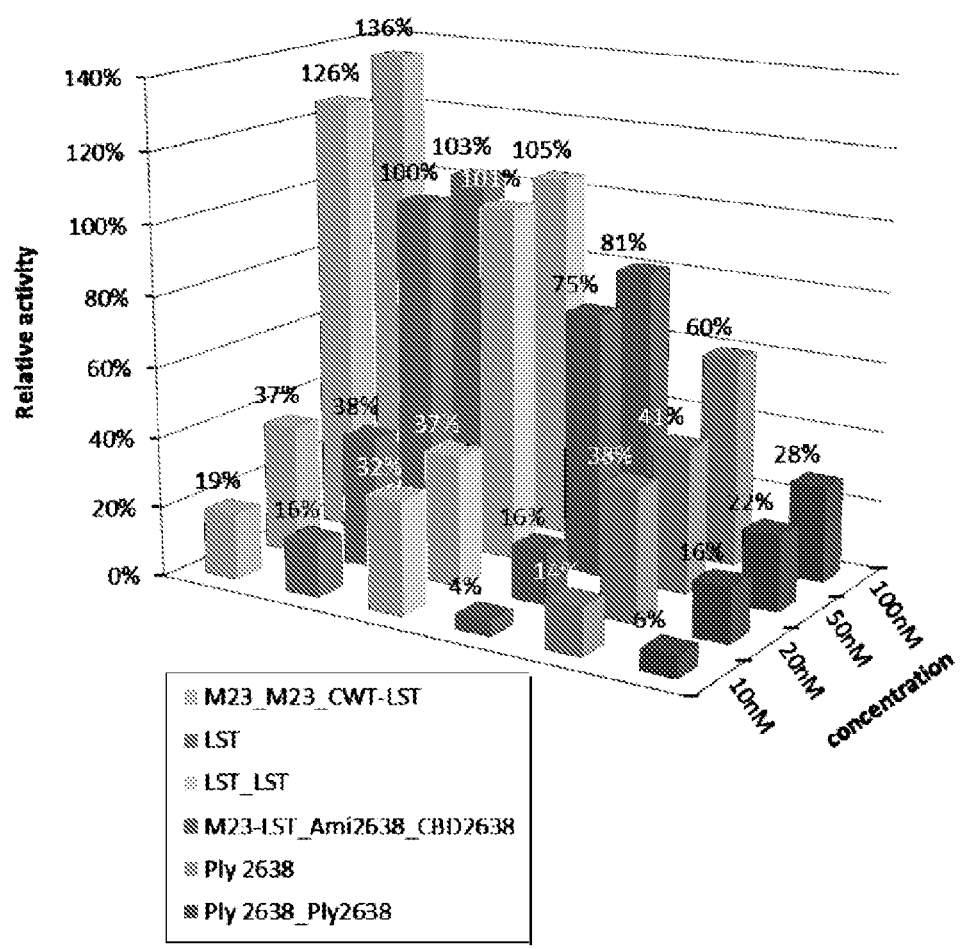
FIG. 5. Relative activity of Lysostaphin (LST; SEQ ID NO: 34, encoded by SEQ ID NO: 33) and Ply2638 derivatives (SEQ ID NO: 31, 30, 29, 21 and 24, encoded by SEQ ID NO: 11, 10, 48, 44 and 4, respectively) in dependency of the concentration. The activity of LST at 50 nM was set as reference. All assays were done under standard conditions (37° C., pH 7.4 and 120 mM sodium chloride concentration) using *S. aureus* SA2638/2854 substrate cells from frozen stock.
Figure 6A:
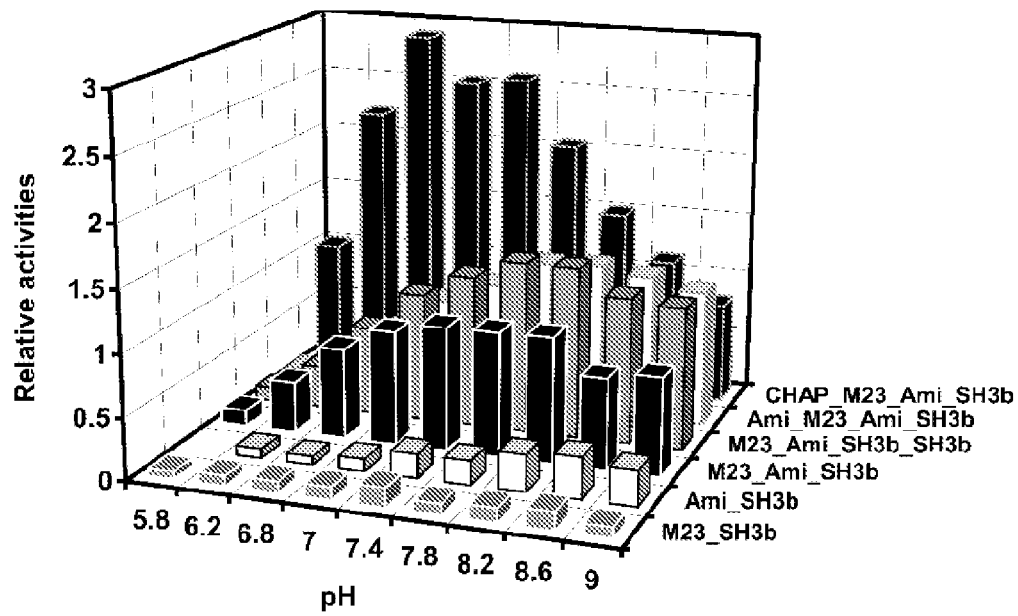
FIG. 6. Relative activities at various pH values (left diagram) and sodium chloride concentrations (right diagram) of truncated and (with PlyTw domains) retrofitted Ply2638 variants determined in turbidity reduction assays. Truncation of the enzyme by one of the two catalytic domains resulted in impaired activities. Duplication of the CBD (M23_Ami_SH3b_SH3b; SEQ ID NO: 32, encoded by SEQ ID NO: 49) accelerates lysis at basic pH values and elevated salt concentrations. Retrofitting of Ply2638 with CHAP11 domain results in an enzyme which is presumed to attack three different bonds in the peptidoglycan layer of *Staphylococcus*. It shifted pH optima to slight acidic conditions and improved antibacterial activity. However, protein stability of the chimeric enzymes remains a challenge. Maximum lysis velocity of Ply2638 at standard conditions (pH 7.4 and 120 mM sodium chloride concentration) was set as reference. Bars represent mean of triplicate assays, standard deviation is not shown. (CHAP_M23_Ami_SH3b=SEQ ID NO: 25, encoded by SEQ ID NO: 45; Ami_M23_Ami_SH3b=SEQ ID NO: 26, encoded by SEQ ID NO: 46; M23_Ami_SH3b_SH3b=SEQ ID NO: 32, encoded by SEQ ID NO: 49; M23_Ami_SH3b=SEQ ID NO: 21, encoded by SEQ ID NO: 44; Ami_SH3b=SEQ ID NO: 22, encoded by SEQ ID NO: 2; M23_SH3b=SEQ ID NO: 23, encoded by SEQ ID NO: 3).
Figure 6B:
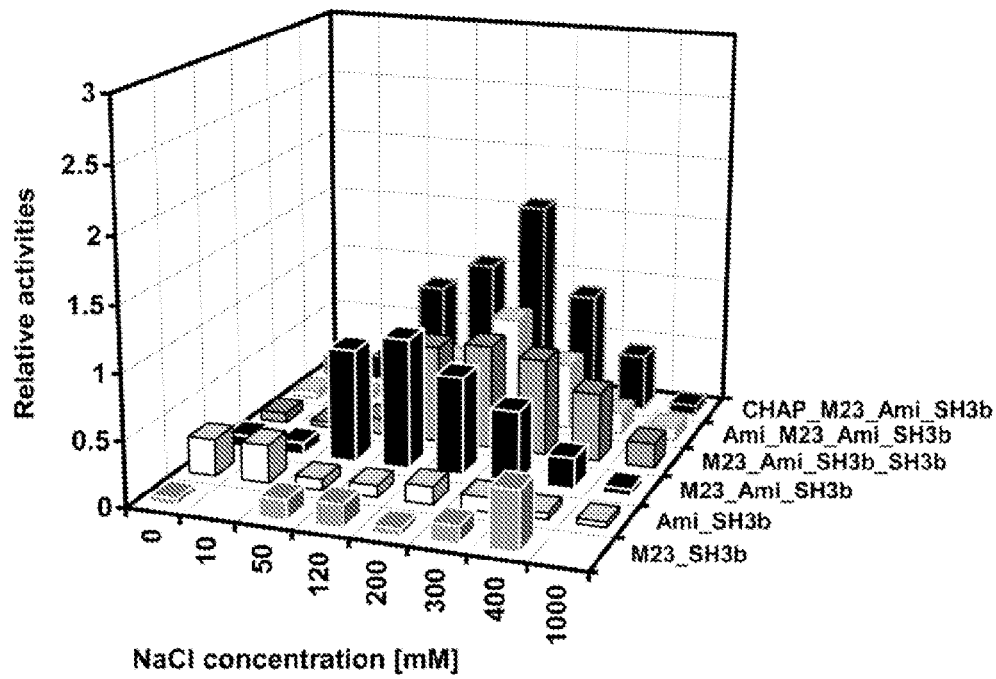
Figure 7:
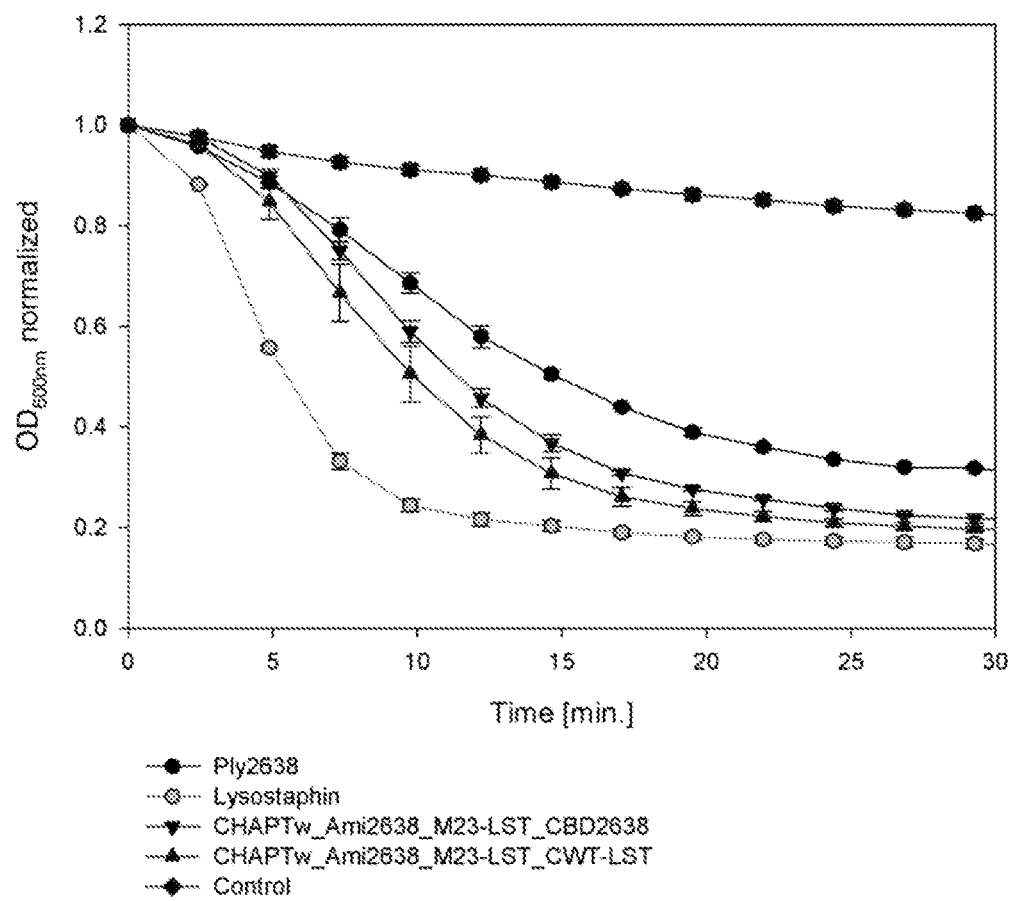
FIG. 7: Activity of 50 nM quadruple domain enzymes (SEQ ID NO: 27 and 28, encoded by SEQ ID NO: 47 and 8, respectively), Ply2638 (SEQ ID NO: 21, encoded by SEQ ID NO: 44), and Lysotaphin (SEQ ID NO: 34, encoded by SEQ ID NO: 33) against using *S. aureus* SA2638/2854 substrate cells under standard conditions. Lyophilization buffer was taken as a control. Quadruple domain enzymes were constructed by combining domains of Ply2638, PlyTw, and Lysostaphin.

Bacterial Strains, Culture Conditions, Phages and Plasmids

*E. coli* XL1BlueMRF' and *E. coli* Sure was used for the over-expression of 6×-His-tagged (SEQ ID NO: 43) fusion proteins. Both strains were cultured in LB-PE medium at 30° C. with 100 µg/ml ampicillin and 30 µg/ml tetracycline for plasmid selection. Phage 2638A lysate were used as template for the amplification of Ply2638A gene or domain coding regions thereof. CHAPTw domain (SEQ ID NO: 19) was amplified from Phage Twort lysate. Cystein-Histidine dependent amidase/peptidase (CHAP) domain and amidase domain from phage 11 (SEQ ID NO 18 and 17, respectively; Donovan, et al., 2006 and 2008; Navarre et al., 1999; Sass and Bierbaum 2007) were amplified from a pet21a vector containing phi11 autolysin gene, a kindly gift from Donovan, D. M. Plasmid LT1215 containing the sequence of mature Lysostaphin (SEQ ID NO: 33) was used as template for domain amplification M23-LST (SEQ ID NO: 15) and CWT-LST (SEQ ID NO: 13).

pQE-30 vector (catalogues number: 32915, Qiagen, Hilden, Germany; SEQ ID NO: 50) was used as cloning and expression vector for the production of 6x-His tagged recombinant fusion proteins in *E. coli* XL1BlueMRF' or *E. coli* Sure respectively.

DNA Techniques and Cloning Procedures

Standard techniques according to Sambrook, Maniatis et al. (1989) were employed for cloning of single genes and the creation of fusion proteins. High Fidelity PCR Enzyme mix (Fermentas) was used in PCR reactions. DNA concentrations were determined with a spectrophotometer (NanoDrop ND-1000 Spectrophotometer).

pHPl2638 is constructed by insertion of Ply2638 (SEQ ID NO: 1) encoding sequence Met1-Lys486 into pQE30 (SEQ ID NO: 50) sites BamHI-SalI. pHPl2638-Pl2638 construct has the same sequence consecutively inserted into BamHI-SacI-SalI sites. CHAP11 (SEQ ID NO: 18), Ami11 (SEQ ID NO: 17) and CHAP_Ami11 were N-terminal introduced into BamHI digested pHPL2638A. Prior to ligation reaction, the vector was dephosphorylated using shrimp alkaline phosphatase (SAP, Fermentas). pHM23_CBD2638 (SEQ ID NO: 3), and pHM23-2638_Ami_2638_CBD2638_CBD2638 (SEQ ID NO: 49) were constructed by a replacement of GFP coding region from pHGFP_CBD2638A_c vector (SEQ ID NO: 59) with the respective inserts using BamHI and SacI restriction sites. pHM23-LST_Ami2638_CBD2638 (SEQ ID NO: 48) has a pQE-30 backbone with mature lysostaphin (SEQ ID NO: 33) coding sequence Ala1-Gly154 inserted into BamHI and SacI and Ply2638 partial sequence encoding Leu138-Lys486 in SacI and SalI sites. pHM23-LST_M23-LST_CWT-LST (SEQ ID NO: 11) has mature Lysostaphin (SEQ ID NO: 33) sequences Ala1-Gly154 inserted into BamHI and SacI and Ala1-Lys246 into SacI and SalI sites of pQE30. pHLST-LST (SEQ ID NO: 10) is constructed the same way having Ala1-Lys246 repeatedly in BamHI-SacI and SacI-SalI sites. In plasmids encoding quadruple domain constructs pHCHAPTw_Ami2638_M23-LST_CBD2638 (SEQ ID NO: 47) and pHCHAPTw_Ami2638_M23-LST_CWT-LST (SEQ ID NO: 8) the domains are directly fused via splicing overlap extension PCR (SOE) and inserted into pQE30 BamHI and SalI sites. In both constructs, boarder regions of individual domains (CHAPTw, SEQ ID NO: 19: Met1-Ile140, Ami2638, SEQ ID NO: 16: Lys141-Gly358 of SEQ ID NO: 1, CBD2638, SEQ ID NO: 12: Trp393-Lys486 of SEQ ID NO: 1, M23-LST, SEQ ID NO: 15: Ala1-Gly154 of SEQ ID NO: 33, CWT-LST, SEQ ID NO: 13: Trp155-Lys246 of SEQ ID NO: 33) were determined with bioinformatics (unpublished data). Plasmids with repetitive sequences were transferred into *E. coli* Sure strain, all other plasmids into *E. coli* XL1BlueMRF'.

Expression and Purification of Recombinant Fusion Proteins

Protein overexpression and partial purification was essentially done as previously described by others (Loessner et al., 1996, Schmelcher et al., 2010). In brief, plasmid bearing *E. coli* were grown in 250 ml modified LB medium (15 g/l tryptose, 8 g/l yeast extract, 5 g/l NaCl, pH 7.8) to an optical density at 600 nm (OD600 nm) of 0.4 to 0.6 and induced with 1 mM IPTG. Cells were further incubated for 4 hours at 30° C., or 18 hours at 20° C., cooled to 4° C., and harvested by centrifugation. Cell pellets were suspended in 5 ml immobilization buffer (50 mM $NaH_2PO_4$, 500 mM NaCl, 5 mM imidazole, 0.1% polysorbate 20, pH 7.4). Cytosolic *E. coli* contents containing soluble recombinant proteins were liberated by a double passage through a French Pressure Cell Press (1200 psi, SLM Aminco, Urbana, Ill., U.S.) operated at 1200 psi. Other downstream processing steps included removal of insoluble cell debris by centrifugation, filter sterilization (0.2 µm PES membrane, Millipore), and Immobilized Metal Affinity Chromatography (IMAC) purification using Micro-Biospin (Bio-Rad, Hercules, Calif., U.S.) columns packet with low density Ni-NTA Superflow resin (Chemie Brunschwig AG, Basel, Switzerland). Ni-NTA immobilized proteins were on-column gravity flow washed with 5-10 column volumes immobilization buffer. Protein fractions were then eluted with elution buffer (50 mM $NaH_2PO_4$, 500 mM NaCl, 125 mM imidazole, 0.1% polysorbate 20, pH 7.4) and dialyzed against two changes of dialysis buffer (50 mM $NaH_2PO_4$, 100 mM NaCl, 0.1% polysorbate 20, pH 7.4). Protein concentrations were defined in a NanoDrop ND-1000 spectrophotometer, corrected for specific absorbance at 280 nm as calculated from the primary amino acid sequence with Vector NTI software (Invitrogen, Carlsbad, Calif., U.S.) and estimated for purity by SDS-PAGE. Aliquots were stored at −20° C. mixed with 50% glycerol.

Lyophilization of Recombinant Proteins

IMAC purified proteins were dialyzed against 3 changes of 300 ml lyophilization buffer (50 mM phosphate or Tris, 500 mM sucrose, 200 mM mannitol, pH 7.4) aliquot and frozen in the gaseous phase of liquid nitrogen. The freeze-drying was done at −40° C. and vacuum at 75 mTorr for 60 minutes, followed by increasing temperature during 5 hours to −10° C. and another 60 minutes at −10° C. at the same vacuum levels. As final step, temperature was increased to 25° C. during 10 hours. Samples were reconstituted prior to testing in lysis assays by the addition of water.

Cell Wall-Binding Assay

As a standard assay to determine the ability of a CBD to direct a GFP fusion to the bacterial surface and mediate tight binding to the cell wall ligand, the following conditions is used: bacteria, preferably *S. aureus* BB255, from late log phase are harvested by centrifugation, resuspended in ¹⁄₁₀th volume of PBS-T (50 mM $NaH_2PO_4$, 120 mM NaCl [pH 8.0], 0.01% polysorbate 20) and stored on ice. GFP-CBD proteins, preferably SEQ ID NO: 64, encoded by SEQ ID NO: 60, are diluted in the same buffer to a concentration of 400 nM (2×GFP-CBD) and also stored on ice. In a 1.5 ml microcentrifuge cup, 100 µl cells and 100 µl of 2×GFP-CBD are mixed and incubated at room temperature for 5 min. Cells are then removed from the supernatant by centrifugation in a microfuge (16000 g, 60 s). The supernatant was discarded and cells were washed twice in 500 µl of PBS-T buffer. For fluorescence microscopy the pellet was finally resuspended in 50 µl of buffer. For fluorometer assays, the pellet is finally resuspended in 200 µl of PBS-T and transferred to a microplate well. Quantitative fluorescence assays can be performed using a multi label counter device (Victor$^3$, Perkin Elmer, Mass., U.S.) with sterile, untreated, black 96-well polystyrene microplates (Nunc, Roskilde, Denmark). As a negative control GFP can be used.

Quantitative Fluorescence Assays

Dependency of pH and salt on CBD2638 to *S. aureus* BB255 cell surface ligand interaction is investigated by incubation of cells from 1 ml volume set to an $OD_{600\,nm}$ 1+/−0.05 (~4×10$^9$ cells) with 7.5 µg GFP-CBDS2638 fusion protein, SEQ ID NO: 64, encoded by SEQ ID NO: 60. This cell to protein ratio is close to saturation point as determined in previous experiments and enables detection of variations in binding efficiencies. Varying pH is tested using citrate buffers pH 4.5 to 6.5 and phosphate buffers pH 6 to 9. After incubation with GFP-CBD2638 protein in pH buffer, cells are washed with respective pH buffer followed by standard PBS-T (pH 8) washing. Finally, cells are adjusted to an $OD_{595\ nm}$=0.3 to detect fluorescence from 200 µl suspensions thereof with a Victor³ multi label counter. Similar experiments are performed using buffers prepared with increasing sodium chloride concentrations (10 mM $NaH_2PO_4$, 0-1000 mM NaCl, 0.1% polysorbate 20, pH 6).

Quantification of CBD binding capacity of *Staphylococcus* strains with altered cell surface properties is tested by recording relative fluorescence units (RFU) of washed and heat killed cells previously incubated with excessive GFP-CBD2638 protein. Fluorescence of equal volumes (200 µl) of GFP-CBD2638 labeled cells, adjusted to an $OD_{595\ nm}$=0.3, are measured using appropriate filter sets in a multi label counter device. Comparison and quantification of absorption levels of GFP-CBD2638 (SEQ ID NO: 64, encoded by SEQ ID NO: 60), GFP-CBD2638-CBD2638 (SEQ ID NO 65 and/or 66, encoded by SEQ ID NO: 61 and 62, respectively), and GFP-CBD2638-CBD2638-CBD2638 (SEQ ID NO: 67, encoded SEQ ID NO: 63) on *S. aureus* BB255 cells and SDS treated cells is done the same way.

Lysis Assays

Substrate cell for lytic activity assays were grown to an optical density at 600 nm (OD600) of 0.4, washed twice with PBST pH 7.4 and re-suspended in 15% glycerol containing PBS buffer pH 7.4 concentrating it at the same time 100 fold. The cells were stored at −20° C. For further use in binding or lytic activity assays the cells were thaw, washed with PBS pH 7.4 and diluted to an OD600 of 1±0.05. In standard lytic activity assays protein samples were diluted to equimolar amounts and distributed in transparent 96-well tissue culture test plates (SPL life sciences, Pocheon, Korea). Substrate cells were added to a final volume and drop in optical density at 595 nm (OD595 nm) were recorded for about 1 hour at 37° C.

Lytic activity of retrofitted and deletion constructs of Ply2638 were tested against Phage 2638A propagation strain *S. aureus* SA2638/2854 from frozen stock in lysis assays. We tested the activity at various buffer conditions. pH values from 4.6 to 9 in 0.4 increments were tested using Citrate/Phosphate buffers (25 mM Citrate, 25 mM Phosphate, 120 mM NaCl, pH 4.6-6.6) and Tris/Phosphate buffers (25 mM Tris, 25 mM Phosphate, 120 mM NaCl). The activity of Ply2638A derivatives at salt concentrations ranging from 0 to 1000 mM Sodium chloride (in 10 mM phosphate buffer pH 7.4) was tested. The Ply2638A derivatives were diluted to 10 µM final concentration with MQ prior to its application in lysis assays. Here, 4 µl of 10 µM Ply2638A derivatives were applied to 196 µl substrate cell suspensions using a multichannel pipette, resulting in an assay concentration of 200 nM protein. The substrate cell suspensions were prepared from frozen stocks, diluting it with pH or salt buffers and standardizing it spectrophotometrically (Libra S22, Biochrom) to an initial OD600 of 1±0.05. Decrease in optical density at 595 nm (OD595) was measured using a Victor3 1420 Multilabel Counter instrument (Perkin Elmer) during 1 hour. Plates were shaken vigorously for 1 second (double orbit, 0.1 mm diameter) after every single read out. As positive control served N-terminal 6×His tagged Lysostaphin (HLST), commercially available Lysostaphin (recombinant, *E. coli* originated, Sigma). As negative control we applied MilliQ water.

Influence of Divalent Metal Ions on the Activity of Ply2638

Partially purified Ply2638 (SEQ ID NO: 21) was dialyzed for 2 hours against EDTA containing buffer (50 mM MOPS, 100 mM sodium chloride, 0.005% polysorbate 20, 10 mM EDTA) followed by dialysis against buffer containing the respective divalent metal ions (50 mM MOPS, 100 mM sodium chloride, 0.005% polysorbate 20, and 10 mM $CaCl_2$, 10 mM $MgCl_2$, 1 mM $CoCl_2$, 1 mM $CuCl_2$, 1 mM $MnSO_4$, or 1 mM $ZnCl_2$ respectively). Cells used as substrate were SDS treated and EDTA washed prior to its application in standard lysis assays.

TABLE 1

SEQ ID NO identification

| enzyme/domain/<br>construct/vector | nucleic acid<br>sequence | amino acid<br>sequence | amino acid<br>sequence<br>of domain<br>with putative<br>linker | nucleic acid<br>sequence of<br>His-tagged<br>construct |
|---|---|---|---|---|
| Mature enzyme | | | | |
| Ply2638 | SEQ ID NO: 1 | SEQ ID NO: 21 | | SEQ ID NO: 44 |
| LST | SEQ ID NO: 33 | SEQ ID NO: 34 | | |
| Domain | | | | |
| CBD-2638 | SEQ ID NO: 12 | SEQ ID NO: 35 | SEQ ID NO: 51 | |
| CWT-LST | SEQ ID NO: 13 | SEQ ID NO: 36 | SEQ ID NO: 52 | |
| M23-2638 | SEQ ID NO: 14 | SEQ ID NO: 37 | SEQ ID NO: 53 | |
| M23-LST | SEQ ID NO: 15 | SEQ ID NO: 38 | SEQ ID NO: 54 | |
| Ami-2638 | SEQ ID NO: 16 | SEQ ID NO: 39 | SEQ ID NO: 55 | |
| Ami-φ11 | SEQ ID NO: 17 | SEQ ID NO: 40 | SEQ ID NO: 56 | |
| CHAP-φ11 | SEQ ID NO: 18 | SEQ ID NO: 41 | SEQ ID NO: 57 | |
| CHAP-φTwort | SEQ ID NO: 19 | SEQ ID NO: 42 | SEQ ID NO: 58 | |

TABLE 1-continued

SEQ ID NO identification

Retrofitted construct

| | | | |
|---|---|---|---|
| CHAP11_M23-2638_Ami2638_CBD2638 | SEQ ID NO: 5 | SEQ ID NO: 25 | SEQ ID NO: 45 |
| Ami11_M23-2638_Ami2638_CBD2638 | SEQ ID NO: 6 | SEQ ID NO: 26 | SEQ ID NO: 46 |
| CHAPTw_Ami2638_M23-LST_CBD2638 | SEQ ID NO: 7 | SEQ ID NO: 27 | SEQ ID NO: 47 |
| M23-LST_Ami2638_CBD2638 | SEQ ID NO: 9 | SEQ ID NO: 29 | SEQ ID NO: 48 |
| M23-2638_Ami2638_CBD2638_CBD2638 | SEQ ID NO: 20 | SEQ ID NO: 32 | SEQ ID NO: 49 |
| Ami2638_CBD2638 | | SEQ ID NO: 22 | SEQ ID NO: 2 |
| M23-2638_CBD2638 | | SEQ ID NO: 23 | SEQ ID NO: 3 |
| Ply2638-Ply2638 | | SEQ ID NO: 24 | SEQ ID NO: 4 |
| CHAPTw_Ami2638_M23-LST_CWT-LST | | SEQ ID NO: 28 | SEQ ID NO: 8 |
| LST_LST | | SEQ ID NO: 30 | SEQ ID NO: 10 |
| M23-LST_M23-LST_CWT-LST | | SEQ ID NO: 31 | SEQ ID NO: 11 |
| GFP_CBD2638 | | SEQ ID NO: 64 | SEQ ID NO: 60 |
| GFP_CBD2638_CBD2638 var.1 | | SEQ ID NO: 65 | SEQ ID NO: 61 |
| GFP_CBD2638_CBD2638 var. 2 | | SEQ ID NO: 66 | SEQ ID NO: 62 |
| GFP_CBD2638_CBD2638_CBD2638 | | SEQ ID NO: 67 | SEQ ID NO: 63 |

Tag

| | |
|---|---|
| 6xHis-tag | SEQ ID NO: 43 |

Vector

| | |
|---|---|
| pQE-30 vector | SEQ ID NO: 50 |
| pHGFP_CBD2638_c vector | SEQ ID NO: 59 |

SEQ ID NO: 1 (Ply2638)

```
ATGCTAACTGCTATTGACTATCTTACGAAAAAAGGTTGGAAAATATCATCT
GACCCTCGCACTTACGATGGTTACCCTAAAAACTACGGCTACAGAAATTAC
CATGAAAACGGCATTAATTATGATGAGTTTTGTGGTGGTTATCATAGAGCTT
TTGATGTTTACAGTAACGAAACTAACGACGTGCCTGCTGTTACTAGCGGAA
CAGTTATTGAAGCAAACGATTACGGTAATTTTGGTGGTACATTCGTTATTAG
AGACGCTAACGATAACGATTGGATATATGGGCATCTACAACGTGGCTCAAT
GCGATTTGTTGTAGGCGACAAAGTCAATCAAGGTGACATTATTGGTTTACA
AGGTAATAGCAACTATTACGACAATCCTATGAGTGTACATTTACATTTACA
ATTACGCCCTAAAGACGCAAAGAAAGATGAAAAATCACAAGTATGTAGTG
GTTTGGCTATGGAAAAATATGACATTACAAATTTAAATGCTAAACAAGATA
AATCAAAGAATGGGAGCGTGAAAGAGTTGAAACATATCTATTCAAACCAT
ATTAAAGGTAACAAGATTACAGCACCAAAACCTAGTATTCAAGGTGTGGTC
ATCCACAATGATTATGGTAGTATGACACCTAGTCAATACTTACCATGGTTAT
ATGCACGTGAGAATAACGGTACACACGTTAACGGTTGGGCTAGTGTTTATG
CAAATAGAAACGAAGTGCTTTGGTATCATCCGACAGACTACGTAGAGTGGC
ATTGTGGTAATCAATGGGCAAATGCTAACTTAATCGGATTTGAAGTGTGTG
AGTCGTATCCTGGTAGAATCTCGGACAAATTATTCTTAGAAAATGAAGAAG
CGACATTGAAAGTAGCTGCGGATGTGATGAAGTCGTACGGATTACCAGTTA
ATCGCAACACTGTACGTCTGCATAACGAATTCTTCGGAACTTCTTGTCCACA
TCGTTCGTGGGACTTGCATGTTGGCAAAGGTGAGCCTTACACAACTACTAA
TATTAATAAAATGAAAGACTACTTCATCAAACGCATCAAACATTATTATGA
CGGTGGAAAGCTAGAAGTAAGCAAAGCAGCAACTATCAAACAATCTGACG
TTAAGCAAGAAGTTAAAAAGCAAGAAGCAAAACAAATTGTGAAAGCAACA
GATTGGAAACAGAATAAAGATGGCATTTGGTATAAAGCTGAACATGCTTCG
TTCACAGTGACAGCACCAGAGGGAATTATCACAAGATACAAAGGTCCTTGG
```

TABLE 1-continued

SEQ ID NO identification

ACTGGTCACCCACAAGCTGGTGTATTACAAAAAGGTCAAACGATTAAATAT
GATGAGGTTCAAAAATTTGACGGTCATGTTTGGGTATCGTGGGAAACGTTT
GAGGGCGAAACTGTATACATGCCGGTACGCACATGGGACGCTAAAACTGG
TAAAGTTGGTAAGTTGTGGGGCGAAATTAAATAA

SEQ ID NO: 2 (Ami2638_CBD2638 + 6xHis and
cloning sites)

ATGAGAGGATCGCATCACCATCACCATCACGGATCCTTACGCCCTAAAGAC
GCAAAGAAAGATGAAAAATCACAAGTATGTAGTGGTTTGGCTATGGAAAA
ATATGACATTACAAATTTAAATGCTAAACAAGATAAATCAAAGAATGGGA
GCGTGAAAGAGTTGAAACATATCTATTCAAACCATATTAAAGGTAACAAGA
TTACAGCACCAAAACCTAGTATTCAAGGTGTGGTCATCCACAATGATTATG
GTAGTATGACACCTAGTCAATACTTACCATGGTTATATGCACGTGAGAATA
ACGGTACACACGTTAACGGTTGGGCTAGTGTTTATGCAAATAGAAACGAAG
TGCTTTGGTATCATCCGACAGACTACGTAGAGTGGCATTGTGGTAATCAAT
GGGCAAATGCTAACTTAATCGGATTTGAAGTGTGTGAGTCGTATCCTGGTA
GAATCTCGGACAAATTATTCTTAGAAAATGAAGAAGCGACATTGAAAGTAG
CTGCGGATGTGATGAAGTCGTACGGATTACCAGTTAATCGCAACACTGTAC
GTCTGCATAACGAATTCTTCGGAACTTCTTGTCCACATCGTTCGTGGGACTT
GCATGTTGGCAAAGGTGAGCCTTACACAACTACTAATATTAATAAAATGAA
AGACTACTTCATCAAACGCATCAAACATTATTATGACGGTGGAAAGCTAGA
AGTAAGCAAAGCAGCAACTATCAAACAATCTGACGTTAAGCAAGAAGTTA
AAAAGCAAGAAGCAAACAAATTGTGAAAGCAACAGATTGGAAACAGAAT
AAAGATGGCATTTGGTATAAAGCTGAACATGCTTCGTTCACAGTGACAGCA
CCAGAGGGAATTATCACAAGATACAAAGGTCCTTGGACTGGTCACCCACAA
GCTGGTGTATTACAAAAAGGTCAAACGATTAAATATGATGAGGTTCAAAAA
TTTGACGGTCATGTTTGGGTATCGTGGGAAACGTTTGAGGGCGAAACTGTA
TACATGCCGGTACGCACATGGGACGCTAAAACTGGTAAAGTTGGTAAGTTG
TGGGGCGAAATTAAATAA

SEQ ID NO: 3 (M23-2638_CBD2638 + 6xHis and
cloning sites)

ATGAGAGGATCGCATCACCATCACCATCACGGATCCATGCTAACTGCTATT
GACTATCTTACGAAAAAAGGTTGGAAAATATCATCTGACCCTCGCACTTAC
GATGGTTACCCTAAAAACTACGGCTACAGAAATTACCATGAAAACGGCATT
AATTATGATGAGTTTTGTGGTGGTTATCATAGAGCTTTTGATGTTTACAGTA
ACGAAACTAACGACGTGCCTGCTGTTACTAGCGGAACAGTTATTGAAGCAA
ACGATTACGGTAATTTTGGTGGTACATTCGTTATTAGAGACGCTAACGATA
ACGATTGGATATATGGGCATCTACAACGTGGCTCAATGCGATTTGTTGTAG
GCGACAAAGTCAATCAAGGTGACATTATTGGTTTACAAGGTAATAGCAACT
ATTACGACAATCCTATGAGTGTACATTTACATTTACAATTACGCCCTAAAGA
CGCAAAGAAAGATGAAAAATCACAAGTATGTAGTGGTTTGGCTATGGAAA
AATATGACATTACAAATTTAAATGCTAAACAAGATAAATCAAAGAATGGG
AGCGTGAAAGAGTTGAAACATATCTATTCAAACCATATTAAAGGTAACAAG
ATTACAGCACCAAAACCTAGTATTCAAGGTGAGCTCGGTGGAAAGCTAGAA
GTAAGCAAAGCAGCAACTATCAAACAATCTGACGTTAAGCAAGAAGTTAA
AAAGCAAGAAGCAAACAAATTGTGAAAGCAACAGATTGGAAACAGAATA
AAGATGGCATTTGGTATAAAGCTGAACATGCTTCGTTCACAGTGACAGCAC
CAGAGGGAATTATCACAAGATACAAAGGTCCTTGGACTGGTCACCCACAAG
CTGGTGTATTACAAAAAGGTCAAACGATTAAATATGATGAGGTTCAAAAAT
TTGACGGTCATGTTTGGGTATCGTGGGAAACGTTTGAGGGCGAAACTGTAT
ACATGCCGGTACGCACATGGGACGCTAAAACTGGTAAAGTTGGTAAGTTGT
GGGGCGAAATTAAATAA

SEQ ID NO: 4 (Ply2638-Ply2638 + 6x His and
cloning sites))

ATGAGAGGATCGCATCACCATCACCATCACGGATCCATGCTAACTGCTATT
GACTATCTTACGAAAAAAGGTTGGAAAATATCATCTGACCCTCGCACTTAC
GATGGTTACCCTAAAAACTACGGCTACAGAAATTACCATGAAAACGGCATT
AATTATGATGAGTTTTGTGGTGGTTATCATAGAGCTTTTGATGTTTACAGTA
ACGAAACTAACGACGTGCCTGCTGTTACTAGCGGAACAGTTATTGAAGCAA
ACGATTACGGTAATTTTGGTGGTACATTCGTTATTAGAGACGCTAACGATA
ACGATTGGATATATGGGCATCTACAACGTGGCTCAATGCGATTTGTTGTAG
GCGACAAAGTCAATCAAGGTGACATTATTGGTTTACAAGGTAATAGCAACT
ATTACGACAATCCTATGAGTGTACATTTACATTTACAATTACGCCCTAAAGA
CGCAAAGAAAGATGAAAAATCACAAGTATGTAGTGGTTTGGCTATGGAAA
AATATGACATTACAAATTTAAATGCTAAACAAGATAAATCAAAGAATGGG
AGCGTGAAAGAGTTGAAACATATCTATTCAAACCATATTAAAGGTAACAAG
ATTACAGCACCAAAACCTAGTATTCAAGGTGTGGTCATCCACAATGATTAT
GGTAGTATGACACCTAGTCAATACTTACCATGGTTATATGCACGTGAGAAT
AACGGTACACACGTTAACGGTTGGGCTAGTGTTTATGCAAATAGAAACGAA
GTGCTTTGGTATCATCCGACAGACTACGTAGAGTGGCATTGTGGTAATCAA
TGGGCAAATGCTAACTTAATCGGATTTGAAGTGTGTGAGTCGTATCCTGGT
AGAATCTCGGACAAATTATTCTTAGAAAATGAAGAAGCGACATTGAAAGTA
GCTGCGGATGTGATGAAGTCGTACGGATTACCAGTTAATCGCAACACTGTA

TABLE 1-continued

SEQ ID NO identification

CGTCTGCATAACGAATTCTTCGGAACTTCTTGTCCACATCGTTCGTGGGACT
TGCATGTTGGCAAAGGTGAGCCTTACACAACTACTAATATTAATAAAATGA
AAGACTACTTCATCAAACGCATCAAACATTATTATGACGGTGGAAAGCTAG
AAGTAAGCAAAGCAGCAACTATCAAACAATCTGACGTTAAGCAAGAAGTT
AAAAAGCAAGAAGCAAAACAAATTGTGAAAGCAACAGATTGGAAACAGA
ATAAAGATGGCATTTGGTATAAAGCTGAACATGCTTCGTTCACAGTGACAG
CACCAGAGGGAATTATCACAAGATACAAAGGTCCTTGGACTGGTCACCCAC
AAGCTGGTGTATTACAAAAAGGTCAAACGATTAAATATGATGAGGTTCAAA
AATTTGACGGTCATGTTTGGGTATCGTGGGAAACGTTTGAGGGCGAAACTG
TATACATGCCGGTACGCACATGGGACGCTAAAACTGGTAAAGTTGGTAAGT
TGTGGGGCGAAATTAAAGAGCTCATGCTAACTGCTATTGACTATCTTACGA
AAAAAGGTTGGAAAATATCATCTGACCCTCGCACTTACGATGGTTACCCTA
AAAACTACGGCTACAGAATTACCATGAAAACGGCATTAATTATGATGAGT
TTTGTGGTGGTTATCATAGAGCTTTTGATGTTTACAGTAACGAAACTAACGA
CGTGCCTGCTGTTACTAGCGGAACAGTTATTGAAGCAAACGATTACGGTAA
TTTTGGTGGTACATTCGTTATTAGAGACGCTAACGATAACGATTGGATATAT
GGGCATCTACAACGTGGCTCAATGCGATTTGTTGTAGGCGACAAAGTCAAT
CAAGGTGACATTATTGGTTTACAAGGTAATAGCAACTATTACGACAATCCT
ATGAGTGTACATTTACATTTCAATTACGCCCTAAAGACGCAAAGAAAGAT
GAAAAATCACAAGTATGTAGTGGTTTGGCTATGGAAAAATATGACATTACA
AATTTAAATGCTAAACAAGATAAATCAAAGAATGGGAGCGTGAAAGAGTT
GAAACATATCTATTCAAACCATATTAAAGGTAACAAGATTACAGCACCAAA
ACCTAGTATTCAAGGTGTGGTCATCCACAATGATTATGGTAGTATGACACC
TAGTCAATACTTACCATGGTTATATGCACGTGAGAATAACGGTACACACGT
TAACGGTTGGGCTAGTGTTTATGCAAATAGAAACGAAGTGCTTTGGTATCA
TCCGACAGACTACGTAGAGTGGCATTGTGGTAATCAATGGGCAAATGCTAA
CTTAATCGGATTTGAAGTGTGTGAGTCGTATCCTGGTAGAATCTCGGACAA
ATTATTCTTAGAAAATGAAGAAGCGACATTGAAAGTAGCTGCGGATGTGAT
GAAGTCGTACGGATTACCAGTTAATCGCAACACTGTACGTCTGCATAACGA
ATTCTTCGGAACTTCTTGTCCACATCGTTCGTGGGACTTGCATGTTGGCAAA
GGTGAGCCTTACACAACTACTAATATTAATAAAATGAAAGACTACTTCATC
AAACGCATCAAACATTATTATGACGGTGGAAAGCTAGAAGTAAGCAAAGC
AGCAACTATCAAACAATCTGACGTTAAGCAAGAAGTTAAAAAGCAAGAAG
CAAAACAAATTGTGAAAGCAACAGATTGGAAACAGAATAAAGATGGCATT
TGGTATAAAGCTGAACATGCTTCGTTCACAGTGACAGCACCAGAGGGAATT
ATCACAAGATACAAAGGTCCTTGGACTGGTCACCCACAAGCTGGTGTATTA
CAAAAAGGTCAAACGATTAAATATGATGAGGTTCAAAAATTTGACGGTCAT
GTTTGGGTATCGTGGGAAACGTTTGAGGGCGAAACTGTATACATGCCGGTA
CGCACATGGGACGCTAAAACTGGTAAAGTTGGTAAGTTGTGGGGCGAAATT
AAATAA

SEQ ID NO: 5 (CHAP11_M23-2638_Ami2638_CBD2638)

ATGCAAGCAAAATTAACTAAAAATGAGTTTATAGAGTGGTTGAAAACTTCT
GAGGGGAAAACAATTCAATGTGGACTTATGGTATGGATTTCAATGCTTTGAT
TATGCCAATGCTGGTTGGAAAGTTTTGTTTGGATTACTTCTAAAAGGTTTAG
GTGCAAAAGATATTCCGTTCGCTAACAACTTCGACGGATTAGCTACTGTAT
ACCAAAATACACCGGACTTCTTAGCACAACCTGGCGACATGGTGGTATTCG
GTAGCAACTACGGTGCTGGATATGGTCACGTTGCATGGGTAATTGAAGCAA
CTTTAGATTACATCATTGTATATGAGCAGAATTGGCTAGGCGGTGGCTGGA
CTGACGGAATCGAACAACCCGGCTGGGGTTGGGAAAAAGTTACAAGACGA
CAACATGCTTATGATTTCCCTATGTGGTTTATCCGTCCGAATTTTAAAAGTG
AGACAGCGCCACGATCAGTTCAATCTCCTACACAAGCACCTAAAAAAGAA
ACAGCTGGATCCATGCTAACTGCTATTGACTATCTTACGAAAAAAGGTTGG
AAAATATCATCTGACCCTCGCACTTACGATGGTTACCCTAAAAACTACGGC
TACAGAATTACCATGAAAACGGCATTAATTATGATGAGTTTTGTGGTGGT
TATCATAGAGCTTTTGATGTTTACAGTAACGAAACTAACGACGTGCCTGCT
GTTACTAGCGGAACAGTTATTGAAGCAAACGATTACGGTAATTTTGGTGGT
ACATTCGTTATTAGAGACGCTAACGATAACGATTGGATATATGGGCATCTA
CAACGTGGCTCAATGCGATTTGTTGTAGGCGACAAAGTCAATCAAGGTGAC
ATTATTGGTTTACAAGGTAATAGCAACTATTACGACAATCCTATGAGTGTA
CATTTACATTTACAATTACGCCCTAAAGACGCAAAGAAAGATGAAAAATCA
CAAGTATGTAGTGGTTTGGCTATGGAAAAATATGACATTACAAATTTAAAT
GCTAAACAAGATAAATCAAAGAATGGGAGCGTGAAAGAGTTGAAACATAT
CTATTCAAACCATATTAAAGGTAACAAGATTACAGCACCAAAACCTAGTAT
TCAAGGTGTGGTCATCCACAATGATTATGGTAGTATGACACCTAGTCAATA
CTTACCATGGTTATATGCACGTGAGAATAACGGTACACACGTTAACGGTTG
GGCTAGTGTTTATGCAAATAGAAACGAAGTGCTTTGGTATCATCCGACAGA
CTACGTAGAGTGGCATTGTGGTAATCAATGGGCAAATGCTAACTTAATCGG
ATTTGAAGTGTGTGAGTCGTATCCTGGTAGAATCTCGGACAAATTATTCTTA
GAAAATGAAGAAGCGACATTGAAAGTAGCTGCGGATGTGATGAAGTCGTA
CGGATTACCAGTTAATCGCAACACTGTACGTCTGCATAACGAATTCTTCGG
AACTTCTTGTCCACATCGTTCGTGGGACTTGCATGTTGGCAAAGGTGAGCCT
TACACAACTACTAATATTAATAAAATGAAAGACTACTTCATCAAACGCATC
AAACATTATTATGACGGTGGAAAGCTAGAAGTAAGCAAAGCAGCAACTAT
CAAACAATCTGACGTTAAGCAAGAAGTTAAAAAGCAAGAAGCAAAACAAA
TTGTGAAAGCAACAGATTGGAAACAGAATAAAGATGGCATTTGGTATAAA
GCTGAACATGCTTCGTTCACAGTGACAGCACCAGAGGGAATTATCACAAGA

TABLE 1-continued

SEQ ID NO identification

TACAAAGGTCCTTGGACTGGTCACCCACAAGCTGGTGTATTACAAAAAGGT
CAAACGATTAAATATGATGAGGTTCAAAAATTTGACGGTCATGTTTGGGTA
TCGTGGGAAACGTTTGAGGGCGAAACTGTATACATGCCGGTACGCACATGG
GACGCTAAAACTGGTAAAGTTGGTAAGTTGTGGGGCGAAATTAAATAA

SEQ ID NO: 6 (Ami11_M23-2638_Ami2638_CBD2638)

AAGCCACAACCTAAAGCAGTAGAACTTAAAATCATCAAAGATGTGGTTAA
AGGTTATGACCTACCTAAGCGTGGTAGTAACCCTAAAGGTATAGTTATACA
CAACGACGCAGGGAGCAAAGGGGCGACTGCTGAAGCATATCGTAACGGAT
TAGTAAATGCACCTTTATCAAGATTAGAAGCGGGCATTGCGCATAGTTACG
TATCAGGCAACACAGTTTGGCAAGCCTTAGATGAATCACAAGTAGGTTGGC
ATACCGCTAATCAAATAGGTAATAAATATTATTACGGTATTGAAGTATGTC
AATCAATGGGCGCAGATAACGCGACATTCTTAAAAAATGAACAGGCAACTT
TCCAAGAATGCGCTAGATTGTTGAAAAAATGGGGATTACCAGCAAACAGA
AATACAATCAGATTGCACAATGAATTTACTTCAACATCATGCCCTCATAGA
AGTTCGGTTTTACACACTGGTTTTGACCCAGTAACTCGCGGTCTATTGCCAG
AAGACAAGCGGTTGCAACTTAAAGACTACTTTATCAAGCAGATTAGGGCGT
ACATGGATGGTAAAATACCGGTTGCCACTGTCTCTAATGAGTCAAGCGCTT
CAAGTAATACAGTTAAACCAGTTGCAAGTGCAGGATCCATGCTAACTGCTA
TTGACTATCTTACGAAAAAGGTTGGAAAATATCATCTGACCCTCGCACTT
ACGATGGTTACCCTAAAAACTACGGCTACAGAATTACCATGAAAACGGCA
TTAATTATGATGAGTTTTGTGGTGGTTATCATAGAGCTTTTGATGTTTACAG
TAACGAAACTAACGACGTGCCTGCTGTTACTAGCGGAACAGTTATTGAAGC
AAACGATTACGGTAATTTTGGTGGTACATTCGTTATTAGAGACGCTAACGA
TAACGATTGGATATATGGGCATCTACAACGTGGCTCAATGCGATTTGTTGT
AGGCGACAAAGTCAATCAAGGTGACATTATTGGTTTACAAGGTAATAGCAA
CTATTACGACAATCCTATGAGTGTACATTTACATTTACAATTACGCCCTAAA
GACGCAAAGAAAGATGAAAAATCACAAGTATGTAGTGGTTTGGCTATGGA
AAAATATGACATTACAAATTTAAATGCTAAACAAGATAAATCAAAGAATG
GGAGCGTGAAAGAGTTGAAACATATCTATTCAAACCATATTAAAGGTAACA
AGATTACAGCACCAAAACCTAGTATTCAAGGTGTGGTCATCCACAATGATT
ATGGTAGTATGACACCTAGTCAATACTTACCATGGTTATATGCACGTGAGA
ATAACGGTACACACGTTAACGGTTGGGCTAGTGTTTATGCAAATAGAAACG
AAGTGCTTTGGTATCATCCGACAGACTACGTAGAGTGGCCATTGTGGTAATC
AATGGGCAAATGCTAACTTAATCGGATTTGAAGTGTGAGTCGTATCCTG
GTAGAATCTCGGACAAATTATTCTTAGAAAATGAAGAAGCGACATTGAAAG
TAGCTGCGGATGTGATGAAGTCGTACGGATTACCAGTTAATCGCAACACTG
TACGTCTGCATAACGAATTCTTCGGAACTTCTTGTCCACATCGTTCGTGGGA
CTTGCATGTTGGCAAAGGTGAGCCTTACACAACTACTAATATTAATAAAT
GAAAGACTACTTCATCAAACGCATCAAACATTATTATGACGGTGGAAAGCT
AGAAGTAAGCAAAGCAGCAACTATCAAACAATCTGACGTTAAGCAAGAAG
TTAAAAAGCAAGAAGCAAAACAAATTGTGAAAGCAACAGATTGGAAACAG
AATAAAGATGGCATTTGGTATAAAGCTGAACATGCTTCGTTCACAGTGACA
GCACCAGAGGGAATTATCACAAGATACAAAGGTCCTTGGACTGGTCACCCA
CAAGCTGGTGTATTACAAAAAGGTCAAACGATTAAATATGATGAGGTTCAA
AAATTTGACGGTCATGTTTGGGTATCGTGGGAAACGTTTGAGGGCGAAACT
GTATACATGCCGGTACGCACATGGGACGCTAAAACTGGTAAAGTTGGTAAG
TTGTGGGGCGAAATTAAATAA

SEQ ID NO: 7 (CHAPTw_Ami2638_M23-LST_CBD2638)

ATGAAAACCCTGAAACAAGCAGAGTCCTACATTAAGAGTAAAGTAAATAC
AGGAACTGATTTTGATGGTTTATATGGGTATCAGTGTATGGACTTAGCAGT
AGATTATATTTACCATGTAACAGATGGTAAAATAAGAATGTGGGGTAATGC
TAAGGATGCGATAAATAACTCTTTTGGTGGTACTGCTACGGTATATAAAAA
CTACCCTGCTTTTAGACCTAAGTACGGTGATGTAGTCGTATGGACTACTGGT
AATTTTGCAACTTATGGTCATATCGCAATAGTTACTAACCCTGACCCTTATG
GAGACCTTCAATATGTTACAGTTCTTGAACAAAACTGGAACGGTAACGGGA
TTTATAAAACCGAGTTAGCTACAATCAGAACACACGATTACACAGGAATTA
CACATTTTATTAAAGACGCAAAGAAAGATGAAAAATCACAAGTATGTAGTG
GTTTGGCTATGGAAAAATATGACATTACAAATTTAAATGCTAAACAAGATA
AATCAAAGAATGGGAGCGTGAAAGAGTTGAAACATATCTATTCAAACCAT
ATTAAAGGTAACAAGATTACAGCACCAAAACCTAGTATTCAAGGTGTGGTC
ATCCACAATGATTATGGTAGTATGACACCTAGTCAATACTTACCATGGTTAT
ATGCACGTGAGAATAACGGTACACACGTTAACGGTTGGGCTAGTGTTTATG
CAAATAGAAACGAAGTGCTTTGGTATCATCCGACAGACTACGTAGAGTGGC
ATTGTGGTAATCAATGGGCAAATGCTAACTTAATCGGATTTGAAGTGTGTG
AGTCGTATCCTGGTAGAATCTCGGACAAATTATTCTTAGAAAATGAAGAAG
CGACATTGAAAGTAGCTGCGGATGTGATGAAGTCGTACGGATTACCAGTTA
ATCGCAACACTGTACGTCTGCATAACGAATTCTTCGGAACTTCTTGTCCACA
TCGTTCGTGGGACTTGCATGTTGGCAAAGGTGAGCCTTACACAACTACTAA
TATTAATAAAATGAAAGACTACTTCATCAAACGCATCAAACATTATTATGA
CGGTGGAAAGCTAGAAGTAAGCAAAGCAGCAACTATCAAACAATCTGACG
TTAAGCAAGAAGTTAAAAGCAAGAAGCAAACAAATTGTGAAAGCAACA
GATGCTGCAACACATGAACATTCAGCACAATGGTTGAATAATTACAAAAAA
GGATATGGTTACGGTCCTTATCCATTAGGTATAAATGGCGGTATGCACTAC
GGAGTTGATTTTTTATGAATATTGGAACACCAGTAAAAGCTATTTCAAGC

GGAAAAATAGTTGAAGCTGGTTGGAGTAATTACGGAGGAGGTAATCAAAT
AGGTCTTATTGAAAATGATGGAGTGCATAGACAATGGTATATGCATCTAAG
TAAATATAATGTTAAAGTAGGAGATTATGTCAAAGCTGGTCAAATAATCGG
TTGGTCTGGAAGCACTGGTTATTCTACAGCACCACATTTACACTTCCAAAGA
ATGGTTAATTCATTTTCAAATTCAACTGCCCAAGATCCAATGCCTTTCTTAA
AGAGCGCAGGATATGGAAAAGCAGGTGGTACAGTAACTCCAACGCCGAAT
ACAGGTTGGAAACAGAATAAAGATGGCATTTGGTATAAAGCTGAACATGCT
TCGTTCACAGTGACAGCACCAGAGGGAATTATCACAAGATACAAAGGTCCT
TGGACTGGTCACCCACAAGCTGGTGTATTACAAAAAGGTCAAACGATTAAA
TATGATGAGGTTCAAAAATTTGACGGTCATGTTTGGGTATCGTGGGAAACG
TTTGAGGGCGAAACTGTATACATGCCGGTACGCACATGGGACGCTAAAACT
GGTAAAGTTGGTAAGTTGTGGGGCGAAATTAAATAA

SEQ ID NO: 8 (CHAPTw_Ami2638_M23-LST_CWT-LST +
6xHis and cloning site)

ATGAGAGGATCGCATCACCATCACCATCACGGATCCATGAAAACCCTGAAA
CAAGCAGAGTCCTACATTAAGAGTAAAGTAAATACAGGAACTGATTTTGAT
GGTTTATATGGGTATCAGTGTATGGACTTAGCAGTAGATTATATTTACCATG
TAACAGATGGTAAAATAAGAATGTGGGGTAATGCTAAGGATGCGATAAAT
AACTCTTTTGGTGGTACTGCTACGGTATATAAAAACTACCCTGCTTTTAGAC
CTAAGTACGGTGATGTAGTCGTATGGACTACTGGTAATTTTGCAACTTATGG
TCATATCGCAATAGTTACTAACCCTGACCCTTATGGAGACCTTCAATATGTT
ACAGTTCTTGAACAAAACTGGAACGGTAACGGGATTTATAAAACCGAGTTA
GCTACAATCAGAACACACGATTACACAGGAATTACACATTTTATTAAAGAC
GCAAAGAAAGATGAAAAATCACAAGTATGTAGTGGTTTGGCTATGGAAAA
ATATGACATTACAAATTTAAATGCTAAACAAGATAAATCAAAGAATGGGA
GCGTGAAAGAGTTGAAACATATCTATTCAAACCATATTAAAGGTAACAAGA
TTACAGCACCAAAACCTAGTATTCAAGGTGTGGTCATCCACAATGATTATG
GTAGTATGACACCTAGTCAATACTTACCATGGTTATATGCACGTGAGAATA
ACGGTACACACGTTAACGGTTGGGCTAGTGTTTATGCAAATAGAAACGAAG
TGCTTTGGTATCATCCGACAGACTACGTAGAGTGGCATTGTGGTAATCAAT
GGGCAAATGCTAACTTAATCGGATTTGAAGTGTGTGAGTCGTATCCTGGTA
GAATCTCGGACAAATTATTCTTAGAAAATGAAGAAGCGACATTGAAAGTAG
CTGCGGATGTGATGAAGTCGTACGGATTACCAGTTAATCGCAACACTGTAC
GTCTGCATAACGAATTCTTCGGAACTTCTTGTCCACATCGTTCGTGGGACTT
GCATGTTGGCAAAGGTGAGCCTTACACAACTACTAATATTAATAAAATGAA
AGACTACTTCATCAAACGCATCAAACATTATTATGACGGTGGAAAGCTAGA
AGTAAGCAAAGCAGCAACTATCAAACAATCTGACGTTAAGCAAGAAGTTA
AAAAGCAAGAAGCAAACAAATTGTGAAAGCAACAGATGCTGCAACACAT
GAACATTCAGCACAATGGTTGAATAATTACAAAAAAGGATATGGTTACGGT
CCTTATCCATTAGGTATAAATGGCGGTATGCACTACGGAGTTGATTTTTTA
TGAATATTGGAACACCAGTAAAAGCTATTTCAAGCGGAAAAATAGTTGAAG
CTGGTTGGAGTAATTACGGAGGAGGTAATCAAATAGGTCTTATTGAAAATG
ATGGAGTGCATAGACAATGGTATATGCATCTAAGTAAATATAATGTTAAAG
TAGGAGATTATGTCAAAGCTGGTCAAATAATCGGTTGGTCTGGAAGCACTG
GTTATTCTACAGCACCACATTTACACTTCCAAAGAATGGTTAATTCATTTTC
AAATTCAACTGCCCAAGATCCAATGCCTTTCTTAAAGAGCGCAGGATATGG
AAAAGCAGGTGGTACAGTAACTCCAACGCCGAATACAGGTTGGAAAACAA
ACAAATATGGCACACTATATAAATCAGAGTCAGCTAGCTTCACACCTAATA
CAGATATAATAACAAGAACGACTGGTCCATTTAGAAGCATGCCGCAGTCAG
GAGTCTTAAAAGCAGGTCAAACAATTCATTATGATGAAGTGATGAAACAAG
ACGGTCATGTTTGGGTAGGTTATACAGGTAACAGTGGCCAACGTATTTACT
TGCCTGTAAGAACATGGAATAAATCTACTAATACTTTAGGTGTTCTTTGGGG
AACTATAAAGTAA

SEQ ID NO: 9 (M23-LST_Ami2638_CBD2638)

GCTGCAACACATGAACATTCAGCACAATGGTTGAATAATTACAAAAAAGG
ATATGGTTACGGTCCTTATCCATTAGGTATAAATGGCGGTATGCACTACGG
AGTTGATTTTTTATGAATATTGGAACACCAGTAAAAGCTATTTCAAGCGG
AAAAATAGTTGAAGCTGGTTGGAGTAATTACGGAGGAGGTAATCAAATAG
GTCTTATTGAAAATGATGGAGTGCATAGACAATGGTATATGCATCTAAGTA
AATATAATGTTAAAGTAGGAGATTATGTCAAAGCTGGTCAAATAATCGGTT
GGTCTGGAAGCACTGGTTATTCTACAGCACCACATTTACACTTCCAAAGAA
TGGTTAATTCATTTTCAAATTCAACTGCCCAAGATCCAATGCCTTTCTTAAA
GAGCGCAGGATATGGAAAAGCAGGTGGTACAGTAACTCCAACGCCGAATA
CAGGTGAGCTCTTACGCCCTAAAGACGCAAAGAAAGATGAAAAATCACAA
GTATGTAGTGGTTTGGCTATGGAAAAATATGACATTACAAATTTAAATGCT
AAACAAGATAAATCAAAGAATGGGAGCGTGAAAGAGTTGAAACATATCTA
TTCAAACCATATTAAAGGTAACAAGATTACAGCACCAAAACCTAGTATTCA
AGGTGTGGTCATCCACAATGATTATGGTAGTATGACACCTAGTCAATACTT
ACCATGGTTATATGCACGTGAGAATAACGGTACACACGTTAACGGTTGGGC
TAGTGTTTATGCAAATAGAAACGAAGTGCTTTGGTATCATCCGACAGACTA
CGTAGAGTGGCATTGTGGTAATCAATGGGCAAATGCTAACTTAATCGGATT
TGAAGTGTGTGAGTCGTATCCTGGTAGAATCTCGGACAAATTATTCTTAGA
AAATGAAGAAGCGACATTGAAAGTAGCTGCGGATGTGATGAAGTCGTACG
GATTACCAGTTAATCGCAACACTGTACGTCTGCATAACGAATTCTTCGGAA

TABLE 1-continued

SEQ ID NO identification

CTTCTTGTCCACATCGTTCGTGGGACTTGCATGTTGGCAAAGGTGAGCCTTA
CACAACTACTAATATTAATAAAATGAAAGACTACTTCATCAAACGCATCAA
ACATTATTATGACGGTGGAAAGCTAGAAGTAAGCAAAGCAGCAACTATCA
AACAATCTGACGTTAAGCAAGAAGTTAAAAAGCAAGAAGCAAAACAAATT
GTGAAAGCAACAGATTGGAAACAGAATAAAGATGGCATTTGGTATAAAGC
TGAACATGCTTCGTTCACAGTGACAGCACCAGAGGGAATTATCACAAGATA
CAAAGGTCCTTGGACTGGTCACCCACAAGCTGGTGTATTACAAAAAGGTCA
AACGATTAAATATGATGAGGTTCAAAAATTTGACGGTCATGTTTGGGTATC
GTGGGAAACGTTTGAGGGCGAAACTGTATACATGCCGGTACGCACATGGG
ACGCTAAAACTGGTAAAGTTGGTAAGTTGTGGGGCGAAATTAAATAA

SEQ ID NO: 10 (LST_LST + 6xHis and cloning sites)

ATGAGAGGATCGCATCACCATCACCATCACGGATCCGCTGCAACACATGAA
CATTCAGCACAATGGTTGAATAATTACAAAAAAGGATATGGTTACGGTCCT
TATCCATTAGGTATAAATGGCGGTATGCACTACGGAGTTGATTTTTTTATGA
ATATTGGAACACCAGTAAAAGCTATTTCAAGCGGAAAAATAGTTGAAGCTG
GTTGGAGTAATTACGGAGGAGGTAATCAAATAGGTCTTATTGAAAATGATG
GAGTGCATAGACAATGGTATATGCATCTAAGTAAATATAATGTTAAAGTAG
GAGATTATGTCAAAGCTGGTCAAATAATCGGTTGGTCTGGAAGCACTGGTT
ATTCTACAGCACCACATTTACACTTCCAAAGAATGGTTAATTCATTTTCAAA
TTCAACTGCCCAAGATCCAATGCCTTTCTTAAAGAGCGCAGGATATGGAAA
AGCAGGTGGTACAGTAACTCCAACGCCGAATACAGGTTGGAAAACAAACA
AATATGGCACACTATATAAATCAGAGTCAGCTAGCTTCACACCTAATACAG
ATATAATAACAAGAACGACTGGTCCATTTAGAAGCATGCCGCAGTCAGGAG
TCTTAAAAGCAGGTCAAACAATTCATTATGATGAAGTGATGAAACAAGACG
GTCATGTTTGGGTAGGTTATACAGGTAACAGTGGCCAACGTATTTACTTGCC
TGTAAGAACATGGAATAAATCTACTAATACTTTAGGTGTTCTTTGGGGAAC
TATAAAGGAGCTCGCTGCAACACATGAACATTCAGCACAATGGTTGAATAA
TTACAAAAAAGGATATGGTTACGGTCCTTATCCATTAGGTATAAATGGCGG
TATGCACTACGGAGTTGATTTTTTTATGAATATTGGAACACCAGTAAAAGCT
ATTTCAAGCGGAAAAATAGTTGAAGCTGGTTGGAGTAATTACGGAGGAGGT
AATCAAATAGGTCTTATTGAAAATGATGGAGTGCATAGACAATGGTATATG
CATCTAAGTAAATATAATGTTAAAGTAGGAGATTATGTCAAAGCTGGTCAA
ATAATCGGTTGGTCTGGAAGCACTGGTTATTCTACAGCACCACATTTACACT
TCCAAAGAATGGTTAATTCATTTTCAAATTCAACTGCCCAAGATCCAATGCC
TTTCTTAAAGAGCGCAGGATATGGAAAAGCAGGTGGTACAGTAACTCCAAC
GCCGAATACAGGTTGGAAAACAAACAAATATGGCACACTATATAAATCAG
AGTCAGCTAGCTTCACACCTAATACAGATATAATAACAAGAACGACTGGTC
CATTTAGAAGCATGCCGCAGTCAGGAGTCTTAAAAGCAGGTCAAACAATTC
ATTATGATGAAGTGATGAAACAAGACGGTCATGTTTGGGTAGGTTATACAG
GTAACAGTGGCCAACGTATTTACTTGCCTGTAAGAACATGGAATAAATCTA
CTAATACTTTAGGTGTTCTTTGGGGAACTATAAAGTGA

SEQ ID NO: 11 (M23-LST_M23-LST_CWT-LST +
6xHis and cloning sites)

ATGAGAGGATCGCATCACCATCACCATCACGGATCCGCTGCAACACATGAA
CATTCAGCACAATGGTTGAATAATTACAAAAAAGGATATGGTTACGGTCCT
TATCCATTAGGTATAAATGGCGGTATGCACTACGGAGTTGATTTTTTTATGA
ATATTGGAACACCAGTAAAAGCTATTTCAAGCGGAAAAATAGTTGAAGCTG
GTTGGAGTAATTACGGAGGAGGTAATCAAATAGGTCTTATTGAAAATGATG
GAGTGCATAGACAATGGTATATGCATCTAAGTAAATATAATGTTAAAGTAG
GAGATTATGTCAAAGCTGGTCAAATAATCGGTTGGTCTGGAAGCACTGGTT
ATTCTACAGCACCACATTTACACTTCCAAAGAATGGTTAATTCATTTTCAAA
TTCAACTGCCCAAGATCCAATGCCTTTCTTAAAGAGCGCAGGATATGGAAA
AGCAGGTGGTACAGTAACTCCAACGCCGAATACAGGTGAGCTCGCTGCAAC
ACATGAACATTCAGCACAATGGTTGAATAATTACAAAAAAGGATATGGTTA
CGGTCCTTATCCATTAGGTATAAATGGCGGTATGCACTACGGAGTTGATTTT
TTTATGAATATTGGAACACCAGTAAAAGCTATTTCAAGCGGAAAAATAGTT
GAAGCTGGTTGGAGTAATTACGGAGGAGGTAATCAAATAGGTCTTATTGAA
AATGATGGAGTGCATAGACAATGGTATATGCATCTAAGTAAATATAATGTT
AAAGTAGGAGATTATGTCAAAGCTGGTCAAATAATCGGTTGGTCTGGAAGC
ACTGGTTATTCTACAGCACCACATTTACACTTCCAAAGAATGGTTAATTCAT
TTTCAAATTCAACTGCCCAAGATCCAATGCCTTTCTTAAAGAGCGCAGGAT
ATGGAAAAGCAGGTGGTACAGTAACTCCAACGCCGAATACAGGTTGGAAA
ACAAACAAATATGGCACACTATATAAATCAGAGTCAGCTAGCTTCACACCT
AATACAGATATAATAACAAGAACGACTGGTCCATTTAGAAGCATGCCGCAG
TCAGGAGTCTTAAAAGCAGGTCAAACAATTCATTATGATGAAGTGATGAAA
CAAGACGGTCATGTTTGGGTAGGTTATACAGGTAACAGTGGCCAACGTATT
TACTTGCCTGTAAGAACATGGAATAAATCTACTAATACTTTAGGTGTTCTTT
GGGGAACTATAAAGTGA

SEQ ID NO: 12 (CBD-2638)

TGGAAACAGAATAAAGATGGCATTTGGTATAAAGCTGAACATGCTTCGTTC
ACAGTGACAGCACCAGAGGGAATTATCACAAGATACAAAGGTCCTTGGAC
TGGTCACCCACAAGCTGGTGTATTACAAAAAGGTCAAACGATTAAATATGA

TABLE 1-continued

SEQ ID NO identification

TGAGGTTCAAAAATTTGACGGTCATGTTTGGGTATCGTGGGAAACGTTTGA
GGGCGAAACTGTATACATGCCGGTACGCACATGGGACGCTAAAACTGGTA
AAGTTGGTAAGTTGTGGGGCGAAATTAAATAA

SEQ ID NO: 13 (CWT-LST)

TGGAAAACAAACAAATATGGCACACTATATAAATCAGAGTCAGCTAGCTTC
ACACCTAATACAGATATAATAACAAGAACGACTGGTCCATTTAGAAGCATG
CCGCAGTCAGGAGTCTTAAAAGCAGGTCAAACAATTCATTATGATGAAGTG
ATGAAACAAGACGGTCATGTTTGGGTAGGTTATACAGGTAACAGTGGCCAA
CGTATTTACTTGCCTGTAAGAACATGGAATAAATCTACTAATACTTTAGGTG
TTCTTTGGGGAACTATAAAGTGA

SEQ ID NO: 14 (M23-2638)

ATGCTAACTGCTATTGACTATCTTACGAAAAAAGGTTGGAAAATATCATCT
GACCCTCGCACTTACGATGGTTACCCTAAAAACTACGGCTACAGAAATTAC
CATGAAAACGGCATTAATTATGATGAGTTTTGTGGTGGTTATCATAGAGCTT
TTGATGTTTACAGTAACGAAACTAACGACGTGCCTGCTGTTACTAGCGAA
CAGTTATTGAAGCAAACGATTACGGTAATTTTGGTGGTACATTCGTTATTAG
AGACGCTAACGATAACGATTGGATATATGGGCATCTACAACGTGGCTCAAT
GCGATTTGTTGTAGGCGACAAAGTCAATCAAGGTGACATTATTGGTTTACA
AGGTAATAGCAACTATTACGACAATCCTATGAGTGTACATTTACATTTACA
ATTACGCCCTAAAGACGCAAAGAAAGAT

SEQ ID NO: 15 (M23-LST)

GCTGCAACACATGAACATTCAGCACAATGGTTGAATAATTACAAAAAAGG
ATATGGTTACGGTCCTTATCCATTAGGTATAAATGGCGGTATGCACTACGG
AGTTGATTTTTTATGAATATTGGAACACCAGTAAAAGCTATTTCAAGCGG
AAAAATAGTTGAAGCTGGTTGGAGTAATTACGGAGGAGGTAATCAAATAG
GTCTTATTGAAAATGATGGAGTGCATAGACAATGGTATATGCATCTAAGTA
AATATAATGTTAAAGTAGGAGATTATGTCAAAGCTGGTCAAATAATCGGTT
GGTCTGGAAGCACTGGTTATTCTACAGCACCACATTTACACTTCCAAAGAA
TGGTTAATTCATTTTCAAATTCAACTGCCCAAGATCCAATGCCTTTCTTAAA
GAGCGCAGGATAT

SEQ ID NO: 16 (Ami-2638)

GGTAACAAGATTACAGCACCAAAACCTAGTATTCAAGGTGTGGTCATCCAC
AATGATTATGGTAGTATGACACCTAGTCAATACTTACCATGGTTATATGCAC
GTGAGAATAACGGTACACACGTTAACGGTTGGGCTAGTGTTTATGCAAATA
GAAACGAAGTGCTTTGGTATCATCCGACAGACTACGTAGAGTGGCATTGTG
GTAATCAATGGGCAAATGCTAACTTAATCGGATTTGAAGTGTGTGAGTCGT
ATCCTGGTAGAATCTCGGACAAATTATTCTTAGAAAATGAAGAAGCGACAT
TGAAAGTAGCTGCGGATGTGATGAAGTCGTACGGATTACCAGTTAATCGCA
ACACTGTACGTCTGCATAACGAATTCTTCGGAACTTCTTGTCCACATCGTTC
GTGGGACTTGCATGTTGGCAAAGGTGAGCCTTACACAACTACTAATATTAA
TAAAATGAAAGACTACTTCATCAAACGCATCAAACATTATTATGACGGT

SEQ ID NO: 17 (Ami-□11)

AAGCCACAACCTAAAGCAGTAGAACTTAAAATCATCAAAGATGTGGTTAA
AGGTTATGACCTACCTAAGCGTGGTAGTAACCCTAAAGGTATAGTTATACA
CAACGACGCAGGGAGCAAAGGGGCGACTGCTGAAGCATATCGTAACGGAT
TAGTAAATGCACCTTTATCAAGATTAGAAGCGGGCATTGCGCATAGTTACG
TATCAGGCAACACAGTTTGGCAAGCCTTAGATGAATCACAAGTAGGTTGGC
ATACCGCTAATCAAATAGGTAATAAATATTATTACGGTATTGAAGTATGTC
AATCAATGGGCGCAGATAACGCGACATTCTTAAAAAATGAACAGGCAACTT
TCCAAGAATGCGCTAGATTGTTGAAAAAATGGGGATTACCAGCAAACAGA
AATACAATCAGATTGCACAATGAATTTACTTCAACATCATGCCCTCATAGA
AGTTCGGTTTTACACACTGGTTTTGACCCAGTAACTCGCGGTCTATTGCCAG
AAGACAAGCGGTTGCAACTTAAAGACTACTTTATCAAGCAGATTAGGGCGT
ACATGGATGGTAAAATACCGGTTGCCACTGTCTCTAATGAGTCAAGCGCTT
CAAGTAATACAGTTAAACCAGTTGCAAGTGCA

SEQ ID NO: 18 (CHAP-□11)

ATGCAAGCAAAATTAACTAAAAATGAGTTTATAGAGTGGTTGAAAACTTCT
GAGGGAAAACAATTCAATGTGGACTTATGGTATGGATTTCAATGCTTTGAT
TATGCCAATGCTGGTTGGAAAGTTTTGTTTGGATTACTTCTAAAAGGTTTAG
GTGCAAAAGATATTCCGTTCGCTAACAACTTCGACGGATTAGCTACTGTAT
ACCAAAATACACCGGACTTCTTAGCACAACCTGGCGACATGGTGGTATTCG
GTAGCAACTACGGTGCTGGATATGGTCACGTTGCATGGGTAATTGAAGCAA
CTTTAGATTACATCATTGTATATGAGCAGAATTGGCTAGGCGGTGGCTGGA
CTGACGGAATCGAACAACCCGGCTGGGGTTGGGAAAAAGTTACAAGACGA

TABLE 1-continued

SEQ ID NO identification

CAACATGCTTATGATTTCCCTATGTGGTTTATCCGTCCGAATTTTAAAAGTG
AGACAGCGCCACGATCAGTTCAATCTCCTACACAAGCACCTAAAAAAGAA
ACAGCT

SEQ ID NO: 19 (CHAP-□Twort)

ATGAAAACCCTGAAACAAGCAGAGTCCTACATTAAGAGTAAAGTAAATAC
AGGAACTGATTTTGATGGTTTATATGGGTATCAGTGTATGGACTTAGCAGT
AGATTATATTTACCATGTAACAGATGGTAAAATAAGAATGTGGGGTAATGC
TAAGGATGCGATAAATAACTCTTTTGGTGGTACTGCTACGGTATATAAAA
CTACCCTGCTTTTAGACCTAAGTACGGTGATGTAGTCGTATGGACTACTGGT
AATTTTGCAACTTATGGTCATATCGCAATAGTTACTAACCCTGACCCTTATG
GAGACCTTCAATATGTTACAGTTCTTGAACAAAACTGGAACGGTAACGGGA
TTTATAAAACCGAGTTAGCTACAATCAGAACACACGATTACACAGGAATTA
CACATTTTATT

SEQ ID NO: 20 (M23-2638_Ami2638_CBD2638_CBD2638)

ATGCTAACTGCTATTGACTATCTTACGAAAAAAGGTTGGAAAATATCATCT
GACCCTCGCACTTACGATGGTTACCCTAAAAACTACGGCTACAGAAATTAC
CATGAAAACGGCATTAATTATGATGAGTTTTGTGGTGGTTATACATAGAGCTT
TTGATGTTTACAGTAACGAAACTAACGACGTGCCTGCTGTTACTAGCGGAA
CAGTTATTGAAGCAAACGATTACGGTAATTTTGGTGGTACATTCGTTATTAG
AGACGCTAACGATAACGATTGGATATATGGGCATCTACAACGTGGCTCAAT
GCGATTTGTTAGGCGACAAAGTCAATCAAGGTGACATTATTGGTTTACA
AGGTAATAGCAACTATTACGACAATCCTATGAGTGTACATTTACATTTACA
ATTACGCCCTAAAGACGCAAAGAAAGATGAAAAATCACAAGTATGTAGTG
GTTTGGCTATGGAAAAATATGACATTACAAATTTAAATGCTAAACAAGATA
AATCAAAGAATGGGAGCGTGAAAGAGTTGAAACATATCTATTCAAACCAT
ATTAAAGGTAACAAGATTACAGCACCAAAACCTAGTATTCAAGGTGTGGTC
ATCCACAATGATTATGGTAGTATGACACCTAGTCAATACTTACCATGGTTAT
ATGCACGTGAGAATAACGGTACACACGTTAACGGTTGGGCTAGTGTTTATG
CAAATAGAAACGAAGTGCTTTGGTATCATCCGACAGACTACGTAGAGTGGC
ATTGTGGTAATCAATGGGCAAATGCTAACTTAATCGGATTTGAAGTGTGTG
AGTCGTATCCTGGTAGAATCTCGGACAAATTATTCTTAGAAAATGAAGAAG
CGACATTGAAAGTAGCTGCGGATGTGATGAAGTCGTACGGATTACCAGTTA
ATCGCAACACTGTACGTCTGCATAACGAATTCTTCGGAACTTCTTGTCCACA
TCGTTCGTGGGACTTGCATGTTGGCAAAGGTGAGCCTTACACAACTACTAA
TATTAATAAAATGAAAGACTACTTCATCAAACGCATCAAACATTATTATGA
CGGTGGAAAGCTAGAAGTAAGCAAAGCAGCAACTATCAAACAATCTGACG
TTAAGCAAGAAGTTAAAAAGCAAGAAGCAAAACAAATTGTGAAAGCAACA
GATTGGAAACAGAATAAAGATGGCATTTGGTATAAAGCTGAACATGCTTCG
TTCACAGTGACAGCACCAGAGGGAATTATCACAAGATACAAAGGTCCTTGG
ACTGGTCACCCACAAGCTGGTGTATTACAAAAAGGTCAAACGATTAAATAT
GATGAGGTTCAAAAATTTGACGGTCATGTTTGGGTATCGTGGGAAACGTTT
GAGGGCGAAACTGTATACATGCCGGTACGCACATGGGACGCTAAAACTGG
TAAAGTTGGTAAGTTGTGGGGCGAAATTAAAGAGCTCGGTGGAAAGCTAG
AAGTAAGCAAAGCAGCAACTATCAAACAATCTGACGTTAAGCAAGAAGTT
AAAAAGCAAGAAGCAAAACAAATTGTGAAAGCAACAGATTGGAAACAGA
ATAAAGATGGCATTTGGTATAAAGCTGAACATGCTTCGTTCACAGTGACAG
CACCAGAGGGAATTATCACAAGATACAAAGGTCCTTGGACTGGTCACCCAC
AAGCTGGTGTATTACAAAAAGGTCAAACGATTAAATATGATGAGGTTCAAA
AATTTGACGGTCATGTTTGGGTATCGTGGGAAACGTTTGAGGGCGAAACTG
TATACATGCCGGTACGCACATGGGACGCTAAAACTGGTAAAGTTGGTAAGT
TGTGGGGCGAAATTAAATAA

SEQ ID NO: 21 (Ply2638)

MRGSHHHHHHGSMLTAIDYLTKKGWKISSDPRTYDGYPKNYGYRNYHENGI
NYDEFCGGYHRAFDVYSNETNDVPAVTSGTVIEANDYGNFGGTFVIRDANDN
DWIYGHLQRGSMRFVVGDKVNQGDIIGLQGNSNYYDNPMSVHLHLQLRPKD
AKKDEKSQVCSGLAMEKYDITNLNAKQDKSKNGSVKELKHIYSNHIKGNKITA
PKPSIQGVVIHNDYGSMTPSQYLPWLYARENNGTHVNGWASVYANRNEVLW
YHPTDYVEWHCGNQWANANLIGFEVCESYPGRISDKLFLENEEATLKVAADV
MKSYGLPVNRNTVRLHNEFFGTSCPHRSWDLHVGKGEPYTTTNINKMKDYFI
KRIKHYYDGGKLEVSKAATIKQSDVKQEVKKQEAKQIVKATDWKQNKDGIW
YKAEHASFTVTAPEGIITRYKGPWTGHPQAGVLQKGQTIKYDEVQKFDGHVW
VSWETFEGETVYMPVRTWDAKTGKVGKLWGEIK

SEQ ID NO: 22 (Ami2638_CBD2638)

MRGSHHHHHHGSLRPKDAKKDEKSQVCSGLAMEKYDITNLNAKQDKSKNG
SVKELKHIYSNHIKGNKITAPKPSIQGVVIHNDYGSMTPSQYLPWLYARENNGT
HVNGWASVYANRNEVLWYHPTDYVEWHCGNQWANANLIGFEVCESYPGRIS
DKLFLENEEATLKVAADVMKSYGLPVNRNTVRLHNEFFGTSCPHRSWDLHVG
KGEPYTTTNINKMKDYFIKRIKHYYDGGKLEVSKAATIKQSDVKQEVKKQEAK
QIVKATDWKQNKDGIWYKAEHASFTVTAPEGIITRYKGPWTGHPQAGVLQKG
QTIKYDEVQKFDGHVWVSWETFEGETVYMPVRTWDAKTGKVGKLWGEIK

TABLE 1-continued

SEQ ID NO identification

SEQ ID NO: 23 (M23-2638_CBD2638)

MRGSHHHHHHGSMLTAIDYLTKKGWKISSDPRTYDGYPKNYGYRNYHENGI
NYDEFCGGYHRAFDVYSNETNDVPAVTSGTVIEANDYGNFGGTFVIRDANDN
DWIYGHLQRGSMRFVVGDKVNQGDIIGLQGNSNYYDNPMSVHLHLQRPKD
AKKDEKSQVCSGLAMEKYDITNLNAKQDKSKNGSVKELKHIYSNHIKGNKITA
PKPSIQGELGGKLEVSKAATIKQSDVKQEVKKQEAKQIVKATDWKQNKDGIW
YKAEHASFTVTAPEGIITRYKGPWTGHPQAGVLQKGQTIKYDEVQKFDGHVW
VSWETFEGETVYMPVRTWDAKTGKVGKLWGEIK

SEQ ID NO: 24 (Ply2638-Ply2638)

MRGSHHHHHHGSMLTAIDYLTKKGWKISSDPRTYDGYPKNYGYRNYHENGI
NYDEFCGGYHRAFDVYSNETNDVPAVTSGTVIEANDYGNFGGTFVIRDANDN
DWIYGHLQRGSMRFVVGDKVNQGDIIGLQGNSNYYDNPMSVHLHLQRPKD
AKKDEKSQVCSGLAMEKYDITNLNAKQDKSKNGSVKELKHIYSNHIKGNKITA
PKPSIQGVVIHNDYGSMTPSQYLPWLYARENNGTHVNGWASVYANRNEVLW
YHPTDYVEWHCGNQWANANLIGFEVCESYPGRISDKLFLENEEATLKVAADV
MKSYGLPVNRNTVRLHNEFFGTSCPHRSWDLHVGKGEPYTTTNINKMKDYFI
KRIKHYYDGGKLEVSKAATIKQSDVKQEVKKQEAKQIVKATDWKQNKDGIW
YKAEHASFTVTAPEGIITRYKGPWTGHPQAGVLQKGQTIKYDEVQKFDGHVW
VSWETFEGETVYMPVRTWDAKTGKVGKLWGEIKELMLTAIDYLTKKGWKISS
DPRTYDGYPKNYGYRNYHENGINYDEFCGGYHRAFDVYSNETNDVPAVTSGT
VIEANDYGNFGGTFVIRDANDNDWIYGHLQRGSMRFVVGDKVNQGDIIGLQG
NSNYYDNPMSVHLHLQRPKDAKKDEKSQVCSGLAMEKYDITNLNAKQDKS
KNGSVKELKHIYSNHIKGNKITAPKPSIQGVVIHNDYGSMTPSQYLPWLYAREN
NGTHVNGWASVYANRNEVLWYHPTDYVEWHCGNQWANANLIGFEVCESYP
GRISDKLFLENEEATLKVAADVMKSYGLPVNRNTVRLHNEFFGTSCPHRSWDL
HVGKGEPYTTTNINKMKDYFIKRIKHYYDGGKLEVSKAATIKQSDVKQEVKK
QEAKQIVKATDWKQNKDGIWYKAEHASFTVTAPEGIITRYKGPWTGHPQAGV
LQKGQTIKYDEVQKFDGHVWVSWETFEGETVYMPVRTWDAKTGKVGKLWG
EIK

SEQ ID NO: 25 (CHAP11_M23-2638_Ami2638_CBD2638)

MRGSHHHHHHGSMQAKLTKNEFIEWLKTSEGKQFNVDLWYGFQCFDYANA
GWKVLFGLLLKGLGAKDIPFANNFDGLATVYQNTPDFLAQPGDMVVFGSNYG
AGYGHVAWVIEATLDYIIVYEQNWLGGGWTDGIEQPGWGWEKVTRRQHAYD
FPMWFIRPNFKSETAPRSVQSPTQAPKKETAGSMLTAIDYLTKKGWKISSDPRT
YDGYPKNYGYRNYHENGINYDEFCGGYHRAFDVYSNETNDVPAVTSGTVIEA
NDYGNFGGTFVIRDANDNDWIYGHLQRGSMRFVVGDKVNQGDIIGLQGNSNY
YDNPMSVHLHLQRPKDAKKDEKSQVCSGLAMEKYDITNLNAKQDKSKNGS
VKELKHIYSNHIKGNKITAPKPSIQGVVIHNDYGSMTPSQYLPWLYARENNGTH
VNGWASVYANRNEVLWYHPTDYVEWHCGNQWANANLIGFEVCESYPGRISD
KLFLENEEATLKVAADVMKSYGLPVNRNTVRLHNEFFGTSCPHRSWDLHVGK
GEPYTTTNINKMKDYFIKRIKHYYDGGKLEVSKAATIKQSDVKQEVKKQEAKQ
IVKATDWKQNKDGIWYKAEHASFTVTAPEGIITRYKGPWTGHPQAGVLQKGQ
TIKYDEVQKFDGHVWVSWETFEGETVYMPVRTWDAKTGKVGKLWGEIK

SEQ ID NO: 26 (Ami_11_M23-2638_Ami2638_CBD2638)

MRGSHHHHHHGSKPQPKAVELKIIKDVVKGYDLPKRGSNPKGIVIHNDAGSK
GATAEAYRNGLVNAPLSRLEAGIAHSYVSGNTVWQALDESQVGWHTANQIGN
KYYYGIEVCQSMGADNATFLKNEQATFQECARLLKKWGLPANRNTIRLHNEF
TSTSCPHRSSVLHTGFDPVTRGLLPEDKRLQLKDYFIKQIRAYMDGKIPVATVS
NESSASSNTVKPVASAGSMLTAIDYLTKKGWKISSDPRTYDGYPKNYGYRNYH
ENGINYDEFCGGYHRAFDVYSNETNDVPAVTSGTVIEANDYGNFGGTFVIRDA
NDNDWIYGHLQRGSMRFVVGDKVNQGDIIGLQGNSNYYDNPMSVHLHLQR
PKDAKKDEKSQVCSGLAMEKYDITNLNAKQDKSKNGSVKELKHIYSNHIKGN
KITAPKPSIQGVVIHNDYGSMTPSQYLPWLYARENNGTHVNGWASVYANRNE
VLWYHPTDYVEWHCGNQWANANLIGFEVCESYPGRISDKLFLENEEATLKVA
ADVMKSYGLPVNRNTVRLHNEFFGTSCPHRSWDLHVGKGEPYTTTNINKMKD
YFIKRIKHYYDGGKLEVSKAATIKQSDVKQEVKKQEAKQIVKATDWKQNKDG
IWYKAEHASFTVTAPEGIITRYKGPWTGHPQAGVLQKGQTIKYDEVQKFDGHV
WVSWETFEGETVYMPVRTWDAKTGKVGKLWGEIK

SEQ ID NO: 27 (CHAPTw_Ami2638_M23-LST_CBD2638)

MRGSHHHHHHGSMKTLKQAESYIKSKVNTGTDFDGLYGYQCMDLAVDYIY
HVTDGKIRMWGNAKDAINNSFGGTATVYKNYPAFRPKYGDVVVWTTGNFAT
YGHIAIVTNPDPYGDLQYVTVLEQNWNGNGIYKTELATIRTHDYTGITHFIKDA
KKDEKSQVCSGLAMEKYDITNLNAKQDKSKNGSVKELKHIYSNHIKGNKITAP
KPSIQGVVIHNDYGSMTPSQYLPWLYARENNGTHVNGWASVYANRNEVLWY
HPTDYVEWHCGNQWANANLIGFEVCESYPGRISDKLFLENEEATLKVAADVM
KSYGLPVNRNTVRLHNEFFGTSCPHRSWDLHVGKGEPYTTTNINKMKDYFIKR
IKHYYDGGKLEVSKAATIKQSDVKQEVKKQEAKQIVKATDAATHEHSAQWLN
NYKKGYGYGPYPLGINGGMHYGVDFFMNIGTPVKAISSGKIVEAGWSNYGGG

TABLE 1-continued

SEQ ID NO identification

NQIGLIENDGVHRQWYMHLSKYNVKVGDYVKAGQIIGWSGSTGYSTAPHLHF
QRMVNSFSNSTAQDPMPFLKSAGYGKAGGTVTPTPNTGWKQNKDGIWYKAE
HASFTVTAPEGIITRYKGPWTGHPQAGVLQKGQTIKYDEVQKFDGHVWVSWE
TFEGETVYMPVRTWDAKTGKVGKLWGEIK

SEQ ID NO: 28 (CHAPTw_Ami2638_M23-LST_CWT-LST)

MRGSHHHHHHGSMKTLKQAESYIKSKVNTGTDFDGLYGYQCMDLAVDYIY
HVTDGKIRMWGNAKDAINNSFGGTATVYKNYPAFRPKYGDVVVWTTGNFAT
YGHIAIVTNPDPYGDLQYVTVLEQNWNGNGIYKTELATIRTHDYTGITHFIKDA
KKDEKSQVCSGLAMEKYDITNLNAKQDKSKNGSVKELKHIYSNHIKGNKITAP
KPSIQGVVIHNDYGSMTPSQYLPWLYARENNGTHVNGWASVYANRNEVLWY
HPTDYVEWHCGNQWANANLIGFEVCESYPGRISDKLFLENEEATLKVAADVM
KSYGLPVNRNTVRLHNEFFGTSCPHRSWDLHVGKGEPYTTTNINKMKDYFIKR
IKHYYDGGKLEVSKAATIKQSDVKQEVKKQEAKQIVKATDAATHEHSAQWLN
NYKKGYGYGPYPLGINGGMHYGVDFFMNIGTPVKAISSGKIVEAGWSNYGGG
NQIGLIENDGVHRQWYMHLSKYNVKVGDYVKAGQIIGWSGSTGYSTAPHLHF
QRMVNSFSNSTAQDPMPFLKSAGYGKAGGTVTPTPNTGWKTNKYGTLYKSES
ASFTPNTDIITRTTGPFRSMPQSGVLKAGQTIHYDEVMKQDGHVWVGYTGNSG
QRIYLPVRTWNKSTNTLGVLWGTIK

SEQ ID NO: 29 (M23-LST_Ami2638_CBD2638)

MRGSHHHHHHGSAATHEHSAQWLNNYKKGYGYGPYPLGINGGMHYGVDFF
MNIGTPVKAISSGKIVEAGWSNYGGGNQIGLIENDGVHRQWYMHLSKYNVKV
GDYVKAGQIIGWSGSTGYSTAPHLHFQRMVNSFSNSTAQDPMPFLKSAGYGK
AGGTVTPTPNTGELLRPKDAKKDEKSQVCSGLAMEKYDITNLNAKQDKSKNG
SVKELKHIYSNHIKGNKITAPKPSIQGVVIHNDYGSMTPSQYLPWLYARENNGT
HVNGWASVYANRNEVLWYHPTDYVEWHCGNQWANANLIGFEVCESYPGRIS
DKLFLENEEATLKVAADVMKSYGLPVNRNTVRLHNEFFGTSCPHRSWDLHVG
KGEPYTTTNINKMKDYFIKRIKHYYDGGKLEVSKAATIKQSDVKQEVKKQEAK
QIVKATDWKQNKDGIWYKAEHASFTVTAPEGIITRYKGPWTGHPQAGVLQKG
QTIKYDEVQKFDGHVWVSWETFEGETVYMPVRTWDAKTGKVGKLWGEIK

SEQ ID NO: 30 (LST_LST)

MRGSHHHHHHGSAATHEHSAQWLNNYKKGYGYGPYPLGINGGMHYGVDFF
MNIGTPVKAISSGKIVEAGWSNYGGGNQIGLIENDGVHRQWYMHLSKYNVKV
GDYVKAGQIIGWSGSTGYSTAPHLHFQRMVNSFSNSTAQDPMPFLKSAGYGK
AGGTVTPTPNTGWKTNKYGTLYKSESASFTPNTDIITRTTGPFRSMPQSGVLKA
GQTIHYDEVMKQDGHVWVGYTGNSGQRIYLPVRTWNKSTNTLGVLWGTIKE
LAATHEHSAQWLNNYKKGYGYGPYPLGINGGMHYGVDFFMNIGTPVKAISSG
KIVEAGWSNYGGGNQIGLIENDGVHRQWYMHLSKYNVKVGDYVKAGQIIGW
SGSTGYSTAPHLHFQRMVNSFSNSTAQDPMPFLKSAGYGKAGGTVTPTPNTG
WKTNKYGTLYKSESASFTPNTDIITRTTGPFRSMPQSGVLKAGQTIHYDEVMK
QDGHVWVGYTGNSGQRIYLPVRTWNKSTNTLGVLWGTIK

SEQ ID NO: 31 (M23-LST_M23-LST_CWT-LST)

MRGSHHHHHHGSAATHEHSAQWLNNYKKGYGYGPYPLGINGGMHYGVDFF
MNIGTPVKAISSGKIVEAGWSNYGGGNQIGLIENDGVHRQWYMHLSKYNVKV
GDYVKAGQIIGWSGSTGYSTAPHLHFQRMVNSFSNSTAQDPMPFLKSAGYGK
AGGTVTPTPNTGELAATHEHSAQWLNNYKKGYGYGPYPLGINGGMHYGVDF
FMNIGTPVKAISSGKIVEAGWSNYGGGNQIGLIENDGVHRQWYMHLSKYNVK
VGDYVKAGQIIGWSGSTGYSTAPHLHFQRMVNSFSNSTAQDPMPFLKSAGYG
KAGGTVTPTPNTGWKTNKYGTLYKSESASFTPNTDIITRTTGPFRSMPQSGVLK
AGQTIHYDEVMKQDGHVWVGYTGNSGQR1YLPVRTWNKSTNTLGVLWGTIK

SEQ ID NO: 32 (M23-2638_Ami2638_CBD2638_CBD2638)

MRGSHHHHHHGSMLTAIDYLTKKGWKISSDPRTYDGYPKNYGYRNYHENGI
NYDEFCGGYHRAFDVYSNETNDVPAVTSGTVIEANDYGNFGGTFVIRDANDN
DWIYGHLQRGSMRFVVGDKVNQGDIIGLQGNSNYYDNPMSVHLHLQLRPKD
AKKDEKSQVCSGLAMEKYDITNLNAKQDKSKNGSVKELKHIYSNHIKGNKITA
PKPSIQGVVIHNDYGSMTPSQYLPWLYARENNGTHVNGWASVYANRNEVLW
YHPTDYVEWHCGNQWANANLIGFEVCESYPGRISDKLFLENEEATLKVAADV
MKSYGLPVNRNTVRLHNEFFGTSCPHRSWDLHVGKGEPYTTTNINKMKDYFI
KRIKHYYDGGKLEVSKAATIKQSDVKQEVKKQEAKQIVKATDWKQNKDGIW
YKAEHASFTVTAPEGIITRYKGPWTGHPQAGVLQKGQTIKYDEVQKFDGHVW
VSWETFEGETVYMPVRTWDAKTGKVGKLWGEIKELGGKLEVSKAATIKQSDV
KQEVKKQEAKQIVKATDWKQNKDGIWYKAEHASFTVTAPEGIITRYKGPWTG
HPQAGVLQKGQTIKYDEVQKFDGHVWVSWETFEGETVYMPVRTWDAKTGK
VGKLWGEIK

SEQ ID NO: 33 (LST)

GCTGCAACACATGAACATTCAGCACAATGGTTGAATAATTACAAAAAAGG
ATATGGTTACGGTCCTTATCCATTAGGTATAAATGGCGGTATGCACTACGG

TABLE 1-continued

SEQ ID NO identification

AGTTGATTTTTTTATGAATATTGGAACACCAGTAAAAGCTATTTCAAGCGG
AAAAATAGTTGAAGCTGGTTGGAGTAATTACGGAGGAGGTAATCAAATAG
GTCTTATTGAAAATGATGGAGTGCATAGACAATGGTATATGCATCTAAGTA
AATATAATGTTAAAGTAGGAGATTATGTCAAAGCTGGTCAAATAATCGGTT
GGTCTGGAAGCACTGGTTATTCTACAGCACCACATTTACACTTCCAAAGAA
TGGTTAATTCATTTTCAAATTCAACTGCCCAAGATCAATGCCTTTCTTAAA
GAGCGCAGGATATGGAAAAGCAGGTGGTACAGTAACTCCAACGCCGAATA
CAGGTTGGAAAACAAACAAATATGGCACACTATATAAATCAGAGTCAGCT
AGCTTCACACCTAATACAGATATAATAACAAGAACGACTGGTCCATTTAGA
AGCATGCCGCAGTCAGGAGTCTTAAAAGCAGGTCAAACAATTCATTATGAT
GAAGTGATGAAACAAGACGGTCATGTTTGGGTAGGTTATACAGGTAACAGT
GGCCAACGTATTTACTTGCCTGTAAGAACATGGAATAAATCTACTAATACT
TTAGGTGTTCTTTGGGGAACTATAAAGTGA

SEQ ID NO: 34 (LST aa)

AATHEHSAQWLNNYKKGYGYGPYPLGINGGMHYGVDFFMNIGTPVKAISSGK
IVEAGWSNYGGGNQIGLIENDGVHRQWYMHLSKYNVKVGDYVKAGQIIGWS
GSTGYSTAPHLHFQRMVNSFSNSTAQDPMPFLKSAGYGKAGGTVTPTPNTGW
KTNKYGTLYKSESASFTPNTDIITRTTGPFRSMPQSGVLKAGQTIHYDEVMKQD
GHVWVGYTGNSGQRIYLPVRTWNKSTNTLGVLWGTIK

SEQ ID NO: 35 (CBD-2638)

WKQNKDGIWYKAEHASFTVTAPEGIITRYKGPWTGHPQAGVLQKGQTIKYDE
VQKFDGHVWVSWETFEGETVYMPVRTWDAKTGKVGKLWGEIK

SEQ ID NO: 36 (CWT-LST)

WKTNKYGTLYKSESASFTPNTDIITRTTGPFRSMPQSGVLKAGQTIHYDEVMK
QDGHVWVGYTGNSGQRIYLPVRTWNKSTNTLGVLWGTIK

SEQ ID NO: 37 (M23-2638)

MLTAIDYLTKKGWKISSDPRTYDGYPKNYGYRNYHENGINYDEFCGGYHRAF
DVYSNETNDVPAVTSGTVIEANDYGNFGGTFVIRDANDNDWIYGHLQRGSMR
FVVGDKVNQGDIIGLQGNSNYYDNPMSVHLHLQLRPKDAKKD

SEQ ID NO: 38 (M23-LST)

AATHEHSAQWLNNYKKGYGYGPYPLGINGGMHYGVDFFMNIGTPVKAISSGK
IVEAGWSNYGGGNQIGLIENDGVHRQWYMHLSKYNVKVGDYVKAGQIIGWS
GSTGYSTAPHLHFQRMVNSFSNSTAQDPMPFLKSAGY

SEQ ID NO: 39 (Ami-2638)

NKITAPKPSIQGVVIHNDYGSMTPSQYLPWLYARENNGTHVNGWASVYANRN
EVLWYHPTDYVEWHCGNQWANANLIGFEVCESYPGRISDKLFLENEEATLKV
AADVMKSYGLPVNRNTVRLHNEFFGTSCPHRSWDLHVGKGEPYTTTNINKMK
DYFIKRIKHYYDG

SEQ ID NO: 40 (Ami-□11)

NPKGIVIHNDAGSKGATAEAYRNGLVNAPLSRLEAGIAHSYVSGNTVWQALD
ESQVGWHTANQIGNKYYYGIEVCQSMGADNATFLKNEQATFQECARLLKKW
GLPANRNTIRLHNEFTSTSCPHRSSVLHTGFDPVTRGLLPEDKRLQLKDYFIKQI
RAYMD

SEQ ID NO: 41 (CHAP-□11)

MSIIMEVATMQAKLTKNEFIEWLKTSEGKQFNVDLWYGFQCFDYANAGWKV
LFGLLLKGLGAKDIPFANNFDGLATVYQNTPDFLAQPGDMVVFGSNYGAGYG
HVAWVIEATLDYIIVYEQNWLGGGWTDGIEQPGWGWEKVTRRQHAYDFPMW
FIRP

SEQ ID NO: 42 (CHAP-□Twort)

MKTLKQAESYIKSKVNTGTDFDGLGYQCMDLAVDYIYHVTDGKIRMWGNA
KDAINNSFGGTATVYKNYPAFRPKYGDVVVWTTGNFATYGHIAIVTNPDPYG
DLQYVTVLEQNWNGNGIYKTELATIRTHDYTGITHFI

SEQ ID NO 43 (6xHis tag N terminal)

MRGSHHHHHHGS

TABLE 1-continued

SEQ ID NO identification

SEQ ID NO: 44 (Ply2638 + 6xHis and cloning sites)

ATGAGAGGATCGCATCACCATCACCATCACGGATCCATGCTAACTGCTATT
GACTATCTTACGAAAAAAGGTTGGAAAATATCATCTGACCCTCGCACTTAC
GATGGTTACCCTAAAAACTACGGCTACAGAAATTACCATGAAAACGGCATT
AATTATGATGAGTTTTGTGGTGGTTATCATAGAGCTTTTGATGTTTACAGTA
ACGAAACTAACGACGTGCCTGCTGTTACTAGCGGAACAGTTATTGAAGCAA
ACGATTACGGTAATTTTGGTGGTACATTCGTTATTAGAGACGCTAACGATA
ACGATTGGATATATGGGCATCTACAACGTGGCTCAATGCGATTTGTTGTAG
GCGACAAAGTCAATCAAGGTGACATTATTGGTTTACAAGGTAATAGCAACT
ATTACGACAATCCTATGAGTGTACATTTACATTTACAATTACGCCCTAAAGA
CGCAAAGAAAGATGAAAAATCACAAGTATGTAGTGGTTTGGCTATGGAAA
AATATGACATTACAAATTTAAATGCTAAACAAGATAAATCAAAGAATGGG
AGCGTGAAAGAGTTGAAACATATCTATTCAAACCATATTAAAGGTAACAAG
ATTACAGCACCAAAACCTAGTATTCAAGGTGTGGTCATCCACAATGATTAT
GGTAGTATGACACCTAGTCAATACTTACCATGGTTATATGCACGTGAGAAT
AACGGTACACACGTTAACGGTTGGGCTAGTGTTTATGCAAATAGAAACGAA
GTGCTTTGGTATCATCCGACAGACTACGTAGAGTGGCATTGTGGTAATCAA
TGGGCAAATGCTAACTTAATCGGATTTGAAGTGTGTGAGTCGTATCCTGGT
AGAATCTCGGACAAATTATTCTTAGAAAATGAAGAAGCGACATTGAAAGTA
GCTGCGGATGTGATGAAGTCGTACGGATTACCAGTTAATCGCAACACTGTA
CGTCTGCATAACGAATTCTTCGGAACTTCTTGTCCACATCGTTCGTGGGACT
TGCATGTTGGCAAAGGTGAGCCTTACACAACTACTAATATTAATAAAATGA
AAGACTACTTCATCAAACGCATCAAACATTATTATGACGGTGGAAAGCTAG
AAGTAAGCAAAGCAGCAACTATCAAACAATCTGACGTTAAGCAAGAAGTT
AAAAAGCAAGAAGCAAACAAATTGTGAAAGCAACAGATTGGAAACAGA
ATAAAGATGGCATTTGGTATAAAGCTGAACATGCTTCGTTCACAGTGACAG
CACCAGAGGGAATTATCACAAGATACAAAGGTCCTTGGACTGGTCACCCAC
AAGCTGGTGTATTACAAAAAGGTCAAACGATTAAATATGATGAGGTTCAAA
AATTTGACGGTCATGTTTGGGTATCGTGGGAAACGTTTGAGGGCGAAACTG
TATACATGCCGGTACGCACATGGGACGCTAAAACTGGTAAAGTTGGTAAGT
TGTGGGGCGAAATTAAATAA

SEQ ID NO: 45 (CHAP11_M23-2638_Ami2638_CBD2638 +
6xHis and cloning sites)

ATGAGAGGATCGCATCACCATCACCATCACGGATCCATGCAAGCAAAATTA
ACTAAAAATGAGTTTATAGAGTGGTTGAAAACTTCTGAGGGAAAACAATTC
AATGTGGACTTATGGTATGGATTTCAATGCTTTGATTATGCCAATGCTGGTT
GGAAAGTTTTGTTTGGATTACTTCTAAAAGGTTTAGGTGCAAAAGATATTCC
GTTCGCTAACAACTTCGACGGATTAGCTACTGTATACCAAAATACACCGGA
CTTCTTAGCACAACCTGGCGACATGGTGGTATTCGGTAGCAACTACGGTGC
TGGATATGGTCACGTTGCATGGGTAATTGAAGCAACTTTAGATTACATCATT
GTATATGAGCAGAATTGGCTAGGCGGTGGCTGGACTGACGGAATCGAACA
ACCCGGCTGGGGTTGGGAAAAAGTTACAAGACGACAAACATGCTTATGATTT
CCCTATGTGGTTTATCCGTCCGAATTTTAAAAGTGAGACAGCGCCACGATC
AGTTCAATCTCCTACACAAGCACCTAAAAAAGAAACAGCTGGATCCATGCT
AACTGCTATTGACTATCTTACGAAAAAAGGTTGGAAAATATCATCTGACCC
TCGCACTTACGATGGTTACCCTAAAAACTACGGCTACAGAAATTACCATGA
AAACGGCATTAATTATGATGAGTTTTGTGGTGGTTATCATAGAGCTTTTGAT
GTTTACAGTAACGAAACTAACGACGTGCCTGCTGTTACTAGCGGAACAGTT
ATTGAAGCAAACGATTACGGTAATTTTGGTGGTACATTCGTTATTAGAGAC
GCTAACGATAACGATTGGATATATGGGCATCTACAACGTGGCTCAATGCGA
TTTGTTGTAGGCGACAAAGTCAATCAAGGTGACATTATTGGTTTACAAGGT
AATAGCAACTATTACGACAATCCTATGAGTGTACATTTACATTTACAATTAC
GCCCTAAAGACGCAAAGAAAGATGAAAAATCACAAGTATGTAGTGGTTTG
GCTATGGAAAAATATGACATTACAAATTTAAATGCTAAACAAGATAAATCA
AAGAATGGGAGCGTGAAAGAGTTGAAACATATCTATTCAAACCATATTAAA
GGTAACAAGATTACAGCACCAAAACCTAGTATTCAAGGTGTGGTCATCCAC
AATGATTATGGTAGTATGACACCTAGTCAATACTTACCATGGTTATATGCAC
GTGAGAATAACGGTACACACGTTAACGGTTGGGCTAGTGTTTATGCAAATA
GAAACGAAGTGCTTTGGTATCATCCGACAGACTACGTAGAGTGGCATTGTG
GTAATCAATGGGCAAATGCTAACTTAATCGGATTTGAAGTGTGTGAGTCGT
ATCCTGGTAGAATCTCGGACAAATTATTCTTAGAAAATGAAGAAGCGACAT
TGAAAGTAGCTGCGGATGTGATGAAGTCGTACGGATTACCAGTTAATCGCA
ACACTGTACGTCTGCATAACGAATTCTTCGGAACTTCTTGTCCACATCGTTC
GTGGGACTTGCATGTTGGCAAAGGTGAGCCTTACACAACTACTAATATTAA
TAAAATGAAAGACTACTTCATCAAACGCATCAAACATTATTATGACGGTGG
AAAGCTAGAAGTAAGCAAAGCAGCAACTATCAAACAATCTGACGTTAAGC
AAGAAGTTAAAAAGCAAGAAGCAAACAAATTGTGAAAGCAACAGATTGG
AAACAGAATAAAGATGGCATTTGGTATAAAGCTGAACATGCTTCGTTCACA
GTGACAGCACCAGAGGGAATTATCACAAGATACAAAGGTCCTTGGACTGGT
CACCCACAAGCTGGTGTATTACAAAAAGGTCAAACGATTAAATATGATGAG
GTTCAAAAATTTGACGGTCATGTTTGGGTATCGTGGGAAACGTTTGAGGGC
GAAACTGTATACATGCCGGTACGCACATGGGACGCTAAAACTGGTAAAGTT
GGTAAGTTGTGGGGCGAAATTAAATAA

TABLE 1-continued

SEQ ID NO identification

SEQ ID NO: 46 (Ami11_M23-2638_Ami2638_CBD2638 + 6xHis and cloning sites)

ATGAGAGGATCGCATCACCATCACCATCACGGATCCAAGCCACAACCTAAA
GCAGTAGAACTTAAAATCATCAAAGATGTGGTTAAAGGTTATGACCTACCT
AAGCGTGGTAGTAACCCTAAAGGTATAGTTATACACAACGACGCAGGGAG
CAAAGGGGCGACTGCTGAAGCATATCGTAACGGATTAGTAAATGCACCTTT
ATCAAGATTAGAAGCGGGCATTGCGCATAGTTACGTATCAGGCAACACAGT
TTGGCAAGCCTTAGATGAATCACAAGTAGGTTGGCATACCGCTAATCAAAT
AGGTAATAAATATTATTACGGTATTGAAGTATGTCAATCAATGGGCGCAGA
TAACGCGACATTCTTAAAAAATGAACAGGCAACTTTCCAAGAATGCGCTAG
ATTGTTGAAAAAATGGGGATTACCAGCAAACAGAAATACAATCAGATTGC
ACAATGAATTTACTTCAACATCATGCCCTCATAGAAGTTCGGTTTTACACAC
TGGTTTTGACCCAGTAACTCGCGGTCTATTGCCAGAAGACAAGCGGTTGCA
ACTTAAAGACTACTTTATCAAGCAGATTAGGGCGTACATGGATGGTAAAAT
ACCGGTTGCCACTGTCTCTAATGAGTCAAGCGCTTCAAGTAATACAGTTAA
ACCAGTTGCAAGTGCAGGATCCATGCTAACTGCTATTGACTATCTTACGAA
AAAAGGTTGGAAAATATCATCTGACCCTCGCACTTACGATGGTTACCCTAA
AAACTACGGCTACAGAAATTACCATGAAAACGGCATTAATTATGATGAGTT
TTGTGGTGGTTATCATAGAGCTTTTGATGTTTACAGTAACGAAACTAACGAC
GTGCCTGCTGTTACTAGCGGAACAGTTATTGAAGCAAACGATTACGGTAAT
TTTGGTGGTACATTCGTTATTAGAGACGCTAACGATAACGATTGGATATAT
GGGCATCTACAACGTGGCTCAATGCGATTTGTTGTAGGCGACAAAGTCAAT
CAAGGTGACATTATTGGTTTACAAGGTAATAGCAACTATTACGACAATCCT
ATGAGTGTACATTTACATTTACAATTACGCCCTAAAGACGCAAAGAAAGAT
GAAAAATCACAAGTATGTAGTGGTTTGGCTATGGAAAAATATGACATTACA
AATTTAAATGCTAAACAAGATAAATCAAAGAATGGGAGCGTGAAAGAGTT
GAAACATATCTATTCAAACCATATTAAAGGTAACAAGATTACAGCACCAAA
ACCTAGTATTCAAGGTGTGGTCATCCACAATGATTATGGTAGTATGACACC
TAGTCAATACTTACCATGGTTATATGCACGTGAGAATAACGGTACACACGT
TAACGGTTGGGCTAGTGTTTATGCAAATAGAAACGAAGTGCTTTGGTATCA
TCCGACAGACTACGTAGAGTGGCATTGTGGTAATCAATGGGCAAATGCTAA
CTTAATCGGATTTGAAGTGTGTGAGTCGTATCCTGGTAGAATCTCGGACAA
ATTATTCTTAGAAAATGAAGAGCGACATTGAAAGTAGCTGCGGATGTGAT
GAAGTCGTACGGATTACCAGTTAATCGCAACACTGTACGTCTGCATAACGA
ATTCTTCGGAACTTCTTGTCCACATCGTTCGTGGGACTTGCATGTTGGCAAA
GGTGAGCCTTACACAACTACTAATATTAATAAAATGAAAGACTACTTCATC
AAACGCATCAAACATTATTATGACGGTGGAAAGCTAGAAGTAAGCAAAGC
AGCAACTATCAAACAATCTGACGTTAAGCAAGAAGTTAAAAAGCAAGAAG
CAAAACAAATTGTGAAAGCAACAGATTGGAAACAGAATAAAGATGGCATT
TGGTATAAAGCTGAACATGCTTCGTTCACAGTGACAGCACCAGAGGGAATT
ATCACAAGATACAAAGGTCCTTGGACTGGTCACCCACAAGCTGGTGTATTA
CAAAAAGGTCAAACGATTAAATATGATGAGGTTCAAAAATTTGACGGTCAT
GTTTGGGTATCGTGGGAAACGTTTGAGGGCGAAACTGTATACATGCCGGTA
CGCACATGGGACGCTAAAACTGGTAAAGTTGGTAAGTTGTGGGGCGAAATT
AAATAA

SEQ ID NO: 47 (CHAPTw_Ami2638_M23-LST_CBD2638 + 6xHis and cloning sites)

ATGAGAGGATCGCATCACCATCACCATCACGGATCCATGAAAACCCTGAAA
CAAGCAGAGTCCTACATTAAGAGTAAAGTAAATACAGGAACTGATTTTGAT
GGTTTATATGGGTATCAGTGTATGGACTTAGCAGTAGATTATATTTACCATG
TAACAGATGGTAAAATAAGAATGTGGGGTAATGCTAAGGATGCGATAAAT
AACTCTTTTGGTGGTACTGCTACGGTATATAAAAACTACCCTGCTTTTAGAC
CTAAGTACGGTGATGTAGTCGTATGGACTACTGGTAATTTTGCAACTTATGG
TCATATCGCAATAGTTACTAAACCCTGACCCTTATGGAGACCTTCAATATGTT
ACAGTTCTTGAACAAAACTGGAACGGTAACGGGATTTATAAAACCGAGTTA
GCTACAATCAGAACACACGATTACACAGGAATTACACATTTTATTAAAGAC
GCAAAGAAAGATGAAAAATCACAAGTATGTAGTGGTTTGGCTATGGAAAA
ATATGACATTACAAATTTAAATGCTAAACAAGATAAATCAAAGAATGGGA
GCGTGAAAGAGTTGAAACATATCTATTCAAACCATATTAAAGGTAACAAGA
TTACAGCACCAAAACCTAGTATTCAAGGTGTGGTCATCCACAATGATTATG
GTAGTATGACACCTAGTCAATACTTACCATGGTTATATGCACGTGAGAATA
ACGGTACACACGTTAACGGTTGGGCTAGTGTTTATGCAAATAGAAACGAAG
TGCTTTGGTATCATCCGACAGACTACGTAGAGTGGCATTGTGGTAATCAAT
GGGCAAATGCTAACTTAATCGGATTTGAAGTGTGTGAGTCGTATCCTGGTA
GAATCTCGGACAAATTATTCTTAGAAAATGAAGAGCGACATTGAAAGTAG
CTGCGGATGTGATGAAGTCGTACGGATTACCAGTTAATCGCAACACTGTAC
GTCTGCATAACGAATTCTTCGGAACTTCTTGTCCACATCGTTCGTGGGACTT
GCATGTTGGCAAAGGTGAGCCTTACACAACTACTAATATTAATAAAATGAA
AGACTACTTCATCAAACGCATCAAACATTATTATGACGGTGGAAAGCTAGA
AGTAAGCAAAGCAGCAACTATCAAACAATCTGACGTTAAGCAAGAAGTTA
AAAAGCAAGAAGCAAAACAAATTGTGAAAGCAACAGATGCTGCAACACAT
GAACATTCAGCACAATGGTTGAATAATTACAAAAAAGGATATGGTTACGGT
CCTTATCCATTAGGTATAAATGGCGGTATGCACTACGGAGTTGATTTTTTA
TGAATATTGGAACACCAGTAAAAGCTATTTCAAGCGGAAAAATAGTTGAAG
CTGGTTGGAGTAATTACGGAGGAGGTAATCAAATAGGTCTTATTGAAAATG

TABLE 1-continued

SEQ ID NO identification

ATGGAGTGCATAGACAATGGTATATGCATCTAAGTAAATATAATGTTAAAG
TAGGAGATTATGTCAAAGCTGGTCAAATAATCGGTTGGTCTGGAAGCACTG
GTTATTCTACAGCACCACATTTACACTTCCAAAGAATGGTTAATTCATTTTC
AAATTCAACTGCCCAAGATCCAATGCCTTTCTTAAAGAGCGCAGGATATGG
AAAAGCAGGTGGTACAGTAACTCCAACGCCGAATACAGGTTGGAAACAGA
ATAAAGATGGCATTTGGTATAAAGCTGAACATGCTTCGTTCACAGTGACAG
CACCAGAGGGAATTATCACAAGATACAAAGGTCCTTGGACTGGTCACCCAC
AAGCTGGTGTATTACAAAAAGGTCAAACGATTAAATATGATGAGGTTCAAA
AATTTGACGGTCATGTTTGGGTATCGTGGGAAACGTTTGAGGGCGAAACTG
TATACATGCCGGTACGCACATGGGACGCTAAAACTGGTAAAGTTGGTAAGT
TGTGGGGCGAAATTAAATAA

SEQ ID NO: 48 (M23-LST_Ami2638_CBD2638 +
6xHis and cloning sites)

ATGAGAGGATCGCATCACCATCACCATCACGGATCCGCTGCAACACATGAA
CATTCAGCACAATGGTTGAATAATTACAAAAAAGGATATGGTTACGGTCCT
TATCCATTAGGTATAAATGGCGGTATGCACTACGGAGTTGATTTTTTTATGA
ATATTGGAACACCAGTAAAAGCTATTTCAAGCGGAAAAATAGTTGAAGCTG
GTTGGAGTAATTACGGAGGAGGTAATCAAATAGGTCTTATTGAAATGATG
GAGTGCATAGACAATGGTATATGCATCTAAGTAAATATAATGTTAAAGTAG
GAGATTATGTCAAAGCTGGTCAAATAATCGGTTGGTCTGGAAGCACTGGTT
ATTCTACAGCACCACATTTACACTTCCAAAGAATGGTTAATTCATTTTCAAA
TTCAACTGCCCAAGATCCAATGCCTTTCTTAAAGAGCGCAGGATATGGAAA
AGCAGGTGGTACAGTAACTCCAACGCCGAATACAGGTGAGCTCTTACGCCC
TAAAGACGCAAAGAAAGATGAAAAATCACAAGTATGTAGTGGTTTGGCTA
TGGAAAAATATGACATTACAAATTTAAATGCTAAACAAGATAAATCAAAG
AATGGGAGCGTGAAAGAGTTGAAACATATCTATTCAAACCATATTAAAGGT
AACAAGATTACAGCACCAAAACCTAGTATTCAAGGTGTGGTCATCCACAAT
GATTATGGTAGTATGACACCTAGTCAATACTTACCATGGTTATATGCACGTG
AGAATAACGGTACACACGTTAACGGTTGGGCTAGTGTTTATGCAAATAGAA
ACGAAGTGCTTTGGTATCATCCGACAGACTACGTAGAGTGGCATTGTGGTA
ATCAATGGGCAAATGCTAACTTAATCGGATTTGAAGTGTGTGAGTCGTATC
CTGGTAGAATCTCGGACAAATTATTCTTAGAAAATGAAGAAGCGACATTGA
AAGTAGCTGCGGATGTGATGAAGTCGTACGGATTACCAGTTAATCGCAACA
CTGTACGTCTGCATAACGAATTCTTCGGAACTTCTTGTCCACATCGTTCGTG
GGACTTGCATGTTGGCAAAGGTGAGCCTTACACAACTACTAATATTAATAA
AATGAAAGACTACTTCATCAAACGCATCAAACATTATTATGACGGTGGAAA
GCTAGAAGTAAGCAAAGCAGCAACTATCAAACAATCTGACGTTAAGCAAG
AAGTTAAAAAGCAAGAAGCAAAACAAATTGTGAAAGCAACAGATTGGAAA
CAGAATAAAGATGGCATTTGGTATAAAGCTGAACATGCTTCGTTCACAGTG
ACAGCACCAGAGGGAATTATCACAAGATACAAAGGTCCTTGGACTGGTCAC
CCACAAGCTGGTGTATTACAAAAAGGTCAAACGATTAAATATGATGAGGTT
CAAAAATTTGACGGTCATGTTTGGGTATCGTGGGAAACGTTTGAGGGCGAA
ACTGTATACATGCCGGTACGCACATGGGACGCTAAAACTGGTAAAGTTGGT
AAGTTGTGGGGCGAAATTAAATAA

SEQ ID NO: 49 (M23-2638_Ami2638_CBD2638_CBD2638 +
6xHis and cloning sites)

ATGAGAGGATCGCATCACCATCACCATCACGGATCCATGCTAACTGCTATT
GACTATCTTACGAAAAAAGGTTGGAAAATATCATCTGACCCTCGCACTTAC
GATGGTTACCCTAAAAACTACGGCTACAGAAATTACCATGAAAACGGCATT
AATTATGATGAGTTTTGTGGTGGTTATCATAGAGCTTTTGATGTTTACAGTA
ACGAAACTAACGACGTGCCTGCTGTTACTAGCGGAACAGTTATTGAAGCAA
ACGATTACGGTAATTTTGGTGGTACATTCGTTATTAGAGACGCTAACGATA
ACGATTGGATATATGGGCATCTACAACGTGGCTCAATGCGATTTGTTGTAG
GCGACAAAGTCAATCAAGGTGACATTATTGGTTTACAAGGTAATAGCAACT
ATTACGACAATCCTATGAGTGTACATTTACATTTACAATTACGCCCTAAAGA
CGCAAAGAAAGATGAAAAATCACAAGTATGTAGTGGTTTGGCTATGGAAA
AATATGACATTACAAATTTAAATGCTAAACAAGATAAATCAAAGAATGGG
AGCGTGAAAGAGTTGAAACATATCTATTCAAACCATATTAAAGGTAACAAG
ATTACAGCACCAAAACCTAGTATTCAAGGTGTGGTCATCCACAATGATTAT
GGTAGTATGACACCTAGTCAATACTTACCATGGTTATATGCACGTGAGAAT
AACGGTACACACGTTAACGGTTGGGCTAGTGTTTATGCAAATAGAAACGAA
GTGCTTTGGTATCATCCGACAGACTACGTAGAGTGGCATTGTGGTAATCAA
TGGGCAAATGCTAACTTAATCGGATTTGAAGTGTGTGAGTCGTATCCTGGT
AGAATCTCGGACAAATTATTCTTAGAAAATGAAGAAGCGACATTGAAAGTA
GCTGCGGATGTGATGAAGTCGTACGGATTACCAGTTAATCGCAACACTGTA
CGTCTGCATAACGAATTCTTCGGAACTTCTTGTCCACATCGTTCGTGGGACT
TGCATGTTGGCAAAGGTGAGCCTTACACAACTACTAATATTAATAAAATGA
AAGACTACTTCATCAAACGCATCAAACATTATTATGACGGTGGAAAGCTAG
AAGTAAGCAAAGCAGCAACTATCAAACAATCTGACGTTAAGCAAGAAGTT
AAAAAGCAAGAAGCAAAACAAATTGTGAAAGCAACAGATTGGAAACAGA
ATAAAGATGGCATTTGGTATAAAGCTGAACATGCTTCGTTCACAGTGACAG
CACCAGAGGGAATTATCACAAGATACAAAGGTCCTTGGACTGGTCACCCAC
AAGCTGGTGTATTACAAAAAGGTCAAACGATTAAATATGATGAGGTTCAAA
AATTTGACGGTCATGTTTGGGTATCGTGGGAAACGTTTGAGGGCGAAACTG

TABLE 1-continued

SEQ ID NO identification

TATACATGCCGGTACGCACATGGGACGCTAAAACTGGTAAAGTTGGTAAGT
TGTGGGGCGAAATTAAAGAGCTCGGTGGAAAGCTAGAAGTAAGCAAAGCA
GCAACTATCAAACAATCTGACGTTAAGCAAGAAGTTAAAAAGCAAGAAGC
AAAACAAATTGTGAAAGCAACAGATTGGAAACAGAATAAAGATGGCATTT
GGTATAAAGCTGAACATGCTTCGTTCACAGTGACAGCACCAGAGGGAATTA
TCACAAGATACAAAGGTCCTTGGACTGGTCACCCACAAGCTGGTGTATTAC
AAAAAGGTCAAACGATTAAATATGATGAGGTTCAAAAATTTGACGGTCATG
TTTGGGTATCGTGGGAACGTTTGAGGGCGAAACTGTATACATGCCGGTAC
GCACATGGGACGCTAAAACTGGTAAAGTTGGTAAGTTGTGGGGCGAAATTA
AATAA

SEQ ID NO: 50 (pQE-30 vector, available under
cat. No.: 32915 at Qiagen - Hilden, Germany)

CTCGAGAAATCATAAAAAATTTATTTGCTTTGTGAGCGGATAACAATTATA
ATAGATTCAATTGTGAGCGGATAACAATTTCACACAGAATTCATTAAAGAG
GAGAAATTAACTATGAGAGGATCGCATCACCATCACCATCACGGATCCGCA
TGCGAGCTCGGTACCCCGGGTCGACCTGCAGCCAAGCTTAATTAGCTGAGC
TTGGACTCCTGTTGATAGATCCAGTAATGACCTCAGAACTCCATCTGGATTT
GTTCAGAACGCTCGGTTGCCGCCGGGCGTTTTTTATTGGTGAGAATCCAAG
CTAGCTTGGCGAGATTTTCAGGAGCTAAGGAAGCTAAAATGGAGAAAAAA
ATCACTGGATATACCACCGTTGATATATCCCAATGGCATCGTAAAGAACAT
TTTGAGGCATTTCAGTCAGTTGCTCAATGTACCTATAACCAGACCGTTCAGC
TGGATATTACGGCCTTTTTAAAGACCGTAAAGAAAAATAAGCACAAGTTTT
ATCCGGCCTTTATTCACATTCTTGCCCGCCTGATGAATGCTCATCCGGAATT
TCGTATGGCAATGAAAGACGGTGAGCTGGTGATATGGGATAGTGTTCACCC
TTGTTACACCGTTTTCCATGAGCAAACTGAAACGTTTTCATCGCTCTGGAGT
GAATACCACGACGATTTCCGGCAGTTTCTACACATATATTCGCAAGATGTG
GCGTGTTACGGTGAAAACCTGGCCTATTTCCCTAAAGGGTTTATTGAGAAT
ATGTTTTTCGTCTCAGCCAATCCCTGGGTGAGTTTCACCAGTTTTGATTTAA
ACGTGGCCAATATGGACAACTTCTTCGCCCCCGTTTTCACCATGGGCAAAT
ATTATACGCAAGGCGACAAGGTGCTGATGCCGCTGGCGATTCAGGTTCATC
ATGCCGTTTGTGATGGCTTCCATGTCGGCAGAATGCTTAATGAATTACAAC
AGTACTGCGATGAGTGGCAGGGCGGGGCGTAATTTTTTTAAGGCAGTTATT
GGTGCCCTTAAACGCCTGGGGTAATGACTCTCTAGCTTGAGGCATCAAATA
AAACGAAAGGCTCAGTCGAAAGACTGGGCCTTTCGTTTTATCTGTTGTTTGT
CGGTGAACGCTCTCCTGAGTAGGACAAATCCGCCCTCTAGAGCTGCCTCGC
GCGTTTCGGTGATGACGGTGAAAACCTCTGACACATGCAGCTCCCGGAGAC
GGTCACAGCTTGTCTGTAAGCGGATGCCGGGAGCAGACAAGCCCGTCAGG
GCGCGTCAGCGGGTGTTGGCGGGTGTCGGGGCGCAGCCATGACCCAGTCAC
GTAGCGATAGCGGAGTGTATACTGGCTTAACTATGCGGCATCAGAGCAGAT
TGTACTGAGAGTGCACCATATGCGGTGTGAAATACCGCACAGATGCGTAAG
GAGAAAATACCGCATCAGGCGCTCTTCCGCTTCCTCGCTCACTGACTCGCTG
CGCTCGGTCGTTCGGCTGCGGCGAGCGGTATCAGCTCACTCAAAGGCGGTA
ATACGGTTATCCACAGAATCAGGGGATAACGCAGGAAAGAACATGTGAGC
AAAAGGCCAGCAAAAGGCCAGGAACCGTAAAAAGGCCGCGTTGCTGGCGT
TTTTCCATAGGCTCCGCCCCCCTGACGAGCATCACAAAAATCGACGCTCAA
GTCAGAGGTGGCGAAACCCGACAGGACTATAAAGATACCAGGCGTTTCCCC
CTGGAAGCTCCCTCGTGCGCTCTCCTGTTCCGACCCTGCCGCTTACCGGATA
CCTGTCCGCCTTTCTCCCTTCGGGAAGCGTGGCGCTTTCTCATAGCTCACGC
TGTAGGTATCTCAGTTCGGTGTAGGTCGTTCGCTCCAAGCTGGGCTGTGTGC
ACGAACCCCCCGTTCAGCCCGACCGCTGCGCCTTATCCGGTAACTATCGTCT
TGAGTCCAACCCGGTAAGACACGACTTATCGCCACTGGCAGCAGCCACTGG
TAACAGGATTAGCAGAGCGAGGTATGTAGGCGGTGCTACAGAGTTCTTGAA
GTGGTGGCCTAACTACGGCTACACTAGAAGGACAGTATTTGGTATCTGCGC
TCTGCTGAAGCCAGTTACCTTCGGAAAAAGAGTTGGTAGCTCTTGATCCGG
CAAACAAACCACCGCTGGTAGCGGTGGTTTTTTTGTTTGCAAGCAGCAGAT
TACGCGCAGAAAAAAAGGATCTCAAGAAGATCCTTTGATCTTTTCTACGGG
GTCTGACGCTCAGTGGAACGAAAACTCACGTTAAGGGATTTTGGTCATGAG
ATTATCAAAAAGGATCTTCACCTAGATCCTTTTAAATTAAAAATGAAGTTTT
AAATCAATCTAAAGTATATATGAGTAAACTTGGTCTGACAGTTACCAATGC
TTAATCAGTGAGGCACCTATCTCAGCGATCTGTCTATTTCGTTCATCCATAG
TTGCCTGACTCCCCGTCGTGTAGATAACTACGATACGGGAGGGCTTACCAT
CTGGCCCCAGTGCTGCAATGATACCGCGAGACCCACGCTCACCGGCTCCAG
ATTTATCAGCAATAAACCAGCCAGCCGGAAGGGCCGAGCGCAGAAGTGGT
CCTGCAACTTTATCCGCCTCCATCCAGTCTATTAATTGTTGCCGGGAAGCTA
GAGTAAGTAGTTCGCCAGTTAATAGTTTGCGCAACGTTGTTGCCATTGCTAC
AGGCATCGTGGTGTCACGCTCGTCGTTTGGTATGGCTTCATTCAGCTCCGGT
TCCCAACGATCAAGGCGAGTTACATGATCCCCCATGTTGTGCAAAAAAGCG
GTTAGCTCCTTCGGTCCTCCGATCGTTGTCAGAAGTAAGTTGGCCGCAGTGT
TATCACTCATGGTTATGGCAGCACTGCATAATTCTCTTACTGTCATGCCATC
CGTAAGATGCTTTTCTGTGACTGGTGAGTACTCAACCAAGTCATTCTGAGA
ATAGTGTATGCGGCGACCGAGTTGCTCTTGCCCGGCGTCAATACGGGATAA
TACCGCGCCACATAGCAGAACTTTAAAAGTGCTCATCATTGGAAAACGTTC
TTCGGGGCGAAAACTCTCAAGGATCTTACCGCTGTTGAGATCCAGTTCGAT
GTAACCCACTCGTGCACCCAACTGATCTTCAGCATCTTTTACTTTCACCAGC
GTTTCTGGGTGAGCAAAAACAGGAAGGCAAATGCCGCAAAAAAGGGAAT
AAGGGCGACACGGAAATGTTGAATACTCATACTCTTCCTTTTTCAATATTAT

TABLE 1-continued

SEQ ID NO identification

```
TGAAGCATTTATCAGGGTTATTGTCTCATGAGCGGATACATATTTGAATGTA
TTTAGAAAAATAAACAAATAGGGGTTCCGCGCACATTTCCCCGAAAAGTGC
CACCTGACGTCTAAGAAACCATTATTATCATGACATTAACCTATAAAATA
GGCGTATCACGAGGCCCTTTCGTCTTCAC
```

SEQ ID NO: 51 (CBD-2638 with putative linker indicated in bold)

GKLEVSKAATIKQSDVKQEVKKQEAKQIVKATDWKQNKDGIWYKAEHASF
TVTAPEGIITRYKGPWTGHPQAGVLQKGQTIKYDEVQKFDGHVWVSWETFEG
ETVYMPVRTWDAKTGKVGKLWGEIK

SEQ ID NO: 52 (CWT-LST with putative linker indicated in bold)

GKAGGTVTPTPNTGWKTNKYGTLYKSESASFTPNTDIITRTTGPFRSMPQSGV
LKAGQTIHYDEVMKQDGHVWVGYTGNSGQRIYLPVRTWNKSTNTLGVLWGT
IK

SEQ ID NO: 53 (M23-2638 with putative linker indicated in bold)

MLTAIDYLTKKGWKISSDPRTYDGYPKNYGYRNYHENGINYDEFCGGYHRAF
DVYSNETNDVPAVTSGTVIEANDYGNFGGTFVIRDANDNDWIYGHLQRGSMR
FVVGDKVNQGDIIGLQGNSNYYDNPMSVHLHLQLRPKDAKKD**EKSQVCSGL
AMEKYDITNLNAKQDKSKNGSVKELKHIYSNHIKG**

SEQ ID NO: 54 (M23-LST with putative linker indicated in bold)

AATHEHSAQWLNNYKKGYGYGPYPLGINGGMHYGVDFFMNIGTPVKAISSGK
IVEAGWSNYGGGNQIGLIENDGVHRQWYMHLSKYNVKVGDYVKAGQIIGWS
GSTGYSTAPHLHFQRMVNSFSNSTAQDPMPFLKSAGYGKAGGTVTPTPNTG

SEQ ID NO: 55 (Ami-2638 with putative linker indicated in bold)

EKSQVCSGLAMEKYDITNLNAKQDKSKNGSVKELKHIYSNHIKGNKITAPK
PSIQGVVIHNDYGSMTPSQYLPWLYARENNGTHVNGWASVYANRNEVLWYH
PTDYVEWHCGNQWANANLIGFEVCESYPGRISDKLFLENEEATLKVAADVMK
SYGLPVNRNTVRLHNEFFGTSCPHRSWDLHVGKGEPYTTTNINKMKDYFIKRI
KHYYDGGKLEVSKAATIKQSDVKQEVKKQEAKQIVKATD

SEQ ID NO: 56 (Ami-□11 with putative linker indicated in bold)

PKKETAKPQPKAVELKIIKDVVKGYDLPKRGSNPKGIVIHNDAGSKGATAE
AYRNGLVNAPLSRLEAGIAHSYVSGNTVWQALDESQVGWHTANQIGNKYYY
GIEVCQSMGADNATFLKNEQATFQECARLLKKWGLPANRNTIRLHNEFTSTSC
PHRSSVLHTGFDPVTRGLLPEDKRLQLKDYFIKQIRAYMD**GKIPVATVSNESSA
SSNTVKPVASA**

SEQ ID NO: 57 (CHAP-□11 with putative linker indicated in bold)

MSIIMEVATMQAKLTKNEFIEWLKTSEGKQFNVDLWYGFQCFDYANAGWKV
LFGLLLKGLGAKDIPFANNFDGLATVYQNTPDFLAQPGDMVVFGSNYGAGYG
HVAWWIEATLDYIIVYEQNWLGGGWTDGIEQPGWGWEKVTRRQHAYDFPMW
FIRPNFKSETAPRSVQSPTQAPKKETAKPQPKAVELKIIKDVVKGYDLPKRG

SEQ ID NO: 58 (CHAP-□Twort with putative linker indicated in bold)

MKTLKQAESYIKSKVNTGTDFDGLYGYQCMDLAVDYIYHVTDGKIRMWGNA
KDAINNSFGGTATVYKNYPAFRPKYGDVVVWTTGNFATYGHIAIVTNPDPYG
DLQYVTVLEQNWNGNGIYKTELATIRTHDYTGITHFI**RPNFATESSVKKKDTK
KKPKPSNRDGINKDKIVYDRTNINYNMVKRG**

SEQ ID NO: 59 (pHGFP_CBD2638_c vector)

```
CTCGAGAAATCATAAAAAATTTATTTGCTTTGTGAGCGGATAACAATTATA
ATAGATTCAATTGTGAGCGGATAACAATTTCACACAGAATTCATTAAAGAG
GAGAAATTAACTATGAGAGGATCGCATCACCATCACCATCACGGATCCATG
AGTAAAGGAGAAGAACTTTTCACTGGAGTTGTCCCAATTCTTGTTGAATTA
GATGGTGATGTTAATGGGCACAAATTTTCTGTCAGTGGAGAGGGTGAAGGT
GATGCAACATACGGAAAACTTACCCTTAAATTTATTTGCACTACTGGAAAA
CTACCTGTTCCATGGCCAACACTTGTCACTACTTTCGCGTATGGTCTTCAAT
GCTTTGCGAGATACCCAGATCATATGAAACGGCATGACTTTTTCAAGAGTG
```

TABLE 1-continued

SEQ ID NO identification

```
CCATGCCCGAAGGTTATGTACAGGAAAGAACTATATTTTTCAAAGATGACG
GGAACTACAAGACACGTGCTGAAGTCAAGTTTGAAGGTGATACCCTTGTTA
ATAGAATCGAGTTAAAAGGTATTGATTTTAAAGAAGATGGAAACATTCTTG
GACACAAATTGGAATACAACTATAACTCACACAATGTATACATCATGGCAG
ACAAACAAAAGAATGGAATCAAAGTTAACTTCAAAATTAGACACAACATT
GAAGATGGAAGCGTTCAACTAGCAGACCATTATCAACAAAATACTCCAATT
GGCGATGGCCCTGTCCTTTTACCAGACAACCATTACCTGTCCACACAATCTG
CCCTTTCGAAAGATCCCAACGAAAAGAGAGACCACATGGTCCTTCTTGAGT
TTGTAACAGCTGCTGGGATTACACATGGCATGGATGAACTATACAAAGAGC
TCGGTGGAAAGCTAGAAGTAAGCAAAGCAGCAACTATCAAACAATCTGAC
GTTAAGCAAGAAGTTAAAAAGCAAGAAGCAAAACAAATTGTGAAAGCAAC
AGATTGGAAACAGAATAAAGATGGCATTTGGTATAAAGCTGAACATGCTTC
GTTCACAGTGACAGCACCAGAGGGAATTATCACAAGATACAAAGGTCCTTG
GACTGGTCACCCACAAGCTGGTGTATTACAAAAAGGTCAAACGATTAAATA
TGATGAGGTTCAAAAATTTGACGGTCATGTTTGGGTATCGTGGGAAACGTT
TGAGGGCGAAACTGTATACATGCCGGTACGCACATGGGACGCTAAAACTG
GTAAAGTTGGTAAGTTGTGGGGCGAAATTAAATAAGTCGACCTGCAGCCAA
GCTTAATTAGCTGAGCTTGGACTCCTGTTGATAGATCCAGTAATGACCTCAG
AACTCCATCTGGATTTGTTCAGAACGCTCGGTTGCCGCCGGGCGTTTTTTAT
TGGTGAGAATCCAAGCTAGCTTGGCGAGATTTTCAGGAGCTAAGGAAGCTA
AAATGGAGAAAAAAATCACTGGATATACCACCGTTGATATATCCCAATGGC
ATCGTAAAGAACATTTTGAGGCATTTCAGTCAGTTGCTCAATGTACCTATAA
CCAGACCGTTCAGCTGGATATTACGGCCTTTTTAAAGACCGTAAAGAAAAA
TAAGCACAAGTTTTATCCGGCCTTTATTCACATTCTTGCCCGCCTGATGAAT
GCTCATCCGGAATTTCGTATGGCAATGAAAGACGGTGAGCTGGTGATATGG
GATAGTGTTCACCCTTGTTACACCGTTTTCCATGAGCAAACTGAAACGTTTT
CATCGCTCTGGAGTGAATACCACGACGATTTCCGGCAGTTTCTACACATAT
ATTCGCAAGATGTGGCGTGTTACGGTGAAAACCTGGCCTATTTCCCTAAAG
GGTTTATTGAGAATATGTTTTTCGTCTCAGCCAATCCCTGGGTGAGTTTCAC
CAGTTTTGATTTAAACGTGGCCAATATGGACAACTTCTTCGCCCCCGTTTTC
ACCATGGGCAAATATTATACGCAAGGCGACAAGGTGCTGATGCCGCTGGCG
ATTCAGGTTCATCATGCCGTTTGTGATGGCTTCCATGTCGGCAGAATGCTTA
ATGAATTACAACAGTACTGCGATGAGTGGCAGGGCGGGGCGTAATTTTTTT
AAGGCAGTTATTGGTGCCCTTAAACGCCTGGGGTAATGACTCTCTAGCTTG
AGGCATCAAATAAAACGAAAGGCTCAGTCGAAAGACTGGGCCTTTCGTTTT
ATCTGTTGTTTGTCGGTGAACGCTCTCCTGAGTAGGACAAATCCGCCCTCTA
GAGCTGCCTCGCGCGTTTCGGTGATGACGGTGAAAACCTCTGACACATGCA
GCTCCCGGAGACGGTCACAGCTTGTCTGTAAGCGGATGCCGGGAGCAGACA
AGCCCGTCAGGGCGCGTCAGCGGGTGTTGGCGGGTGTCGGGGCGCAGCCAT
GACCCAGTCACGTAGCGATAGCGGAGTGTATACTGGCTTAACTATGCGGCA
TCAGAGCAGATTGTACTGAGAGTGCACCATATGCGGTGTGAAATACCGCAC
AGATGCGTAAGGAGAAAATACCGCATCAGGCGCTCTTCCGCTTCCTCGCTC
ACTGACTCGCTGCGCTCGGTCGTTCGGCTGCGGCGAGCGGTATCAGCTCAC
TCAAAGGCGGTAATACGGTTATCCACAGAATCAGGGGATAACGCAGGAAA
GAACATGTGAGCAAAAGGCCAGCAAAAGGCCAGGAACCGTAAAAAGGCCG
CGTTGCTGGCGTTTTTCCATAGGCTCCGCCCCCCTGACGAGCATCACAAAA
ATCGACGCTCAAGTCAGAGGTGGCGAAACCCGACAGGACTATAAAGATAC
CAGGCGTTTCCCCCTGGAAGCTCCCTCGTGCGCTCTCCTGTTCCGACCCTGC
CGCTTACCGGATACCTGTCCGCCTTTCTCCCTTCGGGAAGCGTGGCGCTTTC
TCATAGCTCACGCTGTAGGTATCTCAGTTCGGTGTAGGTCGTTCGCTCCAAG
CTGGGCTGTGTGCACGAACCCCCCGTTCAGCCCGACCGCTGCGCCTTATCC
GGTAACTATCGTCTTGAGTCCAACCCGGTAAGACACGACTTATCGCCACTG
GCAGCAGCCACTGGTAACAGGATTAGCAGAGCGAGGTATGTAGGCGGTGC
TACAGAGTTCTTGAAGTGGTGGCCTAACTACGGCTACACTAGAAGGACAGT
ATTTGGTATCTGCGCTCTGCTGAAGCCAGTTACCTTCGGAAAAAGAGTTGG
TAGCTCTTGATCCGGCAAACAAACCACCGCTGGTAGCGGTGGTTTTTTTGTT
TGCAAGCAGCAGATTACGCGCAGAAAAAAAGGATCTCAAGAAGATCCTTT
GATCTTTTCTACGGGGTCTGACGCTCAGTGGAACGAAAACTCACGTTAAGG
GATTTTGGTCATGAGATTATCAAAAAGGATCTTCACCTAGATCCTTTTAAAT
TAAAAATGAAGTTTTAAATCAATCTAAAGTATATATGAGTAAACTTGGTCT
GACAGTTACCAATGCTTAATCAGTGAGGCACCTATCTCAGCGATCTGTCTAT
TTCGTTCATCCATAGTTGCCTGACTCCCCGTCGTGTAGATAACTACGATACG
GGAGGGCTTACCATCTGGCCCCAGTGCTGCAATGATACCGCGAGACCCACG
CTCACCGGCTCCAGATTTATCAGCAATAAACCAGCCAGCCGGAAGGGCCGA
GCGCAGAAGTGGTCCTGCAACTTTATCCGCCTCCATCCAGTCTATTAATTGT
TGCCGGGAAGCTAGAGTAAGTAGTTCGCCAGTTAATAGTTTGCGCAACGTT
GTTGCCATTGCTACAGGCATCGTGGTGTCACGCTCGTCGTTTGGTATGGCTT
CATTCAGCTCCGGTTCCCAACGATCAAGGCGAGTTACATGATCCCCCATGTT
GTGCAAAAAAGCGGTTAGCTCCTTCGGTCCTCCGATCGTTGTCAGAAGTAA
GTTGGCCGCAGTGTTATCACTCATGGTTATGGCAGCACTGCATAATTCTCTT
ACTGTCATGCCATCCGTAAGATGCTTTTCTGTGACTGGTGAGTACTCAACCA
AGTCATTCTGAGAATAGTGTATGCGGCGACCGAGTTGCTCTTGCCCGGCGT
CAATACGGGATAATACCGCGCCACATAGCAGAACTTTAAAAGTGCTCATCA
TTGGAAAACGTTCTTCGGGGCGAAAACTCTCAAGGATCTTACCGCTGTTGA
GATCCAGTTCGATGTAACCCACTCGTGCACCCAACTGATCTTCAGCATCTTT
TACTTTCACCAGCGTTTCTGGGTGAGCAAAAACAGGAAGGCAAAATGCCGC
AAAAAAGGGAATAAGGGCGACACGGAAATGTTGAATACTCATACTCTTCCT
TTTTCAATATTATTGAAGCATTTATCAGGGTTATTGTCTCATGAGCGGATAC
```

TABLE 1-continued

SEQ ID NO identification

ATATTTGAATGTATTTAGAAAAATAAACAAATAGGGGTTCCGCGCACATTT
CCCCGAAAAGTGCCACCTGACGTCTAAGAAACCATTATTATCATGACATTA
ACCTATAAAAATAGGCGTATCACGAGGCCCTTTCGTCTTCAC

SEQ ID NO: 60 (GFP_CBD2638)

ATGAGAGGATCGCATCACCATCACCATCACGGATCCATGAGTAAAGGAGA
AGAACTTTTCACTGGAGTTGTCCCAATTCTTGTTGAATTAGATGGTGATGTT
AATGGGCACAAATTTTCTGTCAGTGGAGAGGGTGAAGGTGATGCAACATAC
GGAAAACTTACCCTTAAATTTATTTGCACTACTGGAAAACTACCTGTTCCAT
GGCCAACACTTGTCACTACTTTCGCGTATGGTCTTCAATGCTTTGCGAGATA
CCCAGATCATATGAAACGGCATGACTTTTTCAAGAGTGCCATGCCCGAAGG
TTATGTACAGGAAAGAACTATATTTTTCAAAGATGACGGGAACTACAAGAC
ACGTGCTGAAGTCAAGTTTGAAGGTGATACCCTTGTTAATAGAATCGAGTT
AAAAGGTATTGATTTTAAAGAAGATGGAAACATTCTTGGACACAAATTGGA
ATACAACTATAACTCACACAATGTATACATCATGGCAGACAAACAAAAGA
ATGGAATCAAAGTTAACTTCAAAATTAGACACAACATTGAAGATGGAAGC
GTTCAACTAGCAGACCATTATCAACAAAATACTCCAATTGGCGATGGCCCT
GTCCTTTTACCAGACAACCATTACCTGTCCACACAATCTGCCCTTTCGAAAG
ATCCCAACGAAAAGAGAGACCACATGGTCCTTCTTGAGTTTGTAACAGCTG
CTGGGATTACACATGGCATGGATGAACTATACAAAGAGCTCGGTGGAAAG
CTAGAAGTAAGCAAAGCAGCAACTATCAAACAATCTGACGTTAAGCAAGA
AGTTAAAAAGCAAGAAGCAAAACAAATTGTGAAAGCAACAGATTGGAAAC
AGAATAAAGATGGCATTTGGTATAAAGCTGAACATGCTTCGTTCACAGTGA
CAGCACCAGAGGGAATTATCACAAGATACAAAGGTCCTTGGACTGGTCACC
CACAAGCTGGTGTATTACAAAAAGGTCAAACGATTAAATATGATGAGGTTC
AAAAATTTGACGGTCATGTTTGGGTATCGTGGGAAACGTTTGAGGGCGAAA
CTGTATACATGCCGGTACGCACATGGGACGCTAAAACTGGTAAAGTTGGTA
AGTTGTGGGGCGAAATTAAATAA

SEQ ID NO: 61 (GFP_CBD2638_CBD2638 Variant 1.
Restriction sites used for construction:
BamHI - SacI - SacI- SalI. TAA Stop codon
derived from 2$^{nd}$ CBD2638)

ATGAGAGGATCGCATCACCATCACCATCACGGATCCATGAGTAAAGGAGA
AGAACTTTTCACTGGAGTTGTCCCAATTCTTGTTGAATTAGATGGTGATGTT
AATGGGCACAAATTTTCTGTCAGTGGAGAGGGTGAAGGTGATGCAACATAC
GGAAAACTTACCCTTAAATTTATTTGCACTACTGGAAAACTACCTGTTCCAT
GGCCAACACTTGTCACTACTTTCGCGTATGGTCTTCAATGCTTTGCGAGATA
CCCAGATCATATGAAACGGCATGACTTTTTCAAGAGTGCCATGCCCGAAGG
TTATGTACAGGAAAGAACTATATTTTTCAAAGATGACGGGAACTACAAGAC
ACGTGCTGAAGTCAAGTTTGAAGGTGATACCCTTGTTAATAGAATCGAGTT
AAAAGGTATTGATTTTAAAGAAGATGGAAACATTCTTGGACACAAATTGGA
ATACAACTATAACTCACACAATGTATACATCATGGCAGACAAACAAAAGA
ATGGAATCAAAGTTAACTTCAAAATTAGACACAACATTGAAGATGGAAGC
GTTCAACTAGCAGACCATTATCAACAAAATACTCCAATTGGCGATGGCCCT
GTCCTTTTACCAGACAACCATTACCTGTCCACACAATCTGCCCTTTCGAAAG
ATCCCAACGAAAAGAGAGACCACATGGTCCTTCTTGAGTTTGTAACAGCTG
CTGGGATTACACATGGCATGGATGAACTATACAAAGAGCTCGGTGGAAAG
CTAGAAGTAAGCAAAGCAGCAACTATCAAACAATCTGACGTTAAGCAAGA
AGTTAAAAAGCAAGAAGCAAAACAAATTGTGAAAGCAACAGATTGGAAAC
AGAATAAAGATGGCATTTGGTATAAAGCTGAACATGCTTCGTTCACAGTGA
CAGCACCAGAGGGAATTATCACAAGATACAAAGGTCCTTGGACTGGTCACC
CACAAGCTGGTGTATTACAAAAAGGTCAAACGATTAAATATGATGAGGTTC
AAAAATTTGACGGTCATGTTTGGGTATCGTGGGAAACGTTTGAGGGCGAAA
CTGTATACATGCCGGTACGCACATGGGACGCTAAAACTGGTAAAGTTGGTA
AGTTGTGGGGCGAAATTAAAGAGCTCGGTGGAAAGCTAGAAGTAAGCAAA
GCAGCAACTATCAAACAATCTGACGTTAAGCAAGAAGTTAAAAAGCAAGA
AGCAAAACAAATTGTGAAAGCAACAGATTGGAAACAGAATAAAGATGGCA
TTTGGTATAAAGCTGAACATGCTTCGTTCACAGTGACAGCACCAGAGGGAA
TTATCACAAGATACAAAGGTCCTTGGACTGGTCACCCACAAGCTGGTGTAT
TACAAAAAGGTCAAACGATTAAATATGATGAGGTTCAAAAATTTGACGGTC
ATGTTTGGGTATCGTGGGAAACGTTTGAGGGCGAAACTGTATACATGCCGG
TACGCACATGGGACGCTAAAACTGGTAAAGTTGGTAAGTTGTGGGGCGAA
ATTAAATAAGTCGAC

SEQ ID NO: 62 (GFP_CBD2638_CBD2638 Variant 2.
Restriction sites used for construction:
BamHI - SacI - KpnI - SalI. Stop codon
is encoded by vector)

ATGAGAGGATCGCATCACCATCACCATCACGGATCCATGAGTAAAGGAGA
AGAACTTTTCACTGGAGTTGTCCCAATTCTTGTTGAATTAGATGGTGATGTT
AATGGGCACAAATTTTCTGTCAGTGGAGAGGGTGAAGGTGATGCAACATAC
GGAAAACTTACCCTTAAATTTATTTGCACTACTGGAAAACTACCTGTTCCAT
GGCCAACACTTGTCACTACTTTCGCGTATGGTCTTCAATGCTTTGCGAGATA
CCCAGATCATATGAAACAGCATGACTTTTTCAAGAGTGCCATGCCCGAAGG

TABLE 1-continued

SEQ ID NO identification

TTATGTACAGGAAAGAACTATATTTTTCAAAGATGACGGGAACTACAAGAC
ACGTGCTGAAGTCAAGTTTGAAGGTGATACCCTTGTTAATAGAATCGAGTT
AAAAGGTATTGATTTTAAAGAAGATGGAAACATTCTTGGACACAAATTGGA
ATACAACTATAACTCACACAATGTATACATCATGGCAGACAAACAAAAGA
ATGGAATCAAAGTTAACTTCAAAATTAGACACAACATTGAAGATGGAAGC
GTTCAACTAGCAGACCATTATCAACAAAATACTCCAATTGGCGATGGCCCT
GTCCTTTTACCAGACAACCATTACCTGTCCACACAATCTGCCCTTTCGAAAG
ATCCCAACGAAAAGAGAGACCACATGGTCCTTCTTGAGTTTGTAACAGCTG
CTGGGATTACACATGGCATGGATGAACTATACAAAGAGCTCGGTGGAAAG
CTAGAAGTAAGCAAAGCAGCAACTATCAAACAATCTGACGTTAAGCAAGA
AGTTAAAAAGCAAGAAGCAAAACAAATTGTGAAAGCAACAGATTGGAAAC
AGAATAAAGATGGCATTTGGTATAAAGCTGAACATGCTTCGTTCACAGTGA
CAGCACCAGAGGGAATTATCACAAGATACAAAGGTCCTTGGACTGGTCACC
CACAAGCTGGTGTATTACAAAAAGGTCAAACGATTAAATATGATGAGGTTC
AAAAATTTGACGGTCATGTTTGGGTATCGTGGGAAACGTTTGAGGGCGAAA
CTGTATACATGCCGGTACGCACATGGGACGCTAAAACTGGTAAAGTTGGTA
AGTTGTGGGCGAAATTAAAGGTACCGGTGGAAAGCTAGAAGTAAGCAAA
GCAGCAACTATCAAACAATCTGACGTTAAGCAAGAAGTTAAAAAGCAAGA
AGCAAAACAAATTGTGAAAGCAACAGATTGGAAACAGAATAAAGATGGCA
TTTGGTATAAAGCTGAACATGCTTCGTTCACAGTGACAGCACCAGAGGGAA
TTATCACAAGATACAAAGGTCCTTGGACTGGTCACCCACAAGCTGGTGTAT
TACAAAAAGGTCAAACGATTAAATATGATGAGGTTCAAAAATTTGACGGTC
ATGTTTGGGTATCGTGGGAAACGTTTGAGGGCGAAACTGTATACATGCCGG
TACGCACATGGGACGCTAAAACTGGTAAAGTTGGTAAGTTGTGGGGCGAA
ATTAAAGTCGACCTGCAGCCAAGCTTAATTAGCTGA

SEQ ID NO: 63 (GFP_CBD2638_CBD2638_CBD2638.
Restriction sites used for construction:
BamHI - SacI - KpnI- SalI - PstI. Stop codon
is encoded by vector)

ATGAGAGGATCGCATCACCATCACCATCACGGATCCATGAGTAAAGGAGA
AGAACTTTTCACTGGAGTTGTCCCAATTCTTGTTGAATTAGATGGTGATGTT
AATGGGCACAAATTTTCTGTCAGTGGAGAGGGTGAAGGTGATGCAACATAC
GGAAAACTTACCCTTAAATTTATTTGCACTACTGGAAAACTACCTGTTCCAT
GGCCAACACTTGTCACTACTTTCGCGTATGGTCTTCAATGCTTTGCGAGATA
CCCAGATCATATGAAACAGCATGACTTTTTCAAGAGTGCCATGCCCGAAGG
TTATGTACAGGAAAGAACTATATTTTTCAAAGATGACGGGAACTACAAGAC
ACGTGCTGAAGTCAAGTTTGAAGGTGATACCCTTGTTAATAGAATCGAGTT
AAAAGGTATTGATTTTAAAGAAGATGGAAACATTCTTGGACACAAATTGGA
ATACAACTATAACTCACACAATGTATACATCATGGCAGACAAACAAAAGA
ATGGAATCAAAGTTAACTTCAAAATTAGACACAACATTGAAGATGGAAGC
GTTCAACTAGCAGACCATTATCAACAAATACTCCAATTGGCGATGGCCCT
GTCCTTTTACCAGACAACCATTACCTGTCCACACAATCTGCCCTTTCGAAAG
ATCCCAACGAAAAGAGAGACCACATGGTCCTTCTTGAGTTTGTAACAGCTG
CTGGGATTACACATGGCATGGATGAACTATACAAAGAGCTCGGTGGAAAG
CTAGAAGTAAGCAAAGCAGCAACTATCAAACAATCTGACGTTAAGCAAGA
AGTTAAAAAGCAAGAAGCAAAACAAATTGTGAAAGCAACAGATTGGAAAC
AGAATAAAGATGGCATTTGGTATAAAGCTGAACATGCTTCGTTCACAGTGA
CAGCACCAGAGGGAATTATCACAAGATACAAAGGTCCTTGGACTGGTCACC
CACAAGCTGGTGTATTACAAAAAGGTCAAACGATTAAATATGATGAGGTTC
AAAAATTTGACGGTCATGTTTGGGTATCGTGGGAAACGTTTGAGGGCGAAA
CTGTATACATGCCGGTACGCACATGGGACGCTAAAACTGGTAAAGTTGGTA
AGTTGTGGGCGAAATTAAAGGTACCGGTGGAAAGCTAGAAGTAAGCAAA
GCAGCAACTATCAAACAATCTGACGTTAAGCAAGAAGTTAAAAAGCAAGA
AGCAAAACAAATTGTGAAAGCAACAGATTGGAAACAGAATAAAGATGGCA
TTTGGTATAAAGCTGAACATGCTTCGTTCACAGTGACAGCACCAGAGGGAA
TTATCACAAGATACAAAGGTCCTTGGACTGGTCACCCACAAGCTGGTGTAT
TACAAAAAGGTCAAACGATTAAATATGATGAGGTTCAAAAATTTGACGGTC
ATGTTTGGGTATCGTGGGAAACGTTTGAGGGCGAAACTGTATACATGCCGG
TACGCACATGGGACGCTAAAACTGGTAAAGTTGGTAAGTTGTGGGGCGAA
ATTAAAGTCGACGGTGGAAAGCTAGAAGTAAGCAAAGCAGCAACTATCAA
ACAATCTGACGTTAAGCAAGAAGTTAAAAAGCAAGAAGCAAAACAAATTG
TGAAAGCAACAGATTGGAAACAGAATAAAGATGGCATTTGGTATAAAGCT
GAACATGCTTCGTTCACAGTGACAGCACCAGAGGGAATTATCACAAGATAC
AAAGGTCCTTGGACTGGTCACCCACAAGCTGGTGTATTACAAAAAGGTCAA
ACGATTAAATATGATGAGGTTCAAAAATTTGACGGTCATGTTTGGGTATCG
TGGGAAACGTTTGAGGGCGAAACTGTATACATGCCGGTACGCACATGGGAC
GCTAAAACTGGTAAAGTTGGTAAGTTGTGGGGCGAAATTAAACTGCAGCCA
AGCTTAATTAGCTGA

SEQ ID NO: 64 (GFP_CBD2638 aa)

MRGSHHHHHHGSMSKGEELFTGVVPILVELDGDVNGHKFSVSGEGEGDATY
GKLTLKFICTTGKLPVPWPTLVTTFAYGLQCFARYPDHMKRHDFFKSAMPEGY
VQERTIFFKDDGNYKTRAEVKFEGDTLVNRIELKGIDFKEDGNILGHKLEYNYN
SHNVYIMADKQKNGIKVNFKIRHNIEDGSVQLADHYQQNPIGDGPVLLPDNH
YLSTQSALSKDPNEKRDHMVLLEFVTAAGITHGMDELYKELGGKLEVSKAATI

TABLE 1-continued

SEQ ID NO identification

KQSDVKQEVKKQEAKQIVKATDWKQNKDGIWYKAEHASFTVTAPEGIITRYK
GPWTGHPQAGVLQKGQTIKYDEVQKFDGHVWVSWETFEGETVYMPVRTWD
AKTGKVGKLWGEIK

SEQ ID NO: 65 (GFP_CBD2638_CBD2638 Variant 1 aa)

MRGSHHHHHHGSMSKGEELFTGVVPILVELDGDVNGHKFSVSGEGEGDATY
GKLTLKFICTTGKLPVPWPTLVTTFAYGLQCFARYPDHMKRHDFFKSAMPEGY
VQERTIFFKDDGNYKTRAEVKFEGDTLVNRIELKGIDFKEDGNILGHKLEYNYN
SHNVYIMADKQKNGIKVNFKIRHNIEDGSVQLADHYQQNTPIGDGPVLLPDNH
YLSTQSALSKDPNEKRDHMVLLEFVTAAGITHGMDELYKELGGKLEVSKAATI
KQSDVKQEVKKQEAKQIVKATDWKQNKDGIWYKAEHASFTVTAPEGIITRYK
GPWTGHPQAGVLQKGQTIKYDEVQKFDGHVWVSWETFEGETVYMPVRTWD
AKTGKVGKLWGEIKELGGKLEVSKAATIKQSDVKQEVKKQEAKQIVKATDW
KQNKDGIWYKAEHASFTVTAPEGIITRYKGPWTGHPQAGVLQKGQTIKYDEV
QKFDGHVWVSWETFEGETVYMPVRTWDAKTGKVGKLWGEIK

SEQ ID NO: 66 (GFP_CBD2638_CBD2638 Variant 2 aa)

MRGSHHHHHHGSMSKGEELFTGVVPILVELDGDVNGHKFSVSGEGEGDATY
GKLTLKFICTTGKLPVPWPTLVTTFAYGLQCFARYPDHMKQHDFFKSAMPEGY
VQERTIFFKDDGNYKTRAEVKFEGDTLVNRIELKGIDFKEDGNILGHKLEYNYN
SHNVYIMADKQKNGIKVNFKIRHNIEDGSVQLADHYQQNTPIGDGPVLLPDNH
YLSTQSALSKDPNEKRDHMVLLEFVTAAGITHGMDELYKELGGKLEVSKAATI
KQSDVKQEVKKQEAKQIVKATDWKQNKDGIWYKAEHASFTVTAPEGIITRYK
GPWTGHPQAGVLQKGQTIKYDEVQKFDGHVWVSWETFEGETVYMPVRTWD
AKTGKVGKLWGEIKGTGGKLEVSKAATIKQSDVKQEVKKQEAKQIVKATDW
KQNKDGIWYKAEHASFTVTAPEGIITRYKGPWTGHPQAGVLQKGQTIKYDEV
QKFDGHVWVSWETFEGETVYMPVRTWDAKTGKVGKLWGEIKVDLQPSLIS

SEQ ID NO: 67 (GFP_CBD2638_CBD2638_CBD2638 aa)

MRGSHHHHHHGSMSKGEELFTGVVPILVELDGDVNGHKFSVSGEGEGDATY
GKLTLKFICTTGKLPVPWPTLVTTFAYGLQCFARYPDHMKQHDFFKSAMPEGY
VQERTIFFKDDGNYKTRAEVKFEGDTLVNRIELKGIDFKEDGNILGHKLEYNYN
SHNVYIMADKQKNGIKVNFKIRHNIEDGSVQLADHYQQNTPIGDGPVLLPDNH
YLSTQSALSKDPNEKRDHMVLLEFVTAAGITHGMDELYKELGGKLEVSKAATI
KQSDVKQEVKKQEAKQIVKATDWKQNKDGIWYKAEHASFTVTAPEGIITRYK
GPWTGHPQAGVLQKGQTIKYDEVQKFDGHVWVSWETFEGETVYMPVRTWD
AKTGKVGKLWGEIKGTGGKLEVSKAATIKQSDVKQEVKKQEAKQIVKATDW
KQNKDGIWYKAEHASFTVTAPEGIITRYKGPWTGHPQAGVLQKGQTIKYDEV
QKFDGHVWVSWETFEGETVYMPVRTWDAKTGKVGKLWGEIKDGGKLEVS
KAATIKQSDVKQEVKKQEAKQIVKATDWKQNKDGIWYKAEHASFTVTAPEGI
ITRYKGPWTGHPQAGVLQKGQTIKYDEVQKFDGHVWVSWETFEGETVYMPV
RTWDAKTGKVGKLWGEIKLQPSLIS

The invention claimed is:

1. A nucleic acid molecule comprising a first nucleotide sequence, encoding a cell wall-binding domain binding the peptidoglycan cell wall of *Staphylococcus* genera, said nucleic acid molecule further comprising a heterologous nucleotide sequence encoding a lytic domain exhibiting peptidoglycan hydrolase activity, wherein said lytic domain is a second and third nucleotide sequences, and wherein said second nucleotide sequence encodes an M23 endopeptidase domain and said third nucleotide sequence encodes an amidase domain, and wherein said nucleic acid molecule has at least 85% sequence identity with SEQ ID NO: 9.

2. The nucleic acid molecule according to claim 1, wherein said first nucleotide sequence originates from *S. aureus* bacteriophage Φ2638a endolysin.

3. The nucleic acid molecule according to claim 1, further comprising a fourth nucleotide sequence encoding a CHAP (cysteine, histidine-dependent amidohydrolases/peptidases) domain.

4. The nucleic acid molecule according to claim 3, wherein said fourth nucleotide sequences originates from *S. aureus* bacteriophage Φ11 or *S. aureus* bacteriophage Φ Twort endolysin.

5. The nucleic acid molecule according to claim 4, wherein said fourth nucleotide sequences has at least 80% sequence identity with SEQ ID NO: 18 or SEQ ID NO: 19.

6. A polypeptide encoded by a nucleic acid molecule as identified in claim 1, said polypeptide comprising a cell wall-binding domain binding the peptidoglycan cell wall of *Staphylococcus* genera, further comprising a heterologous lytic domain exhibiting peptidoglycan hydrolase activity comprising an M23 endopeptidase domain and an amidase domain.

7. A nucleic acid construct comprising a nucleic acid molecule as identified in claim 1.

8. An expression vector comprising a nucleic acid construct as defined in claim 7 operably linked to one or more control sequences, which direct the production or expression of the encoded polypeptide in a cell, a subject, or a cell-free expression system.

9. A cell comprising the nucleic acid construct as identified in claim 7, said cell being a microbial, prokaryotic or eukaryotic cell.

10. A method for producing, optionally purifying and optionally freeze-drying a polypeptide, said method comprising the steps of:
   i) producing said polypeptide in a cell comprising a nucleic acid construct as defined in claim 7, optionally
   ii) purifying said polypeptide, and optionally
   iii) freeze-drying said purified polypeptide.

11. A method for producing a polypeptide with an enhanced lytic activity comprising treating a polypeptide as obtainable by the method of claim 10 by
   i) dialyzing said polypeptide against a buffer comprising a chelating compound,
   ii) dialyzing said polypeptide against a divalent metal ion-containing buffer, preferably said divalent metal ion being selected from the group consisting of $Co^{2+}$, $Cu^{2+}$, $Mn^{2+}$ and $Zn^{2+}$.

12. A composition comprising a polypeptide as obtainable by a method as identified in claim 10.

13. The composition according to claim 12, comprising one or more additional active ingredients, preferably selected from the group consisting of a bacteriophage and antibiotic.

14. The composition according to claim 12 for use as a medicament.

15. The composition according to claim 14 for use as a medicament in the treatment of an infectious disease.

16. Use of a polypeptide according to claim 6 as an antimicrobial, preferably as a food additive or a disinfectant.

17. Use of a nucleic acid molecule according to claim 1, a polypeptide encoded by such nucleic acid molecule, a nucleic acid construct and/or vector and/or cell comprising such nucleic acid construct or a composition comprising any of such polypeptide, nucleic acid molecule, nucleic acid, vector and/or cell for detecting a *Staphylococcus*, preferably in a diagnostic application.

18. A method for treating, delaying and/or preventing an infectious disease by administering a composition as defined in claim 12.

19. A cell comprising the expression vector as identified in claim 8, said cell being a microbial, prokaryotic or eukaryotic cell.

20. A polypeptide according to claim 6 having at least 85% sequence identity with SEQ ID NO: 29.

21. Use of a polypeptide according to claim 20 as an antimicrobial, preferably as a food additive or a disinfectant.

\* \* \* \* \*